United States Patent
Abrams et al.

(10) Patent No.: US 10,005,836 B2
(45) Date of Patent: Jun. 26, 2018

(54) ANTIBODY DRUG CONJUGATES

(71) Applicants: Tinya Abrams, Acton, MA (US); Steven Bruce Cohen, San Diego, CA (US); Jason Damiano, Oakland, CA (US); Clemens Dürr, Weil am Rhein (DE); Thomas Huber, Allschwil (CH); Daniel Menezes, Berkeley, CA (US); Kathy Miller, San Francisco, CA (US); Katherine Rendahl, Berkeley, CA (US); Jean-Michel Rene Rondeau, Rixheim (FR)

(72) Inventors: Tinya Abrams, Acton, MA (US); Steven Bruce Cohen, San Diego, CA (US); Jason Damiano, Oakland, CA (US); Clemens Dürr, Weil am Rhein (DE); Thomas Huber, Allschwil (CH); Daniel Menezes, Berkeley, CA (US); Kathy Miller, San Francisco, CA (US); Katherine Rendahl, Berkeley, CA (US); Jean-Michel Rene Rondeau, Rixheim (FR)

(73) Assignee: Novartis AG, Basel (CH)

( * ) Notice: Subject to any disclaimer, the term of this patent is extended or adjusted under 35 U.S.C. 154(b) by 173 days.

(21) Appl. No.: 14/940,961

(22) Filed: Nov. 13, 2015

(65) Prior Publication Data
US 2016/0137730 A1 May 19, 2016

Related U.S. Application Data

(60) Provisional application No. 62/079,942, filed on Nov. 14, 2014.

(51) Int. Cl.
*C07K 16/28* (2006.01)
*A61K 47/68* (2017.01)
*C07K 16/30* (2006.01)
*A61K 31/53* (2006.01)
*A61K 31/5365* (2006.01)
*G01N 33/574* (2006.01)

(52) U.S. Cl.
CPC .......... *C07K 16/28* (2013.01); *A61K 31/5365* (2013.01); *A61K 47/6803* (2017.08); *A61K 47/6849* (2017.08); *A61K 47/6851* (2017.08); *C07K 16/30* (2013.01); *G01N 33/57492* (2013.01); *C07K 2299/00* (2013.01); *C07K 2317/21* (2013.01); *C07K 2317/24* (2013.01); *C07K 2317/33* (2013.01); *C07K 2317/51* (2013.01); *C07K 2317/515* (2013.01); *C07K 2317/52* (2013.01); *C07K 2317/55* (2013.01); *C07K 2317/56* (2013.01); *C07K 2317/565* (2013.01); *C07K 2317/622* (2013.01); *C07K 2317/73* (2013.01); *C07K 2317/732* (2013.01); *C07K 2317/76* (2013.01); *C07K 2317/77* (2013.01); *C07K 2317/92* (2013.01); *C07K 2319/00* (2013.01); *G01N 2333/705* (2013.01)

(58) Field of Classification Search
CPC ............ A61K 47/6803; A61K 47/6849; A61K 31/5365; C07K 16/28; C07K 16/30; C07K 2317/21; C07K 2317/24; C07K 2317/33; C07K 2317/52; C07K 2317/55; C07K 2317/73; C07K 2317/732; C07K 2317/76; C07K 2317/77; C07K 2317/92; C07K 2319/00
See application file for complete search history.

(56) References Cited

U.S. PATENT DOCUMENTS

| | | | |
|---|---|---|---|
| 5,895,748 | A | 4/1999 | Johnson |
| 6,169,071 | B1 | 1/2001 | Blaschuk et al. |
| 6,312,686 | B1 | 11/2001 | Staddon et al. |
| 7,452,537 | B2 | 11/2008 | Bauer et al. |
| 7,456,153 | B2 | 11/2008 | Blaschuk et al. |
| 7,928,214 | B2 | 4/2011 | Bauer et al. |
| 8,603,986 | B2 | 12/2013 | Blaschuk et al. |
| 2002/0045591 | A1 | 4/2002 | Geiger et al. |
| 2003/0086934 | A1 | 5/2003 | Botstein et al. |
| 2003/0194406 | A1 | 10/2003 | Reinhard et al. |
| 2004/0137538 | A1 | 7/2004 | Bradford |
| 2004/0137539 | A1 | 7/2004 | Bradford |
| 2005/0002919 | A1 | 1/2005 | Brenner et al. |
| 2005/0037439 | A1 | 2/2005 | Bourner et al. |
| 2005/0129676 | A1 | 6/2005 | Blaschuk et al. |
| 2005/0221398 | A1 | 10/2005 | Jacquemier et al. |
| 2006/0040302 | A1 | 2/2006 | Botstein et al. |
| 2008/0008719 | A1 | 1/2008 | Bowdish et al. |
| 2008/0026481 | A1 | 1/2008 | Mitas |
| 2009/0169572 | A1 | 7/2009 | Nakatsuru et al. |
| 2010/0233187 | A1 | 9/2010 | Chan et al. |
| 2010/0240066 | A1 | 9/2010 | Blaschuk et al. |
| 2012/0128584 | A1 | 5/2012 | Togashi et al. |
| 2012/0136140 | A1 | 5/2012 | Aburatani et al. |
| 2013/0317201 | A1 | 11/2013 | Ishii et al. |
| 2014/0178368 | A1 | 6/2014 | Sharp et al. |
| 2014/0221620 | A1 | 8/2014 | Zhang et al. |
| 2014/0328754 | A1 | 11/2014 | Hino et al. |

FOREIGN PATENT DOCUMENTS

| | | |
|---|---|---|
| EP | 1304377 A1 | 4/2003 |
| EP | 2634194 A1 | 9/2013 |

(Continued)

OTHER PUBLICATIONS

Strop et al., Chemistry and Biology 20: 161-167, 2013.*

(Continued)

*Primary Examiner* — Phuong Huynh

(57) ABSTRACT

This application discloses anti-P-cadherin antibodies, antigen binding fragments thereof, and antibody drug conjugates of said antibodies or antigen binding fragments. The invention also relates to methods of treating cancer using the antibodies, antigen binding fragments, and antibody drug conjugates. Also disclosed herein are methods of making the antibodies, antigen binding fragments, and antibody drug conjugates, and methods of using the antibodies and antigen binding fragments as diagnostic reagents.

22 Claims, 19 Drawing Sheets

(56) References Cited

FOREIGN PATENT DOCUMENTS

| WO | 2002008765 A2 | 1/2002 |
|---|---|---|
| WO | 2004086038 A2 | 10/2004 |
| WO | 2005090572 A2 | 9/2005 |
| WO | 2007075672 A2 | 7/2007 |
| WO | 2008104804 A2 | 9/2008 |
| WO | 2010054007 A1 | 5/2010 |
| WO | 2011080796 A1 | 7/2011 |
| WO | 2012057315 A1 | 5/2012 |
| WO | 2013150623 A1 | 10/2013 |
| WO | 2014126198 A1 | 8/2014 |

OTHER PUBLICATIONS

Delgoffe et al., Molecular Immunology 46: 2694-2698, 2009.*
Shimoyama et al. "Molecular Cloning of a Human $Ca^{2+}$-dependent Cell-Cell Adhesion Molecule Homologous to Mouse Placental Cadherin: Its Low Expression in Human Placental Tissues." Journal of Cell Biology. vol. 109, Oct. 1989. pp. 1787-1794.
Islam et al., "Expression of N-cadherin by human squamous carcinoma cells induces a scattered fibroblastic phenotype with disrupted cell-cell adhesion," J Cell Biol. Dec. 1996;135(6 Pt 1):1643-54.
International Search Report and Written Opinion for International Application No. PCT/IB2015/058801, dated May 3, 2016 (21 pages).
Bouchard et al., "Antibody-drug conjugates—a new wave of cancer drugs," Bioorg Med Chem Lett. Dec. 1, 2014;24(23):5357-63.

* cited by examiner

```
           108           120    ↓   ↓ 130          140          150 ↓    ↓ 160    ↓
human    DWVVAPISVPENGKGPFPQRLNQLKSNKDRDTKIFYSITGPGADSPPEGVFAVEKETGWL
cyno     DWVVAPISVPENGKGPFPQRLNQLKSNKDRDTKIFYSITGPGADSPPEGVFAVEKETGWL
         ************************************************************

170      ↓ 180         190         200         208
human    LLNKPLDREEIAKYELFGHAVSENGASVEDPMNISIIVTDQ
cyno     LLNKPLDREEIAKYELFGHAVSENGASVEDPMNISIIVTDQ
         ****************************************
```

ANTIBODY DRUG CONJUGATES

This application claims priority to, and benefit of under 35 USC § 119, U.S. Provisional Application No. 62/079,942, filed on Nov. 14, 2014, the entire contents of which are incorporated by referenced herein.

SEQUENCE LISTING

The instant application contains a Sequence Listing which has been submitted electronically in ASCII format and is hereby incorporated by reference in its entirety. Said ASCII copy, created on Nov. 12, 2015, is named PAT056506-WO-PCT_SL.txt and is 146,966 bytes in size.

FIELD OF THE INVENTION

The present invention generally relates to anti-P-cadherin antibodies, antibody fragments, antibody drug conjugates, and their uses for the treatment of cancer.

BACKGROUND OF THE INVENTION

P-Cadherin

Classical cadherins represent a family of cell adhesion molecules expressed in adherens-type junctions that mediate calcium-dependent cell-to-cell contacts. Placental cadherin (P-cadherin; also known as cadherin 3, type 1 or "CDH3") has restricted expression in normal tissues but is known to be expressed in undifferentiated or under-differentiated cell types of several tissues, including the basal epithelial cells of the skin, esophagus, lung and oral cavity. (see, e.g., Albergaria et al., Int. J. Dev. Biol. 55:811-822 (2011)).

The structure of P-cadherin consists of 3 distinct domains: an extracellular domain (ECD) containing five cadherin repeats in tandem, a transmembrane domain, and an intracellular tail containing a catenin binding domain. The ECD mediates both cis- and trans interactions between multiple P-cadherin molecules, while the catenin binding domain links P-cadherin to proteins such as p120 catenin and consequently, cellular cytoskeletal elements. (see, e.g., Wu et al., PNAS 107:17592-7 (2010).

P-Cadherin and Cancer

P-cadherin (also referred to as "Pcad" "PCad" "P-Cad, or CDH3), is also known to be overexpressed in a number of malignant tumors, including breast, gastric, endometrial, head and neck, and colorectal cancer, among others. The overexpression of P-cadherin in some breast, endometrial, ovarian, colorectal and bladder tumors has also been correlated with a worse prognosis compared to cases where P-cadherin expression levels are low or absent. In breast cancer, P-cadherin is frequently overexpressed in high grade invasive carcinomas and is a reliable marker of basal-like tumors. (see, e.g., Paredes et al., Br. Can. Res. 9:214-226 (2007); Sanders et al., Int. J. Can. 79:573-579 (1998); Albergaria et al., Int. J. Dev. Biol. 55:811-822 (2011); Sousa et al., Histol. Histopathol. 25:963-975 (2010))

In certain cancer types, such as breast and ovarian cancer, P-cadherin is known to promote tumor cell motility, invasiveness and metastasis. (see, e.g., Cheung et al., Oncogene 30:2964-74 (2011); Ribeiro et al, Oncogene 29:392-402 (2010)).

Numerous cancer-relevant processes are known to promote the expression of P-cadherin mRNA and protein. Inactivation of the tumor suppressor BRCA1 through either mutation or loss of expression has been associated with increased P-cadherin expression in both breast cancer cell lines and patient specimens. The transcription factor C-EBPβ and the anti-estrogen ICI182780 (fulvestrant) are also known to disregulate P-cadherin expression and induce its upregulation in tumor cells, as is hypomethylation of the CDH3 promoter via other processes. In alveolar rhabdomyosarcoma, the chimeric oncogenic transcription factors PAX3-FOXOA1 and PAX7-FOXOA1 (resulting from translocations) directly induce P-cadherin expression, resulting in increased tumor aggressiveness. (see e.g. Albergaria et al., Int. J. Dev. Biol. 55:811-822 (2011); Thuault et al., Oncogene 15:1474-86 (2012); Ames et al., Clin. Can. Res. 11; 4003-11 (2005); Gorski et al., Br. Can. Res. Treat. 122:721-31 (2010); Paredes et al., Clin. Can. Res. 11:5869-5877 (2005); Albergaria et al., Human Mol. Gen. 19:2554-2566 (2010).

Antibody Drug Conjugates

Antibody drug conjugates ("ADCs") have been used for the local delivery of cytotoxic agents in the treatment of cancer (see e.g., Lambert, Curr. Opinion In Pharmacology 5:543-549, 2005). ADCs allow targeted delivery of the drug moiety where maximum efficacy with minimal toxicity may be achieved. As more ADCs show promising clinical results, there is an increased need to develop new therapeutics for cancer therapy. Moreover, not all attempts to make therapeutically effective ADCs to known cancer targets have been successful. Examples of factors that can effect therapeutic effectiveness of ADCs include affinity, ability of an antibody to conjugate, the cleavability or stability of the linker; stability of the antibody-drug conjugate, the tendency of an antibody drug conjugate to aggregate, and the ratio of the drug/payload molecules that conjugate to each antibody ("DAR" or "drug antibody ratio").

Aggregation and lack of stability can increase the possibility of adverse reactions to antibody drug conjugates in a clinical setting, reduce efficacy, as well as add to the cost of making ADCS.

Therefore there is a need for therapeutically effective ADC molecules.

SUMMARY OF THE INVENTION

The present application discloses antibodies, or antigen binding fragments thereof, that bind that bind to human P-cadherin protein. In one embodiment, the antibodies or antigen binding fragments thereof bind to P-cadherin at one or more residues selected from the amino acids at positions 124, 125, 151, 153, 154, 155, 156, 159, 160, 161, 162, 163, 168, 170, 171, and 172 of SEQ ID NO:126. In another embodiment, the antibodies, or antigen binding fragments thereof, bind to human P-cadherin protein at the amino acids at positions 124, 125, 151, 153, 154, 155, 156, 159, 160, 161, 162, 163, 168, 170, 171, and 172 of SEQ ID NO:126. In some embodiments, the antibodies, or antigen binding fragments thereof, comprise a heavy chain variable region that binds to human P-cadherin at one or more amino acid residues selected from positions 124, 151, 153-156, and 172 of SEQ ID NO:126. In a further embodiment, the heavy chain variable region comprises a heavy chain binding paratope for human P-cadherin protein comprising one or more amino acid residues selected from positions 52, 54, 56, 60, 65, 105, or 107 of SEQ ID NO:128. In yet another embodiment, the antibody comprises a light chain variable region that binds to human P-cadherin at one or more amino acid residues selected from positions 124, 125, 155, 156, 159-163, 168, 170, and 171 of SEQ ID NO:126. In a further embodiment, the light chain variable region binding paratope for human P-cadherin protein comprises one or more amino acid residues selected from positions 1, 2, 27, 28, 30, 68, 92, 93, or 94 of SEQ ID NO:129. In a specific embodiment, the antibodies, or antigen binding fragments thereof, comprise a heavy chain variable region and light chain variable region of as discussed above.

In other embodiments, the application discloses antibodies, or antigen binding fragments thereof, that bind human P-cadherin comprising:
a) a heavy chain variable region that comprises a VH CDR1 of SEQ ID NO: 1, a VH CDR2 of SEQ ID NO: 2, and a VH CDR3 of SEQ ID NO: 3, wherein the CDR is defined in accordance with the Kabat definition; and a light chain variable region that comprises a VL CDR1 of SEQ ID NO: 11, a VL CDR2 of SEQ ID NO: 12, and a VL CDR3 of SEQ ID NO: 13, wherein the CDR is defined in accordance with the Kabat definition;
b) a heavy chain variable region that comprises a VH CDR1 of SEQ ID NO: 21, a VH CDR2 of SEQ ID NO: 22, and a VH CDR3 of SEQ ID NO: 23, wherein the CDR is defined in accordance with the Kabat definition; and a light chain variable region that comprises a VL CDR1 of SEQ ID NO: 31, a VL CDR2 of SEQ ID NO: 32, and a VL CDR3 of SEQ ID NO: 33, wherein the CDR is defined in accordance with the Kabat definition;
c) a heavy chain variable region that comprises a VH CDR1 of SEQ ID NO:41, a VH CDR2 of SEQ ID NO:42, and a VH CDR3 of SEQ ID NO:43, wherein the CDR is defined in accordance with the Kabat definition; and a light chain variable region that comprises a VL CDR1 of SEQ ID NO:51, a VL CDR2 of SEQ ID NO:52, and a VL CDR3 of SEQ ID NO:53, wherein the CDR is defined in accordance with the Kabat definition;
d) a heavy chain variable region that comprises a VH CDR1 of SEQ ID NO:61, a VH CDR2 of SEQ ID NO:62, and a VH CDR3 of SEQ ID NO:63, wherein the CDR is defined in accordance with the Kabat definition; and a light chain variable region that comprises a VL CDR1 of SEQ ID NO:71, a VL CDR2 of SEQ ID NO:72, and a VL CDR3 of SEQ ID NO:73, wherein the CDR is defined in accordance with the Kabat definition;
e) a heavy chain variable region that comprises a VH CDR1 of SEQ ID NO:81, a VH CDR2 of SEQ ID NO:82, and a VH CDR3 of SEQ ID NO:83, wherein the CDR is defined in accordance with the Kabat definition; and a light chain variable region that comprises a VL CDR1 of SEQ ID NO:91, a VL CDR2 of SEQ ID NO:92, and a VL CDR3 of SEQ ID NO:93, wherein the CDR is defined in accordance with the Kabat definition; or
f) a heavy chain variable region that comprises a VH CDR1 of SEQ ID NO:101, a VH CDR2 of SEQ ID NO:102, and a VH CDR3 of SEQ ID NO:103, wherein the CDR is defined in accordance with the Kabat definition; and a light chain variable region that comprises a VL CDR1 of SEQ ID NO:111, a VL CDR2 of SEQ ID NO:112, and a VL CDR3 of SEQ ID NO:113, wherein the CDR is defined in accordance with the Kabat definition.

This application also discloses antibodies, or antigen binding fragments thereof, that bind P-cadherin comprising:
a) A heavy chain variable region (VH) comprising the amino acid sequence of SEQ ID NO:7, and a light chain variable region (VL) comprising the amino acid sequence of SEQ ID NO:17;
b) A heavy chain variable region (VH) comprising the amino acid sequence of SEQ ID NO:27, and a light chain variable region (VL) comprising the amino acid sequence of SEQ ID NO:37;
c) A heavy chain variable region (VH) comprising the amino acid sequence of SEQ ID NO:47, and a light chain variable region (VL) comprising the amino acid sequence of SEQ ID NO:57;
d) A heavy chain variable region (VH) comprising the amino acid sequence of SEQ ID NO:67, and a light chain variable region (VL) comprising the amino acid sequence of SEQ ID NO:77;
e) A heavy chain variable region (VH) comprising the amino acid sequence of SEQ ID NO:87, and a light chain variable region (VL) comprising the amino acid sequence of SEQ ID NO:97; or
f) A heavy chain variable region (VH) comprising the amino acid sequence of SEQ ID NO:107, and a light chain variable region (VL) comprising the amino acid sequence of SEQ ID NO:117.

In other embodiments, this application discloses antibodies, or antigen binding fragments thereof, that bind P-cadherin comprising:
a) A heavy chain comprising the amino acid sequence of SEQ ID NO:9, and a light chain comprising the amino acid sequence of SEQ ID NO:19;
b) A heavy chain comprising the amino acid sequence of SEQ ID NO:29, and a light chain comprising the amino acid sequence of SEQ ID NO:39;
c) A heavy chain comprising the amino acid sequence of SEQ ID NO:49, and a light chain comprising the amino acid sequence of SEQ ID NO:59;
d) A heavy chain comprising the amino acid sequence of SEQ ID NO:69, and a light chain comprising the amino acid sequence of SEQ ID NO:79;
e) A heavy chain comprising the amino acid sequence of SEQ ID NO:89, and a light chain comprising the amino acid sequence of SEQ ID NO:99; or
f) A heavy chain comprising the amino acid sequence of SEQ ID NO:109, and a light chain comprising the amino acid sequence of SEQ ID NO:119.

The present application further discloses antibodies, or antigen binding fragments thereof, that bind to the same epitope of human P-cadherin as the antibodies disclosed herein, or that compete with the antibodies disclosed herein for binding to human P-cadherin.

In some embodiments, the P-cadherin antibodies, or antigen binding fragments thereof, are human or humanized antibodies. In other embodiments, the antibodies or antigen binding fragments thereof are monoclonal antibodies. In further embodiments, the antibodies or antigen binding fragments thereof are single chain antibodies (scFv).

This application also discloses antibody drug conjugates (ADCs) comprising the formula:

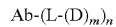

or a pharmaceutically acceptable salt thereof; wherein:
Ab is a P-cadherin antibody, or antigen binding antigen binding fragment thereof, as disclosed herein; L is a linker; D is a drug moiety; m is an integer from 1 to 8; and n is an integer from 1 to 10. In some embodiments, m is 1. In other embodiments, n is 3 or 4.

In some embodiments, the antibody, or antigen binding fragment thereof, of the ADC comprises:
a) a VH region comprising the amino acid sequence of SEQ ID NO:7 and a VL region comprising the amino acid sequence of SEQ I NO:17; or
b) a VH region comprising the amino acid sequence of SEQ ID NO:27 and a VL region comprising the amino acid sequence of SEQ ID NO:37.

In a further embodiment, the antibody, or antigen binding fragment thereof, of the antibody drug conjugate comprises a VH region that comprises:
(a) a VH CDR1 of SEQ ID NO: 1, (b) a VH CDR2 of SEQ ID NO: 2, (c) a VH CDR3 of SEQ ID NO: 3, and a VL region that comprises (d) a VL CDR1 of SEQ ID NO: 11, (e)

a VL CDR2 of SEQ ID NO: 12, and (f) a VL CDR3 of SEQ ID NO: 13, wherein the CDR is defined in accordance with the Kabat definition; or (a) a VH CDR1 of SEQ ID NO: 21, (b) a VH CDR2 of SEQ ID NO: 22, (c) a VH CDR3 of SEQ ID NO: 23, and a VL region that comprises (d) a VL CDR1 of SEQ ID NO: 31, (e) a VL CDR2 of SEQ ID NO: 32, and (f) a VL CDR3 of SEQ ID NO: 33, wherein the CDR is defined in accordance with the Kabat definition In other embodiments, the antibody, or antigen binding fragment thereof, of the antibody drug conjugate comprises:
a) a heavy chain of SEQ ID NO: 9 and a light chain of SEQ ID NO: 19; or
b) a heavy chain of SEQ ID NO: 29 and a light chain of SEQ ID NO: 39.

In further embodiments, the linker of the antibody drug conjugate is selected from the group consisting of a cleavable linker, a non-cleavable linker, a hydrophilic linker, a procharged linker and a dicarboxylic acid based linker. In some embodiments, the linker is derived from a cross-linking reagent selected from the group consisting of N-succinimidyl-3-(2-pyridyldithio)propionate (SPDP), N-succinimidyl 4-(2-pyridyldithio)pentanoate (SPP), N-succinimidyl 4-(2-pyridyldithio)butanoate (SPDB), N-succinimidyl-4-(2-pyridyldithio)-2-sulfo-butanoate (sulfo-SPDB), N-succinimidyl iodoacetate (SIA), N-succinimidyl(4-iodoacetyl) aminobenzoate (SIAB), maleimide PEG NHS, N-succinimidyl 4-(maleimidomethyl)cyclohexanecarboxylate (SMCC), N-sulfosuccinimidyl 4-(maleimidomethyl)cyclohexanecarboxylate (sulfo-SMCC), and 2,5-dioxopyrrolidin-1-yl 17-(2,5-dioxo-2,5-dihydro-1H-pyrrol-1-yl)-5,8,11,14-tetraoxo-4,7,10,13-tetraazaheptadecan-1-oate (CX1-1).

In some embodiments, the drug moiety of the antibody drug conjugate is selected from a group consisting of a V-ATPase inhibitor, a pro-apoptotic agent, a Bcl2 inhibitor, an MCL1 inhibitor, a HSP90 inhibitor, an IAP inhibitor, an mTor inhibitor, a microtubule stabilizer, a microtubule destabilizer, an auristatin, a dolastatin, a maytansinoid, a MetAP (methionine aminopeptidase), an inhibitor of nuclear export of proteins CRM1, a DPPIV inhibitor, proteasome inhibitors, inhibitors of phosphoryl transfer reactions in mitochondria, a protein synthesis inhibitor, a kinase inhibitor, a CDK2 inhibitor, a CDK9 inhibitor, a kinesin inhibitor, an HDAC inhibitor, a DNA damaging agent, a DNA alkylating agent, a DNA intercalator, a DNA minor groove binder and a DHFR inhibitor. In further embodiments, the cytotoxic agent is a maytansinoid. In specific embodiments, the maytansinoid is N(2')-deacetyl-N(2')-(3-mercapto-1-oxopropyl)-maytansine (DM1) or N(2')-deacetyl-N2-(4-mercapto-4-methyl-1-oxopentyl)-maytansine (DM4).

In a specific embodiment, the antibody drug conjugate has the following formula:

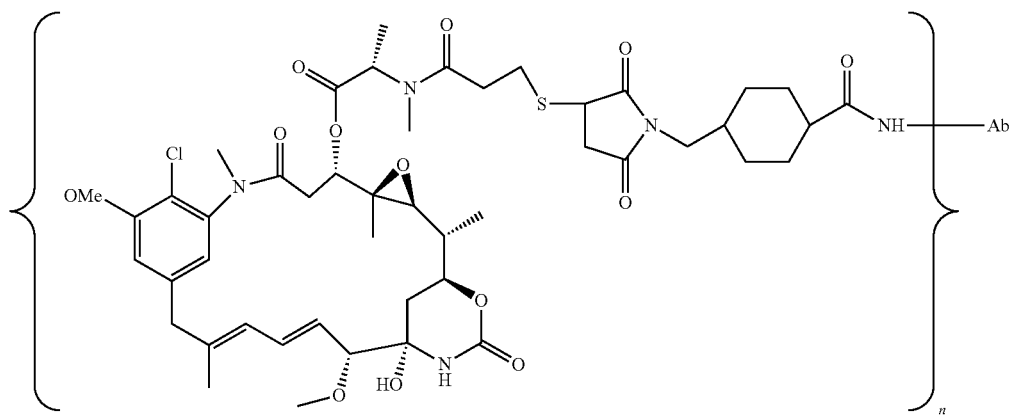

wherein Ab is an antibody or antigen binding fragment thereof comprising a heavy chain CDR1 of SEQ ID NO: 1, a heavy chain CDR2 of SEQ ID NO: 2, a heavy chain CDR3 of SEQ ID NO: 3, and a light chain CDR1 of SEQ ID NO: 11, a light chain CDR2 of SEQ ID NO: 12, a light chain CDR3 of SEQ ID NO: 13, wherein the CDR is defined in accordance with the Kabat definition; and n is 1 to 10; or a pharmaceutically acceptable salt thereof.

This application also discloses pharmaceutical compositions comprising the human P-cadherin antibodies, or antigen binding fragments thereof, as disclosed herein, or antibody drug conjugates comprising these antibodies, and a pharmaceutically acceptable carrier. In some embodiments, the pharmaceutical compositions are prepared as a lyophilisate. In further embodiments, the lyophilisate comprises the antibodies, antigen binding fragments thereof, or antibody drug conjugates of these antibodies, histidine, sucrose, and polysorbate 20. In a specific embodiment, the pharmaceutical composition comprises about 10 mg/mL of the antibody drug conjugate disclosed herein, 20 mM histidine, 240 mM sucrose, and 0.02% polysorbate 20.

The present application also discloses methods of treating cancer in a patient in need thereof, comprising administering to said patient the antibody drug conjugates or pharmaceutical composition disclosed herein. In some embodiments, the methods comprise administering the antibody drug conjugate or pharmaceutical composition to the patient in combination with one or more additional therapeutic compounds.

In other embodiments, this application discloses P-cadherin antibody drug conjugates or the pharmaceutical compositions as disclosed herein for use as a medicament. In specific embodiments, the antibody drug conjugates or the pharmaceutical compositions are for use in the treatment of cancer in a patient in need thereof.

Also disclosed herein is the use of the P-cadherin antibodies, or antigen binding fragments thereof, or antibody drug conjugates as discussed herein to treat cancer in a patient in need thereof, or in the manufacture of a medicament for the treatment of cancer.

In some embodiments, the cancer expresses P-cadherin. In further embodiments, the cancer is selected from the group consisting of adrenocortical carcinoma, bladder cancer, bone cancer, breast cancer, central nervous system atypical teratoid/rhabdoid tumors, colon cancer, colorectal cancer, embryonal tumors, endometrial cancer, esophageal cancer, gastric cancer, head and neck cancer, hepatocellular cancer, Kaposi sarcoma, liver cancer, lung cancer, including small cell lung cancer and non-small cell lung cancer, ovarian cancer, rectal cancer, rhabdomyosarcomasmall intestine cancer, soft tissue sarcoma, squamous cell carcinoma, squamous neck cancer, stomach cancer, uterine cancer, vaginal cancer, and vulvar cancer adrenocortical carcinoma, bladder cancer, bone cancer, breast cancer, central nervous system atypical teratoid/rhabdoid tumors, colon cancer, colorectal cancer, embryonal tumors, endometrial cancer, esophageal cancer, gastric cancer, head and neck cancer, hepatocellular cancer, Kaposi sarcoma, liver cancer, lung cancer, including small cell lung cancer and non-small cell lung cancer, ovarian cancer, rectal cancer, rhabdomyosarcomasmall intestine cancer, soft tissue sarcoma, squamous cell carcinoma, squamous neck cancer, stomach cancer, uterine cancer, vaginal cancer, and vulvar cancer. In specific embodiments, the cancer is selected from the group consisting of bladder, breast, colon, colorectal, endometrial, esophageal, gastric, head and neck, lung, and ovarian cancers.

This application also discloses nucleic acids that encode the P-cadherin antibodies or antigen binding fragments as disclosed herein. In specific embodiments, the nucleic acids comprise the nucleotide sequence of SEQ ID NOs: 8, 28, 48, 68, 88, 108,18, 38, 58, 78, 98, 118, 10, 30, 50, 70, 90, 110, 20, 40, 60, 80, 100, and 120. In a further embodiment, this application contemplates vectors comprising the nucleic acids disclosed here, as well as host cells comprising the vectors or nucleic acids disclosed herein. Further disclosed are processes for producing a P-cadherin antibody or antigen binding fragment comprising cultivating the host cell and recovering the antibody from the culture.

In further embodiments, this application discloses a process for producing an anti-P-cadherin antibody drug conjugate comprising:
(a) chemically linking SMCC to a drug moiety DM-1;
(b) conjugating said linker-drug to the antibody recovered from the cell culture of claim 17 as disclosed herein; and
(c) purifying the antibody drug conjugate.
In another embodiment, the process for producing an anti-P-cadherin antibody drug conjugate comprises:
(a) chemically linking SMCC to a drug moiety DM-1;
(b) conjugating said linker-drug to an antibody as disclosed herein; and
(c) purifying the antibody drug conjugate.
In some embodiments, antibody drug conjugates made according these processes have an average DAR, measured with a UV spectrophotometer, of about 3.8.

In other embodiments, the antibodies, or antigen binding fragments thereof, disclosed herein are used as diagnostic reagents. In some embodiments of the diagnostic reagents, the antibody or antigen binding fragment thereof is labeled with a radiolabel, a fluorophore, a chromophore, an imaging agent, or a metal ion.

BRIEF DESCRIPTION OF THE DRAWINGS

FIG. 5 depicts a sequence alignment of the human (SEQ ID NO: 133) and cynomolgus ("cyno"; *Macaca fascicularis*) (SEQ ID NO: 134) P-cadherin EC1 domains. Amino acid residues in bold black font are involved in direct intermolecular contacts (<4.0 Å) with the NOV169N31Q antibody. Amino acid residues in bold grey font and indicated with arrows are farther away but experience a reduction of their solvent-accessible surface upon antibody binding. Note that both categories of epitope residues are fully conserved in cynomolgus P-cadherin.

FIG. 6 depicts a multiple sequence alignment of the EC1 domain of human cadherins (SEQ ID NOS:135-143, respectively, in order of appearance). Note that P-cadherin is also referred to as "cadherin-3". Boxed residues are located at the antigen-antibody interface as determined by a reduction of their solvent-accessible surface. Boxed in thick lines is the insertion found in human cadherins 1 through 4. Note that the key epitope residue Glu155 is not conserved in other human cadherins.

DETAILED DESCRIPTION OF THE INVENTION

Definitions

Figure 1:
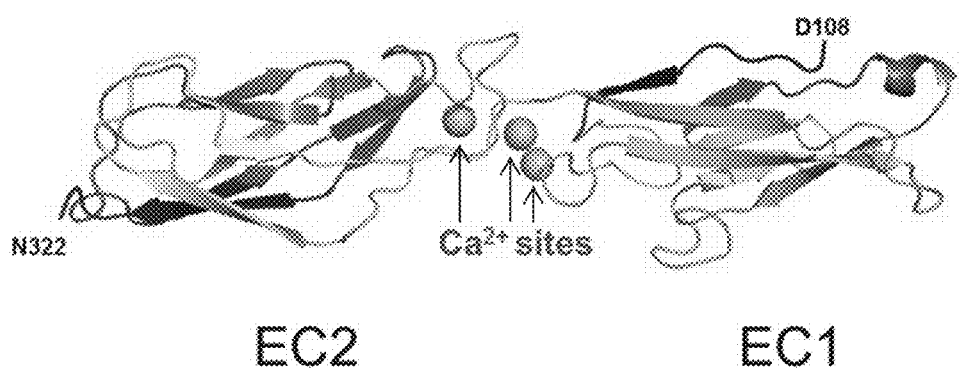
FIG. 1 depicts the overall view of the crystal structure of human P-cadherin EC1_EC2, showing the first two cadherin-repeat domains of the extracellular domain of human P-cadherin, with the three calcium binding sites located at the domain-domain junction.

Unless stated otherwise, the following terms and phrases as used herein are intended to have the following meanings:

The term "alkyl" refers to a monovalent saturated hydrocarbon chain having the specified number of carbon atoms. For example, $C_{1-6}$ alkyl refers to an alkyl group having from 1 to 6 carbon atoms. Alkyl groups may be straight or branched. Representative branched alkyl groups have one, two, or three branches. Examples of alkyl groups include, but are not limited to, methyl, ethyl, propyl (n-propyl and isopropyl), butyl (n-butyl, isobutyl, sec-butyl, and t-butyl), pentyl (n-pentyl, isopentyl, and neopentyl), and hexyl.

The term "antibody" as used herein refers to a polypeptide of the immunoglobulin family that is capable of binding a corresponding antigen non-covalently, reversibly, and in a specific manner. For example, a naturally occurring IgG antibody is a tetramer comprising at least two heavy (H) chains and two light (L) chains inter-connected by disulfide bonds. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs arranged from amino-terminus to carboxy-terminus in the following order: FR1, CDR1, FR2, CDR2, FR3, CDR3, and FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

The term "antibody" includes, but is not limited to, monoclonal antibodies, human antibodies, humanized antibodies, chimeric antibodies, and anti-idiotypic (anti-Id) antibodies (including, e.g., anti-Id antibodies to antibodies of the invention). The antibodies can be of any isotype/class (e.g., IgG, IgE, IgM, IgD, IgA and IgY), or subclass (e.g., IgG1, IgG2, IgG3, IgG4, IgA1 and IgA2).

"Complementarity-determining domains" or "complementary-determining regions" ("CDRs") interchangeably refer to the hypervariable regions of VL and VH. The CDRs are the target protein-binding site of the antibody chains that harbors specificity for such target protein. There are three CDRs (CDR1-3, numbered sequentially from the N-terminus) in each human VL or VH, constituting about 15-20% of the variable domains. The CDRs are structurally complementary to the epitope of the target protein and are thus directly responsible for the binding specificity. The remaining stretches of the VL or VH, the so-called framework regions, exhibit less variation in amino acid sequence (Kuby, Immunology, 4th ed., Chapter 4. W.H. Freeman & Co., New York, 2000).

The positions of the CDRs and framework regions can be determined using various well known definitions in the art, e.g., Kabat, Chothia, international ImMunoGeneTics database (IMGT) (on the worldwide web at www.imgt.org/), and AbM (see, e.g., Johnson et al., Nucleic Acids Res., 29:205-206 (2001); Chothia and Lesk, J. Mol. Biol., 196:901-917 (1987); Chothia et al., Nature, 342:877-883 (1989); Chothia et al., J. Mol. Biol., 227:799-817 (1992); Al-Lazikani et al., J. Mol. Biol., 273:927-748 (1997)). Definitions of antigen combining sites are also described in the following: Ruiz et al., Nucleic Acids Res., 28:219-221 (2000); and Lefranc, M. P., Nucleic Acids Res., 29:207-209 (2001); MacCallum et al., J. Mol. Biol., 262:732-745 (1996); and Martin et al., Proc. Natl. Acad. Sci. USA, 86:9268-9272 (1989); Martin et al., Methods Enzymol., 203:121-153 (1991); and Rees et al., In Sternberg M. J. E. (ed.), Protein Structure Prediction, Oxford University Press, Oxford, 141-172 (1996).

Both the light and heavy chains are divided into regions of structural and functional homology. The terms "constant" and "variable" are used functionally. In this regard, it will be appreciated that the variable domains of both the light (VL) and heavy (VH) chain portions determine antigen recognition and specificity. Conversely, the constant domains of the light chain (CL) and the heavy chain (CH1, CH2 or CH3) confer important biological properties such as secretion, transplacental mobility, Fc receptor binding, complement binding, and the like. By convention, the numbering of the constant region domains increases as they become more distal from the antigen binding site or amino-terminus of the antibody. The N-terminus is a variable region and at the C-terminus is a constant region; the CH3 and CL domains actually comprise the carboxy-terminal domains of the heavy and light chain, respectively.

The term "antigen binding fragment", as used herein, refers to one or more portions of an antibody that retain the ability to specifically interact with (e.g., by binding, steric hindrance, stabilizing/destabilizing, spatial distribution) an epitope of an antigen. Examples of binding fragments include, but are not limited to, single-chain Fvs (scFv), camelid antibodies, disulfide-linked Fvs (sdFv), Fab fragments, F(ab') fragments, a monovalent fragment consisting of the VL, VH, CL and CH1 domains; a F(ab)2 fragment, a bivalent fragment comprising two Fab fragments linked by a disulfide bridge at the hinge region; a Fd fragment consisting of the VH and CH1 domains; a Fv fragment consisting of the VL and VH domains of a single arm of an antibody; a dAb fragment (Ward et al., Nature 341:544-546, 1989), which consists of a VH domain; and an isolated complementarity determining region (CDR), or other epitope-binding fragments of an antibody.

Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv ("scFv"); see, e.g., Bird et al., Science 242:423-426, 1988; and Huston et al., Proc. Natl. Acad. Sci. 85:5879-5883, 1988). Such single chain antibodies are also intended to be encompassed within the term "antigen binding fragment." These antigen binding fragments are obtained using conventional techniques known to those of skill in the art, and the fragments are screened for utility in the same manner as are intact antibodies.

Antigen binding fragments can also be incorporated into single domain antibodies, maxibodies, minibodies, single domain antibodies, intrabodies, diabodies, triabodies, tetrabodies, v-NAR and bis-scFv (see, e.g., Hollinger and Hudson, Nature Biotechnology 23:1126-1136, 2005). Antigen binding fragments can be grafted into scaffolds based on polypeptides such as fibronectin type III (Fn3) (see U.S. Pat. No. 6,703,199, which describes fibronectin polypeptide monobodies).

Antigen binding fragments can be incorporated into single chain molecules comprising a pair of tandem Fv segments (VH-CH1-VH-CH1) which, together with complementary light chain polypeptides, form a pair of antigen binding regions (Zapata et al., Protein Eng. 8:1057-1062, 1995; and U.S. Pat. No. 5,641,870).

The term "monoclonal antibody" or "monoclonal antibody composition" as used herein refers to polypeptides, including antibodies and antigen binding fragments that have substantially identical amino acid sequence or are derived from the same genetic source. This term also includes preparations of antibody molecules of single molecular composition. A monoclonal antibody composition displays a single binding specificity and affinity for a particular epitope.

The term "human antibody", as used herein, includes antibodies having variable regions in which both the framework and CDR regions are derived from sequences of human origin. Furthermore, if the antibody contains a constant region, the constant region also is derived from such human sequences, e.g., human germline sequences, or mutated versions of human germline sequences or antibody containing consensus framework sequences derived from human framework sequences analysis, for example, as described in Knappik et al., J. Mol. Biol. 296:57-86, 2000). Also included are antibodies derived from human sequences wherein one or more CDRs has been mutated for affinity maturation or for manufacturing/payload conjugation purposes. See Hybridoma. 1997 August; 16(4):381-9. Rapid development of affinity matured monoclonal antibodies using RIMMS. Kilpatrick K E, Wring S A, Walker D H, Macklin M D, Payne J A, Su J L, Champion B R, Caterson B, McIntyre G D. Department of Molecular Sciences, Glaxo Wellcome, Research Triangle Park, N.C. 27709, USA The human antibodies of the invention may include amino acid residues not encoded by human sequences (e.g., mutations introduced by random or site-specific mutagenesis in vitro or by somatic mutation in vivo, or a conservative substitution to promote stability or manufacturing).

The term "recognize" as used herein refers to an antibody or antigen binding fragment thereof that finds and interacts (e.g., binds) with its epitope, whether that epitope is linear or conformational. The term "epitope" refers to a site on an antigen to which an antibody or antigen binding fragment of the invention specifically binds. Epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, 4, 5, 6, 7, 8, 9, 10, 11, 12, 13, 14 or 15 amino acids in a unique spatial conformation. Methods of determining spatial conformation of epitopes include techniques in the art, for example, x-ray crystallography and 2-dimensional nuclear magnetic resonance (see, e.g., Epitope Mapping Protocols in Methods in Molecular Biology, Vol. 66, G. E. Morris, Ed. (1996)).

The term "affinity" as used herein refers to the strength of interaction between antibody and antigen at single antigenic sites. Within each antigenic site, the variable region of the antibody "arm" interacts through weak non-covalent forces with antigen at numerous sites; the more interactions, the stronger the affinity.

The term "isolated antibody" refers to an antibody that is substantially free of other antibodies having different antigenic specificities. An isolated antibody that specifically binds to one antigen may, however, have cross-reactivity to other antigens. Moreover, an isolated antibody may be substantially free of other cellular material and/or chemicals.

The term "corresponding human germline sequence" refers to the nucleic acid sequence encoding a human variable region amino acid sequence or subsequence that shares the highest determined amino acid sequence identity with a reference variable region amino acid sequence or subsequence in comparison to all other all other known variable region amino acid sequences encoded by human germline immunoglobulin variable region sequences. The corresponding human germline sequence can also refer to the human variable region amino acid sequence or subsequence with the highest amino acid sequence identity with a reference variable region amino acid sequence or subsequence in comparison to all other evaluated variable region amino acid sequences. The corresponding human germline sequence can be framework regions only, complementarity determining regions only, framework and complementarity determining regions, a variable segment (as defined above), or other combinations of sequences or subsequences that comprise a variable region. Sequence identity can be determined using the methods described herein, for example, aligning two sequences using BLAST, ALIGN, or another alignment algorithm known in the art. The corresponding human germline nucleic acid or amino acid sequence can have at least about 90%, 91, 92%, 93%, 94%, 95%, 96%, 97%, 98%, 99%, or 100% sequence identity with the reference variable region nucleic acid or amino acid sequence. Corresponding human germline sequences can be determined, for example, through the publicly available international ImMunoGeneTics database (IMGT) (on the worldwide web at www.imgt.org/) and V-base (on the worldwide web at vbase.mrc-cpe.cam.ac.uk).

The phrase "specifically binds" or "selectively binds," when used in the context of describing the interaction between an antigen (e.g., a protein) and an antibody, antibody fragment, or antibody-derived binding agent, refers to a binding reaction that is determinative of the presence of the antigen in a heterogeneous population of proteins and other biologics, e.g., in a biological sample, e.g., a blood, serum, plasma or tissue sample. Thus, under certain designated immunoassay conditions, the antibodies or binding agents with a particular binding specificity bind to a particular antigen at least two times the background and do not substantially bind in a significant amount to other antigens present in the sample. In one embodiment, under designated immunoassay conditions, the antibody or binding agent with a particular binding specificity binds to a particular antigen at least ten (10) times the background and does not substantially bind in a significant amount to other antigens present in the sample. Specific binding to an antibody or binding agent under such conditions may require the antibody or agent to have been selected for its specificity for a particular protein. As desired or appropriate, this selection may be achieved by subtracting out antibodies that cross-react with molecules from other species (e.g., mouse or rat) or other subtypes. Alternatively, in some embodiments, antibodies or antibody fragments are selected that cross-react with certain desired molecules.

A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Using Antibodies, A Laboratory Manual (1998), for a description of immunoassay formats and conditions that can be used to determine specific immunoreactivity). Typically a specific or selective binding reaction will produce a signal at least twice over the background signal and more typically at least 10 to 100 times over the background.

The term "equilibrium dissociation constant (KD, M)" refers to the dissociation rate constant (kd, time−1) divided by the association rate constant (ka, time−1, M−1). Equilibrium dissociation constants can be measured using any known method in the art. The antibodies of the present invention generally will have an equilibrium dissociation constant of less than about $10^{-7}$ or $10^{-8}$ M, for example, less than about $10^{-9}$ M or $10^{-10}$ M, in some embodiments, less than about $10^{-11}$ M, $10^{-12}$ M or $10^{-13}$ M.

The term "bioavailability" refers to the systemic availability (i.e., blood/plasma levels) of a given amount of drug administered to a patient. Bioavailability is an absolute term that indicates measurement of both the time (rate) and total amount (extent) of drug that reaches the general circulation from an administered dosage form.

As used herein, the phrase "consisting essentially of" refers to the genera or species of active pharmaceutical agents included in a method or composition, as well as any excipients inactive for the intended purpose of the methods or compositions. In some embodiments, the phrase "consisting essentially of" expressly excludes the inclusion of one or more additional active agents other than an antibody drug conjugate of the invention. In some embodiments, the phrase "consisting essentially of" expressly excludes the inclusion of one or more additional active agents other than an antibody drug conjugate of the invention and a second co-administered agent.

The term "amino acid" refers to naturally occurring, synthetic, and unnatural amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refer to compounds that have the same basic chemical structure as a naturally occurring amino acid, i.e., an α-carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

The term "conservatively modified variant" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

For polypeptide sequences, "conservatively modified variants" include individual substitutions, deletions or additions to a polypeptide sequence which result in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention. The following eight groups contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)). In some embodiments, the term "conservative sequence modifications" are used to refer to amino acid modifications that do not significantly affect or alter the binding characteristics of the antibody containing the amino acid sequence.

The term "optimized" as used herein refers to a nucleotide sequence that has been altered to encode an amino acid sequence using codons that are preferred in the production cell or organism, generally a eukaryotic cell, for example, a yeast cell, a *Pichia* cell, a fungal cell, a *Trichoderma* cell, a Chinese Hamster Ovary cell (CHO) or a human cell. The optimized nucleotide sequence is engineered to retain completely or as much as possible the amino acid sequence originally encoded by the starting nucleotide sequence, which is also known as the "parental" sequence.

The terms "percent identical" or "percent identity," in the context of two or more nucleic acids or polypeptide sequences, refers to the extent to which two or more sequences or subsequences that are the same. Two sequences are "identical" if they have the same sequence of amino acids or nucleotides over the region being compared. Two sequences are "substantially identical" if two sequences have a specified percentage of amino acid residues or nucleotides that are the same (i.e., 60% identity, optionally 65%, 70%, 75%, 80%, 85%, 90%, 95%, or 99% identity over a specified region, or, when not specified, over the entire sequence), when compared and aligned for maximum correspondence over a comparison window, or designated region as measured using one of the following sequence comparison algorithms or by manual alignment and visual inspection. Optionally, the identity exists over a region that is at least about 30 nucleotides (or 10 amino acids) in length, or more preferably over a region that is 100 to 500 or 1000 or more nucleotides (or 20, 50, 200 or more amino acids) in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman, Adv. Appl. Math. 2:482c (1970), by the homology alignment algorithm of Needleman and Wunsch, J. Mol. Biol. 48:443 (1970), by the search for similarity method of Pearson and Lipman, Proc. Natl. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Brent et al., Current Protocols in Molecular Biology, 2003).

Two examples of algorithms that are suitable for determining percent sequence identity and sequence similarity are the BLAST and BLAST 2.0 algorithms, which are described in Altschul et al., Nuc. Acids Res. 25:3389-3402, 1977; and Altschul et al., J. Mol. Biol. 215:403-410, 1990, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) or 10, M=5, N=−4 and a comparison of both strands. For amino acid sequences, the BLASTP program uses as defaults a word length of 3, and expectation (E) of 10, and the BLOSUM62 scoring matrix (see Henikoff and Henikoff, (1989) Proc. Natl. Acad. Sci. USA 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul, Proc. Natl. Acad. Sci. USA 90:5873-5787, 1993). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

The percent identity between two amino acid sequences can also be determined using the algorithm of E. Meyers and W. Miller, Comput. Appl. Biosci. 4:11-17, 1988) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch, J. Mol. Biol. 48:444-453, 1970) algorithm which has been incorporated into the GAP program in the GCG software package (available at www.gcg.com), using either a Blossom 62 matrix or a PAM250 matrix, and a gap weight of 16, 14, 12, 10, 8, 6, or 4 and a length weight of 1, 2, 3, 4, 5, or 6.

Other than percentage of sequence identity noted above, another indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The term "nucleic acid" is used herein interchangeably with the term "polynucleotide" and refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, as detailed below, degenerate codon substitutions may be achieved by generating sequences in which the third position of one or more selected (or all) codons is substituted with mixed-base and/or deoxyinosine residues (Batzer et al., (1991) Nucleic Acid Res. 19:5081; Ohtsuka et al., (1985) J. Biol. Chem. 260: 2605-2608; and Rossolini et al., (1994) Mol. Cell. Probes 8:91-98).

The term "operably linked" in the context of nucleic acids refers to a functional relationship between two or more polynucleotide (e.g., DNA) segments. Typically, it refers to the functional relationship of a transcriptional regulatory sequence to a transcribed sequence. For example, a promoter or enhancer sequence is operably linked to a coding sequence if it stimulates or modulates the transcription of the coding sequence in an appropriate host cell or other expression system. Generally, promoter transcriptional regulatory sequences that are operably linked to a transcribed sequence are physically contiguous to the transcribed sequence, i.e., they are cis-acting. However, some transcriptional regulatory sequences, such as enhancers, need not be physically contiguous or located in close proximity to the coding sequences whose transcription they enhance.

The terms "polypeptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer. Unless otherwise indicated, a particular polypeptide sequence also implicitly encompasses conservatively modified variants thereof.

The term "antibody drug conjugate" or "immunoconjugate" as used herein refers to the linkage of an antibody or an antigen binding fragment thereof with another agent, such as a chemotherapeutic agent, a toxin, an immunotherapeutic agent, an imaging probe, and the like. The linkage can be covalent bonds, or non-covalent interactions such as through electrostatic forces. Various linkers, known in the art, can be employed in order to form the antibody drug conjugate. Additionally, the antibody drug conjugate can be provided in the form of a fusion protein that may be expressed from a polynucleotide encoding the immunoconjugate. As used herein, "fusion protein" refers to proteins created through the joining of two or more genes or gene fragments which originally coded for separate proteins (including peptides and polypeptides). Translation of the fusion gene results in a single protein with functional properties derived from each of the original proteins.

The term "subject" includes human and non-human animals. Non-human animals include all vertebrates, e.g., mammals and non-mammals, such as non-human primates, sheep, dog, cow, chickens, amphibians, and reptiles. Except when noted, the terms "patient" or "subject" are used herein interchangeably.

The term "cytotoxin", or "cytotoxic agent" as used herein, refers to any agent that is detrimental to the growth and proliferation of cells and may act to reduce, inhibit, or destroy a cell or malignancy.

The term "anti-cancer agent" as used herein refers to any agent that can be used to treat a cell proliferative disorder such as cancer, including but not limited to, cytotoxic agents, chemotherapeutic agents, radiotherapy and radiotherapeutic agents, targeted anti-cancer agents, and immunotherapeutic agents.

The term "drug moiety" or "payload" as used herein refers to a chemical moiety that is conjugated to an antibody or antigen binding fragment of the invention, and can include any therapeutic or diagnostic agent, for example, an anti-cancer, anti-inflammatory, anti-infective (e.g., anti-fungal, antibacterial, anti-parasitic, anti-viral), or an anesthetic agent. For example, the drug moiety can be an anti-cancer agent, such as a cytotoxin. In certain embodiments, a drug moiety is selected from a V-ATPase inhibitor, a HSP90 inhibitor, an IAP inhibitor, an mTor inhibitor, a microtubule stabilizer, a microtubule destabilizer, an auristatin, a dolastatin, a maytansinoid, a MetAP (methionine aminopeptidase), an inhibitor of nuclear export of proteins CRM1, a DPPIV inhibitor, an inhibitor of phosphoryl transfer reactions in mitochondria, a protein synthesis inhibitor, a kinase inhibitor, a CDK2 inhibitor, a CDK9 inhibitor, a proteasome inhibitor, a kinesin inhibitor, an HDAC inhibitor, a DNA damaging agent, a DNA alkylating agent, a DNA intercalator, a DNA minor groove binder and a DHFR inhibitor. Methods for attaching each of these to a linker compatible with the antibodies and method of the invention are known in the art. See, e.g., Singh et al., (2009) Therapeutic Antibodies: Methods and Protocols, vol. 525, 445-457. In addition, a payload can be a biophysical probe, a fluorophore, a spin label, an infrared probe, an affinity probe, a chelator, a spectroscopic probe, a radioactive probe, a lipid molecule, a polyethylene glycol, a polymer, a spin label, DNA, RNA, a protein, a peptide, a surface, an antibody, an antibody fragment, a nanoparticle, a quantum dot, a liposome, a PLGA particle, a saccharide or a polysaccharide.

The term "maytansinoid drug moiety" means the substructure of an antibody-drug conjugate that has the structure of a maytansinoid compound. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and maytansinol analogues have been reported. See U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533, and Kawai et al (1984) Chem. Pharm. Bull. 3441-3451), each of which are expressly incorporated by reference. Examples of specific maytansinoids useful for conjugation include DM1, DM3 and DM4.

"Tumor" refers to neoplastic cell growth and proliferation, whether malignant or benign, and all pre-cancerous and cancerous cells and tissues.

The term "anti-tumor activity" means a reduction in the rate of tumor cell proliferation, viability, or metastatic activity. For example, anti-tumor activity can be shown by a decline in growth rate of abnormal cells that arises during therapy or tumor size stability or reduction, or longer survival due to therapy as compared to control without therapy. Such activity can be assessed using accepted in vitro or in vivo tumor models, including but not limited to xenograft models, allograft models, MMTV models, and other known models known in the art to investigate anti-tumor activity.

The term "malignancy" refers to a non-benign tumor or a cancer. As used herein, the term "cancer" includes a malignancy characterized by deregulated or uncontrolled cell growth. Exemplary cancers include: carcinomas, sarcomas, leukemias, and lymphomas.

The term "cancer" includes primary malignant tumors (e.g., those whose cells have not migrated to sites in the subject's body other than the site of the original tumor) and secondary malignant tumors (e.g., those arising from metastasis, the migration of tumor cells to secondary sites that are different from the site of the original tumor).

The term "P-cadherin" (also known as Pcad, PCad, or CDH3) refers to the nucleic acid and amino acid sequence of P-cadherin, which have been published in GenBank Accession Nos. NP_ 001784, NP_001784.2 (amino acid sequence), and NM_001793.4, GenBank Accession Nos. AA14462, NG_009096, and NG_009096.1 (nucleotide sequences). Sequence information for human P-cadherin domains 1-5 are extracellular and are published in GenBank Accession Nos. NM_001793.4 and NP_001784.

"P-cadherin" also refers to proteins and amino acid sequences that over their full length have at least about 90%, 91%, 92%, 93%, 94%, 95%, 96%, 97%, 98%, 99%, or 100% sequence identity with the amino acid sequence of the above GenBank accession Nos. NP_001784, NP_001784.2.

Structurally, a P-cadherin nucleic acid sequence has over its extracellular domain at least about 90%, 91%, 92%, 93%, 94%, 95%, 96%, 97%, 98%, 99%, or 100% sequence identity with the nucleic acid sequence of GenBank accession numbers NM_001793.4, GenBank Accession Nos. AA4462, NG_009096, and NG_009096.1.

As used herein, the terms "treat," "treating," or "treatment" of any disease or disorder refers in one embodiment, to ameliorating the disease or disorder (i.e., slowing or arresting or reducing the development of the disease or at least one of the clinical symptoms thereof). In another embodiment, "treat," "treating," or "treatment" refers to alleviating or ameliorating at least one physical parameter including those which may not be discernible by the patient. In yet another embodiment, "treat," "treating," or "treatment" refers to modulating the disease or disorder, either physically, (e.g., stabilization of a discernible symptom), physiologically, (e.g., stabilization of a physical parameter), or both. In yet another embodiment, "treat," "treating," or "treatment" refers to preventing or delaying the onset or development or progression of the disease or disorder.

The term "therapeutically acceptable amount" or "therapeutically effective dose" interchangeably refers to an amount sufficient to effect the desired result (i.e., a reduction in tumor size, inhibition of tumor growth, prevention of metastasis, inhibition or prevention of viral, bacterial, fungal or parasitic infection). In some embodiments, a therapeutically acceptable amount does not induce or cause undesirable side effects. In some embodiments, a therapeutically acceptable amount induces or causes side effects but only those that are acceptable by the healthcare providers in view of a patient's condition. A therapeutically acceptable amount can be determined by first administering a low dose, and then incrementally increasing that dose until the desired effect is achieved. A "prophylactically effective dosage," and a "therapeutically effective dosage," of the molecules of the invention can prevent the onset of, or result in a decrease in severity of, respectively, disease symptoms, including symptoms associated with cancer.

The term "co-administer" refers to the presence of two active agents in the blood of an individual. Active agents that are co-administered can be concurrently or sequentially delivered.

The present invention provides antibodies, antibody fragments (e.g., antigen binding fragments), and drug conjugates thereof, i.e. antibody drug conjugates or ADCs, that bind to P-cadherin. In particular, the present invention provides antibodies and antibody fragments (e.g., antigen binding fragments) that bind to P-cadherin, and internalize upon such binding. The antibodies and antibody fragments (e.g., antigen binding fragments) of the present invention can be used for producing antibody drug conjugates. Furthermore, the present invention provides antibody drug conjugates that have desirable pharmacokinetic characteristics and other desirable attributes, and thus can be used for treating cancer expressing P-cadherin. The present invention further provides pharmaceutical compositions comprising the antibody drug conjugates of the invention, and methods of making and using such pharmaceutical compositions for the treatment of cancer.

Antibody Drug Conjugates

The present invention provides antibody drug conjugates also referred to as immunoconjugates, where an antibody, antigen binding fragment or its functional equivalent that specifically binds to P-cadherin is linked to a drug moiety. In one aspect, the antibodies, antigen binding fragments or their functional equivalents of the invention are linked, via covalent attachment by a linker, to a drug moiety that is an anti-cancer agent. The antibody drug conjugates of the invention can selectively deliver an effective dose of an anti-cancer agent (e.g., a cytotoxic agent) to tumor tissues expressing P-cadherin, whereby greater selectivity (and lower efficacious dose) may be achieved.

In one aspect, the invention provides an immunoconjugate of Formula (I):

Wherein Ab represents P-cadherin binding antibody described herein;
L is a linker;
D is a drug moiety;
m is an integer from 1 to 8; and
n is an integer from 1-20. In one embodiment, n is an integer from 1 to 10, 2 to 8, or 2 to 5. In a specific embodiment, n is 2, 3, or 4. In some embodiments, m is 1; in other embodiments m is 2, 3 or 4.

While the drug to antibody ratio has an exact value for a specific conjugate molecule (e.g., n multiplied by m in Formula (I)), it is understood that the value will often be an average value when used to describe a sample containing many molecules, due to some degree of inhomogeneity, typically associated with the conjugation step. The average loading for a sample of an immunoconjugate is referred to herein as the drug to antibody ratio, or "DAR." In some embodiments, when the drug is maytansinoid, it is referred to as "MAR." In some embodiments, the DAR is between about 2 and about 6, and typically is about 3, 3.5, 4, 4.5, 5, 5.5, 6, 6.5, 7.0, 7.5. 8.0. In some embodiments, at least 50% of a sample by weight is compound having the average DAR plus or minus 2, and preferably at least 50% of the sample is a conjugate that contains the average DAR plus or minus 1. Embodiments include immunoconjugates wherein the DAR is about 3.5, 3.6, 3.7, 3.8 or 3.9. In some embodiments, a DAR of 'about n' means the measured value for DAR is within 20% of n.

The present invention is also directed to immunoconjugates comprising the antibodies, antibody fragments (e.g., antigen binding fragments) and their functional equivalents as disclosed herein, linked or conjugated to a drug moiety. In one embodiment, the drug moiety D is a maytansinoid drug moiety, including those having the structure:

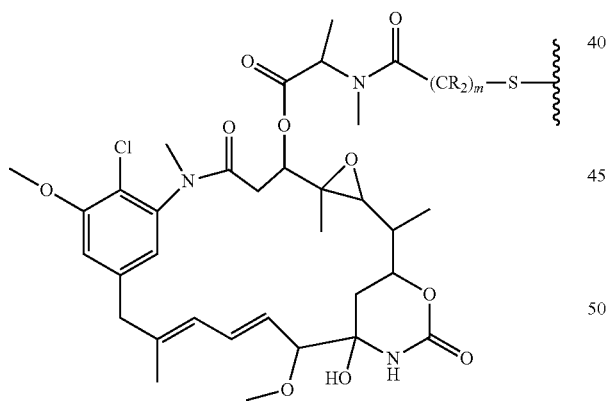

where the wavy line indicates the covalent attachment of the sulfur atom of the maytansinoid to a linker of an antibody drug conjugate. R at each occurrence is independently H or a $C_1$-$C_6$ alkyl. The alkylene chain attaching the amide group to the sulfur atom may be methanyl, ethanyl, or propyl, i.e. m is 1, 2, or 3. (U.S. Pat. No. 633,410, U.S. Pat. No. 5,208,020, Chari et al. (1992) Cancer Res. 52; 127-131, Lui et al. (1996) Proc. Natl. Acad. Sci. 93:8618-8623).

All stereoisomers of the maytansinoid drug moiety are contemplated for the immunoconjugates of the invention, i.e. any combination of R and S configurations at the chiral carbons of the maytansinoid. In one embodiment the maytansinoid drug moiety has the following stereochemistry.

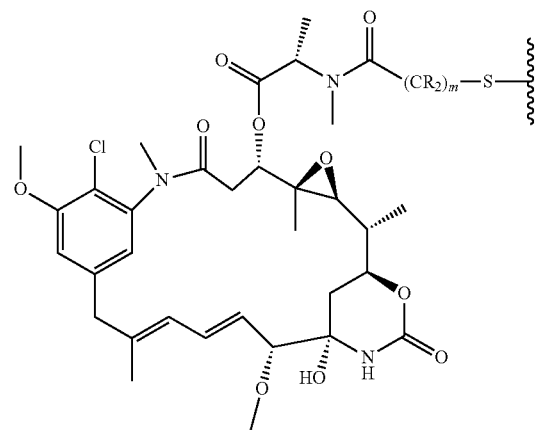

In one embodiment, the maytansinoid drug moiety is $N^{2'}$-deacetyl-$N^{2'}$-(3-mercapto-1-oxopropyl)-maytansine (also known as DM1). DM1 is represented by the following structural formula.

DM1

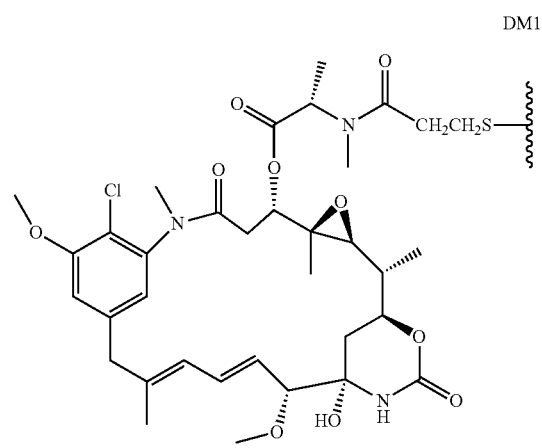

In another embodiment the maytansinoid drug moiety is $N^{2'}$-deacetyl-$N^{2'}$-(4-mercapto-1-oxopentyl)-maytansine (also known as DM3). DM3 is represented by the following structural formula.

DM3

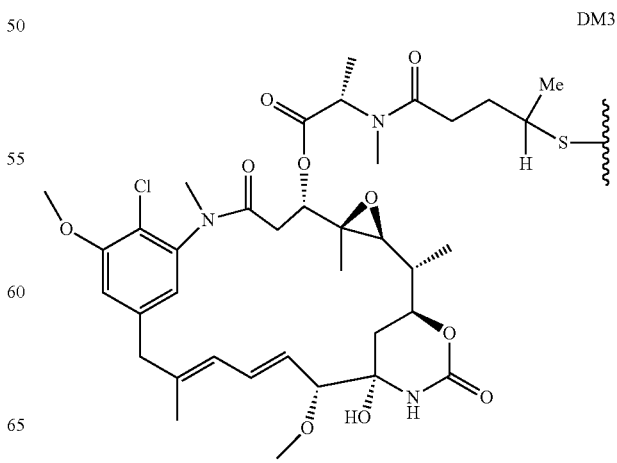

In another embodiment the maytansinoid drug moiety is $N^{2'}$-deacetyl-$N^{2'}$-(4-methyl-4-mercapto-1-oxopentyl)-maytansine (also known as DM4). DM4 is represented by the following structural formula.

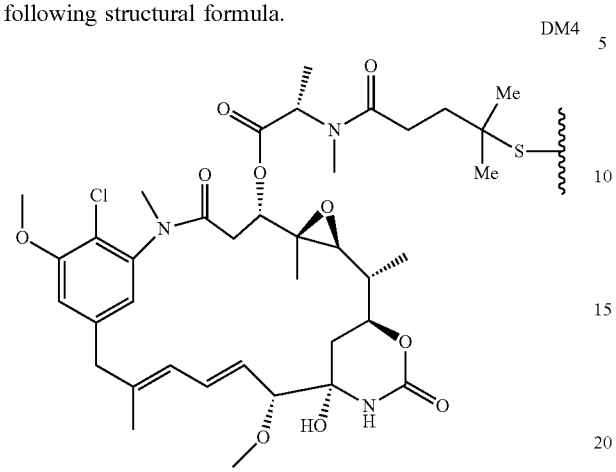

DM4

The drug moiety D can be linked to the antibody Ab through linker L. L is any chemical moiety capable of linking the drug moiety to the antibody through covalent bonds. A cross-linking reagent is a bifunctional or multifunctional reagent that can be used to link a drug moiety and an antibody to form antibody drug conjugates. Antibody drug conjugates can be prepared using a cross-linking reagent having a reactive functionality capable of binding to both the drug moiety and the antibody. For example, a cysteine, thiol or an amine, e.g. N-terminus or an amino acid side chain, such as lysine of the antibody, can form a bond with a functional group of a cross-linking reagent.

In one embodiment, L is a cleavable linker. In another embodiment, L is a non-cleavable linker. In some embodiments, L is an acid-labile linker, photo-labile linker, peptidase cleavable linker, esterase cleavable linker, a disulfide bond cleavable linker, a hydrophilic linker, a procharged linker, or a dicarboxylic acid based linker.

Suitable cross-linking reagents that form a non-cleavable linker between the drug moiety, for example maytansinoid, and the antibody are well known in the art, and can form non-cleavable linkers that comprise a sulfur atom (such as SMCC) or those that are without a sulfur atom. Preferred cross-linking reagents that form non-cleavable linkers between the drug moiety, for example maytansinoid, and the antibody comprise a maleimido- or haloacetyl-based moiety. According to the present invention, such non-cleavable linkers are said to be derived from maleimido- or haloacetyl-based moieties.

Cross-linking reagents comprising a maleimido-based moiety include but not limited to, N-succinimidyl-4-(maleimidomethyl)cyclohexanecarboxylate (SMCC), sulfosuccinimidyl 4-(N-maleimidomethyl)cyclohexane-1-carboxylate (sulfo-SMCC), N-succinimidyl-4-(maleimidomethyl)cyclohexane-1-carboxy-(6-amidocaproate), which is a "long chain" analog of SMCC (LC-SMCC), κ-maleimidoundecanoic acid N-succinimidyl ester (KMUA), γ-maleimidobutyric acid N-succinimidyl ester (GMBS), ε-maleimidocaproic acid N-succinimidyl ester (EMCS), m-maleimidobenzoyl-N-hydroxysuccinimide ester (MBS), N-(-maleimidoacetoxy)-succinimide ester (AMSA), succinimidyl-6-(β-maleimidopropionamido)hexanoate (SMPH), N-succinimidyl-4-(p-maleimidophenyl)-butyrate (SMPB), N-(-p-maleomidophenyl)isocyanate (PMIP) and maleimido-based cross-linking reagents containing a polyethythene glycol spacer, such as MAL-PEG-NHS. These cross-linking reagents form non-cleavable linkers derived from maleimido-based moieties. Representative structures of maleimido-based cross-linking reagents are shown below.

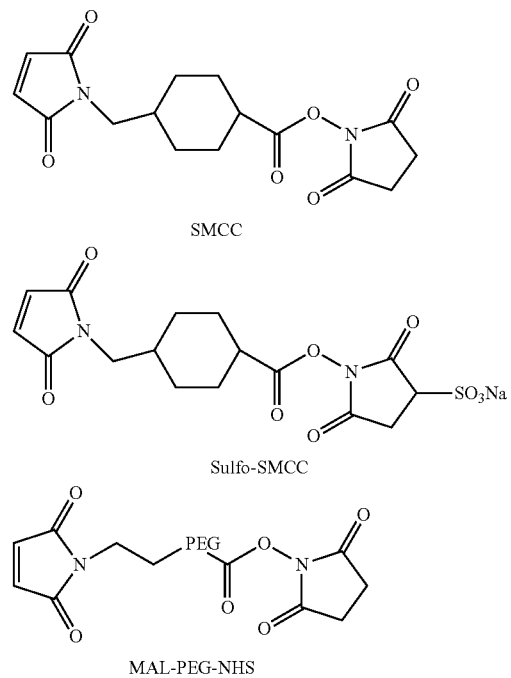

SMCC

Sulfo-SMCC

MAL-PEG-NHS

In another embodiment, the linker L is derived from N-succinimidyl-4-(maleimidomethyl)cyclohexanecarboxylate (SMCC), sulfosuccinimidyl 4-(N-maleimidomethyl)cyclohexane-1-carboxylate (sulfo-SMCC) or MAL-PEG-NHS.

Cross-linking reagents comprising a haloacetyle-based moiety include N-succinimidyl iodoacetate (SIA), N-succinimidyl(4-iodoacetyl)aminobenzoate (SIAB), N-succinimidyl bromoacetate (SBA) and N-succinimidyl 3-(bromoacetamido)propionate (SBAP). These cross-linking reagents form a non-cleavable linker derived from haloacetyl-based moieties. Representative structures of haloacetyl-based cross-linking reagents are shown below.

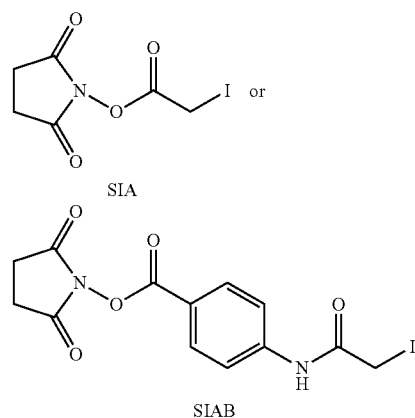

SIA

SIAB

In one embodiment, the linker L is derived from N-succinimidyl iodoacetate (SIA) or N-succinimidyl(4-iodoacetyl)aminobenzoate (SIAB).

Suitable cross-linking reagents that form a cleavable linker between the drug moiety, for example maytansinoid, and the antibody are well known in the art. Disulfide containing linkers are linkers cleavable through disulfide exchange, which can occur under physiological conditions. According to the present invention, such cleavable linkers are said to be derived from disulfide-based moieties. Suitable disulfide cross-linking reagents include N-succinimidyl-3-(2-pyridyldithio)propionate (SPDP), N-succinimidyl-4-(2-pyridyldithio)pentanoate (SPP), N-succinimidyl-4-(2-pyridyldithio)butanoate (SPDB) and N-succinimidyl-4-(2-pyridyldithio)-2-sulfo-butanoate (sulfo-SPDB), the structures of which are shown below. These disulfide cross-linking reagents form a cleavable linker derived from disulfide-based moieties.

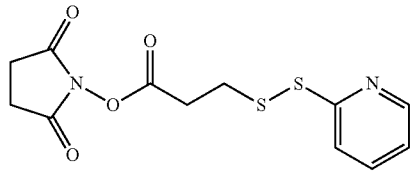

N-succinimidyl-3-(2-pyridyldithio)
propionate (SPDP)

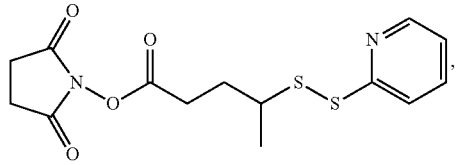

N-succinimidyl-4-(2-pyridyldithio)
pentanoate (SPP)

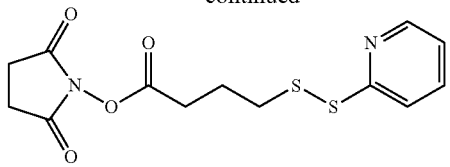

N-succinimidyl-4-(2-pyridyldithio)
butanoate (SPDB) and

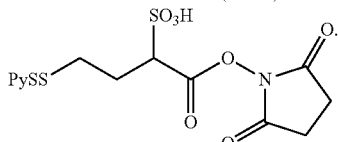

N-succinimidyl-4-(2-pyridyldithio)-
2-sulfo-butanoate (sulfo-SPDB)

In one embodiment, the linker L is derived from N-succinimidyl-4-(2-pyridyldithio)butanoate (SPDB).

Suitable cross-linking reagents that form a charged linker between the drug moiety, for example maytansinoid, and the antibody are known as procharged cross-linking reagents. In one embodiment, the linker L is derived from the procharged cross-linking reagent CX1-1. The structure of CX1-1 is below.

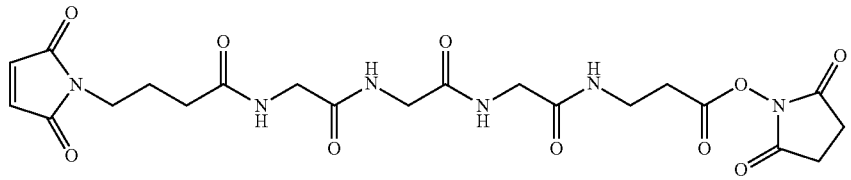 [SMILES: O=C(CCCN1C(=O)C=CC1=O)NCC(=O)NCC(=O)NCC(=O)NCCC(=O)ON1C(=O)CCC1=O]

2,5-dioxopyrrolidin-1-yl 17-(2,5-dioxo-2,5-dihydro-1H-pyrrol-1-yl)-5,8,11,14-tetraoxo-4,7,10,13-tetraazaheptadecan-1-oate (CX1-1)

Each of the cross-linking reagents depicted above contains, at one end of the cross-linking reagent, a NHS-ester which reacts with a primary amine of the antibody to form an amide bond and, at the other end, a maleimide group or pyridinyldisulfide group which reacts with the sulfhydryl of the maytansionoid drug moiety to form a thioether or disulfide bond.

In one embodiment, the conjugate of the present invention is represented by any one of the following structural formulae

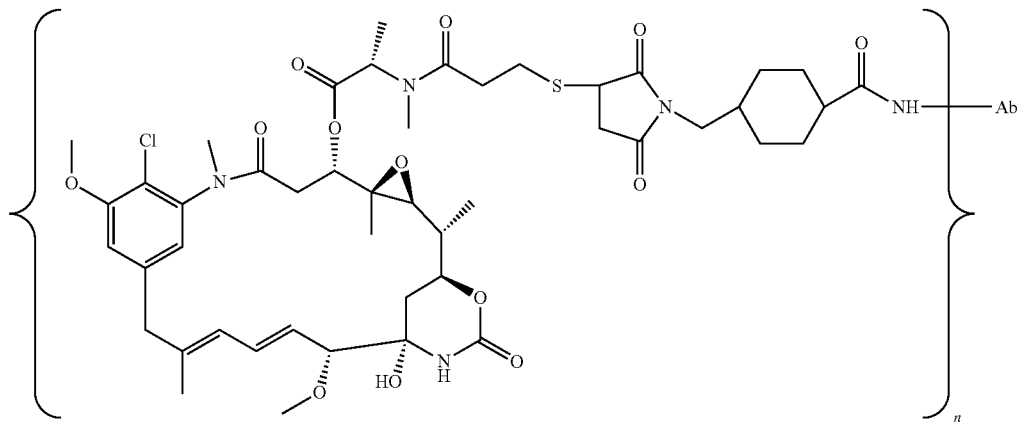

Ab-MCC-DM1

-continued

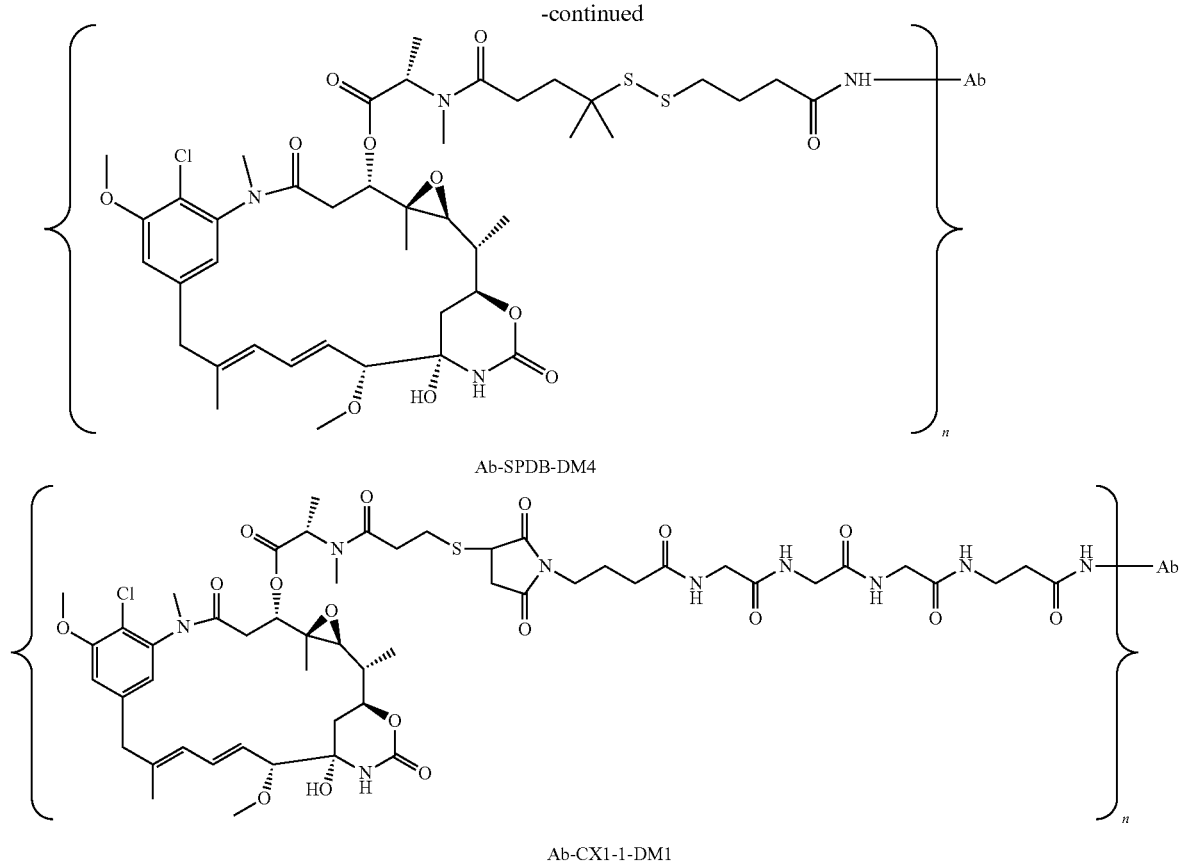

Ab-SPDB-DM4

Ab-CX1-1-DM1 wherein:

Ab is an antibody or antigen binding fragment thereof that specifically binds P-cadherin;

n, which indicates the number of D-L groups attached the Ab through the formation of an amide bond with a primary amine of the Ab, is an integer from 1 to 20. In one embodiment, n is an integer from 1 to 10, 2 to 8 or 2 to 5. In a specific embodiment, n is 3 or 4.

In one embodiment, the average molar ratio of drug (e.g., DM1 or DM4) to the antibody in the conjugate (i.e., average n value, also known as Maytansinoid Antibody Ratio (MAR)) is about 1 to about 10, about 2 to about 8 (e.g., 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, or 8.1), about 2.5 to about 7, about 3 to about 5, about 2.5 to about 4.5 (e.g., about 2.5, about 2.6, about 2.7, about 2.8, about 2.9, about 3.0, about 3.1, about 3.3, about 3.4, about 3.5, about 3.6, about 3.7, about 3.8, about 3.9, about 4.0, about 4.1, about 4.2, about 4.3, about 4.4, about 4.5), about 3.0 to about 4.0, about 3.2 to about 4.2, or about 4.5 to 5.5 (e.g., about 4.5, about 4.6, about 4.7, about 4.8, about 4.9, about 5.0, about 5.1, about 5.2, about 5.3, about 5.4, or about 5.5).

In an aspect of the invention, the conjugate of the present invention has substantially high purity and has one or more of the following features: (a) greater than about 90% (e.g., greater than or equal to about 91%, 92%, 93%, 94%, 95%, 96%, 97%, 98%, 99%, or 100%), preferably greater than about 95%, of conjugate species are monomeric, (b) unconjugated linker level in the conjugate preparation is less than about 10% (e.g., less than or equal to about 9%, 8%, 7%, 6%, 5%, 4%, 3%, 2%, 1%, or 0%) (relative to total linker), (c) less than 10% of conjugate species are crosslinked (e.g., less than or equal to about 9%, 8%, 7%, 6%, 5%, 4%, 3%, 2%, 1%, or 0%), (d) free drug (e.g., DM1 or DM4) level in the conjugate preparation is less than about 2% (e.g., less than or equal to about 1.5%, 1.4%, 1.3%, 1.2%, 1.1%, 1.0%, 0.9%, 0.8%, 0.7%, 0.6%, 0.5%, 0.4%, 0.3%, 0.2%, 0.1%, or 0%) (mol/mol relative to total cytotoxic agent) and/or (e) no substantial increase in the level of free drug (e.g., DM1 or DM4) occurs upon storage (e.g., after about 1 week, about 2 weeks, about 3 weeks, about 1 month, about 2 months, about 3 months, about 4 months, about 5 months, about 6 months, about 1 year, about 2 years, about 3 years, about 4 years, or about 5 years). "Substantial increase" in the level of free drug (e.g., DM1 or DM4) means that after certain storage time (e.g., about 1 week, about 2 weeks, about 3 weeks, about 1 month, about 2 months, about 3 months, about 4 months, about 5 months, about 6 months, about 1 year, about 2 years, about 3 years, about 4 years, or about 5 years), the increase in the level of free drug (e.g., DM1 or DM4) is less than about 0.1%, about 0.2%, about 0.3%, about 0.4%, about 0.5%, about 0.6%, about 0.7%, about 0.8%, about 0.9%, about 1.0%, about 1.1%, about 1.2%, about 1.3%, about 1.4%, about 1.5%, about 1.6%, about 1.7%, about 1.8%, about 1.9%, about 2.0%, about 2.2%, about 2.5%, about 2.7%, about 3.0%, about 3.2%, about 3.5%, about 3.7%, or about 4.0%.

As used herein, the term "unconjugated linker" refers to the antibody that is covalently linked with a linker derived from a cross-linking reagent (e.g., SMCC, Sulfo-SMCC, SPDB, Sulfo-SPDB or CX1-1), wherein the antibody is not covalently coupled to the drug (e.g., DM1 or DM4) through a linker (i.e., the "unconjugated linker" can be represented by Ab-MCC, Ab-SPDB, or Ab-CX1-1).

1. Drug Moiety

The present invention provides immunoconjugates that specifically bind to P-cadherin. The antibody drug conjugates of the invention comprise anti-P-cadherin antibodies, antibody fragments (e.g., antigen binding fragments) or functional equivalents that are conjugated to a drug moiety, e.g., an anti-cancer agent, an autoimmune treatment agent, an anti-inflammatory agent, an antifungal agent, an antibacterial agent, an anti-parasitic agent, an anti-viral agent, or an anesthetic agent. The antibodies, antibody fragments (e.g., antigen binding fragments) or functional equivalents of the invention can be conjugated to several identical or different drug moieties using any methods known in the art.

In certain embodiments, the drug moiety of the immunoconjugates of the present invention is selected from a group consisting of a V-ATPase inhibitor, a pro-apoptotic agent, a Bcl2 inhibitor, an MCL1 inhibitor, a HSP90 inhibitor, an IAP inhibitor, an mTor inhibitor, a microtubule stabilizer, a microtubule destabilizer, an auristatin, a dolastatin, a maytansinoid, a MetAP (methionine aminopeptidase), an inhibitor of nuclear export of proteins CRM1, a DPPIV inhibitor, an Eg5 inhibitor, proteasome inhibitors, an inhibitor of phosphoryl transfer reactions in mitochondria, a protein synthesis inhibitor, a kinase inhibitor, a CDK2 inhibitor, a CDK9 inhibitor, a kinesin inhibitor, an HDAC inhibitor, a DNA damaging agent, a DNA alkylating agent, a DNA intercalator, a DNA minor groove binder and a DHFR inhibitor.

In one embodiment, the drug moiety of the immunoconjugates of the present invention is a maytansinoid drug moiety, such as but not limited to, DM1, DM3, or DM4.

Further, the antibodies, antibody fragments (e.g., antigen binding fragments) or functional equivalents of the present invention may be conjugated to a drug moiety that modifies a given biological response. Drug moieties are not to be construed as limited to classical chemical therapeutic agents. For example, the drug moiety may be a protein, peptide, or polypeptide possessing a desired biological activity. Such proteins may include, for example, a toxin such as abrin, ricin A, *pseudomonas* exotoxin, cholera toxin, or diphtheria toxin, a protein such as tumor necrosis factor, α-interferon, β-interferon, nerve growth factor, platelet derived growth factor, tissue plasminogen activator, a cytokine, an apoptotic agent, an anti-angiogenic agent, or, a biological response modifier such as, for example, a lymphokine.

In one embodiment, the antibodies, antibody fragments (e.g., antigen binding fragments) or functional equivalents of the present invention are conjugated to a drug moiety, such as a cytotoxin, a drug (e.g., an immunosuppressant) or a radiotoxin. Examples of cytotoxins include but are not limited to, taxanes (see, e.g., International (PCT) Patent Application Nos. WO 01/38318 and PCT/US03/02675), DNA-alkylating agents (e.g., CC-1065 analogs), anthracyclines, tubulysin analogs, duocarmycin analogs, auristatin E, auristatin F, maytansinoids, and cytotoxic agents comprising a reactive polyethylene glycol moiety (see, e.g., Sasse et al., J. Antibiot. (Tokyo), 53, 879-85 (2000), Suzawa et al., Bioorg. Med. Chem., 8, 2175-84 (2000), Ichimura et al., J. Antibiot. (Tokyo), 44, 1045-53 (1991), Francisco et al., Blood (2003) (electronic publication prior to print publication), U.S. Pat. Nos. 5,475,092, 6,340,701, 6,372,738, and 6,436,931, U.S. Patent Application Publication No. 2001/0036923 A1, Pending U.S. patent application Ser. Nos. 10/024,290 and 10/116,053, and International (PCT) Patent Application No. WO 01/49698), taxon, cytochalasin B, gramicidin D, ethidium bromide, emetine, mitomycin, etoposide, tenoposide, vincristine, vinblastine, t. colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents also include, for example, antimetabolites (e.g., methotrexate, 6-mercaptopurine, 6-thioguanine, cytarabine, 5-fluorouracil decarbazine), ablating agents (e.g., mechlorethamine, thiotepa chlorambucil, meiphalan, carmustine (BSNU) and lomustine (CCNU), cyclophosphamide, busulfan, dibromomannitol, streptozotocin, mitomycin C, and cis-dichlorodiamine platinum (II) (DDP) cisplatin, anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine). (See e.g., Seattle Genetics US20090304721).

Other examples of cytotoxins that can be conjugated to the antibodies, antibody fragments (antigen binding fragments) or functional equivalents of the invention include duocarmycins, calicheamicins, maytansines and auristatins, and derivatives thereof.

Various types of cytotoxins, linkers and methods for conjugating therapeutic agents to antibodies are known in the art, see, e.g., Saito et al., (2003) Adv. Drug Deliv. Rev. 55:199-215; Trail et al., (2003) Cancer Immunol. Immunother. 52:328-337; Payne, (2003) Cancer Cell 3:207-212; Allen, (2002) Nat. Rev. Cancer 2:750-763; Pastan and Kreitman, (2002) Curr. Opin. Investig. Drugs 3:1089-1091; Senter and Springer, (2001) Adv. Drug Deliv. Rev. 53:247-264.

The antibodies, antibody fragments (e.g., antigen binding fragments) or functional equivalents of the present invention can also be conjugated to a radioactive isotope to generate cytotoxic radiopharmaceuticals, referred to as radioimmunoconjugates. Examples of radioactive isotopes that can be conjugated to antibodies for use diagnostically or therapeutically include, but are not limited to, iodine-131, indium-111, yttrium-90, and lutetium-177. Methods for preparing radioimmunoconjugates are established in the art. Examples of radioimmunoconjugates are commercially available, including Zevalin™ (DEC Pharmaceuticals) and Bexxar™ (Corixa Pharmaceuticals), and similar methods can be used to prepare radioimmunoconjugates using the antibodies of the invention. In certain embodiments, the macrocyclic chelator is 1,4,7,10-tetraazacyclododecane-N,N',N'',N'''-tetraacetic acid (DOTA) which can be attached to the antibody via a linker molecule. Such linker molecules are commonly known in the art and described in Denardo et al., (1998) Clin Cancer Res. 4(10):2483-90; Peterson et al., (1999) Bioconjug. Chem. 10(4):553-7; and Zimmerman et al., (1999) Nucl. Med. Biol. 26(8):943-50, each incorporated by reference in their entireties.

The antibodies, antibody fragments (e.g., antigen binding fragments) or functional equivalents of the present invention can also conjugated to a heterologous protein or polypeptide (or fragment thereof, preferably to a polypeptide of at least 10, at least 20, at least 30, at least 40, at least 50, at least 60, at least 70, at least 80, at least 90 or at least 100 amino acids) to generate fusion proteins. In particular, the invention provides fusion proteins comprising an antibody fragment (e.g., antigen binding fragment) described herein (e.g., a Fab fragment, Fd fragment, Fv fragment, F(ab)2 fragment, a VH domain, a VH CDR, a VL domain or a VL CDR) and a heterologous protein, polypeptide, or peptide.

Additional fusion proteins may be generated through the techniques of gene-shuffling, motif-shuffling, exon-shuffling, and/or codon-shuffling (collectively referred to as "DNA shuffling"). DNA shuffling may be employed to alter the activities of antibodies of the invention or fragments thereof (e.g., antibodies or fragments thereof with higher affinities and lower dissociation rates). See, generally, U.S. Pat. Nos. 5,605,793, 5,811,238, 5,830,721, 5,834,252, and 5,837,458; Patten et al., (1997) Curr. Opinion Biotechnol. 8:724-33; Harayama, (1998) Trends Biotechnol. 16(2):76-82; Hansson et al., (1999) J. Mol. Biol. 287:265-76; and Lorenzo and Blasco, (1998) Biotechniques 24(2):308-313 (each of these patents and publications are hereby incorporated by reference in its entirety). Antibodies or fragments thereof, or the encoded antibodies or fragments thereof, may be altered by being subjected to random mutagenesis by error-prone PCR, random nucleotide insertion or other methods prior to recombination. A polynucleotide encoding an antibody or fragment thereof that specifically binds to an antigen may be recombined with one or more components, motifs, sections, parts, domains, fragments, etc. of one or more heterologous molecules.

Moreover, the antibodies, antibody fragments (e.g., antigen binding fragments) or functional equivalents of the present invention can be conjugated to marker sequences, such as a peptide, to facilitate purification. In preferred embodiments, the marker amino acid sequence is a hexa-histidine peptide (SEQ ID NO: 130), such as the tag provided in a pQE vector (QIAGEN, Inc., 9259 Eton Avenue, Chatsworth, Calif., 91311), among others, many of which are commercially available. As described in Gentz et al., (1989) Proc. Natl. Acad. Sci. USA 86:821-824, for instance, hexa-histidine (SEQ ID NO: 130) provides for convenient purification of the fusion protein. Other peptide tags useful for purification include, but are not limited to, the hemagglutinin ("HA") tag, which corresponds to an epitope derived from the influenza hemagglutinin protein (Wilson et al., (1984) Cell 37:767), and the "FLAG" tag (A. Einhauer et al., J. Biochem. Biophys. Methods 49: 455-465, 2001). According to the present invention, antibodies or antigen binding fragments can also be conjugated to tumor-penetrating peptides in order to enhance their efficacy.

In other embodiments, the antibodies, antibody fragments (e.g., antigen binding fragments) or functional equivalents of the present invention are conjugated to a diagnostic or detectable agent. Such immunoconjugates can be useful for monitoring or prognosing the onset, development, progression and/or severity of a disease or disorder as part of a clinical testing procedure, such as determining the efficacy of a particular therapy. Such diagnosis and detection can be accomplished by coupling the antibody to detectable substances including, but not limited to, various enzymes, such as, but not limited to, horseradish peroxidase, alkaline phosphatase, beta-galactosidase, or acetylcholinesterase; prosthetic groups, such as, but not limited to, streptavidin/biotin and avidin/biotin; fluorescent materials, such as, but not limited to, Alexa Fluor 350, Alexa Fluor 405, Alexa Fluor 430, Alexa Fluor 488, Alexa Fluor 500, Alexa Fluor 514, Alexa Fluor 532, Alexa Fluor 546, Alexa Fluor 555, Alexa Fluor 568, Alexa Fluor 594, Alexa Fluor 610, Alexa Fluor 633, Alexa Fluor 647, Alexa Fluor 660, Alexa Fluor 680, Alexa Fluor 700, Alexa Fluor 750, umbelliferone, fluorescein, fluorescein isothiocyanate, rhodamine, dichlorotriazinylamine fluorescein, dansyl chloride or phycoerythrin; luminescent materials, such as, but not limited to, luminol; bioluminescent materials, such as but not limited to, luciferase, luciferin, and aequorin; radioactive materials, such as, but not limited to, iodine ($^{131}$I, $^{125}$I, $^{123}$I, and $^{121}$I), carbon ($^{14}$C) sulfur ($^{35}$S), tritium ($^{3}$H), indium ($^{115}$In, $^{113}$In, $^{112}$In, and $^{111}$In), technetium ($^{99}$Tc), thallium ($^{201}$Ti), gallium ($^{68}$Ga, $^{67}$Ga), palladium ($^{103}$Pd), molybdenum ($^{99}$Mo), xenon ($^{133}$Xe) fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, $^{97}$Ru, $^{68}$Ge, $^{57}$Co, $^{65}$Zn, $^{85}$Sr, $^{32}$P, $^{153}$Gd, $^{169}$Yb, $^{51}$Cr, $^{54}$Mn, $^{75}$Se, $^{64}$Cu, $^{113}$Sn, and $^{117}$Sn; and positron emitting metals using various positron emission tomographies, and non-radioactive paramagnetic metal ions.

The antibodies, antibody fragments (e.g., antigen binding fragments) or functional equivalents of the invention may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

2. Linker

As used herein, a "linker" is any chemical moiety that is capable of linking an antibody, antibody fragment (e.g., antigen binding fragments) or functional equivalent to another moiety, such as a drug moiety. Linkers can be susceptible to cleavage (cleavable linker), such as, acid-induced cleavage, photo-induced cleavage, peptidase-induced cleavage, esterase-induced cleavage, and disulfide bond cleavage, at conditions under which the compound or the antibody remains active. Alternatively, linkers can be substantially resistant to cleavage (e.g., stable linker or noncleavable linker). In some aspects, the linker is a procharged linker, a hydrophilic linker, or a dicarboxylic acid based linker.

In one aspect, the linker used in the present invention is derived from a crosslinking reagent such as N-succinimidyl-3-(2-pyridyldithio)propionate (SPDP), N-succinimidyl 4-(2-pyridyldithio)pentanoate (SPP), N-succinimidyl 4-(2-pyridyldithio)butanoate (SPDB), N-succinimidyl-4-(2-pyridyldithio)-2-sulfo-butanoate (sulfo-SPDB), N-succinimidyl iodoacetate (SIA), N-succinimidyl(4-iodoacetyl)aminobenzoate (SIAB), maleimide PEG NHS, N-succinimidyl 4-(maleimidomethyl)cyclohexanecarboxylate (SMCC), N-sulfosuccinimidyl 4-(maleimidomethyl)cyclohexanecarboxylate (sulfo-SMCC) or 2,5-dioxopyrrolidin-1-yl 17-(2,5-dioxo-2,5-dihydro-1H-pyrrol-1-yl)-5,8,11,14-tetraoxo-4,7,10,13-tetraazaheptadecan-1-oate (CX1-1).

Non-cleavable linkers are any chemical moiety capable of linking a drug, such as a maytansinoid, to an antibody in a stable, covalent manner and does not fall off under the categories listed above for cleaveable linkers. Thus, non-cleavable linkers are substantially resistant to acid-induced cleavage, photo-induced cleavage, peptidase-induced cleavage, esterase-induced cleavage and disulfide bond cleavage. Furthermore, non-cleavable refers to the ability of the chemical bond in the linker or adjoining to the linker to withstand cleavage induced by an acid, photolabile-cleaving agent, a peptidase, an esterase, or a chemical or physiological compound that cleaves a disulfide bond, at conditions under which the drug, such as maytansionoid or the antibody does not lose its activity.

Acid-labile linkers are linkers cleavable at acidic pH. For example, certain intracellular compartments, such as endosomes and lysosomes, have an acidic pH (pH 4-5), and provide conditions suitable to cleave acid-labile linkers.

Photo-labile linkers are linkers that are useful at the body surface and in many body cavities that are accessible to light. Furthermore, infrared light can penetrate tissue.

Some linkers can be cleaved by peptidases, i.e. peptidase cleavable linkers. Only certain peptides are readily cleaved inside or outside cells, see e.g. Trout et al., 79 Proc. Natl. Acad. Sci. USA, 626-629 (1982) and Umemoto et al. 43 Int. J. Cancer, 677-684 (1989). Furthermore, peptides are composed of α-amino acids and peptidic bonds, which chemically are amide bonds between the carboxylate of one amino acid and the amino group of a second amino acid. Other amide bonds, such as the bond between a carboxylate and the α-amino group of lysine, are understood not to be peptidic bonds and are considered non-cleavable.

Some linkers can be cleaved by esterases, i.e. esterase cleavable linkers. Again, only certain esters can be cleaved by esterases present inside or outside of cells. Esters are formed by the condensation of a carboxylic acid and an alcohol. Simple esters are esters produced with simple alcohols, such as aliphatic alcohols, and small cyclic and small aromatic alcohols.

Procharged linkers are derived from charged cross-linking reagents that retain their charge after incorporation into an antibody drug conjugate. Examples of procharged linkers can be found in US 2009/0274713.

3. Conjugation and Preparation of ADCs

The conjugates of the present invention can be prepared by any methods known in the art, such as those described in U.S. Pat. Nos. 7,811,572, 6,411,163, 7,368,565, and 8,163,888, and US application publications 2011/0003969, 2011/0166319, 2012/0253021 and 2012/0259100. The entire teachings of these patents and patent application publications are herein incorporated by reference.

One-Step Process

In one embodiment, the conjugates of the present invention can be prepared by a one-step process. The process comprises combining the antibody, drug and cross-linking agent in a substantially aqueous medium, optionally containing one or more co-solvents, at a suitable pH. In one embodiment, the process comprises the step of contacting the antibody of the present invention with a drug (e.g., DM1 or DM4) to form a first mixture comprising the antibody and the drug, and then contacting the first mixture comprising the antibody and the drug with a cross-linking agent (e.g., SMCC, Sulfo-SMCC, SPDB, Sulfo-SPDB or CX1-1) in a solution having a pH of about 4 to about 9 to provide a mixture comprising (i) the conjugate (e.g., Ab-MCC-DM1, Ab-SPDB-DM4, or Ab-CX1-1-DM1), (ii) free drug (e.g., DM1 or DM4), and (iii) reaction by-products.

In one embodiment, the one-step process comprises contacting the antibody with the drug (e.g., DM1 or DM4) and then the cross-linking agent (e.g., SMCC, Sulfo-SMCC, SPDB, Sulfo-SPDB or CX1-1) in a solution having a pH of about 6 or greater (e.g., about 6 to about 9, about 6 to about 7, about 7 to about 9, about 7 to about 8.5, about 7.5 to about 8.5, about 7.5 to about 8.0, about 8.0 to about 9.0, or about 8.5 to about 9.0). For example, the inventive process comprises contacting a cell-binding agent with the drug (DM1 or DM4) and then the cross-linking agent (e.g., SMCC, Sulfo-SMCC, SPDB, Sulfo-SPDB or CX1-1) in a solution having a pH of about 6.0, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, about 7.6, about 7.7, about 7.8, about 7.9, about 8.0, about 8.1, about 8.2, about 8.3, about 8.4, about 8.5, about 8.6, about 8.7, about 8.8, about 8.9, or about 9.0. In a specific embodiment, the inventive process comprises contacting a cell-binding agent with the drug (e.g., DM1 or DM4) and then the cross-linking agent (e.g., SMCC, Sulfo-SMCC, SPDB, Sulfo-SPDB or CX1-1) in a solution having a pH of about 7.6 to about 8.0 or a pH of 7.7 to 7.9).

The one-step process (i.e., contacting the antibody with the drug (e.g., DM1 or DM4) and then the cross-linking agent (e.g., SMCC, Sulfo-SMCC, SPDB, Sulfo-SPDB or CX1-1) can be carried out at any suitable temperature known in the art. For example, the one-step process can occur at about 20° C. or less (e.g., about −10° C. (provided that the solution is prevented from freezing, e.g., by the presence of organic solvent used to dissolve the cytotoxic agent and the bifunctional crosslinking reagent) to about 20° C., about 0° C. to about 18° C., about 4° C. to about 16° C.), at room temperature (e.g., about 20° C. to about 30° C. or about 20° C. to about 25° C.), or at an elevated temperature (e.g., about 30° C. to about 37° C.). In one embodiment, the one-step process occurs at a temperature of about 16° C. to about 24° C. (e.g., about 16° C., about 17° C., about 18° C., about 19° C., about 20° C., about 21° C., about 22° C., about 23° C., about 24° C., or about 25° C.). In another embodiment, the one-step process is carried out at a temperature of about 15° C. or less (e.g., about −10° C. to about 15° C., or about 0° C. to about 15° C.). For example, the process comprises contacting the antibody with the drug (e.g., DM1 or DM4) and then the cross-linking agent (e.g., SMCC, Sulfo-SMCC, SPDB, Sulfo-SPDB or CX1-1) at a temperature of about 15° C., about 14° C., about 13° C., about 12° C., about 11° C., about 10° C., about 9° C., about 8° C., about 7° C., about 6° C., about 5° C., about 4° C., about 3° C., about 2° C., about 1° C., about 0° C., about −1° C., about −2° C., about −3° C., about −4° C., about −5° C., about −6° C., about −7° C., about −8° C., about −9° C., or about −10° C., provided that the solution is prevented from freezing, e.g., by the presence of organic solvent(s) used to dissolve the cross-linking agent (e.g., SMCC, Sulfo-SMCC, Sulfo-SPDB SPDB, or CX1-1). In one embodiment, the process comprises contacting the antibody with the drug (e.g., DM1 or DM4) and then the cross-linking agent (e.g., SMCC, Sulfo-SMCC, SPDB, Sulfo-SPDB or CX1-1) at a temperature of about −10° C. to about 15° C., about 0° C. to about 15° C., about 0° C. to about 10° C., about 0° C. to about 5° C., about 5° C. to about 15° C., about 10° C. to about 15° C., or about 5° C. to about 10° C. In another embodiment, the process comprises contacting the antibody with the drug (e.g., DM1 or DM4) and then the cross-linking agent (e.g., SMCC, Sulfo-SMCC, SPDB, Sulfo-SPDB or CX1-1) at a temperature of about 10° C. (e.g., a temperature of 8° C. to 12° C. or a temperature of 9° C. to 11° C.).

In one embodiment, the contacting described above is effected by providing the antibody, then contacting the antibody with the drug (e.g., DM1 or DM4) to form a first mixture comprising the antibody and the drug (e.g., DM1 or DM4), and then contacting the first mixture comprising the antibody and the drug (e.g., DM1 or DM4) with the cross-linking agent (e.g., SMCC, Sulfo-SMCC, SPDB, Sulfo-SPDB or CX1-1). For example, in one embodiment, the antibody is provided in a reaction vessel, the drug (e.g., DM1 or DM4) is added to the reaction vessel (thereby contacting the antibody), and then the cross-linking agent (e.g., SMCC, Sulfo-SMCC, SPDB, Sulfo-SPDB or CX1-1) is added to the mixture comprising the antibody and the drug (e.g., DM1 or DM4) (thereby contacting the mixture comprising the antibody and the drug). In one embodiment, the antibody is provided in a reaction vessel, and the drug (e.g., DM1 or DM4) is added to the reaction vessel immediately following providing the antibody to the vessel. In another embodiment, the antibody is provided in a reaction vessel, and the drug (e.g., DM1 or DM4) is added to the reaction vessel after a time interval following providing the antibody to the vessel (e.g., about 5 minutes, about 10 minutes, about 20 minutes, about 30 minutes, about 40 minutes, about 50 minutes, about 1 hour, about 1 day or longer after providing the cell-binding agent to the space). The drug (e.g., DM1 or DM4) can be added quickly (i.e., within a short time interval, such as about 5 minutes, about 10 minutes) or slowly (such as by using a pump).

The mixture comprising the antibody and the drug (e.g., DM1 or DM4) can then be contacted with the cross-linking agent (e.g., SMCC, Sulfo-SMCC, SPDB, Sulfo-SPDB or CX1-1) either immediately after contacting the antibody with the drug (e.g., DM1 or DM4) or at some later point (e.g., about 5 minutes to about 8 hours or longer) after contacting the antibody with the drug (e.g., DM1 or DM4). For example, in one embodiment, the cross-linking agent (e.g., SMCC, Sulfo-SMCC, SPDB, Sulfo-SPDB or CX1-1) is added to the mixture comprising the antibody and the drug (e.g., DM1 or DM4) immediately after the addition of the drug (e.g., DM1 or DM4) to the reaction vessel comprising the antibody. Alternatively, the mixture comprising the antibody and the drug (e.g., DM1 or DM4) can be contacted with the cross-linking agent (e.g., SMCC, Sulfo-SMCC, SPDB, Sulfo-SPDB or CX1-1) at about 5 minutes, about 10 minutes, about 20 minutes, about 30 minutes, about 1 hour, about 2 hours, about 3 hours, about 4 hours, about 5 hours, about 6 hours, about 7 hours, about 8 hours, or longer after contacting the antibody with the drug (e.g., DM1 or DM4).

After the mixture comprising the antibody and the drug (e.g., DM1 or DM4) is contacted with the cross-linking agent (e.g., SMCC, Sulfo-SMCC, SPDB, Sulfo-SPDB or CX1-1) the reaction is allowed to proceed for about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, or longer (e.g., about 30 hours, about 35 hours, about 40 hours, about 45 hours, or about 48 hrs).

In one embodiment, the one-step process further comprises a quenching step to quench any unreacted drug (e.g., DM1 or DM4) and/or unreacted cross-linking agent (e.g., SMCC, Sulfo-SMCC, SPDB, Sulfo-SPDB or CX1-1). The quenching step is typically performed prior to purification of the conjugate. In one embodiment, the mixture is quenched by contacting the mixture with a quenching reagent. As used herein, the "quenching reagent" refers to a reagent that reacts with the free drug (e.g., DM1 or DM4) and/or cross-linking agent (e.g., SMCC, Sulfo-SMCC, SPDB, Sulfo-SPDB or CX1-1). In one embodiment, maleimide or haloacetamide quenching reagents, such as 4-maleimidobutyric acid, 3-maleimidopropionic acid, N-ethylmaleimide, iodoacetamide, or iodoacetamidopropionic acid, can be used to ensure that any unreacted group (such as thiol) in the drug (e.g., DM1 or DM4) is quenched. The quenching step can help prevent the dimerization of the drug (e.g., DM1). The dimerized DM1 can be difficult to remove. Upon quenching with polar, charged thiol-quenching reagents (such as 4-maleimidobutyric acid or 3-maleimidopropionic acid), the excess, unreacted DM1 is converted into a polar, charged, water-soluble adduct that can be easily separated from the covalently-linked conjugate during the purification step. Quenching with non-polar and neutral thiol-quenching reagents can also be used. In one embodiment, the mixture is quenched by contacting the mixture with a quenching reagent that reacts with the unreacted cross-linking agent (e.g., SMCC, Sulfo-SMCC, SPDB, Sulfo-SPDB or CX1-1). For example, nucleophiles can be added to the mixture in order to quench any unreacted SMCC. The nucleophile preferably is an amino group containing nucleophile, such as lysine, taurine and hydroxylamine.

In a preferred embodiment, the reaction (i.e., contacting the antibody with the drug (e.g., DM1 or DM4) and then cross-linking agent (e.g., SMCC, Sulfo-SMCC, SPDB, Sulfo-SPDB or CX1-1)) is allowed to proceed to completion prior to contacting the mixture with a quenching reagent. In this regard, the quenching reagent is added to the mixture about 1 hour to about 48 hours (e.g., about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, or about 25 hours to about 48 hours) after the mixture comprising the antibody and the drug (e.g., DM1 or DM4) is contacted with the cross-linking agent (e.g., SMCC, Sulfo-SMCC, SPDB, Sulfo-SPDB or CX1-1).

Alternatively, the mixture is quenched by lowering the pH of the mixture to about 5.0 (e.g., 4.8, 4.9, 5.0, 5.1 or 5.2). In another embodiment, the mixture is quenched by lowering the pH to less than 6.0, less than 5.5, less than 5.0, less than 4.8, less than 4.6, less than 4.4, less than 4.2, less than 4.0. Alternatively, the pH is lowered to about 4.0 (e.g., 3.8, 3.9, 4.0, 4.1 or 4.2) to about 6.0 (e.g., 5.8, 5.9, 6.0, 6.1 or 6.2), about 4.0 to about 5.0, about 4.5 (e.g., 4.3, 4.4, 4.5, 4.6 or 4.7) to about 5.0. In one embodiment, the mixture is quenched by lowering the pH of the mixture to 4.8. In another embodiment, the mixture is quenched by lowering the pH of the mixture to 5.5.

In one embodiment, the one-step process further comprises a holding step to release the unstably bound linkers from the antibody. The holding step comprises holding the mixture prior to purification of the conjugate (e.g., after the reaction step, between the reaction step and the quenching step, or after the quenching step). For example, the process comprises (a) contacting the antibody with the drug (e.g., DM1 or DM4) to form a mixture comprising the antibody and the drug (e.g., DM1 or DM4); and then contacting the mixture comprising the antibody and drug (e.g., DM1 or DM4) with the cross-linking agent (e.g., SMCC, Sulfo-SMCC, SPDB, Sulfo-SPDB or CX1-1), in a solution having a pH of about 4 to about 9 to provide a mixture comprising (i) the conjugate (e.g., Ab-MCC-DM1, Ab-SPDB-DM4 or Ab-CX1-1-DM1), (ii) free drug (e.g., DM1 or DM4), and (iii) reaction by-products, (b) holding the mixture prepared in step (a) to release the unstably bound linkers from the cell-binding agent, and (c) purifying the mixture to provide a purified conjugate.

In another embodiment, the process comprises (a) contacting the antibody with the drug (e.g., DM1 or DM4) to form a mixture comprising the antibody and the drug (e.g., DM1 or DM4); and then contacting the mixture comprising the antibody and the drug (e.g., DM1 or DM4) with the cross-linking agent (e.g., SMCC, Sulfo-SMCC, SPDB, Sulfo-SPDB or CX1-1), in a solution having a pH of about 4 to about 9 to provide a mixture comprising (i) the conjugate, (ii) free drug (e.g., DM1 or DM4), and (iii) reaction by-products, (b) quenching the mixture prepared in step (a) to quench any unreacted drug (e.g., DM1 or DM4) and/or unreacted cross-linking agent (e.g., SMCC, Sulfo- SMCC, SPDB, Sulfo-SPDB or CX1-1), (c) holding the mixture prepared in step (b) to release the unstably bound linkers from the cell-binding agent, and (d) purifying the mixture to provide a purified conjugate (e.g., Ab-MCC-DM1, Ab-SPDB-DM4 or Ab-CX1-1-DM1).

Alternatively, the holding step can be performed after purification of the conjugate, followed by an additional purification step.

In a preferred embodiment, the reaction is allowed to proceed to completion prior to the holding step. In this regard, the holding step can be performed about 1 hour to about 48 hours (e.g., about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, or about 24 hours to about 48 hours) after the mixture comprising the antibody and the drug (e.g., DM1 or DM4) is contacted with the cross-linking agent (e.g., SMCC, Sulfo-SMCC, SPDB, Sulfo-SPDB or CX1-1).

The holding step comprises maintaining the solution at a suitable temperature (e.g., about 0° C. to about 37° C.) for a suitable period of time (e.g., about 1 hour to about 1 week, about 1 hour to about 24 hours, about 1 hour to about 8 hours, or about 1 hour to about 4 hours) to release the unstably bound linkers from the antibody while not substantially releasing the stably bound linkers from the antibody. In one embodiment, the holding step comprises maintaining the solution at about 20° C. or less (e.g., about 0° C. to about 18° C., about 4° C. to about 16° C.), at room temperature (e.g., about 20° C. to about 30° C. or about 20° C. to about 25° C.), or at an elevated temperature (e.g., about 30° C. to about 37° C.). In one embodiment, the holding step comprises maintaining the solution at a temperature of about 16° C. to about 24° C. (e.g., about 15° C., about 16° C., about 17° C., about 18° C., about 19° C., about 20° C., about 21° C., about 22° C., about 23° C., about 24° C., or about 25° C.). In another embodiment, the holding step comprises maintaining the solution at a temperature of about 2° C. to about 8° C. (e.g., about 0° C., about 1° C., about 2° C., about 3° C., about 4° C., about 5° C., about 6° C., about 7° C., about 8° C., about 9° C., or about 10° C.). In another embodiment, the holding step comprises maintaining the solution at a temperature of about 37° C. (e.g., about 34° C., about 35° C., about 36° C., about 37° C., about 38° C., about 39° C., or about 40° C.).

The duration of the holding step depends on the temperature and the pH at which the holding step is performed. For example, the duration of the holding step can be substantially reduced by performing the holding step at elevated temperature, with the maximum temperature limited by the stability of the cell-binding agent-cytotoxic agent conjugate. The holding step can comprise maintaining the solution for about 1 hour to about 1 day (e.g., about 1 hour, about 2 hours, about 3 hours, about 4 hours, about 5 hours, about 6 hours, about 7 hours, about 8 hours, about 9 hours, about 10 hours, about 12 hours, about 14 hours, about 16 hours, about 18 hours, about 20 hours, about 22 hours, or about 24 hours), about 10 hours to about 24 hours, about 12 hours to about 24 hours, about 14 hours to about 24 hours, about 16 hours to about 24 hours, about 18 hours to about 24 hours, about 20 hours to about 24 hours, about 5 hours to about 1 week, about 20 hours to about 1 week, about 12 hours to about 1 week (e.g., about 12 hours, about 16 hours, about 20 hours, about 24 hours, about 2 days, about 3 days, about 4 days, about 5 days, about 6 days, or about 7 days), or about 1 day to about 1 week.

In one embodiment, the holding step comprises maintaining the solution at a temperature of about 2° C. to about 8° C. for a period of at least about 12 hours for up to a week. In another embodiment, the holding step comprises maintaining the solution at a temperature of about 2° C. to about 8° C. overnight (e.g., about 12 to about 24 hours, preferably about 20 hours).

The pH value for the holding step preferably is about 4 to about 10. In one embodiment, the pH value for the holding step is about 4 or more, but less than about 6 (e.g., 4 to 5.9) or about 5 or more, but less than about 6 (e.g., 5 to 5.9). In another embodiment, the pH values for the holding step range from about 6 to about 10 (e.g., about 6.5 to about 9, about 6 to about 8). For example, pH values for the holding step can be about 6, about 6.5, about 7, about 7.5, about 8, about 8.5, about 9, about 9.5, or about 10.

In specific embodiments, the holding step can comprise incubating the mixture at 25° C. at a pH of about 6-7.5 for about 12 hours to about 1 week, incubating the mixture at 4° C. at a pH of about 4.5-5.9 for about 5 hours to about 5 days, or incubating the mixture at 25° C. at a pH of about 4.5-5.9 for about 5 hours to about 1 day.

The one-step process may optionally include the addition of sucrose to the reaction step to increase solubility and recovery of the conjugates. Desirably, sucrose is added at a concentration of about 0.1% (w/v) to about 20% (w/v) (e.g., about 0.1% (w/v), 1% (w/v), 5% (w/v), 10% (w/v), 15% (w/v), or 20% (w/v)). Preferably, sucrose is added at a concentration of about 1% (w/v) to about 10% (w/v) (e.g., about 0.5% (w/v), about 1% (w/v), about 1.5% (w/v), about 2% (w/v), about 3% (w/v), about 4% (w/v), about 5% (w/v), about 6% (w/v), about 7% (w/v), about 8% (w/v), about 9% (w/v), about 10% (w/v), or about 11% (w/v)). In addition, the reaction step also can comprise the addition of a buffering agent. Any suitable buffering agent known in the art can be used. Suitable buffering agents include, for example, a citrate buffer, an acetate buffer, a succinate buffer, and a phosphate buffer. In one embodiment, the buffering agent is selected from the group consisting of HEPPSO (N-(2-hydroxyethyl)piperazine-N'-(2-hydroxypropanesulfonic acid)), POPSO (piperazine-1,4-bis-(2-hydroxy-propane-sulfonic acid) dehydrate), HEPES (4-(2-hydroxyethyl)piperazine-1-ethanesulfonic acid), HEPPS (EPPS) (4-(2-hydroxyethyl)piperazine-1-propanesulfonic acid), TES (N-[tris(hydroxymethyl)methyl]-2-aminoethanesulfonic acid), and a combination thereof.

In one embodiment, the one-step process can further comprise the step of purifying the mixture to provide purified conjugate (e.g., Ab-MCC-DM1, Ab-SPDB-DM4 or Ab-CX1-1-DM1). Any purification methods known in the art can be used to purify the conjugates of the present invention. In one embodiment, the conjugates of the present invention using tangential flow filtration (TFF), non-adsorptive chromatography, adsorptive chromatography, adsorptive filtration, selective precipitation, or any other suitable purification process, as well as combinations thereof. In another embodiment, prior to subjecting the conjugates to purification process described above, the conjugates are first filtered through one or more PVDF membranes. Alternatively, the conjugates are filtered through one or more PVDF membranes after subjecting the conjugates to the purification process described above. For example, in one embodiment, the conjugates are filtered through one or more PVDF membranes and then purified using tangential flow filtration.

Alternatively, the conjugates are purified using tangential flow filtration and then filtered through one or more PVDF membranes.

Any suitable TFF systems may be utilized for purification, including a Pellicon type system (Millipore, Billerica, Mass.), a Sartocon Cassette system (Sartorius AG, Edgewood, N.Y.), and a Centrasette type system (Pall Corp., East Hills, N.Y.).

Any suitable adsorptive chromatography resin may be utilized for purification. Preferred adsorptive chromatography resins include hydroxyapatite chromatography, hydrophobic charge induction chromatography (HCIC), hydrophobic interaction chromatography (HIC), ion exchange chromatography, mixed mode ion exchange chromatography, immobilized metal affinity chromatography (IMAC), dye ligand chromatography, affinity chromatography, reversed phase chromatography, and combinations thereof. Examples of suitable hydroxyapatite resins include ceramic hydroxyapatite (CHT Type I and Type II, Bio-Rad Laboratories, Hercules, Calif.), HA Ultrogel hydroxyapatite (Pall Corp., East Hills, N.Y.), and ceramic fluoroapatite (CFT Type I and Type II, Bio-Rad Laboratories, Hercules, Calif.). An example of a suitable HCIC resin is MEP Hypercel resin (Pall Corp., East Hills, N.Y.). Examples of suitable HIC resins include Butyl-Sepharose, Hexyl-Sepaharose, Phenyl-Sepharose, and Octyl Sepharose resins (all from GE Healthcare, Piscataway, N.J.), as well as Macro-prep Methyl and Macro-Prep t-Butyl resins (Biorad Laboratories, Hercules, Calif.). Examples of suitable ion exchange resins include SP-Sepharose, CM-Sepharose, and Q-Sepharose resins (all from GE Healthcare, Piscataway, N.J.), and Unosphere S resin (Bio-Rad Laboratories, Hercules, Calif.). Examples of suitable mixed mode ion exchangers include Bakerbond ABx resin (JT Baker, Phillipsburg N.J.). Examples of suitable IMAC resins include Chelating Sepharose resin (GE Healthcare, Piscataway, N.J.) and Profinity IMAC resin (Bio-Rad Laboratories, Hercules, Calif.). Examples of suitable dye ligand resins include Blue Sepharose resin (GE Healthcare, Piscataway, N.J.) and Affi-gel Blue resin (Bio-Rad Laboratories, Hercules, Calif.). Examples of suitable affinity resins include Protein A Sepharose resin (e.g., MabSelect, GE Healthcare, Piscataway, N.J.) and lectin affinity resins, e.g. Lentil Lectin Sepharose resin (GE Healthcare, Piscataway, N.J.), where the antibody bears appropriate lectin binding sites. Examples of suitable reversed phase resins include C4, C8, and C18 resins (Grace Vydac, Hesperia, Calif.).

Any suitable non-adsorptive chromatography resin may be utilized for purification. Examples of suitable non-adsorptive chromatography resins include, but are not limited to, SEPHADEX™ G-25, G-50, G-100, SEPHACRYL™ resins (e.g., S-200 and S-300), SUPERDEX™ resins (e.g., SUPERDEX™ 75 and SUPERDEX™ 200), BIO-GEL® resins (e.g., P-6, P-10, P-30, P-60, and P-100), and others known to those of ordinary skill in the art.

Two-Step Process and One-Pot Process

In one embodiment, the conjugates of the present invention can be prepared as described in the U.S. Pat. No. 7,811,572 and U.S. Patent Application Publication No. 2006/0182750. The process comprises the steps of (a) contacting the antibody of the present invention with the cross-linking agent (e.g., SMCC, Sulfo-SMCC, SPDB, Sulfo-SPDB or CX1-1) to covalently attach the linker (i.e., Ab-SMCC, Ab-SPDB, or Ab-CX1-1) to the antibody and thereby prepare a first mixture comprising the antibody having the linker bound thereto; (b) optionally subjecting the first mixture to a purification process to prepare a purified first mixture of the antibody having the linker bound thereto; (c) conjugating the drug (e.g., DM1 or DM4) to the antibody having the linker bound thereto in the first mixture by reacting the antibody having the linker bound thereto with the drug (e.g., DM1 or DM4) in a solution having a pH of about 4 to about 9 to prepare a second mixture comprising (i) conjugate (e.g., Ab-MCC-DM1, Ab-SPDB-DM4 or Ab-CX1-1-DM1), (ii) free drug (e.g., DM1 or DM4); and (iii) reaction by-products; and (d) subjecting the second mixture to a purification process to purify the conjugate from the other components of the second mixture. Alternatively, the purification step (b) can be omitted. Any purification methods described herein can be used for steps (b) and (d). In one embodiment, TFF is used for both steps (b) and (d). In another embodiment, TFF is used for step (b) and absorptive chromatography (e.g., CHT) is used for step (d).

One-Step Reagent and In-Situ Process

In one embodiment, the conjugates of the present invention can be prepared by conjugating pre-formed drug-linker compound (e.g., SMCC-DM1, Sulfo-SMCC-DM1, SPDB-DM4 or CX1-1-DM1) to the antibody of the present invention, as described in U.S. Pat. No. 6,441,163 and U.S. Patent Application Publication Nos. 2011/0003969 and 2008/0145374, followed by a purification step. Any purification methods described herein can be used. The drug-linker compound is prepared by reacting the drug (e.g., DM1 or DM4) with the cross-linking agent (e.g., SMCC, Sulfo-SMCC, SPDB, Sulfo-SPDB or CX1-1). The drug-linker compound (e.g., SMCC-DM1, Sulfo-SMCC-DM1, SPDB-DM4 or CX1-1-DM1) is optionally subjected to purification before being conjugated to the antibody.

Anti-P-Cadherin Antibodies

The present invention provides antibodies or antibody fragments (e.g., antigen binding fragments) that specifically bind to human P-cadherin. Antibodies or antibody fragments (e.g., antigen binding fragments) of the invention include, but are not limited to, the human monoclonal antibodies or fragments thereof, isolated as described in the Examples.

The present invention in certain embodiments provides antibodies or antibody fragments (e.g., antigen binding fragments) that specifically bind P-cadherin, said antibodies or antibody fragments (e.g., antigen binding fragments) comprise a VH domain having an amino acid sequence of SEQ ID NO: 7, 27, 47, 67, 87, or 107. The present invention in certain embodiments also provides antibodies or antibody fragments (e.g., antigen binding fragments) that specifically bind to P-cadherin, said antibodies or antibody fragments (e.g., antigen binding fragments) comprise a VH CDR having an amino acid sequence of any one of the VH CDRs listed in Table 1, infra. In particular embodiments, the invention provides antibodies or antibody fragments (e.g., antigen binding fragments) that specifically bind to P-cadherin, said antibodies comprising (or alternatively, consist of) one, two, three, four, five or more VH CDRs having an amino acid sequence of any of the VH CDRs listed in Table 1, infra.

The present invention provides antibodies or antibody fragments (e.g., antigen binding fragments) that specifically bind to P-cadherin, said antibodies or antibody fragments (e.g., antigen binding fragments) comprise a VL domain having an amino acid sequence of SEQ ID NO: 17, 37, 57, 77, 97, or 117. The present invention also provides antibodies or antibody fragments (e.g., antigen binding fragments) that specifically bind to P-cadherin, said antibodies or antibody fragments (e.g., antigen binding fragments) comprise a VL CDR having an amino acid sequence of any one of the VL CDRs listed in Table 1, infra. In particular, the invention provides antibodies or antibody fragments (e.g., antigen binding fragments) that specifically bind to P-cadherin, said antibodies or antibody fragments (e.g., antigen binding fragments) comprise (or alternatively, consist of) one, two, three or more VL CDRs having an amino acid sequence of any of the VL CDRs listed in Table 1, infra.

Other antibodies or antibody fragments (e.g., antigen binding fragments) of the invention include amino acids that have been mutated, yet have at least 60, 70, 80, 90 or 95 percent identity in the CDR regions with the CDR regions depicted in the sequences described in Table 1. In some embodiments, the antibodies comprise mutant amino acid sequences wherein no more than 1, 2, 3, 4 or 5 amino acids have been mutated in the CDR regions when compared with the CDR regions depicted in the sequence described in Table 1.

The present invention also provides nucleic acid sequences that encode the VH, VL, the full length heavy chain, and the full length light chain of the antibodies that specifically bind to P-cadherin. Such nucleic acid sequences can be optimized for expression in mammalian cells.

TABLE 1

Examples of anti-P-cadherin Antibodies of the Present Invention

| SEQ ID NO. | Description | Sequence |
|---|---|---|
| | NOV169N31Q | |
| SEQ ID NO: 1 | HCDR1 (Kabat) | SQSAAWN |
| SEQ ID NO: 2 | HCDR2 (Kabat) | RIYYRSKWYNDYALSVKS |
| SEQ ID NO: 3 | HCDR3 (Kabat) | GEGYGREGFAI |
| SEQ ID NO: 4 | HCDR1 (Chothia) | GDSVSSQSA |
| SEQ ID NO: 5 | HCDR2 (Chothia) | YYRSKWY |
| SEQ ID NO: 6 | HCDR3 (Chothia) | GEGYGREGFAI |
| SEQ ID NO: 7 | VH | QVQLQQSGPGLVKPSQTLSLTCAISGDSVSSQSAAWNWI RQSPSRGLEWLGRIYYRSKWYNDYALSVKSRITINPDTS KNQFSLQLNSVTPEDTAVYYCARGEGYGREGFAIWGQGT LVTVSS |
| SEQ ID NO: 8 | DNA VH | CAGGTGCAGCTGCAGCAGTCAGGCCCTGGCCTGGTCAAG CCTAGTCAGACCCTGAGCCTGACCTGCGCTATTAGCGGC GATAGTGTGTCTAGTCAGTCAGCCGCCTGGAACTGGATT AGACAGTCACCCTCTAGGGGCCTGGAGTGGCTGGGTAGA ATCTACTATAGGTCTAAGTGGTATAACGACTACGCCCTG AGCGTGAAGTCTAGGATCACTATTAACCCCGACACCTCT AAGAATCAGTTTAGCCTGCAGCTGAATAGCGTGACCCCC GAGGACACCGCCGTCTACTACTGCGCTAGAGGCGAGGGC TACGGTAGAGAGGGCTTCGCTATCTGGGGTCAGGGCACC CTGGTCACCGTGTCTAGC |
| SEQ ID NO: 9 | Heavy Chain | QVQLQQSGPGLVKPSQTLSLTCAISGDSVSSQSAAWNWI RQSPSRGLEWLGRIYYRSKWYNDYALSVKSRITINPDTS KNQFSLQLNSVTPEDTAVYYCARGEGYGREGFAIWGQGT LVTVSSASTKGPSVFPLAPSSKSTSGGTAALGCLVKDYF PEPVTVSWNSGALTSGVHTFPAVLQSSGLYSLSSVVTVP SSSLGTQTYICNVNHKPSNTKVDKRVEPKSCDKTHTCPP CPAPELLGGPSVFLFPPKPKDTLMISRTPEVTCVVVDVS HEDPEVKFNWYVDGVEVHNAKTKPREEQYNSTYRVVSVL TVLHQDWLNGKEYKCKVSNKALPAPIEKTISKAKGQPRE PQVYTLPPSREEMTKNQVSLTCLVKGFYPSDIAVEWESN GQPENNYKTTPPVLDSDGSFFLYSKLTVDKSRWQQGNVF SCSVMHEALHNHYTQKSLSLSPGK |
| SEQ ID NO: 10 | DNA Heavy Chain | CAGGTGCAGCTGCAGCAGTCAGGCCCTGGCCTGGTCAAG CCTAGTCAGACCCTGAGCCTGACCTGCGCTATTAGCGGC GATAGTGTGTCTAGTCAGTCAGCCGCCTGGAACTGGATT AGACAGTCACCCTCTAGGGGCCTGGAGTGGCTGGGTAGA ATCTACTATAGGTCTAAGTGGTATAACGACTACGCCCTG AGCGTGAAGTCTAGGATCACTATTAACCCCGACACCTCT AAGAATCAGTTTAGCCTGCAGCTGAATAGCGTGACCCCC GAGGACACCGCCGTCTACTACTGCGCTAGAGGCGAGGGC TACGGTAGAGAGGGCTTCGCTATCTGGGGTCAGGGCACC CTGGTCACCGTGTCTAGCGCTAGCACTAAGGGCCCAAGT GTGTTTCCCCTGGCCCCAGCAGCAAGTCTACTTCCGGC GGAACTGCTGCCCTGGGTTGCCTGGTGAAGGACTACTTC CCCGAGCCCGTGACAGTGTCCTGGAACTCTGGGGCTCTG |

TABLE 1-continued

Examples of anti-P-cadherin Antibodies of the Present Invention

| SEQ ID NO. | Description | Sequence |
|---|---|---|
| | | ACTTCCGGCGTGCACACCTTCCCCGCCGTGCTGCAGAGC<br>AGCGGCCTGTACAGCCTGAGCAGCGTGGTGACAGTGCCC<br>TCCAGCTCTCTGGGAACCCAGACCTATATCTGCAACGTG<br>AACCACAAGCCCAGCAACACCAAGGTGGACAAGAGAGTG<br>GAGCCCAAGAGCTGCGACAAGACCCACACCTGCCCCCCC<br>TGCCCAGCTCCAGAACTGCTGGGAGGGCCTTCCGTGTTC<br>CTGTTCCCCCCCAAGCCCAAGGACACCCTGATGATCAGC<br>AGGACCCCCGAGGTGACCTGCGTGGTGGTGGACGTGTCC<br>CACGAGGACCCAGAGGTGAAGTTCAACTGGTACGTGGAC<br>GGCGTGGAGGTGCACAACGCCAAGACCAAGCCCAGAGAG<br>GAGCAGTACAACAGCACCTACAGGGTGGTGTCCGTGCTG<br>ACCGTGCTGCACCAGGACTGGCTGAACGGCAAAGAATAC<br>AAGTGCAAAGTCTCCAACAAGGCCCTGCCAGCCCCAATC<br>GAAAAGACAATCAGCAAGGCCAAGGGCCAGCCACGGGAG<br>CCCCAGGTGTACACCCTGCCCCCCAGCCGGGAGGAGATG<br>ACCAAGAACCAGGTGTCCCTGACCTGTCTGGTGAAGGGC<br>TTCTACCCCAGCGATATCGCCGTGGAGTGGGAGAGCAAC<br>GGCCAGCCCGAGAACAACTACAAGACCACCCCCCCCAGTG<br>CTGGACAGCGACGGCAGCTTCTTCCTGTACAGCAAGCTG<br>ACCGTGGACAAGTCCAGGTGGCAGCAGGGCAACGTGTTC<br>AGCTGCAGCGTGATGCACGAGGCCCTGCACAACCACTAC<br>ACCCAGAAGTCCCTGAGCCTGAGCCCCGGCAAG |
| SEQ ID NO: 11 | LCDR1<br>(Kabat) | RASQTISNTLA |
| SEQ ID NO: 12 | LCDR2<br>(Kabat) | AASNLQS |
| SEQ ID NO: 13 | LCDR3<br>(Kabat) | QQYLSWFT |
| SEQ ID NO: 14 | LCDR1<br>(Chothia) | SQTISNT |
| SEQ ID NO: 15 | LCDR2<br>(Chothia) | AAS |
| SEQ ID NO: 16 | LCDR3<br>(Chothia) | YLSWF |
| SEQ ID NO: 17 | VL | DIQMTQSPSSLSASVGDRVTITCRASQTISNTLAWYQQK<br>PGKAPKLLIYAASNLQSGVPSRFSGSGSGTDFTLTISSL<br>QPEDFATYYCQQYLSWFTFGQGTKVEIK |
| SEQ ID NO: 18 | DNAVL | GATATTCAGATGACTCAGTCACCTAGTAGCCTGAGCGCT<br>AGTGTGGGCGATAGAGTGACTATCACCTGTAGAGCCTCT<br>CAGACTATCTCTAACACCCTGGCCTGGTATCAGCAGAAG<br>CCCGGTAAAGCCCCTAAGCTGCTGATCTACGCCGCCTCT<br>AACCTGCAGTCAGGCGTGCCCTCTAGGTTTAGCGGTAGC<br>GGTAGTGGCACCGACTTCACCCTGACTATTAGTAGCCTG<br>CAGCCCGAGGACTTCGCTACCTACTACTGTCAGCAGTAC<br>CTGAGCTGGTTCACCTTCGGTCAGGGCACTAAGGTCGAG<br>ATTAAG |
| SEQ ID NO: 19 | Light<br>Chain | DIQMTQSPSSLSASVGDRVTITCRASQTISNTLAWYQQK<br>PGKAPKLLIYAASNLQSGVPSRFSGSGSGTDFTLTISSL<br>QPEDFATYYCQQYLSWFTFGQGTKVEIKRTVAAPSVFIF<br>PPSDEQLKSGTASVVCLLNNFYPREAKVQWKVDNALQSG<br>NSQESVTEQDSKDSTYSLSSTLTLSKADYEKHKVYACEV<br>THQGLSSPVTKSFNRGEC |
| SEQ ID NO 20: | DNA Light<br>Chain | GATATTCAGATGACTCAGTCACCTAGTAGCCTGAGCGCT<br>AGTGTGGGCGATAGAGTGACTATCACCTGTAGAGCCTCT<br>CAGACTATCTCTAACACCCTGGCCTGGTATCAGCAGAAG<br>CCCGGTAAAGCCCCTAAGCTGCTGATCTACGCCGCCTCT<br>AACCTGCAGTCAGGCGTGCCCTCTAGGTTTAGCGGTAGC<br>GGTAGTGGCACCGACTTCACCCTGACTATTAGTAGCCTG<br>CAGCCCGAGGACTTCGCTACCTACTACTGTCAGCAGTAC<br>CTGAGCTGGTTCACCTTCGGTCAGGGCACTAAGGTCGAG<br>ATTAAGCGTACGGTGGCCGCTCCCAGCGTGTTCATCTTC<br>CCCCCAGCGACGAGCAGCTGAAGAGCGGCACCGCCAGC<br>GTGGTGTGCCTGCTGAACAACTTCTACCCCGGGAGGCC<br>AAGGTGCAGTGGAAGGTGGACAACGCCCTGCAGAGCGGC<br>AACAGCCAGGAGAGCGTCACCGAGCAGGACAGCAAGGAC<br>TCCACCTACAGCCTGAGCAGCACCCTGACCCTGAGCAAG |

TABLE 1-continued

Examples of anti-P-cadherin Antibodies of the Present Invention

| SEQ ID NO. | Description | Sequence |
|---|---|---|
| | | GCCGACTACGAGAAGCATAAGGTGTACGCCTGCGAGGTG ACCCACCAGGGCCTGTCCAGCCCCGTGACCAAGAGCTTC AACAGGGGCGAGTGC |

NEG0012

| SEQ ID NO: 21 | HCDR1 (Kabat) | DHTIH |
| --- | --- | --- |
| SEQ ID NO: 22 | HCDR2 (Kabat) | YIYPRSGSINYNEKFKG |
| SEQ ID NO: 23 | HCDR3 (Kabat) | RNLFLPMEY |
| SEQ ID NO: 24 | HCDR1 (Chothia) | GYTFTDH |
| SEQ ID NO: 25 | HCDR2 (Chothia) | YPRSGS |
| SEQ ID NO: 26 | HCDR3 (Chothia) | RNLFLPMEY |
| SEQ ID NO: 27 | VH | EVQLVQSGAEVKKPGESLKISCKVSGYTFTDHTIHWMRQ MPGKGLEWMGYIYPRSGSINYNEKFKGQVTISADKSSST AYLQWSSLKASDTAMYYCARRNLFLPMEYWGQGTLVTVS S |
| SEQ ID NO: 28 | DNA VH | GAGGTGCAGCTGGTGCAGTCAGGCGCCGAAGTGAAGAAG CCCGGCGAGTCACTGAAGATTAGCTGTAAAGTCTCAGGC TACACCTTCACCGATCACACTATTCACTGGATGAGACAG ATGCCCGGTAAAGGCCTGGAGTGGATGGGCTATATCTAC CCTAGATCAGGCTCTATTAACTATAACGAGAAGTTTAAG GGTCAGGTCACAATTAGCGCCGATAAGTCTAGCTCTACC GCCTACCTGCAGTGGTCTAGCCTGAAGGCTAGTGACACC GCTATGTACTACTGCGCTAGACGTAACCTGTTCCTGCCT ATGGAATACTGGGGTCAGGGCACCCTGGTCACCGTGTCT AGC |
| SEQ ID NO: 29 | Heavy Chain | EVQLVQSGAEVKKPGESLKISCKVSGYTFTDHTIHWMRQ MPGKGLEWMGYIYPRSGSINYNEKFKGQVTISADKSSST AYLQWSSLKASDTAMYYCARRNLFLPMEYWGQGTLVTVS SASTKGPSVFPLAPSSKSTSGGTAALGCLVKDYFPEPVT VSWNSGALTSGVHTFPAVLQSSGLYSLSSVVTVPSSSLG TQTYICNVNHKPSNTKVDKRVEPKSCDKTHTCPPCPAPE LLGGPSVFLFPPKPKDTLMISRTPEVTCVVVDVSHEDPE VKFNWYVDGVEVHNAKTKPREEQYNSTYRVVSVLTVLHQ DWLNGKEYKCKVSNKALPAPIEKTISKAKGQPREPQVYT LPPSREEMTKNQVSLTCLVKGFYPSDIAVEWESNGQPEN NYKTTPPVLDSDGSFFLYSKLTVDKSRWQQGNVFSCSVM HEALHNHYTQKSLSLSPGK |
| SEQ ID NO: 30 | DNA Heavy Chain | GAGGTGCAGCTGGTGCAGTCAGGCGCCGAAGTGAAGAAG CCCGGCGAGTCACTGAAGATTAGCTGTAAAGTCTCAGGC TACACCTTCACCGATCACACTATTCACTGGATGAGACAG ATGCCCGGTAAAGGCCTGGAGTGGATGGGCTATATCTAC CCTAGATCAGGCTCTATTAACTATAACGAGAAGTTTAAG GGTCAGGTCACAATTAGCGCCGATAAGTCTAGCTCTACC GCCTACCTGCAGTGGTCTAGCCTGAAGGCTAGTGACACC GCTATGTACTACTGCGCTAGACGTAACCTGTTCCTGCCT ATGGAATACTGGGGTCAGGGCACCCTGGTCACCGTGTCT AGCGCTAGCACTAAGGGCCCAAGTGTGTTTCCCCTGGCC CCCAGCAGCAAGTCTACTTCCGGCGGAACTGCTGCCCTG GGTTGCCTGGTGAAGGACTACTTCCCCGAGCCCGTGACA GTGTCCTGGAACTCTGGGGCTCTGACTTCCGGCGTGCAC ACCTTCCCCGCCGTGCTGCAGAGCAGCGGCCTGTACAGC CTGAGCAGCGTGGTGACAGTGCCCTCCAGCTCTCTGGGA ACCCAGACCTATATCTGCAACGTGAACCACAAGCCCAGC AACACCAAGGTGGACAAGAGAGTGGAGCCCAAGAGCTGC GACAAGACCCACACCTGCCCCCCCTGCCCAGCTCCAGAA CTGCTGGGAGGGCCTTCCGTGTTCCTGTTCCCCCCCAAG CCCAAGGACACCCTGATGATCAGCAGGACCCCCGAGGTG ACCTGCGTGGTGGTGGACGTGTCCCACGAGGACCCAGAG GTGAAGTTCAACTGGTACGTGGACGGCGTGGAGGTGCAC AACGCCAAGACCAAGCCCAGAGAGGAGCAGTACAACAGC |

TABLE 1-continued

Examples of anti-P-cadherin Antibodies of the Present Invention

| SEQ ID NO. | Description | Sequence |
|---|---|---|
| | | ACCTACAGGGTGGTGTCCGTGCTGACCGTGCTGCACCAG<br>GACTGGCTGAACGGCAAAGAATACAAGTGCAAAGTCTCC<br>AACAAGGCCCTGCCAGCCCCAATCGAAAAGACAATCAGC<br>AAGGCCAAGGGCCAGCCACGGGAGCCCCAGGTGTACACC<br>CTGCCCCCCAGCCGGGAGGAGATGACCAAGAACCAGGTG<br>TCCCTGACCTGTCTGGTGAAGGGCTTCTACCCCAGCGAT<br>ATCGCCGTGGAGTGGGAGAGCAACGGCCAGCCCGAGAAC<br>AACTACAAGACCACCCCCCCAGTGCTGGACAGCGACGGC<br>AGCTTCTTCCTGTACAGCAAGCTGACCGTGGACAAGTCC<br>AGGTGGCAGCAGGGCAACGTGTTCAGCTGCAGCGTGATG<br>CACGAGGCCCTGCACAACCACTACACCCAGAAGTCCCTG<br>AGCCTGAGCCCCGGCAAG |
| SEQ ID NO: 31 | LCDR1 (Kabat) | RSSQSLLSSGDQKNYLT |
| SEQ ID NO: 32 | LCDR2 (Kabat) | WASTRES |
| SEQ ID NO: 33 | LCDR3 (Kabat) | QNDYRYPLT |
| SEQ ID NO: 34 | LCDR1 (Chothia) | SQSLLSSGDQKNY |
| SEQ ID NO: 35 | LCDR2 (Chothia) | WAS |
| SEQ ID NO: 36 | LCDR3 (Chothia) | DYRYPL |
| SEQ ID NO: 37 | VL | DIVMTQTPLSLPVTPGEPASISCRSSQSLLSSGDQKNYL<br>TWYLQKPGQSPQLLIYWASTRESGVPDRFSGSGSGTDFT<br>LKISRVEAEDVGVYYCQNDYRYPLTFGQGTKLEIK |
| SEQ ID NO: 38 | DNA VL | GATATCGTGATGACTCAGACCCCCCTGAGCCTGCCCGTG<br>ACCCCTGGCGAGCCTGCCTCTATTAGCTGTAGATCTAGT<br>CAGTCACTGCTGTCTAGCGGCGATCAGAAGAACTACCTG<br>ACCTGGTATCTGCAGAAGCCCGGTCAGTCACCTCAGCTG<br>CTGATCTACTGGGCCTCTACTAGAGAATCAGGCGTGCCC<br>GATAGGTTTAGCGGTAGCGGTAGTGGCACCGACTTCACC<br>CTGAAGATCTCTAGGGTGGAAGCCGAGGACGTGGGCGTC<br>TACTACTGTCAGAACGACTATAGATACCCCCTGACCTTC<br>GGTCAGGGCACTAAGCTGGAGATTAAG |
| SEQ ID NO: 39 | Light Chain | DIVMTQTPLSLPVTPGEPASISCRSSQSLLSSGDQKNYL<br>TWYLQKPGQSPQLLIYWASTRESGVPDRFSGSGSGTDFT<br>LKISRVEAEDVGVYYCQNDYRYPLTFGQGTKLEIKRTVA<br>APSVFIFPPSDEQLKSGTASVVCLLNNFYPREAKVQWKV<br>DNALQSGNSQESVTEQDSKDSTYSLSSTLTLSKADYEKH<br>KVYACEVTHQGLSSPVTKSFNRGEC |
| SEQ ID NO 40: | DNA Light Chain | GATATCGTGATGACTCAGACCCCCCTGAGCCTGCCCGTG<br>ACCCCTGGCGAGCCTGCCTCTATTAGCTGTAGATCTAGT<br>CAGTCACTGCTGTCTAGCGGCGATCAGAAGAACTACCTG<br>ACCTGGTATCTGCAGAAGCCCGGTCAGTCACCTCAGCTG<br>CTGATCTACTGGGCCTCTACTAGAGAATCAGGCGTGCCC<br>GATAGGTTTAGCGGTAGCGGTAGTGGCACCGACTTCACC<br>CTGAAGATCTCTAGGGTGGAAGCCGAGGACGTGGGCGTC<br>TACTACTGTCAGAACGACTATAGATACCCCCTGACCTTC<br>GGTCAGGGCACTAAGCTGGAGATTAAGCGTACGGTGGCC<br>GCTCCCAGCGTGTTCATCTTCCCCCCCAGCGACGAGCAG<br>CTGAAGAGCGGCACCGCCAGCGTGGTGTGCCTGCTGAAC<br>AACTTCTACCCCGGGAGGCCAAGGTGCAGTGGAAGGTG<br>GACAACGCCCTGCAGAGCGGCAACAGCCAGGAGAGCGTC<br>ACCGAGCAGGACAGCAAGGACTCCACCTACAGCCTGAGC<br>AGCACCCTGACCCTGAGCAAGGCCGACTACGAGAAGCAT<br>AAGGTGTACGCCTGCGAGGTGACCCACCAGGGCCTGTCC<br>AGCCCCGTGACCAAGAGCTTCAACAGGGGCGAGTGC |

TABLE 1-continued

Examples of anti-P-cadherin Antibodies of the Present Invention

| SEQ ID NO. | Description | Sequence |
|---|---|---|
| | | NEG0013 |
| SEQ ID NO: 41 | HCDR1 (Kabat) | DHTIH |
| SEQ ID NO: 42 | HCDR2 (Kabat) | YIYPRSGSINYNEKFKG |
| SEQ ID NO: 43 | HCDR3 (Kabat) | RNLFLPMEY |
| SEQ ID NO: 44 | HCDR1 (Chothia) | GYTFTDH |
| SEQ ID NO: 45 | HCDR2 (Chothia) | YPRSGS |
| SEQ ID NO: 46 | HCDR3 (Chothia) | RNLFLPMEY |
| SEQ ID NO: 47 | VH | EVQLVQSGAEVKKPGESLKISCKVSGYTFTDHTIHWMRQ MPGKGLEWMGYIYPRSGSINYNEKFKGQVTISADKSSST AYLQWSSLKASDTAMYYCARRNLFLPMEYWGQGTLVTVS S |
| SEQ ID NO: 48 | DNA VH | GAGGTGCAGCTGGTGCAGTCAGGCGCCGAAGTGAAGAAG CCCGGCGAGTCACTGAAGATTAGCTGTAAAGTCTCAGGC TACACCTTCACCGATCACACTATTCACTGGATGAGACAG ATGCCCGGTAAAGGCCTGGAGTGGATGGGCTATATCTAC CCTAGATCAGGCTCTATTAACTATAACGAGAAGTTTAAG GGTCAGGTCACAATTAGCGCCGATAAGTCTAGCTCTACC GCCTACCTGCAGTGGTCTAGCCTGAAGGCTAGTGACACC GCTATGTACTACTGCGCTAGACGTAACCTGTTCCTGCCT ATGGAATACTGGGGTCAGGGCACCCTGGTCACCGTGTCT AGC |
| SEQ ID NO: 49 | Heavy Chain | EVQLVQSGAEVKKPGESLKISCKVSGYTFTDHTIHWMRQ MPGKGLEWMGYIYPRSGSINYNEKFKGQVTISADKSSST AYLQWSSLKASDTAMYYCARRNLFLPMEYWGQGTLVTVS SASTKGPSVFPLAPSSKSTSGGTAALGCLVKDYFPEPVT VSWNSGALTSGVHTFPAVLQSSGLYSLSSVVTVPSSSLG TQTYICNVNHKPSNTKVDKRVEPKSCDKTHTCPPCPAPE LLGGPSVFLFPPKPKDTLMISRTPEVTCVVVDVSHEDPE VKFNWYVDGVEVHNAKTKPREEQYNSTYRVVSVLTVLHQ DWLNGKEYKCKVSNKALPAPIEKTISKAKGQPREPQVYT LPPSREEMTKNQVSLTCLVKGFYPSDIAVEWESNGQPEN NYKTTPPVLDSDGSFFLYSKLTVDKSRWQQGNVFSCSVM HEALHNHYTQKSLSLSPGK |
| SEQ ID NO: 50 | DNA Heavy Chain | GAGGTGCAGCTGGTGCAGTCAGGCGCCGAAGTGAAGAAG CCCGGCGAGTCACTGAAGATTAGCTGTAAAGTCTCAGGC TACACCTTCACCGATCACACTATTCACTGGATGAGACAG ATGCCCGGTAAAGGCCTGGAGTGGATGGGCTATATCTAC CCTAGATCAGGCTCTATTAACTATAACGAGAAGTTTAAG GGTCAGGTCACAATTAGCGCCGATAAGTCTAGCTCTACC GCCTACCTGCAGTGGTCTAGCCTGAAGGCTAGTGACACC GCTATGTACTACTGCGCTAGACGTAACCTGTTCCTGCCT ATGGAATACTGGGGTCAGGGCACCCTGGTCACCGTGTCT AGCGCTAGCACTAAGGGCCCAAGTGTGTTTCCCCTGGCC CCCAGCAGCAAGTCTACTTCCGGCGGAACTGCTGCCCTG GGTTGCCTGGTGAAGGACTACTTCCCCGAGCCCGTGACA GTGTCCTGGAACTCTGGGGCTCTGACTTCCGGCGTGCAC ACCTTCCCCGCCGTGCTGCAGAGCAGCGGCCTGTACAGC CTGAGCAGCGTGGTGACAGTGCCCTCCAGCTCTCTGGGA ACCCAGACCTATATCTGCAACGTGAACCACAAGCCCAGC AACACCAAGGTGGACAAGAGAGTGGAGCCCAAGAGCTGC GACAAGACCCACACCTGCCCCCCCTGCCCAGCTCCAGAA CTGCTGGGAGGGCCTTCCGTGTTCCTGTTCCCCCCCAAG CCCAAGGACACCCTGATGATCAGCAGGACCCCCGAGGTG ACCTGCGTGGTGGTGGACGTGTCCCACGAGGACCCAGAG GTGAAGTTCAACTGGTACGTGGACGGCGTGGAGGTGCAC AACGCCAAGACCAAGCCCAGAGAGGAGCAGTACAACAGC ACCTACAGGGTGGTGTCCGTGCTGACCGTGCTGCACCAG GACTGGCTGAACGGCAAGGAATACAAGTGCAAAGTCTCC AACAAGGCCCTGCCAGCCCCAATCGAAAAGACAATCAGC AAGGCCAAGGGCCAGCCACGGGAGCCCCAGGTGTACACC |

TABLE 1-continued

Examples of anti-P-cadherin Antibodies of the Present Invention

| SEQ ID NO. | Description | Sequence |
|---|---|---|
| | | CTGCCCCCAGCCGGGAGGAGATGACCAAGAACCAGGTG<br>TCCCTGACCTGTCTGGTGAAGGGCTTCTACCCCAGCGAT<br>ATCGCCGTGGAGTGGGAGAGCAACGGCCAGCCCGAGAAC<br>AACTACAAGACCACCCCCCCAGTGCTGGACAGCGACGGC<br>AGCTTCTTCCTGTACAGCAAGCTGACCGTGGACAAGTCC<br>AGGTGGCAGCAGGGCAACGTGTTCAGCTGCAGCGTGATG<br>CACGAGGCCCTGCACAACCACTACACCCAGAAGTCCCTG<br>AGCCTGAGCCCCGGCAAG |
| SEQ ID NO: 51 | LCDR1 (Kabat) | RSSQSLLSSGNQKNYLT |
| SEQ ID NO: 52 | LCDR2 (Kabat) | WASTRES |
| SEQ ID NO: 53 | LCDR3 (Kabat) | QNDYSYPLT |
| SEQ ID NO: 54 | LCDR1 (Chothia) | SQSLLSSGNQKNY |
| SEQ ID NO: 55 | LCDR2 (Chothia) | WAS |
| SEQ ID NO: 56 | LCDR3 (Chothia) | DYSYPL |
| SEQ ID NO: 57 | VL | DIVMTQTPLSLPVTPGEPASISCRSSQSLLSSGNQKNYL<br>TWYLQKPGQSPQLLIYWASTRESGVPDRFSGSGSGTDFT<br>LKISRVEAEDVGVYYCQNDYSYPLTFGQGTKLEIK |
| SEQ ID NO: 58 | DNAVL | GATATCGTGATGACTCAGACCCCCCTGAGCCTGCCCGTG<br>ACCCCTGGCGAGCCTGCCTCTATTAGCTGTAGATCTAGT<br>CAGTCACTGCTGTCTAGCGGTAATCAGAAGAACTACCTG<br>ACCTGGTATCTGCAGAAGCCCGGTCAGTCACCTCAGCTG<br>CTGATCTACTGGGCCTCTACTAGAGAATCAGGCGTGCCC<br>GATAGGTTTAGCGGTAGCGGTAGTGGCACCGACTTCACC<br>CTGAAGATCTCTAGGGTGGAAGCCGAGGACGTGGGCGTC<br>TACTACTGTCAGAACGACTATAGCTACCCCCTGACCTTC<br>GGTCAGGGCACTAAGCTGGAGATTAAG |
| SEQ ID NO: 59 | Light Chain | DIVMTQTPLSLPVTPGEPASISCRSSQSLLSSGNQKNYL<br>TWYLQKPGQSPQLLIYWASTRESGVPDRFSGSGSGTDFT<br>LKISRVEAEDVGVYYCQNDYSYPLTFGQGTKLEIKRTVA<br>APSVFIFPPSDEQLKSGTASVVCLLNNFYPREAKVQWKV<br>DNALQSGNSQESVTEQDSKDSTYSLSSTLTLSKADYEKH<br>KVYACEVTHQGLSSPVTKSFNRGEC |
| SEQ ID NO 60: | DNA Light Chain | GATATCGTGATGACTCAGACCCCCCTGAGCCTGCCCGTG<br>ACCCCTGGCGAGCCTGCCTCTATTAGCTGTAGATCTAGT<br>CAGTCACTGCTGTCTAGCGGTAATCAGAAGAACTACCTG<br>ACCTGGTATCTGCAGAAGCCCGGTCAGTCACCTCAGCTG<br>CTGATCTACTGGGCCTCTACTAGAGAATCAGGCGTGCCC<br>GATAGGTTTAGCGGTAGCGGTAGTGGCACCGACTTCACC<br>CTGAAGATCTCTAGGGTGGAAGCCGAGGACGTGGGCGTC<br>TACTACTGTCAGAACGACTATAGCTACCCCCTGACCTTC<br>GGTCAGGGCACTAAGCTGGAGATTAAGCGTACGGTGGCC<br>GCTCCCAGCGTGTTCATCTTCCCCCCCAGCGACGAGCAG<br>CTGAAGAGCGGCACCGCCAGCGTGGTGTGCCTGCTGAAC<br>AACTTCTACCCCGGGAGGCCAAGGTGCAGTGGAAGGTG<br>GACAACGCCCTGCAGAGCGGCAACAGCCAGGAGAGCGTC<br>ACCGAGCAGGACAGCAAGGACTCCACCTACAGCCTGAGC<br>AGCACCCTGACCCTGAGCAAGGCCGACTACGAGAAGCAT<br>AAGGTGTACGCCTGCGAGGTGACCCACCAGGGCCTGTCC<br>AGCCCCGTGACCAAGAGCTTCAACAGGGGCGAGTGC |

NEG0016

| SEQ ID NO: 61 | HCDR1 (Kabat) | DHTLH |
| SEQ ID NO: 62 | HCDR2 (Kabat) | YIYPRSGSTKYNENFRG |
| SEQ ID NO: 63 | HCDR3 (Kabat) | RLLFLPLDY |

TABLE 1-continued

Examples of anti-P-cadherin Antibodies of the Present Invention

| SEQ ID NO. | Description | Sequence |
| --- | --- | --- |
| SEQ ID NO: 64 | HCDR1 (Chothia) | GYTFTDH |
| SEQ ID NO: 65 | HCDR2 (Chothia) | YPRSGS |
| SEQ ID NO: 66 | HCDR3 (Chothia) | RLLFLPLDY |
| SEQ ID NO: 67 | VH | QIQLVQSGAEVKKPGSSVKVSCKVSGYTFTDHTLHWMRQ APGQGLEWMGYIYPRSGSTKYNENFRGRVTITADTSSST AYMELSSLRSEDTAVYYCARRLLFLPLDYWGQGTLVTVS S |
| SEQ ID NO: 68 | DNA VH | CAGATTCAGCTGGTGCAGTCAGGCGCCGAAGTGAAGAAA CCCGGCTCTAGCGTGAAAGTCAGCTGTAAAGTCTCAGGC TACACCTTCACCGATCACACCCTGCACTGGATGAGACAG GCCCCAGGTCAGGGCCTGGAGTGGATGGGCTATATCTAC CCTAGATCAGGCTCTACTAAGTATAACGAGAACTTTAGG GGTAGAGTGACTATCACCGCCGACACTAGCTCTAGCACC GCCTATATGGAACTGTCTAGCCTGAGATCAGAGGACACC GCCGTCTACTACTGCGCTAGACGGCTGCTGTTCCTGCCC CTGGACTACTGGGGTCAGGGCACCCTGGTCACCGTGTCT AGC |
| SEQ ID NO: 69 | Heavy Chain | QIQLVQSGAEVKKPGSSVKVSCKVSGYTFTDHTLHWMRQ APGQGLEWMGYIYPRSGSTKYNENFRGRVTITADTSSST AYMELSSLRSEDTAVYYCARRLLFLPLDYWGQGTLVTVS SASTKGPSVFPLAPSSKSTSGGTAALGCLVKDYFPEPVT VSWNSGALTSGVHTFPAVLQSSGLYSLSSVVTVPSSSLG TQTYICNVNHKPSNTKVDKRVEPKSCDKTHTCPPCPAPE LLGGPSVFLFPPKPKDTLMISRTPEVTCVVVDVSHEDPE VKFNWYVDGVEVHNAKTKPREEQYNSTYRVVSVLTVLHQ DWLNGKEYKCKVSNKALPAPIEKTISKAKGQPREPQVYT LPPSREEMTKNQVSLTCLVKGFYPSDIAVEWESNGQPEN NYKTTPPVLDSDGSFFLYSKLTVDKSRWQQGNVFSCSVM HEALHNHYTQKSLSLSPGK |
| SEQ ID NO: 70 | DNA Heavy Chain | CAGATTCAGCTGGTGCAGTCAGGCGCCGAAGTGAAGAAA CCCGGCTCTAGCGTGAAAGTCAGCTGTAAAGTCTCAGGC TACACCTTCACCGATCACACCCTGCACTGGATGAGACAG GCCCCAGGTCAGGGCCTGGAGTGGATGGGCTATATCTAC CCTAGATCAGGCTCTACTAAGTATAACGAGAACTTTAGG GGTAGAGTGACTATCACCGCCGACACTAGCTCTAGCACC GCCTATATGGAACTGTCTAGCCTGAGATCAGAGGACACC GCCGTCTACTACTGCGCTAGACGGCTGCTGTTCCTGCCC CTGGACTACTGGGGTCAGGGCACCCTGGTCACCGTGTCT AGCGCTAGCACTAAGGGCCCAAGTGTGTTTCCCCTGGCC CCCAGCAGCAAGTCTACTTCCGGCGGAACTGCTGCCCTG GGTTGCCTGGTGAAGGACTACTTCCCCGAGCCCGTGACA GTGTCCTGGAACTCTGGGGCTCTGACTTCCGGCGTGCAC ACCTTCCCCGCCGTGCTGCAGAGCAGCGGCCTGTACAGC CTGAGCAGCGTGGTGACAGTGCCCTCCAGCTCTCTGGGA ACCCAGACCTATATCTGCAACGTGAACCACAAGCCCAGC AACACCAAGGTGGACAAGAGAGTGGAGCCCAAGAGCTGC GACAAGACCCACACCTGCCCCCCCTGCCCAGCTCCAGAA CTGCTGGGAGGGCCTTCCGTGTTCCTGTTCCCCCCCAAG CCCAAGGACACCCTGATGATCAGCAGGACCCCCGAGGTG ACCTGCGTGGTGGTGGACGTGTCCCACGAGGACCCAGAG GTGAAGTTCAACTGGTACGTGGACGGCGTGGAGGTGCAC AACGCCAAGACCAAGCCCAGAGAGGAGCAGTACAACAGC ACCTACAGGGTGGTGTCCGTGCTGACCGTGCTGCACCAG GACTGGCTGAACGGCAAAGAATACAAGTGCAAAGTCTCC AACAAGGCCCTGCCAGCCCCAATCGAAAAGACAATCAGC AAGGCCAAGGGCCAGCCACGGGAGCCCCAGGTGTACACC CTGCCCCCCAGCCGGGAGGAGATGACCAAGAACCAGGTG TCCCTGACCTGTCTGGTGAAGGGCTTCTACCCCAGCGAT ATCGCCGTGGAGTGGGAGAGCAACGGCCAGCCCGAGAAC AACTACAAGACCACCCCCCCAGTGCTGGACAGCGACGGC AGCTTCTTCCTGTACAGCAAGCTGACCGTGGACAAGTCC AGGTGGCAGCAGGGCAACGTGTTCAGCTGCAGCGTGATG CACGAGGCCCTGCACAACCACTACACCCAGAAGTCCCTG AGCCTGAGCCCCGGCAAG |
| SEQ ID NO: 71 | LCDR1 (Kabat) | RSSQSLLSSGNQKSYLT |

TABLE 1-continued

Examples of anti-P-cadherin Antibodies of the Present Invention

| SEQ ID NO. | Description | Sequence |
| --- | --- | --- |
| SEQ ID NO: 72 | LCDR2 (Kabat) | WASTRES |
| SEQ ID NO: 73 | LCDR3 (Kabat) | QNDYSYPFT |
| SEQ ID NO: 74 | LCDR1 (Chothia) | SQSLLSSGNQKSY |
| SEQ ID NO: 75 | LCDR2 (Chothia) | WAS |
| SEQ ID NO: 76 | LCDR3 (Chothia) | DYSYPF |
| SEQ ID NO: 77 | VL | EIVMTQSPATLSLSPGERATLSCRSSQSLLSSGNQKSYL TWYQQKPGQAPRLLIYWASTRESGIPARFSGSGSGTDFT LTISSLQPEDFAVYYCQNDYSYPFTFGQGTKLEIK |
| SEQ ID NO: 78 | DNA VL | GAGATCGTGATGACTCAGTCACCCGCTACCCTGAGCCTG AGCCCTGGCGAGAGAGCTACACTGAGCTGTAGATCTAGT CAGTCACTGCTGTCTAGCGGTAATCAGAAGTCCTACCTG ACCTGGTATCAGCAGAAGCCCGGTCAGGCCCCTAGACTG CTGATCTACTGGGCCTCTACTAGAGAGTCAGGGATCCCC GCTAGGTTTAGCGGTAGCGGTAGTGGCACCGACTTCACC CTGACTATCTCTAGCCTGCAGCCCGAGGACTTCGCCGTC TACTACTGTCAGAACGACTATAGCTACCCCTTCACCTTC GGTCAGGGCACTAAGCTGGAGATTAAG |
| SEQ ID NO: 79 | Light Chain | EIVMTQSPATLSLSPGERATLSCRSSQSLLSSGNQKSYL TWYQQKPGQAPRLLIYWASTRESGIPARFSGSGSGTDFT LTISSLQPEDFAVYYCQNDYSYPFTFGQGTKLEIKRTVA APSVFIFPPSDEQLKSGTASVVCLLNNFYPREAKVQWKV DNALQSGNSQESVTEQDSKDSTYSLSSTLTLSKADYEKH KVYACEVTHQGLSSPVTKSFNRGEC |
| SEQ ID NO 80: | DNA Light Chain | GAGATCGTGATGACTCAGTCACCCGCTACCCTGAGCCTG AGCCCTGGCGAGAGAGCTACACTGAGCTGTAGATCTAGT CAGTCACTGCTGTCTAGCGGTAATCAGAAGTCCTACCTG ACCTGGTATCAGCAGAAGCCCGGTCAGGCCCCTAGACTG CTGATCTACTGGGCCTCTACTAGAGAGTCAGGGATCCCC GCTAGGTTTAGCGGTAGCGGTAGTGGCACCGACTTCACC CTGACTATCTCTAGCCTGCAGCCCGAGGACTTCGCCGTC TACTACTGTCAGAACGACTATAGCTACCCCTTCACCTTC GGTCAGGGCACTAAGCTGGAGATTAAGCGTACGGTGGCC GCTCCCAGCGTGTTCATCTTCCCCCCCAGCGACGAGCAG CTGAAGAGCGGCACCGCCAGCGTGGTGTGCCTGCTGAAC AACTTCTACCCCCGGGAGGCCAAGGTGCAGTGGAAGGTG GACAACGCCCTGCAGAGCGGCAACAGCCAGGAGAGCGTC ACCGAGCAGGACAGCAAGGACTCCACCTACAGCCTGAGC AGCACCCTGACCCTGAGCAAGGCCGACTACGAGAAGCAT AAGGTGTACGCCTGCGAGGTGACCCACCAGGGCCTGTCC AGCCCCGTGACCAAGAGCTTCAACAGGGGCGAGTGC |
| NECX064 | | |
| SEQ ID NO: 81 | HCDR1 (Kabat) | DHTLH |
| SEQ ID NO: 82 | HCDR2 (Kabat) | YIYPRSGSTKYNENFRG |
| SEQ ID NO: 83 | HCDR3 (Kabat) | RLLFLPLDY |
| SEQ ID NO: 84 | HCDR1 (Chothia) | GYTFTDH |
| SEQ ID NO: 85 | HCDR2 (Chothia) | YPRSGS |
| SEQ ID NO: 86 | HCDR3 (Chothia) | RLLFLPLDY |

TABLE 1-continued

Examples of anti-P-cadherin Antibodies of the Present Invention

| SEQ ID NO. | Description | Sequence |
| --- | --- | --- |
| SEQ ID NO: 87 | VH | QIQLVQSGAEVKKPGSSVKVSCKVSGYTFTDHTLHWMRQ APGQGLEWMGYIYPRSGSTKYNENFRGRVTITADTSSST AYMELSSLRSEDTAVYYCVRRLLFLPLDYWGQGTLVTVS S |
| SEQ ID NO: 88 | DNA VH | CAGATTCAGCTGGTGCAGTCAGGCGCCGAAGTGAAGAAA CCCGGCTCTAGCGTGAAAGTCAGCTGTAAAGTCTCAGGC TACACCTTCACCGATCACACCCTGCACTGGATGAGACAG GCCCCAGGTCAGGGCCTGGAGTGGATGGGCTATATCTAC CCTAGATCAGGCTCTACTAAGTATAACGAGAACTTTAGG GGTAGAGTGACTATCACCGCCGACACTAGCTCTAGCACC GCCTATATGGAACTGTCTAGCCTGAGATCAGAGGACACC GCCGTCTACTACTGCGTCAGACGGCTGCTGTTCCTGCCC CTGGACTACTGGGGTCAGGGCACCCTGGTCACCGTGTCT AGC |
| SEQ ID NO: 89 | Heavy Chain | QIQLVQSGAEVKKPGSSVKVSCKVSGYTFTDHTLHWMRQ APGQGLEWMGYIYPRSGSTKYNENFRGRVTITADTSSST AYMELSSLRSEDTAVYYCVRRLLFLPLDYWGQGTLVTVS SASTKGPSVFPLAPSSKSTSGGTAALGCLVKDYFPEPVT VSWNSGALTSGVHTFPAVLQSSGLYSLSSVVTVPSSSLG TQTYICNVNHKPSNTKVDKRVEPKSCDKTHTCPPCPAPE LLGGPSVFLFPPKPKDTLMISRTPEVTCVVVDVSHEDPE VKFNWYVDGVEVHNAKTKPREEQYNSTYRVVSVLTVLHQ DWLNGKEYKCKVSNKALPAPIEKTISKAKGQPREPQVYT LPPSREEMTKNQVSLTCLVKGFYPSDIAVEWESNGQPEN NYKTTPPVLDSDGSFFLYSKLTVDKSRWQQGNVFSCSVM HEALHNHYTQKSLSLSPGK |
| SEQ ID NO: 90 | DNA Heavy Chain | CAGATTCAGCTGGTGCAGTCAGGCGCCGAAGTGAAGAAA CCCGGCTCTAGCGTGAAAGTCAGCTGTAAAGTCTCAGGC TACACCTTCACCGATCACACCCTGCACTGGATGAGACAG GCCCCAGGTCAGGGCCTGGAGTGGATGGGCTATATCTAC CCTAGATCAGGCTCTACTAAGTATAACGAGAACTTTAGG GGTAGAGTGACTATCACCGCCGACACTAGCTCTAGCACC GCCTATATGGAACTGTCTAGCCTGAGATCAGAGGACACC GCCGTCTACTACTGCGTCAGACGGCTGCTGTTCCTGCCC CTGGACTACTGGGGTCAGGGCACCCTGGTCACCGTGTCT AGCGCTAGCACTAAGGGCCCAAGTGTGTTTCCCCTGGCC CCCAGCAGCAAGTCTACTTCCGGCGGAACTGCTGCCCTG GGTTGCCTGGTGAAGGACTACTTCCCCGAGCCCGTGACA GTGTCCTGGAACTCTGGGGCTCTGACTTCCGGCGTGCAC ACCTTCCCCGCCGTGCTGCAGAGCAGCGGCCTGTACAGC CTGAGCAGCGTGGTGACAGTGCCCTCCAGCTCTCTGGGA ACCCAGACCTATATCTGCAACGTGAACCACAAGCCCAGC AACACCAAGGTGGACAAGAGAGTGGAGCCCAAGAGCTGC GACAAGACCCACACCTGCCCCCCCTGCCCAGCTCCAGAA CTGCTGGGAGGGCCTTCCGTGTTCCTGTTCCCCCCCAAG CCCAAGGACACCCTGATGATCAGCAGGACCCCCGAGGTG ACCTGCGTGGTGGTGGACGTGTCCCACGAGGACCCAGAG GTGAAGTTCAACTGGTACGTGGACGGCGTGGAGGTGCAC AACGCCAAGACCAAGCCCAGAGAGGAGCAGTACAACAGC ACCTACAGGGTGGTGTCCGTGCTGACCGTGCTGCACCAG GACTGGCTGAACGGCAAAGAATACAAGTGCAAAGTCTCC AACAAGGCCCTGCCAGCCCCAATCGAAAAGACAATCAGC AAGGCCAAGGGCCAGCCACGGGAGCCCCAGGTGTACACC CTGCCCCCAGCCGGGAGGAGATGACCAAGAACCAGGTG TCCCTGACCTGTCTGGTGAAGGGCTTCTACCCCAGCGAT ATCGCCGTGGAGTGGGAGAGCAACGGCCAGCCCGAGAAC AACTACAAGACCACCCCCCCAGTGCTGGACAGCGACGGC AGCTTCTTCCTGTACAGCAAGCTGACCGTGGACAAGTCC AGGTGGCAGCAGGGCAACGTGTTCAGCTGCAGCGTGATG CACGAGGCCCTGCACAACCACTACACCCAGAAGTCCCTG AGCCTGAGCCCCGGCAAG |
| SEQ ID NO: 91 | LCDR1 (Kabat) | RSSQSLLSSGNQKSYLT |
| SEQ ID NO: 92 | LCDR2 (Kabat) | WASTRES |
| SEQ ID NO: 93 | LCDR3 (Kabat) | QNDYSYPFT |
| SEQ ID NO: 94 | LCDR1 (Chothia) | SQSLLSSGNQKSY |

TABLE 1-continued

Examples of anti-P-cadherin Antibodies of the Present Invention

| SEQ ID NO. | Description | Sequence |
|---|---|---|
| SEQ ID NO: 95 | LCDR2 (Chothia) | WAS |
| SEQ ID NO: 96 | LCDR3 (Chothia) | DYSYPF |
| SEQ ID NO: 97 | VL | EIVMTQSPATLSLSPGERATLSCRSSQSLLSSGNQKSYL TWYQQKPGQAPRLLIYWASTRESGIPARFSGSGSGTDFT LTISSLQPEDFAVYYCQNDYSYPFTFGQGTKLEIK |
| SEQ ID NO: 98 | DNA VL | GAGATCGTGATGACTCAGTCACCCGCTACCCTGAGCCTG AGCCCTGGCGAGAGAGCTACACTGAGCTGTAGATCTAGT CAGTCACTGCTGTCTAGCGGTAATCAGAAGTCCTACCTG ACCTGGTATCAGCAGAAGCCCGGTCAGGCCCCTAGACTG CTGATCTACTGGGCCTCTACTAGAGAGTCAGGGATCCCC GCTAGGTTTAGCGGTAGCGGTAGTGGCACCGACTTCACC CTGACTATCTCTAGCCTGCAGCCCGAGGACTTCGCCGTC TACTACTGTCAGAACGACTATAGCTACCCCTTCACCTTC GGTCAGGGCACTAAGCTGGAGATTAAG |
| SEQ ID NO: 99 | Light Chain | EIVMTQSPATLSLSPGERATLSCRSSQSLLSSGNQKSYL TWYQQKPGQAPRLLIYWASTRESGIPARFSGSGSGTDFT LTISSLQPEDFAVYYCQNDYSYPFTFGQGTKLEIKRTVA APSVFIFPPSDEQLKSGTASVVCLLNNFYPREAKVQWKV DNALQSGNSQESVTEQDSKDSTYSLSSTLTLSKADYEKH KVYACEVTHQGLSSPVTKSFNRGEC |
| SEQ ID NO: 100 | DNA Light Chain | GAGATCGTGATGACTCAGTCACCCGCTACCCTGAGCCTG AGCCCTGGCGAGAGAGCTACACTGAGCTGTAGATCTAGT CAGTCACTGCTGTCTAGCGGTAATCAGAAGTCCTACCTG ACCTGGTATCAGCAGAAGCCCGGTCAGGCCCCTAGACTG CTGATCTACTGGGCCTCTACTAGAGAGTCAGGGATCCCC GCTAGGTTTAGCGGTAGCGGTAGTGGCACCGACTTCACC CTGACTATCTCTAGCCTGCAGCCCGAGGACTTCGCCGTC TACTACTGTCAGAACGACTATAGCTACCCCTTCACCTTC GGTCAGGGCACTAAGCTGGAGATTAAGCGTACGGTGGCC GCTCCCAGCGTGTTCATCTTCCCCCCCAGCGACGAGCAG CTGAAGAGCGGCACCGCCAGCGTGGTGTGCCTGCTGAAC AACTTCTACCCCGGGAGGCCAAGGTGCAGTGGAAGGTG GACAACGCCCTGCAGAGCGGCAACAGCCAGGAGAGCGTC ACCGAGCAGGACAGCAAGGACTCCACCTACAGCCTGAGC AGCACCCTGACCCTGAGCAAGGCCGACTACGAGAAGCAT AAGGTGTACGCCTGCGAGGTGACCCACCAGGGCCTGTCC AGCCCCGTGACCAAGAGCTTCAACAGGGGCGAGTGC |

NEG0067

| SEQ ID NO: 101 | HCDR1 (Kabat) | DHTLH |
| SEQ ID NO: 102 | HCDR2 (Kabat) | YIYPRSGSTKYNENFKG |
| SEQ ID NO: 103 | HCDR3 (Kabat) | RLLFLPLDY |
| SEQ ID NO: 104 | HCDR1 (Chothia) | GYTFTDH |
| SEQ ID NO: 105 | HCDR2 (Chothia) | YPRSGS |
| SEQ ID NO: 106 | HCDR3 (Chothia) | RLLFLPLDY |
| SEQ ID NO: 107 | VH | QIQLVQSGAEVKKPGSSVKVSCKVSGYTFTDHTLHWMRQ APGQGLEWMGYIYPRSGSTKYNENFKGRVTITADTSSST AYMELSSLRSEDTAVYYCVRRLLFLPLDYWGQGTLVTVS S |
| SEQ ID NO: 108 | DNA VH | CAGATTCAGCTGGTGCAGTCAGGCGCCGAAGTGAAGAAA CCCGGCTCTAGCGTGAAAGTCAGCTGTAAAGTCTCAGGC TACACCTTCACCGATCACACCCTGCACTGGATGAGACAG GCCCCAGGTCAGGGCCTGGAGTGGATGGGCTATATCTAC CCTAGATCAGGCTCTACTAAGTATAACGAGAACTTTAAG GGTAGAGTGACTATCACCGCCGACACTAGCTCTAGCACC |

TABLE 1-continued

Examples of anti-P-cadherin Antibodies of the Present Invention

| SEQ ID NO. | Description | Sequence |
| --- | --- | --- |
| | | GCCTATATGGAACTGTCTAGCCTGAGATCAGAGGACACC<br>GCCGTCTACTACTGCGTCAGACGGCTGCTGTTCCTGCCC<br>CTGGACTACTGGGGTCAGGGCACCCTGGTCACCGTGTCT<br>AGC |
| SEQ ID NO: 109 | Heavy<br>Chain | QIQLVQSGAEVKKPGSSVKVSCKVSGYTFTDHTLHWMRQ<br>APGQGLEWMGYIYPRSGSTKYNENFKGRVTITADTSSST<br>AYMELSSLRSEDTAVYYCVRRLLFLPLDYWGQGTLVTVS<br>SASTKGPSVFPLAPSSKSTSGGTAALGCLVKDYFPEPVT<br>VSWNSGALTSGVHTFPAVLQSSGLYSLSSVVTVPSSSLG<br>TQTYICNVNHKPSNTKVDKRVEPKSCDKTHTCPPCPAPE<br>LLGGPSVFLFPPKPKDTLMISRTPEVTCVVVDVSHEDPE<br>VKFNWYVDGVEVHNAKTKPREEQYNSTYRVVSVLTVLHQ<br>DWLNGKEYKCKVSNKALPAPIEKTISKAKGQPREPQVYT<br>LPPSREEMTKNQVSLTCLVKGFYPSDIAVEWESNGQPEN<br>NYKTTPPVLDSDGSFFLYSKLTVDKSRWQQGNVFSCSVM<br>HEALHNHYTQKSLSLSPGK |
| SEQ ID NO: 110 | DNA<br>Heavy<br>Chain | CAGATTCAGCTGGTGCAGTCAGGCGCCGAAGTGAAGAAA<br>CCCGGCTCTAGCGTGAAAGTCAGCTGTAAAGTCTCAGGC<br>TACACCTTCACCGATCACACCCTGCACTGGATGAGACAG<br>GCCCCAGGTCAGGGCCTGGAGTGGATGGGCTATATCTAC<br>CCTAGATCAGGCTCTACTAAGTATAACGAGAACTTTAAG<br>GGTAGAGTGACTATCACCGCCGACACTAGCTCTAGCACC<br>GCCTATATGGAACTGTCTAGCCTGAGATCAGAGGACACC<br>GCCGTCTACTACTGCGTCAGACGGCTGCTGTTCCTGCCC<br>CTGGACTACTGGGGTCAGGGCACCCTGGTCACCGTGTCT<br>AGCGCTAGCACTAAGGGCCCAAGTGTGTTTCCCCTGGCC<br>CCCAGCAGCAAGTCTACTTCCGGCGGAACTGCTGCCCTG<br>GGTTGCCTGGTAAGGACTACTTCCCCGAGCCCGTGACA<br>GTGTCCTGGAACTCTGGGGCTCTGACTTCCGGCGTGCAC<br>ACCTTCCCCGCCGTGCTGCAGAGCAGCGGCCTGTACAGC<br>CTGAGCAGCGTGGTGACAGTGCCCTCCAGCTCTCTGGGA<br>ACCCAGACCTATATCTGCAACGTGAACCACAAGCCCAGC<br>AACACCAAGGTGGACAAGAGAGTGGAGCCCAAGAGCTGC<br>GACAAGACCCACACCTGCCCCCCCTGCCCAGCTCCAGAA<br>CTGCTGGGAGGGCCTTCCGTGTTCCTGTTCCCCCCCAAG<br>CCCAAGGACACCCTGATGATCAGCAGGACCCCCGAGGTG<br>ACCTGCGTGGTGGTGGACGTGTCCCACGAGGACCCAGAG<br>GTGAAGTTCAACTGGTACGTGGACGGCGTGGAGGTGCAC<br>AACGCCAAGACCAAGCCCAGAGAGGAGCAGTACAACAGC<br>ACCTACAGGGTGGTGTCCGTGCTGACCGTGCTGCACCAG<br>GACTGGCTGAACGGCAAGAATACAAGTGCAAAGTCTCC<br>AACAAGGCCCTGCCAGCCCCAATCGAAAAGACAATCAGC<br>AAGGCCAAGGGCCAGCCACGGGAGCCCCAGGTGTACACC<br>CTGCCCCCCAGCCGGGAGGAGATGACCAAGAACCAGGTG<br>TCCCTGACCTGTCTGGTGAAGGGCTTCTACCCCAGCGAT<br>ATCGCCGTGGAGTGGGAGAGCAACGGCCAGCCCGAGAAC<br>AACTACAAGACCACCCCCCCAGTGCTGGACAGCGACGGC<br>AGCTTCTTCCTGTACAGCAAGCTGACCGTGGACAAGTCC<br>AGGTGGCAGCAGGGCAACGTGTTCAGCTGCAGCGTGATG<br>CACGAGGCCCTGCACAACCACTACACCCAGAAGTCCCTG<br>AGCCTGAGCCCCGGCAAG |
| SEQ ID NO: 111 | LCDR1<br>(Kabat) | RSSQSLLSSGNQKSYLT |
| SEQ ID NO: 112 | LCDR2<br>(Kabat) | WASTRES |
| SEQ ID NO: 113 | LCDR3<br>(Kabat) | QNDYSYPFT |
| SEQ ID NO: 114 | LCDR1<br>(Chothia) | SQSLLSSGNQKSY |
| SEQ ID NO: 115 | LCDR2<br>(Chothia) | WAS |
| SEQ ID NO: 116 | LCDR3<br>(Chothia) | DYSYPF |
| SEQ ID NO: 117 | VL | EIVMTQSPATLSLSPGERATLSCRSSQSLLSSGNQKSYL<br>TWYQQKPGQAPRLLIYWASTRESGIPARFSGSGSGTDFT<br>LTISSLQPEDFAVYYCQNDYSYPFTFGQGTKLEIK |

TABLE 1-continued

Examples of anti-P-cadherin Antibodies of the Present Invention

| SEQ ID NO. | Description | Sequence |
|---|---|---|
| SEQ ID NO: 118 | DNA VL | GAGATCGTGATGACTCAGTCACCCGCTACCCTGAGCCTG<br>AGCCCTGGCGAGAGAGCTACACTGAGCTGTAGATCTAGT<br>CAGTCACTGCTGTCTAGCGGTAATCAGAAGTCCTACCTG<br>ACCTGGTATCAGCAGAAGCCCGGTCAGGCCCCTAGACTG<br>CTGATCTACTGGGCCTCTACTAGAGAGTCAGGGATCCCC<br>GCTAGGTTTAGCGGTAGCGGTAGTGGCACCGACTTCACC<br>CTGACTATCTCTAGCCTGCAGCCCGAGGACTTCGCCGTC<br>TACTACTGTCAGAACGACTATAGCTACCCCTTCACCTTC<br>GGTCAGGGCACTAAGCTGGAGATTAAG |
| SEQ ID NO: 119 | Light Chain | EIVMTQSPATLSLSPGERATLSCRSSQSLLSSGNQKSYL<br>TWYQQKPGQAPRLLIYWASTRESGIPARFSGSGSGTDFT<br>LTISSLQPEDFAVYYCQNDYSYPFTFGQGTKLEIKRTVA<br>APSVFIFPPSDEQLKSGTASVVCLLNNFYPREAKVQWKV<br>DNALQSGNSQESVTEQDSKDSTYSLSSTLTLSKADYEKH<br>KVYACEVTHQGLSSPVTKSFNRGEC |
| SEQ ID NO: 120 | DNA Light Chain | GAGATCGTGATGACTCAGTCACCCGCTACCCTGAGCCTG<br>AGCCCTGGCGAGAGAGCTACACTGAGCTGTAGATCTAGT<br>CAGTCACTGCTGTCTAGCGGTAATCAGAAGTCCTACCTG<br>ACCTGGTATCAGCAGAAGCCCGGTCAGGCCCCTAGACTG<br>CTGATCTACTGGGCCTCTACTAGAGAGTCAGGGATCCCC<br>GCTAGGTTTAGCGGTAGCGGTAGTGGCACCGACTTCACC<br>CTGACTATCTCTAGCCTGCAGCCCGAGGACTTCGCCGTC<br>TACTACTGTCAGAACGACTATAGCTACCCCTTCACCTTC<br>GGTCAGGGCACTAAGCTGGAGATTAAGCGTACGGTGGCC<br>GCTCCCAGCGTGTTCATCTTCCCCCCCAGCGACGAGCAG<br>CTGAAGAGCGGCACCGCCAGCGTGGTGTGCCTGCTGAAC<br>AACTTCTACCCCCGGGAGGCCAAGGTGCAGTGGAAGGTG<br>GACAACGCCCTGCAGAGCGGCAACAGCCAGGAGAGCGTC<br>ACCGAGCAGGACAGCAAGGACTCCACCTACAGCCTGAGC<br>AGCACCCTGACCCTGAGCAAGGCCGACTACGAGAAGCAT<br>AAGGTGTACGCCTGCGAGGTGACCCACCAGGGCCTGTCC<br>AGCCCCGTGACCAAGAGCTTCAACAGGGGCGAGTGC |

Other antibodies of the invention include those where the amino acids or nucleic acids encoding the amino acids have been mutated, yet have at least 60, 70, 80, 90 or 95 percent identity to the sequences described in Table 1. In some embodiments, 1, 2, 3, 4 or 5 amino acids have been mutated in the variable regions when compared with the variable regions depicted in the sequence described in Table 1, while retaining substantially the same therapeutic activity as the antibodies listed in Table 1.

Since each of these antibodies can bind to P-cadherin, the VH, VL, full length light chain, and full length heavy chain sequences (amino acid sequences and the nucleotide sequences encoding the amino acid sequences) can be "mixed and matched" to create other P-cadherin-binding antibodies of the invention. Such "mixed and matched" P-cadherin-binding antibodies can be tested using the binding assays known in the art (e.g., ELISAs, and other assays described in the Example section). When these chains are mixed and matched, a VH sequence from a particular VH/VL pairing should be replaced with a structurally similar VH sequence. Likewise a full length heavy chain sequence from a particular full length heavy chain/full length light chain pairing should be replaced with a structurally similar full length heavy chain sequence. Likewise, a VL sequence from a particular VH/VL pairing should be replaced with a structurally similar VL sequence. Likewise a full length light chain sequence from a particular full length heavy chain/full length light chain pairing should be replaced with a structurally similar full length light chain sequence. Accordingly, in one aspect, the invention provides an isolated monoclonal antibody or antigen binding region thereof having: a heavy chain variable region comprising an amino acid sequence selected from the group consisting of SEQ ID NOs: 7, 27, 47, 67, 87 and 107; and a light chain variable region comprising an amino acid sequence selected from the group consisting of SEQ ID NOs: 17, 37, 57, 77, 97, and 117; wherein the antibody specifically binds to P-cadherin.

In another aspect, the invention provides (i) an isolated monoclonal antibody having: a full length heavy chain comprising an amino acid sequence that has been optimized for expression in the cell of a mammalian expression system selected from the group consisting of SEQ ID NOs: 9, 29, 49, 69, 89, and 109; and a full length light chain comprising an amino acid sequence that has been optimized for expression in the cell of a mammalian selected from the group consisting of SEQ ID NOs: 19, 39, 59, 79, 99, and 119; or (ii) a functional protein comprising an antigen binding portion thereof.

In another aspect, the present invention provides P-cadherin-binding antibodies that comprise the heavy chain and light chain CDR1s, CDR2s and CDR3s as described in Table 1, or combinations thereof. The amino acid sequences of the VH CDR1s of the antibodies are shown in SEQ ID NOs: 1, 21, 41, 61, 81, and 101. The amino acid sequences of the VH CDR2s of the antibodies and are shown in SEQ ID NOs: 2, 22, 42, 62, 82, and 102. The amino acid sequences of the VH CDR3s of the antibodies are shown in SEQ ID NOs: 3, 23, 43, 63, 83, and 103. The amino acid sequences of the VL CDR1s of the antibodies are shown in SEQ ID NOs: 11, 31, 51, 71, 91, and 111. The amino acid sequences of the VL CDR2s of the antibodies are shown in SEQ ID NOs 12, 32, 52, 72, 92, and 112. The amino acid sequences of the VL CDR3s of the antibodies are shown in SEQ ID NOs: 13, 33, 53, 73, 93, and 113.

Given that each of these antibodies can bind to P-cadherin and that antigen-binding specificity is provided primarily by the CDR1, 2 and 3 regions, the VH CDR1, CDR2 and CDR3 sequences and VL CDR1, CDR2 and CDR3 sequences can be "mixed and matched" (i.e., CDRs from different antibodies can be mixed and matched. Such "mixed and matched" P-cadherin-binding antibodies can be tested using the binding assays known in the art and those described in the Examples (e.g., ELISAs). When VH CDR sequences are mixed and matched, the CDR1, CDR2 and/or CDR3 sequence from a particular VH sequence should be replaced with a structurally similar CDR sequence(s). Likewise, when VL CDR sequences are mixed and matched, the CDR1, CDR2 and/or CDR3 sequence from a particular VL sequence should be replaced with a structurally similar CDR sequence(s). It will be readily apparent to the ordinarily skilled artisan that novel VH and VL sequences can be created by substituting one or more VH and/or VL CDR region sequences with structurally similar sequences from the CDR sequences shown herein for monoclonal antibodies of the present invention.

Accordingly, the present invention provides an isolated monoclonal antibody or antigen binding region thereof comprising a heavy chain CDR1 comprising an amino acid sequence selected from the group consisting of SEQ ID NOs: 1, 21, 41, 61, 81, and 101; a heavy chain CDR2 comprising an amino acid sequence selected from the group consisting of SEQ ID NOs: 2, 22, 42, 62, 82, and 102; a heavy chain CDR3 comprising an amino acid sequence selected from the group consisting of SEQ ID NOs: 3, 23, 43, 63, 83, and 103; a light chain CDR1 comprising an amino acid sequence selected from the group consisting of SEQ ID NOs: 11, 31, 51, 71, 91, and 111; a light chain CDR2 comprising an amino acid sequence selected from the group consisting of SEQ ID NOs: 12, 32, 52, 72, 92, and 112; and a light chain CDR3 comprising an amino acid sequence selected from the group consisting of SEQ ID NOs: 13, 33, 53, 73, 93, and 113; wherein the antibody specifically binds P-cadherin.

In a specific embodiment, an antibody or antibody fragment (e.g., antigen binding fragments) that specifically binds to P-cadherin comprises a heavy chain CDR1 of SEQ ID NO:1, a heavy chain CDR2 of SEQ ID NO: 2; a heavy chain CDR3 of SEQ ID NO:3; a light chain CDR1 of SEQ ID NO:11; a light chain CDR2 of SEQ ID NO: 12; and a light chain CDR3 of SEQ ID NO: 13.

In another specific embodiment, an antibody or antibody fragment (e.g., antigen binding fragments) that specifically binds to P-cadherin comprising a heavy chain CDR1 of SEQ ID NO:21, a heavy chain CDR2 of SEQ ID NO: 22; a heavy chain CDR3 of SEQ ID NO:23; a light chain CDR1 of SEQ ID NO:31; a light chain CDR2 of SEQ ID NO: 32; and a light chain CDR3 of SEQ ID NO: 33.

In a yet another embodiment, an antibody or antibody fragment (e.g., antigen binding fragments) that specifically binds to P-cadherin comprising a heavy chain CDR1 of SEQ ID NO:41, a heavy chain CDR2 of SEQ ID NO: 42; a heavy chain CDR3 of SEQ ID NO:43; a light chain CDR1 of SEQ ID NO:51; a light chain CDR2 of SEQ ID NO: 52; and a light chain CDR3 of SEQ ID NO: 53.

In a further embodiment, an antibody or antibody fragment (e.g., antigen binding fragments) that specifically binds to P-cadherin comprising a heavy chain CDR1 of SEQ ID NO:61, a heavy chain CDR2 of SEQ ID NO: 62; a heavy chain CDR3 of SEQ ID NO:63; a light chain CDR1 of SEQ ID NO:71; a light chain CDR2 of SEQ ID NO: 72; and a light chain CDR3 of SEQ ID NO: 73.

In another specific embodiment, an antibody or antibody fragment (e.g., antigen binding fragments) that specifically binds to P-cadherin comprising a heavy chain CDR1 of SEQ ID NO:81, a heavy chain CDR2 of SEQ ID NO: 82; a heavy chain CDR3 of SEQ ID NO:83; a light chain CDR1 of SEQ ID NO:91; a light chain CDR2 of SEQ ID NO: 92; and a light chain CDR3 of SEQ ID NO: 93.

In a further specific embodiment, an antibody or antibody fragment (e.g., antigen binding fragments) that specifically binds to P-cadherin comprising a heavy chain CDR1 of SEQ ID NO:101, a heavy chain CDR2 of SEQ ID NO: 102; a heavy chain CDR3 of SEQ ID NO:103; a light chain CDR1 of SEQ ID NO:111; a light chain CDR2 of SEQ ID NO: 112; and a light chain CDR3 of SEQ ID NO: 113.

In certain embodiments, an antibody that specifically binds to P-cadherin is an antibody or antibody fragment (e.g., antigen binding fragment) that is described in Table 1.

1. Identification of Epitopes and Antibodies that Bind to the Same Epitope

In one embodiment, the present invention provides antibodies or antibody fragments (e.g., antigen binding fragments) that specifically bind to an epitope on human P-cadherin comprising one or more residues selected from the amino acids at positions 124, 125, 151, 153, 154, 155, 156, 159, 160, 161, 162, 163, 168, 170, 171, and 172 of SEQ ID NO:126. In some embodiments, the present invention provides antibodies or antibody fragments (e.g., antigen binding fragments) comprising a heavy chain that binds to human P-cadherin at one or more amino acid residues selected from positions 124, 151, 153-156, and 172 of SEQ ID NO:126. In other embodiments, the present invention provides antibodies or antibody fragments (e.g., antigen binding fragments) comprising a light chain that binds to human P-cadherin at one or more amino acid residues selected from positions 124, 125, 155, 156, 159-163, 168, 170, and 171 of SEQ ID NO:126. In some embodiments, the antibodies or antibody fragments comprise a heavy chain binding paratop for human P-cadherin protein comprising one or more amino acid residues selected from positions 52, 54, 56, 60, 65, 105, or 107 of SEQ ID NO:128. In other embodiments, the antibodies or antibody fragments comprise a light chain binding paratope for human P-cadherin protein comprising one or more amino acid residues selected from positions 1, 2, 27, 28, 30, 68, 92, 93, or 94 of SEQ ID NO:129

The present invention also provides antibodies and antibody fragments (e.g., antigen binding fragments) that specifically bind to the same epitope as the anti-P-cadherin antibodies described in Table 1, or cross compete with the antibodies described in Table 1. Additional antibodies and antibody fragments (e.g., antigen binding fragments) can therefore be identified based on their ability to cross-compete (e.g., to competitively inhibit the binding of, in a statistically significant manner) with other antibodies of the invention in P-cadherin binding assays, for example, via BIACORE or assays known to persons skilled in the art for measuring binding. The ability of a test antibody to inhibit the binding of antibodies and antibody fragments (e.g., antigen binding fragments) of the present invention to a P-cadherin (e.g., human P-cadherin) demonstrates that the test antibody can compete with that antibody or antibody fragment (e.g., antigen binding fragments) for binding to P-cadherin; such an antibody may, according to non-limiting theory, bind to the same or a related (e.g., a structurally similar or spatially proximal or overlapping) epitope on the P-cadherin protein as the antibody or antibody fragment (e.g., antigen binding fragments) with which it competes. In certain embodiments, the antibodies that bind to the same epitope on P-cadherin as the antibodies or antibody fragments (e.g., antigen binding fragments) described in Table 1 are human or humanized monoclonal antibodies. Such human or humanized monoclonal antibodies can be prepared and isolated as described herein.

2. Further Alteration of the Framework of Fc Region

The immunoconjugates of the invention may comprise modified antibodies or antigen binding fragments thereof that further comprise modifications to framework residues within VH and/or VL, e.g. to improve the properties of the antibody. In some embodiments, the framework modifications are made to decrease the immunogenicity of the antibody. For example, one approach is to "back-mutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived. To return the framework region sequences to their germline configuration, the somatic mutations can be "back-mutated" to the germline sequence by, for example, site-directed mutagenesis. Such "back-mutated" antibodies are also intended to be encompassed by the invention.

Another type of framework modification involves mutating one or more residues within the framework region, or even within one or more CDR regions, to remove T-cell epitopes to thereby reduce the potential immunogenicity of the antibody. This approach is also referred to as "deimmunization" and is described in further detail in U.S. Patent Publication No. 20030153043 by Carr et al.

In addition or in the alternative to modifications made within the framework or CDR regions, antibodies of the invention may be engineered to include modifications within the Fc region, typically to alter one or more functional properties of the antibody, such as serum half-life, complement fixation, Fc receptor binding, and/or antigen-dependent cellular cytotoxicity. Furthermore, an antibody of the invention may be chemically modified (e.g., one or more chemical moieties can be attached to the antibody) or be modified to alter its glycosylation, again to alter one or more functional properties of the antibody. Each of these embodiments is described in further detail below.

In one embodiment, the hinge region of CH1 is modified such that the number of cysteine residues in the hinge region is altered, e.g., increased or decreased. This approach is described further in U.S. Pat. No. 5,677,425 by Bodmer et al. The number of cysteine residues in the hinge region of CH1 is altered to, for example, facilitate assembly of the light and heavy chains or to increase or decrease the stability of the antibody.

In another embodiment, the Fc hinge region of an antibody is mutated to decrease the biological half-life of the antibody. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745 by Ward et al.

In yet other embodiments, the Fc region is altered by replacing at least one amino acid residue with a different amino acid residue to alter the effector functions of the antibody. For example, one or more amino acids can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in, e.g., U.S. Pat. Nos. 5,624,821 and 5,648,260, both by Winter et al.

In another embodiment, one or more amino acids selected from amino acid residues can be replaced with a different amino acid residue such that the antibody has altered C1q binding and/or reduced or abolished complement dependent cytotoxicity (CDC). This approach is described in, e.g., U.S. Pat. No. 6,194,551 by Idusogie et al.

In another embodiment, one or more amino acid residues are altered to thereby alter the ability of the antibody to fix complement. This approach is described in, e.g., the PCT Publication WO 94/29351 by Bodmer et al. In a specific embodiment, one or more amino acids of an antibody or antigen binding fragment thereof of the present invention are replaced by one or more allotypic amino acid residues, such as those shown in FIG. 4 for the IgG1 subclass and the kappa isotype. Allotypic amino acid residues also include, but are not limited to, the constant region of the heavy chain of the IgG1, IgG2, and IgG3 subclasses as well as the constant region of the light chain of the kappa isotype as described by Jefferis et al., MAbs. 1:332-338 (2009).

In yet another embodiment, the Fc region is modified to increase the ability of the antibody to mediate antibody dependent cellular cytotoxicity (ADCC) and/or to increase the affinity of the antibody for an Fcγ receptor by modifying one or more amino acids. This approach is described in, e.g., the PCT Publication WO 00/42072 by Presta. Moreover, the binding sites on human IgG1 for FcγRI, FcγRII, FcγRIII and FcRn have been mapped and variants with improved binding have been described (see Shields et al., J. Biol. Chem. 276:6591-6604, 2001).

In still another embodiment, the glycosylation of an antibody is modified. For example, an aglycosylated antibody can be made (i.e., the antibody lacks glycosylation). Glycosylation can be altered to, for example, increase the affinity of the antibody for "antigen." Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in, e.g., U.S. Pat. Nos. 5,714,350 and 6,350,861 by Co et al.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the invention to thereby produce an antibody with altered glycosylation. For example, EP 1,176,195 by Hang et al. describes a cell line with a functionally disrupted FUT8 gene, which encodes a fucosyl transferase, such that antibodies expressed in such a cell line exhibit hypofucosylation. PCT Publication WO 03/035835 by Presta describes a variant CHO cell line, Lec13 cells, with reduced ability to attach fucose to Asn(297)-linked carbohydrates, also resulting in hypofucosylation of antibodies expressed in that host cell (see also Shields et al., (2002) J. Biol. Chem. 277: 26733-26740). PCT Publication WO 99/54342 by Umana et al. describes cell lines engineered to express glycoprotein-modifying glycosyl transferases (e.g., beta(1,4)-N acetylglucosaminyltransferase III (GnTIII)) such that antibodies expressed in the engineered cell lines exhibit increased bisecting GlcNac structures which results in increased ADCC activity of the antibodies (see also Umana et al., Nat. Biotech. 17:176-180, 1999).

In another embodiment, the antibody is modified to increase its biological half-life. Various approaches are possible. For example, one or more of the following mutations can be introduced: T252L, T254S, T256F, as described in U.S. Pat. No. 6,277,375 to Ward. Alternatively, to increase the biological half-life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al.

3. Production of the P-Cadherin Antibodies

Anti-P-cadherin antibodies and antibody fragments (e.g., antigen binding fragments) thereof can be produced by any means known in the art, including but not limited to, recombinant expression, chemical synthesis, and enzymatic digestion of antibody tetramers, whereas full-length monoclonal antibodies can be obtained by, e.g., hybridoma or recombinant production. Recombinant expression can be from any appropriate host cells known in the art, for example, mammalian host cells, bacterial host cells, yeast host cells, insect host cells, etc.

The invention further provides polynucleotides encoding the antibodies described herein, e.g., polynucleotides encoding heavy or light chain variable regions or segments comprising the complementarity determining regions as described herein. In some embodiments, the polynucleotide encoding the heavy chain variable regions has at least 85%, 89%, 90%, 91%, 92%, 93%, 94%, 95%, 96%, 97%, 98%, 99%, or 100% nucleic acid sequence identity with a polynucleotide selected from the group consisting of SEQ ID NOs: 8, 28, 48, 68, 88, and 108. In some embodiments, the polynucleotide encoding the light chain variable regions has at least 85%, 89%, 90%, 91%, 92%, 93%, 94%, 95%, 96%, 97%, 98%, 99%, or 100% nucleic acid sequence identity with a polynucleotide selected from the group consisting of SEQ ID NOs:18, 38, 58, 78, 98, and 118.

In some embodiments, the polynucleotide encoding the heavy chain has at least 85%, 89%, 90%, 91%, 92%, 93%, 94%, 95%, 96%, 97%, 98%, 99%, or 100% nucleic acid sequence identity with a polynucleotide of SEQ ID NO: 10, 30, 50, 70, 90, or 110. In some embodiments, the polynucleotide encoding the light chain has at least 85%, 89%, 90%, 91%, 92%, 93%, 94%, 95%, 96%, 97%, 98%, 99%, or 100% nucleic acid sequence identity with a polynucleotide of SEQ ID NO: 20, 40, 60, 80, 100, or 120.

The polynucleotides of the invention can encode only the variable region sequence of an anti-P-cadherin antibody. They can also encode both a variable region and a constant region of the antibody. Some of the polynucleotide sequences encode a polypeptide that comprises variable regions of both the heavy chain and the light chain of one of the exemplified mouse anti-P-cadherin antibody. Some other polynucleotides encode two polypeptide segments that respectively are substantially identical to the variable regions of the heavy chain and the light chain of one of the mouse antibodies.

The polynucleotide sequences can be produced by de novo solid-phase DNA synthesis or by PCR mutagenesis of an existing sequence (e.g., sequences as described in the Examples below) encoding an anti-P-cadherin antibody or its binding fragment. Direct chemical synthesis of nucleic acids can be accomplished by methods known in the art, such as the phosphotriester method of Narang et al., Meth. Enzymol. 68:90, 1979; the phosphodiester method of Brown et al., Meth. Enzymol. 68:109, 1979; the diethylphosphoramidite method of Beaucage et al., Tetra. Lett., 22:1859, 1981; and the solid support method of U.S. Pat. No. 4,458, 066. Introducing mutations to a polynucleotide sequence by PCR can be performed as described in, e.g., PCR Technology: Principles and Applications for DNA Amplification, H. A. Erlich (Ed.), Freeman Press, NY, N.Y., 1992; PCR Protocols: A Guide to Methods and Applications, Innis et al. (Ed.), Academic Press, San Diego, Calif., 1990; Mattila et al., Nucleic Acids Res. 19:967, 1991; and Eckert et al., PCR Methods and Applications 1:17, 1991.

Also provided in the invention are expression vectors and host cells for producing the anti-P-cadherin antibodies described above. Various expression vectors can be employed to express the polynucleotides encoding the anti-P-cadherin antibody chains or binding fragments. Both viral-based and nonviral expression vectors can be used to produce the antibodies in a mammalian host cell. Nonviral vectors and systems include plasmids, episomal vectors, typically with an expression cassette for expressing a protein or RNA, and human artificial chromosomes (see, e.g., Harrington et al., Nat Genet 15:345, 1997). For example, nonviral vectors useful for expression of the anti-P-cadherin polynucleotides and polypeptides in mammalian (e.g., human) cells include pThioHis A, B & C, pcDNA™3.1/His, pEBVHis A, B & C (Invitrogen, San Diego, Calif.), MPSV vectors, and numerous other vectors known in the art for expressing other proteins. Useful viral vectors include vectors based on retroviruses, adenoviruses, adenoassociated viruses, herpes viruses, vectors based on SV40, papilloma virus, HBP Epstein Barr virus, vaccinia virus vectors and Semliki Forest virus (SFV). See, Brent et al., supra; Smith, Annu. Rev. Microbiol. 49:807, 1995; and Rosenfeld et al., Cell 68:143, 1992.

The choice of expression vector depends on the intended host cells in which the vector is to be expressed. Typically, the expression vectors contain a promoter and other regulatory sequences (e.g., enhancers) that are operably linked to the polynucleotides encoding an anti-P-cadherin antibody chain or fragment. In some embodiments, an inducible promoter is employed to prevent expression of inserted sequences except under inducing conditions. Inducible promoters include, e.g., arabinose, lacZ, metallothionein promoter or a heat shock promoter. Cultures of transformed organisms can be expanded under noninducing conditions without biasing the population for coding sequences whose expression products are better tolerated by the host cells. In addition to promoters, other regulatory elements may also be required or desired for efficient expression of an anti-P-cadherin antibody chain or fragment. These elements typically include an ATG initiation codon and adjacent ribosome binding site or other sequences. In addition, the efficiency of expression may be enhanced by the inclusion of enhancers appropriate to the cell system in use (see, e.g., Scharf et al., Results Probl. Cell Differ. 20:125, 1994; and Bittner et al., Meth. Enzymol., 153:516, 1987). For example, the SV40 enhancer or CMV enhancer may be used to increase expression in mammalian host cells.

The expression vectors may also provide a secretion signal sequence position to form a fusion protein with polypeptides encoded by inserted anti-P-cadherin antibody sequences. More often, the inserted anti-P-cadherin antibody sequences are linked to a signal sequences before inclusion in the vector. Vectors to be used to receive sequences encoding anti-P-cadherin antibody light and heavy chain variable domains sometimes also encode constant regions or parts thereof. Such vectors allow expression of the variable regions as fusion proteins with the constant regions thereby leading to production of intact antibodies or fragments thereof. Typically, such constant regions are human.

The host cells for harboring and expressing the anti-P-cadherin antibody chains can be either prokaryotic or eukaryotic. E. coli is one prokaryotic host useful for cloning and expressing the polynucleotides of the present invention. Other microbial hosts suitable for use include bacilli, such as Bacillus subtilis, and other enterobacteriaceae, such as Salmonella, Serratia, and various Pseudomonas species. In these prokaryotic hosts, one can also make expression vectors, which typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters typically control expression, optionally with an operator sequence, and have ribosome binding site sequences and the like, for initiating and completing transcription and translation. Other microbes, such as yeast, can also be employed to express anti-P-cadherin polypeptides of the invention. Insect cells in combination with baculovirus vectors can also be used.

In some preferred embodiments, mammalian host cells are used to express and produce the anti-P-cadherin polypeptides of the present invention. For example, they can be either a hybridoma cell line expressing endogenous immunoglobulin genes (e.g., the myeloma hybridoma clones as described in the Examples) or a mammalian cell line harboring an exogenous expression vector (e.g., the SP2/0 myeloma cells exemplified below). These include any normal mortal or normal or abnormal immortal animal or human cell. For example, a number of suitable host cell lines capable of secreting intact immunoglobulins have been developed, including the CHO cell lines, various Cos cell lines, HeLa cells, myeloma cell lines, transformed B-cells and hybridomas. The use of mammalian tissue cell culture to express polypeptides is discussed generally in, e.g., Winnacker, From Genes to Clones, VCH Publishers, N.Y., N.Y., 1987. Expression vectors for mammalian host cells can include expression control sequences, such as an origin of replication, a promoter, and an enhancer (see, e.g., Queen et al., Immunol. Rev. 89:49-68, 1986), and necessary processing information sites, such as ribosome binding sites, RNA splice sites, polyadenylation sites, and transcriptional terminator sequences. These expression vectors usually contain promoters derived from mammalian genes or from mammalian viruses. Suitable promoters may be constitutive, cell type-specific, stage-specific, and/or modulatable or regulatable. Useful promoters include, but are not limited to, the metallothionein promoter, the constitutive adenovirus major late promoter, the dexamethasone-inducible MMTV promoter, the SV40 promoter, the MRP polIII promoter, the constitutive MPSV promoter, the tetracycline-inducible CMV promoter (such as the human immediate-early CMV promoter), the constitutive CMV promoter, and promoter-enhancer combinations known in the art.

Methods for introducing expression vectors containing the polynucleotide sequences of interest vary depending on the type of cellular host. For example, calcium chloride transfection is commonly utilized for prokaryotic cells, whereas calcium phosphate treatment or electroporation may be used for other cellular hosts (see generally Sambrook et al., supra). Other methods include, e.g., electroporation, calcium phosphate treatment, liposome-mediated transformation, injection and microinjection, ballistic methods, virosomes, immunoliposomes, polycation:nucleic acid conjugates, naked DNA, artificial virions, fusion to the herpes virus structural protein VP22 (Elliot and O'Hare, Cell 88:223, 1997), agent-enhanced uptake of DNA, and ex vivo transduction. For long-term, high-yield production of recombinant proteins, stable expression will often be desired. For example, cell lines which stably express anti-P-cadherin antibody chains or binding fragments can be prepared using expression vectors of the invention which contain viral origins of replication or endogenous expression elements and a selectable marker gene. Following introduction of the vector, cells may be allowed to grow for 1-2 days in an enriched media before they are switched to selective media. The purpose of the selectable marker is to confer resistance to selection, and its presence allows growth of cells which successfully express the introduced sequences in selective media. Resistant, stably transfected cells can be proliferated using tissue culture techniques appropriate to the cell type.

Therapeutic and Diagnostic Uses

The antibodies, antibody fragments (e.g., antigen binding fragments), and antibody drug conjugates of the invention are useful in a variety of applications including, but not limited to, treatment of cancer, such as solid cancers. In certain embodiments, the antibodies, antibody fragments (e.g., antigen binding fragments), and antibody drug conjugates of the invention are useful for inhibiting tumor growth, inducing differentiation, reducing tumor volume, and/or reducing the tumorigenicity of a tumor. The methods of use can be in vitro, ex vivo, or in vivo methods.

In one aspect, the antibodies, antibody fragments (e.g., antigen binding fragments), and antibody drug conjugates of the invention are useful for detecting the presence of P-cadherin in a biological sample. The term "detecting" as used herein encompasses quantitative or qualitative detection. In certain embodiments, a biological sample comprises a cell or tissue. In certain embodiments, such tissues include normal and/or cancerous tissues that express P-cadherin at higher levels relative to other tissues.

In one aspect, the invention provides a method of detecting the presence of P-cadherin in a biological sample. In certain embodiments, the method comprises contacting the biological sample with an anti-P-cadherin antibody under conditions permissive for binding of the antibody to the antigen, and detecting whether a complex is formed between the antibody and the antigen.

In one aspect, the invention provides a method of diagnosing a disorder associated with increased expression of P-cadherin. In certain embodiments, the method comprises contacting a test cell with an anti-P-cadherin antibody; determining the level of expression (either quantitatively or qualitatively) of P-cadherin on the test cell by detecting binding of the anti-P-cadherin antibody to the P-cadherin antigen; and comparing the level of expression of P-cadherin in the test cell with the level of expression of P-cadherin on a control cell (e.g., a normal cell of the same tissue origin as the test cell or a cell that expresses P-cadherin at levels comparable to such a normal cell), wherein a higher level of expression of P-cadherin on the test cell as compared to the control cell indicates the presence of a disorder associated with increased expression of P-cadherin. In certain embodiments, the test cell is obtained from an individual suspected of having a disorder associated with increased expression of P-cadherin. In certain embodiments, the disorder is a cell proliferative disorder, such as a cancer or a tumor. In certain embodiments, the method comprises measuring the copy number of the P-cadherin gene in a test cell. In certain embodiments, the method comprises detecting a PAX-FOXO translocation mutation. Copy number of a gene and/or translocation mutations can be detected using standard methods known in the art, for example, PCR, RTPCR, etc.

In certain embodiments, a method of diagnosis or detection, such as those described above, comprises detecting binding of an anti-P-cadherin antibody to P-cadherin expressed on the surface of a cell or in a membrane preparation obtained from a cell expressing P-cadherin on its surface. An exemplary assay for detecting binding of an anti-P-cadherin antibody to P-cadherin expressed on the surface of a cell is a "FACS" assay.

Certain other methods can be used to detect binding of anti-P-cadherin antibodies to P-cadherin. Such methods include, but are not limited to, antigen-binding assays that are well known in the art, such as western blots, radioimmunoassays, ELISA (enzyme linked immunosorbent assay), "sandwich" immunoassays, immunoprecipitation assays, fluorescent immunoassays, protein A immunoassays, and immunohistochemistry (IHC).

In certain embodiments, anti-P-cadherin antibodies are labeled. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction.

In certain embodiments, anti-P-cadherin antibodies are immobilized on an insoluble matrix. Immobilization entails separating the anti-P-cadherin antibody from any P-cadherin protein that remains free in solution. This conventionally is accomplished by either insolubilizing the anti-P-cadherin antibody before the assay procedure, as by adsorption to a water-insoluble matrix or surface (Bennich et al, U.S. Pat. No. 3,720,760), or by covalent coupling (for example, using glutaraldehyde cross-linking), or by insolubilizing the anti-P-cadherin antibody after formation of a complex between the anti-P-cadherin antibody and P-cadherin protein, e.g., by immunoprecipitation.

Any of the above embodiments of diagnosis or detection can be carried out using an immunoconjugate of the invention in place of or in addition to an anti-P-cadherin antibody.

In one embodiment, the invention provides a method of treating, or preventing a disease comprising administering the antibodies, antibody fragments (e.g., antigen binding fragments), or antibody drug conjugates of the invention to a patient. The invention also provides use of the antibodies, antibody fragments (e.g. antigen binding fragments, or antibody drug conjugates of the invention to treat or prevent disease in a patient. In some embodiments, the invention provides antibodies, antibody fragments (e.g. antigen binding fragments, or antibody drug conjugates of the invention for use in the treatment or prevention of disease in a patient. In further embodiments, the invention provides use of the antibodies, antibody fragments (e.g. antigen binding fragments, or antibody drug conjugates of the invention in the manufacture of a medicament for treatment or prevention of disease in a patient.

In certain embodiments, the disease treated with the antibodies, antibody fragments (e.g., antigen binding fragments), and antibody drug conjugates of the invention is a cancer. In certain embodiments, the cancer is characterized by P-cadherin expressing cells to which the antibodies, antibody fragments (e.g., antigen binding fragments), and antibody drug conjugates of the invention binds. In certain embodiments, the cancer is characterized by an increase in expression of P-cadherin relative to a healthy patient. In some embodiments, the expression of P-cadherin may be measured by an increase in P-cadherin RNA. In other embodiments, the cancer is characterized by an increase in DNA copy number of P-cadherin. Other methods of measuring or determining levels of p-Cadherin expression are known to persons skilled in the art. Examples of diseases which can be treated and/or prevented include, but are not limited to, adrenocortical carcinoma, bladder cancer, bone cancer, breast cancer, central nervous system atypical teratoid/rhabdoid tumors, colon cancer, colorectal cancer, embryonal tumors, endometrial cancer, esophageal cancer, gastric cancer, head and neck cancer, hepatocellular cancer, Kaposi sarcoma, liver cancer, lung cancer, including small cell lung cancer and non-small cell lung cancer, ovarian cancer, rectal cancer, rhabdomyosarcomasmall intestine cancer, soft tissue sarcoma, squamous cell carcinoma, squamous neck cancer, stomach cancer, uterine cancer, vaginal cancer, and vulvar cancer.

The present invention provides for methods of treating cancer comprising administering a therapeutically effective amount of the antibodies, antibody fragments (e.g., antigen binding fragments), or antibody drug conjugates of the invention. In certain embodiments, the cancer is a solid cancer. In certain embodiments, the subject is a human. In certain embodiments, the cancer is a resistant cancer and/or relapsed cancer. In certain aspects, for example, the resistant cancer is resistant to tyrosine kinase inhibitors, including but not limited to, EGFR inhibitors, Her2 inhibitors, Her3 inhibitors, IGFR inhibitors and Met inhibitors. In certain embodiments the cancer is a Her2 resistant cancer.

In certain embodiments, the invention provides for methods of inhibiting tumor growth comprising administering to a subject a therapeutically effective amount of the antibodies, antibody fragments (e.g., antigen binding fragments), or antibody drug conjugates of the invention. In certain embodiments, the subject is a human. In certain embodiments, the subject has a tumor or has had a tumor removed. In certain embodiments, the tumor is resistant to other tyrosine kinase inhibitors, including but not limited to, EGFR inhibitors, Her2 inhibitors, Her3 inhibitors, IGFR inhibitors and Met inhibitors.

In certain embodiments, the tumor expresses the P-cadherin to which the anti-P-cadherin antibody binds. In certain embodiments, the tumor overexpresses the human P-cadherin. In certain embodiments, the tumor has an increase copy number of the P-cadherin gene.

The present invention also provides for methods of selecting patients for treatment with antibodies, antibody fragments (e.g., antigen binding fragments), or antibody drug conjugates of the invention comprising administering a therapeutically effective amount of said antibodies, antibody fragments (e.g., antigen binding fragments), or antibody drug conjugates. In certain aspects the method comprises selecting patients with a tyrosine kinase inhibitor resistant cancer. In certain aspects it is contemplated that the tyrosine kinase inhibitor resistant cancer is resistant to EGFR inhibitors, Her2 inhibitors, Her3 inhibitors, IGFR inhibitors and/or Met inhibitors. In certain aspects it is contemplated that the resistant cancer is a Her2 resistant cancer. More specifically it is contemplated that the Her2 resistant cancer does not respond to trastuzumab or trastuzumab emtansine. In certain aspects it is contemplated that the cancer is a de novo resistant cancer, and in still other aspects it is contemplated that the cancer is a relapsed cancer, for example a Her2 relapsed cancer. In certain aspects of the invention the methods comprise selecting a patient with a de novo resistant or relapsed cancer and measuring for expression of P-cadherin. It is contemplated that in certain aspects the relapsed cancer or tumor was not initially a P-cadherin expressing cancer or tumor, but becomes a P-cadherin positive cancer that is a tyrosine kinase resistant or relapsed cancer or tumor after treatment with tyrosine kinase inhibitors (for example, trastuzumab or trastuzumab emtansine).

For the treatment of the disease, the appropriate dosage of the antibodies, antibody fragments (e.g., antigen binding fragments), or antibody drug conjugates of the present invention depends on various factors, such as the type of disease to be treated, the severity and course of the disease, the responsiveness of the disease, previous therapy, patient's clinical history, and so on. The antibody or agent can be administered one time or over a series of treatments lasting from several days to several months, or until a cure is effected or a diminution of the disease state is achieved (e.g., reduction in tumor size). Optimal dosing schedules can be calculated from measurements of drug accumulation in the body of the patient and will vary depending on the relative potency of an individual antibody, antibody fragment (e.g., antigen binding fragment), or antibody drug conjugates. The treating physician can estimate repetition rates for dosing based on measured residence times and concentrations of the drug in bodily fluids or tissues.

Combination Therapy

In certain instances, an antibody, antibody fragment (e.g., antigen binding fragment), or antibody drug conjugate of the present invention is combined with other therapeutic agents, such as other anti-cancer agents, anti-allergic agents, anti-nausea agents (or anti-emetics), pain relievers, cytoprotective agents, and combinations thereof.

In one embodiment, an antibody, antibody fragment (e.g., antigen binding fragment), or antibody drug conjugate of the present invention is combined in a pharmaceutical combination formulation, or dosing regimen as combination therapy, with a second compound having anti-cancer properties. The second compound of the pharmaceutical combination formulation or dosing regimen can have complementary activities to the antibody or immunoconjugate of the combination such that they do not adversely affect each other. For example, an antibody, antibody fragment (e.g., antigen binding fragment), or antibody drug conjugate of the present invention can be administered in combination with, but not limited to, a chemotherapeutic agent, a tyrosine kinase inhibitor, a P-cadherin downstream signaling pathway inhibitor, IAP inhibitors, Bcl2 inhibitors, Mcl1 inhibitors, and other P-cadherin inhibitors.

The term "pharmaceutical combination" as used herein refers to either a fixed combination in one dosage unit form, or non-fixed combination or a kit of parts for the combined administration where two or more therapeutic agents may be administered independently at the same time or separately within time intervals, especially where these time intervals allow that the combination partners show a cooperative, e.g. synergistic effect.

The term "combination therapy" refers to the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients. Alternatively, such administration encompasses co-administration in multiple, or in separate containers (e.g., capsules, powders, and liquids) for each active ingredient. Powders and/or liquids may be reconstituted or diluted to a desired dose prior to administration. In addition, such administration also encompasses use of each type of therapeutic agent in a sequential manner, either at approximately the same time or at different times. In either case, the treatment regimen will provide beneficial effects of the drug combination in treating the conditions or disorders described herein.

The combination therapy can provide "synergy" and prove "synergistic", i.e., the effect achieved when the active ingredients used together is greater than the sum of the effects that results from using the compounds separately. A synergistic effect can be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect can be attained when the compounds are administered or delivered sequentially, e.g., by different injections in separate syringes. In general, during alternation therapy, an effective dosage of each active ingredient is administered sequentially, i.e., serially, whereas in combination therapy, effective dosages of two or more active ingredients are administered together.

General Chemotherapeutic agents considered for use in combination therapies include anastrozole (Arimidex®), bicalutamide (Casodex®), bleomycin sulfate (Blenoxane®), busulfan (Myleran®), busulfan injection (Busulfex®), capecitabine (Xeloda®), N4-pentoxycarbonyl-5-deoxy-5-fluorocytidine, carboplatin (Paraplatin®), carmustine (BiCNU®), chlorambucil (Leukeran®), cisplatin (Platinol®), cladribine (Leustatin®), cyclophosphamide (Cytoxan® or Neosar®), cytarabine, cytosine arabinoside (Cytosar-U®), cytarabine liposome injection (DepoCyt®), dacarbazine (DTIC-Dome®), dactinomycin (Actinomycin D, Cosmegan), daunorubicin hydrochloride (Cerubidine®), daunorubicin citrate liposome injection (DaunoXome®), dexamethasone, docetaxel (Taxotere®), doxorubicin hydrochloride (Adriamycin®, Rubex®), etoposide (Vepesid®) fludarabine phosphate (Fludara®), 5-fluorouracil (Adrucil®, Efudex®), flutamide (Eulexin®), tezacitibine, Gemcitabine (difluorodeoxycitidine), hydroxyurea (Hydrea®), Idarubicin (Idamycin®), ifosfamide (IFEX®), irinotecan (Camptosar®), L-asparaginase (ELSPAR®) leucovorin calcium, melphalan (Alkeran®), 6-mercaptopurine (Purinethol®), methotrexate (Folex®), mitoxantrone (Novantrone®), mylotarg, paclitaxel (Taxol®), phoenix (Yttrium90/MX-DTPA), pentostatin, polifeprosan 20 with carmustine implant (Gliadel®), tamoxifen citrate (Nolvadex®), teniposide (Vumon®), 6-thioguanine, thiotepa, tirapazamine (Tirazone®), topotecan hydrochloride for injection (Hycamptin®), vinblastine (Velban®), vincristine (Oncovin®), and vinorelbine (Navelbine®).

In one aspect, the present invention provides a method of treating cancer by administering to a subject in need thereof an antibody drug conjugate of the present invention in combination with one or more tyrosine kinase inhibitors, including but not limited to, EGFR inhibitors, Her2 inhibitors, Her3 inhibitors, IGFR inhibitors, and Met inhibitors.

For example, tyrosine kinase inhibitors include but are not limited to, Erlotinib hydrochloride (Tarceva®); Linifanib (N-[4-(3-amino-1H-indazol-4-yl)phenyl]-N'-(2-fluoro-5-methylphenyl)urea, also known as ABT 869, available from Genentech); Sunitinib malate (Sutent®); Bosutinib (4-[(2,4-dichloro-5-methoxyphenyl)amino]-6-methoxy-7-[3-(4-methylpiperazin-1-yl)propoxy]quinoline-3-carbonitrile, also known as SKI-606, and described in U.S. Pat. No. 6,780,996); Dasatinib (Sprycel®); Pazopanib (Votrient®); Sorafenib (Nexavar®); Zactima (ZD6474); and Imatinib or Imatinib mesylate (Gilvec® and Gleevec®).

Epidermal growth factor receptor (EGFR) inhibitors include but are not limited to, Erlotinib hydrochloride (Tarceva®), Gefitinib (Iressa®); N-[4-[(3-Chloro-4-fluorophenyl)amino]-7-[[(3"S")-tetrahydro-3-furanyl]oxy]-6-quinazolinyl]-4(dimethylamino)-2-butenamide, Tovok®); Vandetanib (Caprelsa®); Lapatinib (Tykerb®); (3R,4R)-4-Amino-1-((4-((3-methoxyphenyl)amino)pyrrolo[2,1-f][1,2,4]triazin-5-yl)methyl)piperidin-3-ol (BMS690514); Canertinib dihydrochloride (CI-1033); 6-[4-[(4-Ethyl-1-piperazinyl)methyl]phenyl]-N-[(1R)-1-phenylethyl]-7H-Pyrrolo[2,3-d]pyrimidin-4-amine (AEE788, CAS 497839-62-0); Mubritinib (TAK165); Pelitinib (EKB569); Afatinib (BIBW2992); Neratinib (HKI-272); N-[4-[[1-[(3-Fluorophenyl)methyl]-1H-indazol-5-yl]amino]-5-methylpyrrolo[2,1-f][1,2,4]triazin-6-yl]-carbamic acid, (3S)-3-morpholinylmethyl ester (BMS599626); N-(3,4-Dichloro-2-fluorophenyl)-6-methoxy-7-[[(3aα,5β,6aα)-octahydro-2-methylcyclopenta[c]pyrrol-5-yl]methoxy]-4-quinazolinamine (XL647, CAS 781613-23-8); and 4-[4-[[(1R)-1-Phenylethyl]amino]-7H-pyrrolo[2,3-d]pyrimidin-6-yl]-phenol (PKI166, CAS 187724-61-4).

EGFR antibodies include but are not limited to, Cetuximab (Erbitux®); Panitumumab (Vectibix®); Matuzumab (EMD-72000); Trastuzumab (Herceptin®); Nimotuzumab (hR3); Zalutumumab; TheraCIM h-R3; MDX0447 (CAS 339151-96-1); and ch806 (mAb-806, CAS 946414-09-1).

Human Epidermal Growth Factor Receptor 2 (Her2 receptor) (also known as Neu, ErbB-2, CD340, or p185) inhibitors include but are not limited to, Trastuzumab (Herceptin®); Pertuzumab (Omnitarg®); trastuzumab emtansine (Kadcyla®); Neratinib (HKI-272, (2E)-N-[4-[[3-chloro-4-[(pyridin-2-yl)methoxy]phenyl]amino]-3-cyano-7-ethoxyquinolin-6-yl]-4-(dimethylamino)but-2-enamide, and described PCT Publication No. WO 05/028443); Lapatinib or Lapatinib ditosylate (Tykerb®); (3R,4R)-4-amino-1-((4-((3-methoxyphenyl)amino)pyrrolo[2,1-f][1,2,4]triazin-5-yl) methyl)piperidin-3-ol (BMS690514); (2E)-N-[4-[(3-Chloro-4-fluorophenyl)amino]-7-[[(3S)-tetrahydro-3-furanyl]oxy]-6-quinazolinyl]-4-(dimethylamino)-2-butenamide (BIBW-2992, CAS 850140-72-6); N-[4-[[1-[(3-Fluorophenyl)methyl]-1H-indazol-5-yl]amino]-5-methylpyrrolo[2,1-f][1,2,4]triazin-6-yl]-carbamic acid, (3S)-3-morpholinylmethyl ester (BMS 599626, CAS 714971-09-2); Canertinib dihydrochloride (PD183805 or CI-1033); and N-(3,4-Dichloro-2-fluorophenyl)-6-methoxy-7-[[(3aα,5β,6aα)-octahydro-2-methylcyclopenta[c]pyrrol-5-yl]methoxy]-4-quinazolinamine (XL647, CAS 781613-23-8).

Her3 inhibitors include but are not limited to, LJM716, MM-121, AMG-888, RG7116, REGN-1400, AV-203, MP-RM-1, MM-111, and MEHD-7945A.

MET inhibitors include but are not limited to, Cabozantinib (XL184, CAS 849217-68-1); Foretinib (GSK1363089, formerly XL880, CAS 849217-64-7); Tivantinib (ARQ197, CAS 1000873-98-2); 1-(2-Hydroxy-2-methylpropyl)-N-(5-(7-methoxyquinolin-4-yloxy)pyridin-2-yl)-5-methyl-3-oxo-2-phenyl-2,3-dihydro-1H-pyrazole-4-carboxamide (AMG 458); Cryzotinib (Xalkori®, PF-02341066); (3Z)-5-(2,3-Dihydro-1H-indol-1-ylsulfonyl)-3-({3,5-dimethyl-4-[(4-methylpiperazin-1-yl)carbonyl]-1H-pyrrol-2-yl}methylene)-1,3-dihydro-2H-indol-2-one (SU11271); (3Z)—N-(3-Chlorophenyl)-3-({3,5-dimethyl-4-[(4-methylpiperazin-1-yl)carbonyl]-1H-pyrrol-2-yl}methylene)-N-methyl-2-oxoindoline-5-sulfonamide (SU11274); (3Z)—N-(3-Chlorophenyl)-3-{[3,5-dimethyl-4-(3-morpholin-4-ylpropyl)-1H-pyrrol-2-yl]methylene}-N-methyl-2-oxoindoline-5-sulfonamide (SU11606); 6-[Difluoro[6-(1-methyl-1H-pyrazol-4-yl)-1,2,4-triazolo[4,3-b]pyridazin-3-yl]methyl]-quinoline (JNJ38877605, CAS 943540-75-8); 2-[4-[1-(Quinolin-6-ylmethyl)-1H-[1,2,3]triazolo[4,5-b]pyrazin-6-yl]-1H-pyrazol-1-yl]ethanol (PF04217903, CAS 956905-27-4); N-((2R)-1,4-Dioxan-2-ylmethyl)-N-methyl-N'-[3-(1-methyl-1H-pyrazol-4-yl)-5-oxo-5H-benzo[4,5]cyclohepta[1,2-b]pyridin-7-yl]sulfamide (MK2461, CAS 917879-39-1); 6-[[6-(1-Methyl-1H-pyrazol-4-yl)-1,2,4-triazolo[4,3-b]pyridazin-3-yl]thio]-quinoline (SGX523, CAS 1022150-57-7); and (3Z)-5-[[(2,6-Dichlorophenyl)methyl]sulfonyl]-3-[[3,5-dimethyl-4-[[(2R)-2-(1-pyrrolidinylmethyl)-1-pyrrolidinyl]carbonyl]-1H-pyrrol-2-yl]methylene]-1,3-dihydro-2H-indol-2-one (PHA665752, CAS 477575-56-7).

IGF1R inhibitors include but are not limited to, BMS-754807, XL-228, OSI-906, GSK0904529A, A-928605, AXL1717, KW-2450, MK0646, AMG479, IMCA12, MEDI-573, and BI836845. See e.g., Yee, JNCI, 104; 975 (2012) for review.

In another aspect, the present invention provides a method of treating cancer by administering to a subject in need thereof an antibody drug conjugate of the present invention in combination with one or more P-cadherin downstream signaling pathway inhibitors, including but not limited to, MEK inhibitors, Braf inhibitors, PI3K/Akt inhibitors, SHP2 inhibitors, and also mTor.

For example, mitogen-activated protein kinase (MEK) inhibitors include but are not limited to, XL-518 (also known as GDC-0973, Cas No. 1029872-29-4, available from ACC Corp.); 2-[(2-Chloro-4-iodophenyl)amino]-N-(cyclopropylmethoxy)-3,4-difluoro-benzamide (also known as CI-1040 or PD184352 and described in PCT Publication No. WO2000035436); N-[(2R)-2,3-Dihydroxypropoxy]-3,4-difluoro-2-[(2-fluoro-4-iodophenyl)amino]-benzamide (also known as PD0325901 and described in PCT Publication No. WO2002006213); 2,3-Bis[amino[(2-aminophenyl) thio]methylene]-butanedinitrile (also known as U0126 and described in U.S. Pat. No. 2,779,780); N-[3,4-Difluoro-2-[(2-fluoro-4-iodophenyl)amino]-6-methoxyphenyl]-1-[(2R)-2,3-dihydroxypropyl]-cyclopropanesulfonamide (also known as RDEA119 or BAY869766 and described in PCT Publication No. WO2007014011); (3S,4R,5Z,8S,9S,11E)-14-(Ethylamino)-8,9,16-trihydroxy-3,4-dimethyl-3,4,9,19-tetrahydro-1H-2-benzoxacyclotetradecine-1,7(8H)-dione] (also known as E6201 and described in PCT Publication No. WO2003076424); 2'-Amino-3'-methoxyflavone (also known as PD98059 available from Biaffin GmbH & Co., KG, Germany); Vemurafenib (PLX-4032, CAS 918504-65-1); (R)-3-(2,3-Dihydroxypropyl)-6-fluoro-5-(2-fluoro-4-iodophenylamino)-8-methylpyrido[2,3-d]pyrimidine-4,7(3H,8H)-dione (TAK-733, CAS 1035555-63-5); Pimasertib (AS-703026, CAS 1204531-26-9); and Trametinib dimethyl sulfoxide (GSK-1120212, CAS 1204531-25-80).

Phosphoinositide 3-kinase (PI3K) inhibitors include but are not limited to, 4-[2-(1H-Indazol-4-yl)-6-[[4-(methylsulfonyl)piperazin-1-yl]methyl]thieno[3,2-d]pyrimidin-4-yl]morpholine (also known as GDC 0941 and described in PCT Publication Nos. WO 09/036082 and WO 09/055730); 2-Methyl-2-[4-[3-methyl-2-oxo-8-(quinolin-3-yl)-2,3-dihydroimidazo[4,5-c]quinolin-1-yl]phenyl]propionitrile (also known as BEZ 235 or NVP-BEZ 235, and described in PCT Publication No. WO 06/122806); 4-(trifluoromethyl)-5-(2,6-dimorpholinopyrimidin-4-yl)pyridin-2-amine (also known as BKM120 or NVP-BKM120, and described in PCT Publication No. WO2007/084786); Tozasertib (VX680 or MK-0457, CAS 639089-54-6); (5Z)-5-[[4-(4-Pyridinyl)-6-quinolinyl]methylene]-2,4-thiazolidinedione (GSK1059615, CAS 958852-01-2); (1E,4S,4aR,5R,6aS,9aR)-5-(Acetyloxy)-1-[(di-2-propenylamino)methylene]-4,4a,5,6,6a,8,9,9a-octahydro-11-hydroxy-4-(methoxymethyl)-4a,6a-dimethyl-cyclopenta[5,6]naphtho[1,2-c]pyran-2,7,10(1H)-trione (PX866, CAS 502632-66-8); and 8-Phenyl-2-(morpholin-4-yl)-chromen-4-one (LY294002, CAS 154447-36-6).

mTor include but are not limited to, Temsirolimus (Torisel®); Ridaforolimus (formally known as deferolimus, (1R,2R,4S)-4-[(2R)-2[(1R,9S,12S,15R,16E,18R,19R,21R,23S,24E,26E,28Z,30S,32S,35R)-1,18-dihydroxy-19,30-dimethoxy-15,17,21,23,29,35-hexamethyl-2,3,10,14,20-pentaoxo-11,36-dioxa-4-azatricyclo[30.3.1.0$^{4,9}$]hexatriaconta-16,24,26,28-tetraen-12-yl]propyl]-2-methoxycyclohexyl dimethylphosphinate, also known as AP23573 and MK8669, and described in PCT Publication No. WO 03/064383); Everolimus (Afinitor® or RAD001); Rapamycin (AY22989, Sirolimus®); Simapimod (CAS 164301-51-3); (5-{2,4-Bis[(3S)-3-methylmorpholin-4-yl]pyrido[2,3-d]pyrimidin-7-yl}-2-methoxyphenyl)methanol (AZD8055); 2-Amino-8-[trans-4-(2-hydroxyethoxy)cyclohexyl]-6-(6-methoxy-3-pyridinyl)-4-methyl-pyrido[2,3-d]pyrimidin-7(8H)-one (PF04691502, CAS 1013101-36-4); and N$^2$-[1,4-dioxo-4-[[4-(4-oxo-8-phenyl-4H-1-benzopyran-2-yl)morpholinium-4-yl]methoxy]butyl]-L-arginylglycyl-L-α-aspartylL-serine-(SEQ ID NO: 131), inner salt (SF1126, CAS 936487-67-1).

In yet another aspect, the present invention provides a method of treating cancer by administering to a subject in need thereof an antibody drug conjugate of the present invention in combination with one or more pro-apoptotics, including but not limited to, IAP inhibitors, Bcl2 inhibitors, MC11 inhibitors, Trail agents, Chk inhibitors.

For examples, IAP inhibitors include but are not limited to, LCL161, GDC-0917, AEG-35156, AT406, and TL32711. Other examples of IAP inhibitors include but are not limited to those disclosed in WO04/005284, WO 04/007529, WO05/097791, WO 05/069894, WO 05/069888, WO 05/094818, US2006/0014700, US2006/0025347, WO 06/069063, WO 06/010118, WO 06/017295, and WO08/134679, all of which are incorporated herein by reference.

BCL-2 inhibitors include but are not limited to, 4-[4-[[2-(4-Chlorophenyl)-5,5-dimethyl-1-cyclohexen-1-yl]methyl]-1-piperazinyl]-N-[[4-[[(1R)-3-(4-morpholinyl)-1-[(phenylthio)methyl]propyl]amino]-3-[(trifluoromethyl)sulfonyl]phenyl]sulfonyl]benzamide (also known as ABT-263 and described in PCT Publication No. WO 09/155386); Tetrocarcin A; Antimycin; Gossypol ((−)BL-193); Obatoclax; Ethyl-2-amino-6-cyclopentyl-4-(1-cyano-2-ethoxy-2-oxoethyl)-4Hchromone-3-carboxylate (HA14-1); Oblimersen (G3139, Genasense®); Bak BH3 peptide; (−)-Gossypol acetic acid (AT-101); 4-[4-[(4'-Chloro[1,1'-biphenyl]-2-yl)methyl]-1-piperazinyl]-N-[[4-[[(1R)-3-(dimethylamino)-1-[(phenylthio)methyl]propyl]amino]-3-nitrophenyl]sulfonyl]-benzamide (ABT-737, CAS 852808-04-9); and Navitoclax (ABT-263, CAS 923564-51-6).

Proapoptotic receptor agonists (PARAs) including DR4 (TRAILR1) and DR5 (TRAILR2), including but are not limited to, Dulanermin (AMG-951, RhApo2L/TRAIL); Mapatumumab (HRS-ETR1, CAS 658052-09-6); Lexatumumab (HGS-ETR2, CAS 845816-02-6); Apomab (Apomab®); Conatumumab (AMG655, CAS 896731-82-1); and Tigatuzumab (CS1008, CAS 946415-34-5, available from Daiichi Sankyo).

Checkpoint Kinase (CHK) inhibitors include but are not limited to, 7-Hydroxystaurosporine (UCN-01); 6-Bromo-3-(1-methyl-1H-pyrazol-4-yl)-5-(3R)-3-piperidinyl-pyrazolo[1,5-a]pyrimidin-7-amine (SCH900776, CAS 891494-63-6); 5-(3-Fluorophenyl)-3-ureidothiophene-2-carboxylic acid N—[(S)-piperidin-3-yl]amide (AZD7762, CAS 860352-01-8); 4-[((3S)-1-Azabicyclo[2.2.2]oct-3-yl)amino]-3-(1H-benzimidazol-2-yl)-6-chloroquinolin-2(1H)-one (CHIR 124, CAS 405168-58-3); 7-Aminodactinomycin (7-AAD), Isogranulatimide, debromohymenialdisine; N-[5-Bromo-4-methyl-2-[(2S)-2-morpholinylmethoxy]-phenyl]-N'-(5-methyl-2-pyrazinyl)urea (LY2603618, CAS 911222-45-2); Sulforaphane (CAS 4478-93-7, 4-Methylsulfinylbutyl isothiocyanate); 9,10,11,12-Tetrahydro-9,12-epoxy-1H-diindolo[1,2,3-fg:3',2',1'-kl]pyrrolo[3,4-i][1,6]benzodiazocine-1,3(2H)-dione (SB-218078, CAS 135897-06-2); and TAT-S216A (YGRKKRRQRRRLYRSPAMPENL (SEQ ID NO: 132)), and CBP501 ((d-Bpa)sws(d-Phe-F5)(d-Cha)rrrqrr).

In a further embodiment, the present invention provides a method of treating cancer by administering to a subject in need thereof an antibody drug conjugate of the present invention in combination with one or more immunomodulators (e.g., one or more of: an activator of a costimulatory molecule or an inhibitor of an immune checkpoint molecule).

In certain embodiments, the immunomodulator is an activator of a costimulatory molecule. In one embodiment, the agonist of the costimulatory molecule is chosen from an agonist (e.g., an agonistic antibody or antigen-binding fragment thereof, or a soluble fusion) of OX40, CD2, CD27, CDS, ICAM-1, LFA-1 (CD11a/CD18), ICOS (CD278), 4-1BB (CD137), GITR, CD30, CD40, BAFFR, HVEM, CD7, LIGHT, NKG2C, SLAMF7, NKp80, CD160, B7-H3 or CD83 ligand.

In certain embodiments, the immunomodulator is an inhibitor of an immune checkpoint molecule. In one embodiment, the immunomodulator is an inhibitor of PD-1, PD-L1, PD-L2, CTLA4, TIM3, LAG3, VISTA, BTLA, TIGIT, LAIR1, CD160, 2B4 and/or TGFR beta. In one embodiment, the inhibitor of an immune checkpoint molecule inhibits PD-1, PD-L1, LAG-3, TIM-3 or CTLA4, or any combination thereof. The term "inhibition" or "inhibitor" includes a reduction in a certain parameter, e.g., an activity, of a given molecule, e.g., an immune checkpoint inhibitor. For example, inhibition of an activity, e.g., a PD-1 or PD-L1 activity, of at least 5%, 10%, 20%, 30%, 40%, 50% or more is included by this term. Thus, inhibition need not be 100%.

Inhibition of an inhibitory molecule can be performed at the DNA, RNA or protein level. In some embodiments, an inhibitory nucleic acid (e.g., a dsRNA, siRNA or shRNA), can be used to inhibit expression of an inhibitory molecule. In other embodiments, the inhibitor of an inhibitory signal is a polypeptide e.g., a soluble ligand (e.g., PD-1-Ig or CTLA-4 Ig), or an antibody or antigen-binding fragment thereof, that binds to the inhibitory molecule; e.g., an antibody or fragment thereof (also referred to herein as "an antibody molecule") that binds to PD-1, PD-L1, PD-L2, CTLA4, TIM3, LAG3, VISTA, BTLA, TIGIT, LAIR1, CD160, 2B4 and/or TGFR beta, or a combination thereof.

In one embodiment, the antibody molecule is a full antibody or fragment thereof (e.g., a Fab, F(ab')$_2$, Fv, or a single chain Fv fragment (scFv)). In yet other embodiments, the antibody molecule has a heavy chain constant region (Fc) chosen from, e.g., the heavy chain constant regions of IgG1, IgG2, IgG3, IgG4, IgM, IgA1, IgA2, IgD, and IgE; particularly, chosen from, e.g., the heavy chain constant regions of IgG1, IgG2, IgG3, and IgG4, more particularly, the heavy chain constant region of IgG1 or IgG4 (e.g., human IgG1 or IgG4). In one embodiment, the heavy chain constant region is human IgG1 or human IgG4. In one embodiment, the constant region is altered, e.g., mutated, to modify the properties of the antibody molecule (e.g., to increase or decrease one or more of: Fc receptor binding, antibody glycosylation, the number of cysteine residues, effector cell function, or complement function).

In certain embodiments, the antibody molecule is in the form of a bispecific or multispecific antibody molecule. In one embodiment, the bispecific antibody molecule has a first binding specificity to PD-1 or PD-L1 and a second binding specifity, e.g., a second binding specificity to TIM-3, LAG-3, or PD-L2. In one embodiment, the bispecific antibody molecule binds to PD-1 or PD-L1 and TIM-3. In another embodiment, the bispecific antibody molecule binds to PD-1 or PD-L1 and LAG-3. In another embodiment, the bispecific antibody molecule binds to PD-1 and PD-L1. In yet another embodiment, the bispecific antibody molecule binds to PD-1 and PD-L2. In another embodiment, the bispecific antibody molecule binds to TIM-3 and LAG-3. Any combination of the aforesaid molecules can be made in a multispecific antibody molecule, e.g., a trispecific antibody that includes a first binding specificity to PD-1 or PD-1, and a second and third binding specifities to two or more of: TIM-3, LAG-3, or PD-L2.

In certain embodiments, the immunomodulator is an inhibitor of PD-1, e.g., human PD-1. In another embodiment, the immunomodulator is an inhibitor of PD-L1, e.g., human PD-L1. In one embodiment, the inhibitor of PD-1 or PD-L1 is an antibody molecule to PD-1 or PD-L1. The PD-1 or PD-L1 inhibitor can be administered alone, or in combination with other immunomodulators, e.g., in combination with an inhibitor of LAG-3, TIM-3 or CTLA4. In an exemplary embodiment, the inhibitor of PD-1 or PD-L1, e.g., the anti-PD-1 or PD-L1 antibody molecule, is administered in combination with a LAG-3 inhibitor, e.g., an anti-LAG-3 antibody molecule. In another embodiment, the inhibitor of PD-1 or PD-L1, e.g., the anti-PD-1 or PD-L1 antibody molecule, is administered in combination with a TIM-3 inhibitor, e.g., an anti-TIM-3 antibody molecule. In yet other embodiments, the inhibitor of PD-1 or PD-L1, e.g., the anti-PD-1 antibody molecule, is administered in combination with a LAG-3 inhibitor, e.g., an anti-LAG-3 antibody molecule, and a TIM-3 inhibitor, e.g., an anti-TIM-3 antibody molecule. Other combinations of immunomodulators with a PD-1 inhibitor (e.g., one or more of PD-L2, CTLA4, TIM3, LAG3, VISTA, BTLA, TIGIT, LAIR1, CD160, 2B4 and/or TGFR) are also within the present invention. Any of the antibody molecules known in the art or disclosed herein can be used in the aforesaid combinations of inhibitors of checkpoint molecule.

In one embodiment, the PD-1 inhibitor is an anti-PD-1 antibody chosen from Nivolumab, Pembrolizumab or Pidilizumab. In some embodiments, the anti-PD-1 antibody is Nivolumab. Alternative names for Nivolumab include MDX-1106, MDX-1106-04, ONO-4538, or BMS-936558. In some embodiments, the anti-PD-1 antibody is Nivolumab (CAS Registry Number: 946414-94-4). Nivolumab is a fully human IgG4 monoclonal antibody which specifically blocks PD1. Nivolumab (clone 5C4) and other human monoclonal antibodies that specifically bind to PD1 are disclosed in U.S. Pat. No. 8,008,449 and PCT Publication No. WO2006/121168.

In other embodiments, the anti-PD-1 antibody is Pembrolizumab. Pembrolizumab (Trade name KEYTRUDA formerly Lambrolizumab, also known as Merck 3745, MK-3475 or SCH-900475) is a humanized IgG4 monoclonal antibody that binds to PD1. Pembrolizumab is disclosed, e.g., in Hamid, O. et al. (2013) *New England Journal of Medicine* 369 (2): 134-44, PCT Publication No. WO2009/114335, and U.S. Pat. No. 8,354,509.

In some embodiments, the anti-PD-1 antibody is Pidilizumab. Pidilizumab (CT-011; Cure Tech) is a humanized IgG1k monoclonal antibody that binds to PD1. Pidilizumab and other humanized anti-PD-1 monoclonal antibodies are disclosed in PCT Publication No. WO2009/101611. Other anti-PD1 antibodies are disclosed in U.S. Pat. No. 8,609,089, US Publication No. 2010028330, and/or US Publication No. 20120114649. Other anti-PD1 antibodies include AMP 514 (Amplimmune).

In some embodiments, the PD-1 inhibitor is an immunoadhesin (e.g., an immunoadhesin comprising an extracellular or PD-1 binding portion of PD-L1 or PD-L2 fused to a constant region (e.g., an Fc region of an immunoglobulin sequence). In some embodiments, the PD-1 inhibitor is AMP-224.

In some embodiments, the PD-L1 inhibitor is anti-PD-L1 antibody. In some embodiments, the anti-PD-L1 inhibitor is chosen from YW243.55.570, MPDL3280A, MEDI-4736, or MDX-1105MSB-0010718C (also referred to as A09-246-2) disclosed in, e.g., WO 2013/0179174, and having a sequence disclosed herein (or a sequence substantially identical or similar thereto, e.g., a sequence at least 85%, 90%, 95% identical or higher to the sequence specified).

In one embodiment, the PD-L1 inhibitor is MDX-1105. MDX-1105, also known as BMS-936559, is an anti-PD-L1 antibody described in PCT Publication No. WO2007/005874.

In one embodiment, the PD-L1 inhibitor is YW243.55.570. The YW243.55.570 antibody is an anti-PD-L1 described in PCT Publication No. WO 2010/077634 (heavy and light chain variable region sequences shown in SEQ ID Nos. 20 and 21, respectively).

In one embodiment, the PD-L1 inhibitor is MDPL3280A (Genentech/Roche). MDPL3280A is a human Fc optimized IgG1 monoclonal antibody that binds to PD-L1. MDPL3280A and other human monoclonal antibodies to PD-L1 are disclosed in U.S. Pat. No. 7,943,743 and U.S Publication No.: 20120039906.

In other embodiments, the PD-L2 inhibitor is AMP-224. AMP-224 is a PD-L2 Fc fusion soluble receptor that blocks the interaction between PD1 and B7-H1 (B7-DCIg; Amplimmune; e.g., disclosed in PCT Publication Nos. WO2010/027827 and WO2011/066342).

In one embodiment, the LAG-3 inhibitor is an anti-LAG-3 antibody molecule. In one embodiment, the LAG-3 inhibitor is BMS-986016.

Pharmaceutical Compositions

To prepare pharmaceutical or sterile compositions including immunoconjugates, the immunoconjugates of the invention are mixed with a pharmaceutically acceptable carrier or excipient. The compositions can additionally contain one or more other therapeutic agents that are suitable for treating or preventing cancer (including, but not limited to bladder cancer, breast cancer, colon cancer, colorectal cancer, endometrial cancer, esophageal cancer, Barrett's esophageal cancer, gastric cancer, head and neck cancer, lung cancer, multiple myeloma, ovarian cancer, liver cancer, pancreatic cancer, acute myeloid leukemia, chronic myeloid leukemia, osteosarcoma, squamous cell carcinoma, peripheral nerve sheath tumors schwannoma, glioblastoma, clear cell sarcoma of soft tissue, malignant mesothelioma, neurofibromatosis, renal cancer, melanoma, prostate cancer, benign prostatic hyperplasia (BPH), gynacomastica, and rhabdomyosarcoma).

Formulations of therapeutic and diagnostic agents can be prepared by mixing with physiologically acceptable carriers, excipients, or stabilizers in the form of, e.g., lyophilized powders, slurries, aqueous solutions, lotions, or suspensions (see, e.g., Hardman et al., Goodman and Gilman's The Pharmacological Basis of Therapeutics, McGraw-Hill, New York, N.Y., 2001; Gennaro, Remington: The Science and Practice of Pharmacy, Lippincott, Williams, and Wilkins, New York, N.Y., 2000; Avis, et al. (eds.), Pharmaceutical Dosage Forms: Parenteral Medications, Marcel Dekker, N Y, 1993; Lieberman, et al. (eds.), Pharmaceutical Dosage Forms: tablets, Marcel Dekker, N Y, 1990; Lieberman, et al. (eds.) Pharmaceutical Dosage Forms: Disperse Systems, Marcel Dekker, N Y, 1990; Weiner and Kotkoskie, Excipient Toxicity and Safety, Marcel Dekker, Inc., New York, N.Y., 2000).

In one embodiment, the clinical service form (CSF) of the antibody drug conjugates of the present invention is a lyophilisate in vial containing the ADC, histidine, sucrose, and polysorbate 20. The lyophilisate can be reconstituted with water for injection, the solution comprises the ADC, histidine, sucrose, and polysorbate 20 at a pH of about 5.0. In one specific embodiment, the lyophilisate comprises 10 mg/ml of the ADC, 20 mM histidine, 240 mM sucrose, and 0.02% polysorbate 20, at pH 5.3.

Selecting an administration regimen for a therapeutic depends on several factors, including the serum or tissue turnover rate of the entity, the level of symptoms, the immunogenicity of the entity, and the accessibility of the target cells in the biological matrix. In certain embodiments, an administration regimen maximizes the amount of therapeutic delivered to the patient consistent with an acceptable level of side effects. Accordingly, the amount of biologic delivered depends in part on the particular entity and the severity of the condition being treated. Guidance in selecting appropriate doses of antibodies, cytokines, and small molecules are available (see, e.g., Wawrzynczak, Antibody Therapy, Bios Scientific Pub. Ltd, Oxfordshire, U K, 1996; Kresina (ed.), Monoclonal Antibodies, Cytokines and Arthritis, Marcel Dekker, New York, N.Y., 1991; Bach (ed.), Monoclonal Antibodies and Peptide Therapy in Autoimmune Diseases, Marcel Dekker, New York, N.Y., 1993; Baert et al., New Engl. J. Med. 348:601-608, 2003; Milgrom et al., New Engl. J. Med. 341:1966-1973, 1999; Slamon et al., New Engl. J. Med. 344:783-792, 2001; Beniaminovitz et al., New Engl. J. Med. 342:613-619, 2000; Ghosh et al., New Engl. J. Med. 348:24-32, 2003; Lipsky et al., New Engl. J. Med. 343:1594-1602, 2000).

Determination of the appropriate dose is made by the clinician, e.g., using parameters or factors known or suspected in the art to affect treatment or predicted to affect treatment. Generally, the dose begins with an amount somewhat less than the optimum dose and it is increased by small increments thereafter until the desired or optimum effect is achieved relative to any negative side effects. Important diagnostic measures include those of symptoms of, e.g., the inflammation or level of inflammatory cytokines produced.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors known in the medical arts.

Compositions comprising antibodies or fragments thereof of the invention can be provided by continuous infusion, or by doses at intervals of, e.g., one day, one week, or 1-7 times per week, once every other week, once every three weeks, once every four weeks, once every five weeks, once every six weeks, once every seven weeks, or once very eight weeks. Doses may be provided intravenously, subcutaneously, topically, orally, nasally, rectally, intramuscular, intracerebrally, or by inhalation. A specific dose protocol is one involving the maximal dose or dose frequency that avoids significant undesirable side effects.

For the immunoconjugates of the invention, the dosage administered to a patient may be 0.0001 mg/kg to 100 mg/kg of the patient's body weight. The dosage may be between 0.0001 mg/kg and 30 mg/kg, 0.0001 mg/kg and 20 mg/kg, 0.0001 mg/kg and 10 mg/kg, 0.0001 mg/kg and 5 mg/kg, 0.0001 and 2 mg/kg, 0.0001 and 1 mg/kg, 0.0001 mg/kg and 0.75 mg/kg, 0.0001 mg/kg and 0.5 mg/kg, 0.0001 mg/kg to 0.25 mg/kg, 0.0001 to 0.15 mg/kg, 0.0001 to 0.10 mg/kg, 0.001 to 0.5 mg/kg, 0.01 to 0.25 mg/kg or 0.01 to 0.10 mg/kg of the patient's body weight. The dosage of the antibodies or fragments thereof of the invention may be calculated using the patient's weight in kilograms (kg) multiplied by the dose to be administered in mg/kg.

Doses of the immunoconjugates the invention may be repeated and the administrations may be separated by less than 1 day, at least 1 day, 2 days, 3 days, 5 days, 10 days, 15 days, 30 days, 45 days, 2 months, 75 days, 3 months, 4 months, 5 months, or at least 6 months. In some embodiments, the immunoconjugates of the invention may be given twice weekly, once weekly, once every two weeks, once every three weeks, once every four weeks, or less frequently. In a specific embodiment, doses of the immunoconjugates of the invention are repeated every 2 weeks.

An effective amount for a particular patient may vary depending on factors such as the condition being treated, the overall health of the patient, the method, route and dose of administration and the severity of side effects (see, e.g., Maynard et al., A Handbook of SOPs for Good Clinical Practice, Interpharm Press, Boca Raton, Fla., 1996; Dent, Good Laboratory and Good Clinical Practice, Urch Publ., London, U K, 2001).

The route of administration may be by, e.g., topical or cutaneous application, injection or infusion by subcutaneous, intravenous, intraperitoneal, intracerebral, intramuscular, intraocular, intraarterial, intracerebrospinal, intralesional administration, or by sustained release systems or an implant (see, e.g., Sidman et al., Biopolymers 22:547-556, 1983; Langer et al., J. Biomed. Mater. Res. 15:167-277, 1981; Langer, Chem. Tech. 12:98-105, 1982; Epstein et al., Proc. Natl. Acad. Sci. USA 82:3688-3692, 1985; Hwang et al., Proc. Natl. Acad. Sci. USA 77:4030-4034, 1980; U.S. Pat. Nos. 6,350,466 and 6,316,024). Where necessary, the composition may also include a solubilizing agent or a local anesthetic such as lidocaine to ease pain at the site of the injection, or both. In addition, pulmonary administration can also be employed, e.g., by use of an inhaler or nebulizer, and formulation with an aerosolizing agent. See, e.g., U.S. Pat. Nos. 6,019,968, 5,985,320, 5,985,309, 5,934,272, 5,874, 064, 5,855,913, 5,290,540, and 4,880,078; and PCT Publication Nos. WO 92/19244, WO 97/32572, WO 97/44013, WO 98/31346, and WO 99/66903, each of which is incorporated herein by reference their entirety.

A composition of the present invention may also be administered via one or more routes of administration using one or more of a variety of methods known in the art. As will be appreciated by the skilled artisan, the route and/or mode of administration will vary depending upon the desired results. Selected routes of administration for the immunoconjugates of the invention include intravenous, intramuscular, intradermal, intraperitoneal, subcutaneous, spinal or other parenteral routes of administration, for example by injection or infusion. Parenteral administration may represent modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. Alternatively, a composition of the invention can be administered via a non-parenteral route, such as a topical, epidermal or mucosal route of administration, for example, intranasally, orally, vaginally, rectally, sublingually or topically. In one embodiment, the immunoconjugates of the invention is administered by infusion. In another embodiment, the immunoconjugates of the invention is administered subcutaneously.

If the immunoconjugates of the invention are administered in a controlled release or sustained release system, a pump may be used to achieve controlled or sustained release (see Langer, supra; Sefton, CRC Crit. Ref Biomed. Eng. 14:20, 1987; Buchwald et al., Surgery 88:507, 1980; Saudek et al., N. Engl. J. Med. 321:574, 1989). Polymeric materials can be used to achieve controlled or sustained release of the therapies of the invention (see e.g., Medical Applications of Controlled Release, Langer and Wise (eds.), CRC Pres., Boca Raton, Fla., 1974; Controlled Drug Bioavailability, Drug Product Design and Performance, Smolen and Ball (eds.), Wiley, New York, 1984; Ranger and Peppas, J. Macromol. Sci. Rev. Macromol. Chem. 23:61, 1983; see also Levy et al., Science 228:190, 1985; During et al., Ann. Neurol. 25:351, 1989; Howard et al., J. Neurosurg. 7 1:105, 1989; U.S. Pat. No. 5,679,377; U.S. Pat. No. 5,916,597; U.S. Pat. No. 5,912,015; U.S. Pat. No. 5,989,463; U.S. Pat. No. 5,128,326; PCT Publication No. WO 99/15154; and PCT Publication No. WO 99/20253. Examples of polymers used in sustained release formulations include, but are not limited to, poly(-hydroxy ethyl methacrylate), poly(methyl methacrylate), poly(acrylic acid), poly(ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and poly-orthoesters. In one embodiment, the polymer used in a sustained release formulation is inert, free of leachable impurities, stable on storage, sterile, and biodegradable. A controlled or sustained release system can be placed in proximity of the prophylactic or therapeutic target, thus requiring only a fraction of the systemic dose (see, e.g., Goodson, in Medical Applications of Controlled Release, supra, vol. 2, pp. 115-138, 1984).

Controlled release systems are discussed in the review by Langer, Science 249:1527-1533, 1990). Any technique known to one of skill in the art can be used to produce sustained release formulations comprising one or more immunoconjugates of the invention. See, e.g., U.S. Pat. No. 4,526,938, PCT publication WO 91/05548, PCT publication WO 96/20698, Ning et al., Radiotherapy & Oncology 39:179-189, 1996; Song et al., PDA Journal of Pharmaceutical Science & Technology 50:372-397, 1995; Cleek et al., Pro. Int'l. Symp. Control. Rel. Bioact. Mater. 24:853-854, 1997; and Lam et al., Proc. Int'l. Symp. Control Rel. Bioact. Mater. 24:759-760, 1997, each of which is incorporated herein by reference in their entirety.

If the immunoconjugates of the invention are administered topically, they can be formulated in the form of an ointment, cream, transdermal patch, lotion, gel, spray, aerosol, solution, emulsion, or other form well-known to one of skill in the art. See, e.g., Remington's Pharmaceutical Sciences and Introduction to Pharmaceutical Dosage Forms, 19th ed., Mack Pub. Co., Easton, Pa. (1995). For non-sprayable topical dosage forms, viscous to semi-solid or solid forms comprising a carrier or one or more excipients compatible with topical application and having a dynamic viscosity, in some instances, greater than water are typically employed. Suitable formulations include, without limitation, solutions, suspensions, emulsions, creams, ointments, powders, liniments, salves, and the like, which are, if desired, sterilized or mixed with auxiliary agents (e.g., preservatives, stabilizers, wetting agents, buffers, or salts) for influencing various properties, such as, for example, osmotic pressure. Other suitable topical dosage forms include sprayable aerosol preparations wherein the active ingredient, in some instances, in combination with a solid or liquid inert carrier, is packaged in a mixture with a pressurized volatile (e.g., a gaseous propellant, such as freon) or in a squeeze bottle. Moisturizers or humectants can also be added to pharmaceutical compositions and dosage forms if desired. Examples of such additional ingredients are well-known in the art.

If the compositions comprising the immunoconjugates are administered intranasally, it can be formulated in an aerosol form, spray, mist or in the form of drops. In particular, prophylactic or therapeutic agents for use according to the present invention can be conveniently delivered in the form of an aerosol spray presentation from pressurized packs or a nebuliser, with the use of a suitable propellant (e.g., dichlorodifluoromethane, trichlorofluoromethane, dichlorotetrafluoroethane, carbon dioxide or other suitable gas). In the case of a pressurized aerosol the dosage unit may be determined by providing a valve to deliver a metered amount. Capsules and cartridges (composed of, e.g., gelatin) for use in an inhaler or insufflator may be formulated containing a powder mix of the compound and a suitable powder base such as lactose or starch.

Methods for co-administration or treatment with a second therapeutic agent, e.g., a cytokine, steroid, chemotherapeutic agent, antibiotic, or radiation, are known in the art (see, e.g., Hardman et al., (eds.) (2001) Goodman and Gilman's The Pharmacological Basis of Therapeutics, 10.sup.th ed., McGraw-Hill, New York, N.Y.; Poole and Peterson (eds.) (2001) Pharmacotherapeutics for Advanced Practice: A Practical Approach, Lippincott, Williams & Wilkins, Phila., Pa.; Chabner and Longo (eds.) (2001) Cancer Chemotherapy and Biotherapy, Lippincott, Williams & Wilkins, Phila., Pa.). An effective amount of therapeutic may decrease the symptoms by at least 10%; by at least 20%; at least about 30%; at least 40%, or at least 50%.

Additional therapies (e.g., prophylactic or therapeutic agents), which can be administered in combination with the immunoconjugates of the invention may be administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours apart from the immunoconjugates of the invention. The two or more therapies may be administered within one same patient visit.

In certain embodiments, the immunoconjugates of the invention can be formulated to ensure proper distribution in vivo. For example, the blood-brain barrier (BBB) excludes many highly hydrophilic compounds. To ensure that the therapeutic compounds of the invention cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., Ranade, (1989) J. Clin. Pharmacol. 29:685). Exemplary targeting moieties include folate or biotin (see, e.g., U.S. Pat. No. 5,416,016 to Low et al.); mannosides (Umezawa et al., (1988) Biochem. Biophys. Res. Commun. 153:1038); antibodies (Bloeman et al., (1995) FEBS Lett. 357:140; Owais et al., (1995) Antimicrob. Agents Chemother. 39:180); surfactant protein A receptor (Briscoe et al., (1995) Am. J. Physiol. 1233:134); p 120 (Schreier et al, (1994) J. Biol. Chem. 269:9090); see also K. Keinanen; M. L. Laukkanen (1994) FEBS Lett. 346:123; J. J. Killion; I. J. Fidler (1994) Immunomethods 4:273.

The invention provides protocols for the administration of pharmaceutical composition comprising immunoconjugates of the invention alone or in combination with other therapies to a subject in need thereof. The therapies (e.g., prophylactic or therapeutic agents) of the combination therapies of the present invention can be administered concomitantly or sequentially to a subject. The therapy (e.g., prophylactic or therapeutic agents) of the combination therapies of the present invention can also be cyclically administered. Cycling therapy involves the administration of a first therapy (e.g., a first prophylactic or therapeutic agent) for a period of time, followed by the administration of a second therapy (e.g., a second prophylactic or therapeutic agent) for a period of time and repeating this sequential administration, i.e., the cycle, in order to reduce the development of resistance to one of the therapies (e.g., agents) to avoid or reduce the side effects of one of the therapies (e.g., agents), and/or to improve, the efficacy of the therapies.

The therapies (e.g., prophylactic or therapeutic agents) of the combination therapies of the invention can be administered to a subject concurrently.

The term "concurrently" is not limited to the administration of therapies (e.g., prophylactic or therapeutic agents) at exactly the same time, but rather it is meant that a pharmaceutical composition comprising antibodies or fragments thereof the invention are administered to a subject in a sequence and within a time interval such that the antibody drug conjugates of the invention can act together with the other therapy(ies) to provide an increased benefit than if they were administered otherwise. For example, each therapy may be administered to a subject at the same time or sequentially in any order at different points in time; however, if not administered at the same time, they should be administered sufficiently close in time so as to provide the desired therapeutic or prophylactic effect. Each therapy can be administered to a subject separately, in any appropriate form and by any suitable route. In various embodiments, the therapies (e.g., prophylactic or therapeutic agents) are administered to a subject less than 5 minutes apart, less than 15 minutes apart, less than 30 minutes apart, less than 1 hour apart, at about 1 hour apart, at about 1 hour to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, 24 hours apart, 48 hours apart, 72 hours apart, or 1 week apart. In other embodiments, two or more therapies (e.g., prophylactic or therapeutic agents) are administered to a within the same patient visit.

The prophylactic or therapeutic agents of the combination therapies can be administered to a subject in the same pharmaceutical composition. Alternatively, the prophylactic or therapeutic agents of the combination therapies can be administered concurrently to a subject in separate pharmaceutical compositions. The prophylactic or therapeutic agents may be administered to a subject by the same or different routes of administration. The prophylactic or therapeutic agents of the combination therapies can be administered to a subject in the same pharmaceutical composition. Alternatively, the prophylactic or therapeutic agents of the combination therapies can be administered concurrently to a subject in separate pharmaceutical compositions. The prophylactic or therapeutic agents may be administered to a subject by the same or different routes of administration.

EXAMPLES

Example 1: Generation of Antibodies

Generation of Expression Constructs for Human, Cynomolgus Monkey, Mouse and Rat P-Cadherin Proteins Human, mouse and rat P-cadherin extracellular domains (ECD) were gene synthesized based on amino acid sequences from the GenBank or Uniprot databases (see Table 2 below). Cynomolgus monkey P-cadherin ECD cDNA template were gene synthesized based on amino acid sequence information generated using mRNA isolated from various cyno tissues. All synthesized DNA fragments were cloned into appropriate expression vectors with C-terminal hexa-histidine tag (SEQ ID NO: 130) to allow for purification.

TABLE 2

Amino Acid Sequence Information for P-cadherin

| Name | Description | Accession Number or Sequence | SEQ ID NO |
|---|---|---|---|
| Human P-cadherin (CDH3) D1-5 | Human CDH3, residues 108-652-TAG | NM_001793.4, NP_001784 | 121 |
| Rat P-cadherin (CDH3) D1-5 | Rat CDH3, residues 100-647-TAG | NM_053938.1, NP_446390 | 122 |
| Mouse P-cadherin (CDH3) D1-5 | Mouse CDH3 isoform a, residues 100-647-TAG | NM_001037809.5, NP_001032898 | 123 |
| Cynomolgus Monkey P-cadherin var. 1 (CDH3) D1-5 | Cynomolgus monkey CDH3 variant1, residues 108-654-TAG | MKFLVNVALVFMVVYISYIYADHQTSLY KKAGFEGDRTDWVVAPISVPENGKGPFP QRLNQLKSNKDRDTKIFYSITGPGADSP PEGVFAVEKETGWLLLNKPLDREEIAKY ELFGHAVSENGASVEDPMNISIIVTDQN DHKPKFTQDTFRGSVLEGVLPGTSVMQV TATDEDDAIHTYNGVVAYSIHSQEPKDP HDLMFTIHRSTGTISVISSGLDREKVPE YTLTIQATDMDGDGSTTTAVAVVEILDA NDNAPVFDPQKYESHVPENAVGHEVQRL TVTDLDAPNSPAWRATYLIVGGDDGDHF TIATHPESNQGILTTRKGLDFEAKNQHT LYVEVTNEAPFVLKLPTSTATIVVHVED VNEAPVFVPPSKVVEVQEGIPTGEAVCV YTAKDPDKENQKISYRILRDPAGWLAMD PDSGQVTVAGTLDREDERFVRNNIYEVM VLAVDNGSPPTTGTGTLLLTLIDVNDHG PVPEPREITICNQSPESQVLNITDKDLS PHTSPFQAQLTDDSDIYWMAEVNEKDDT VVLSLKKFLKQDTYDVHLSLSDHGNKEQ LTVIRATVCDCHGHVEKCPDPWKGGGAH HHHHHGA | 124 |
| Cynomolgus Monkey P-cadherin var. 2 (CDH3) D1-5 | Cynomolgus monkey CDH3 variant2, residues 108-654-TAG | MKFLVNVALVFMVVYISYIYADHQTSLY KKAGFEGDRTDWVVAPISVPENGKGPFP QRLNQLKSNKDRDTKIFYSITGPGADSP PEGVFAVEKETGWLLLNKPLDREEIAKY ELFGHAVSENGASVEDPMNISIIVTDQN DHKPKFTQDTFRGSVLEGVLPGTSVMQV TATDEDDAIHTYNGVVAYSIHSQEPKDP HDLMFTIHRSTGTISVISSGLDREKVPE YTLTIQATDMDGDGSTTTAVAVVEILDA NDNAPVFDPQKYESHVPENAVGHEVQRL TVTDLDAPNSPAWRATYLIVGGDDGDHF TIATHPESNQGILTTRKGLDFEAKNQHT LYVEVTNEAPFVLKLPTSTATIVVHVED VNEAPVFVPPSKVVEVQEGIPTGEAVCV YTAKDPDKENQKISYRILRDPAGWLAMD PDSGQVTVAGTLDREDERFVRNNIYEVM VLAVDNGSPPTTGTGTLLLTLIDVNDHG PVPEPREITICNQSPESQVLNITDKDLS PHTSPFQAQLTDDSDIYWMAEVNEKDDT VVLSLKKFLKQGTYDVHLSLSDHGNKEQ LTVIRATVCDCHGHVEKCPDPWKGGGAH HHHHHGA | 125 |

P-Cadherin Baculovirus Generation

Baculovirus expressing recombinant P-cadherin ECD proteins were generated by either the co-transfection/plaque purification method (O'Reilly et. al., 1992) or Bac-To-Bac Expression System method (Invitrogen) following manufacturer's protocol. Virus generated from the transfected insect cells was amplified using a standard low MOI infection method.

Expression of Recombinant P-Cadherin Proteins

Suspension cultures of Tn5 cells growing in serum-free media (proprietary, in-house made recipe) were seeded at a density of 1.5e6 cells/ml and synchronously infected with recombinant P-cadherin baculovirus at either a MOI of 10 pfu/ml or a volume of 3%. The P-cadherin baculovirus culture preps were propagated in either 2 L glass Erlenmyer flasks or Wave bioreactor (GE Healthcare Life Sciences). The P-cadherin preps expressed in 2 L flasks were shaken at 120 rpm at 27° C. in serum-free media. The preps expressed in the Wave bioreactor were shaken at 25 rpm with an angle of 7.5° at 28° C. The supernatant harvested from either flasks or Wave bioreactor was harvested 2 days post-infection by centrifuging the culture at 4° C. for 10 minutes at 1800 rpm. The supernatant was then filtered with a 0.2 μM filter unit. For expression greater than 1 L, the cell culture supernatant is concentrated to 2-10x using AKTAcrossflow system (GE Healthcare Life Sciences) with KvickStart Ultrafilteration Flat sheet Cassette. The concentrated material was filtered with a 0.2 μM filter unit.

Purification of Human, Cynomolgus Monkey, Mouse and Rat pCAD ECD Proteins

Recombinant hexa-histidine (SEQ ID NO: 130) tagged pCAD extracellular domain proteins (e.g., human pCAD-6×His ("6×His" disclosed as SEQ ID NO: 130), cyno1 pCAD-6×His ("6×His" disclosed as SEQ ID NO: 130), cyno2 pCAD-6×His ("6×His" disclosed as SEQ ID NO: 130), mouse pCAD-6×His ("6×His" disclosed as SEQ ID NO: 130), rat pCAD-6×His ("6×His" disclosed as SEQ ID NO: 130)) were purified from the cell culture supernatant. The clarified supernatant was passed over an immobilized metal affinity chromatography (IMAC) on nickel Sepharose resin (GE Healthcare Life Sciences) column which had been equilibrated with 25 mM bisTrisPropane, 0.3 M NaCl, 1 mM CaCl2, pH 6.2. The supernatant is applied to an IMAC column at a flow rate of 5-8 mL/minute. After base-line washing with 25 mM bisTrisPropane, 0.3 M NaCl, 1 mM CaCl2, pH 6.2, switched to wash buffer (20 mM Tris, 0.3 M NaCl, 1 mM CaCl2, pH 7.5) for five column volumes. The pooled protein was concentrated if necessary using Amicon Ultra 15 mL centrifugal concentrators with 10 kD or 30 kD nominal molecular weight cut-offs. The pool protein was then purified by gel filtration utilizing a Superdex 200 26/60 column (GE Healthcare Life Sciences) pre-equilibrated in 20 mM Tris, 0.3 M NaCl, 1 mM CaCl2, pH 7.5. Pertinent fractions were pooled and analyzed by SDS-PAGE. Protein concentrations were determined by Bradford protein assay (Thermal Fisher).

Immunization of Mice and Production of Hybridomas

Purified human P-cadherin ECD was diluted 1:1 with Freund's Complete Adjuvant prior to immunization of Bcl-2 transgenic mice (C57BL/6-Tgn (bcl-2) 22 wehi strain). Mice were immunized using a procedure that calls for Repetitive Immunization at Multiple Sites (RIMMS) (McIntyre G D. Hybridoma 1997). Briefly, mice were injected with 1-3 µg of antigen at 8 specific sites proximal to peripheral lymph nodes (PLN). This procedure was repeated 8 times over a 12-day period. On Day 12, a test bleed was collected and the serum antibody titer was analyzed by ELISA. Pooled PLN were removed from high titer mice on Day 15. To harvest lymphocytes, PLN were washed twice with plain DMEM and then dissociated by passage through a 0.22 micron screen (Falcon #352350). The resulting lymphocytes were washed 2 additional times prior to fusion in Cytofusion media (BTXpress Cytofusion® Electroporation Medium cat#47001). F0 myeloma cells were mixed with lymphocytes at a ratio of 4 lymphocytes to 1 FO cell. The cell mixture was centrifuged, suspended in 7 ml of Cytofusion media and subsequently added to a 9 ml electrofusion chamber (Harvard Apparatus Coaxial Chamber 9ML Part #470020). Electrofusion was carried out per manufacturer's instructions using Cyto Pulse Sciences, Inc CEEF-50B Hybrimune/Hybridoma System. Fused cells were allowed to recover 5 min in chamber, diluted 1/10 in Fusion media without HAT (DMEM+20% FBS, Pen/Strep/Glu, 1×NEAA, 0.5×HFCS) and placed at 37° C. for one hour. 4×HAT media (DMEM+20% FBS, Pen/Strep/Glu, 1×NEAA, 4×HAT, 0.5× HFCS) was added to make a 1× solution and density was adjusted to $1.67 \times 10^4$ cells/ml. The cells were then plated in 384-well plates at 60 µL/well.

Screening of Hybridomas Secreting Antibodies to P-Cadherin

Ten days after fusion, hybridoma plates were screened for the presence of P-cadherin-specific antibodies. For the ELISA screen, Maxisorp 384-well plates (Nunc #464718) were coated with 50 µL of human P-cadherin (diluted to 15 ng/well in PBS) and incubated overnight at 4° C. The remaining protein was aspirated and wells were blocked with 1% BSA in PBS. After 30 min incubation at room temperature, the wells were washed four times with PBS+ 0.05% Tween (PBST). 15 µL of hybridoma supernatant was transferred to the ELISA plates. 15 µL of mouse serum, taken at the time of PLN removal, was diluted 1:1000 in PBS and added as a positive control. PBST. 50 µL of secondary antibody (goat anti mouse IgG-HRP (Jackson Immuno Research #115-035-071), diluted 1:5000 in PBS) was added to all wells on the ELISA plates. After incubation at room temperature for 1 h, the plates were washed eight times with PBST. 25 µL of TMB (KPL #50-76-05) was added and after 30 min incubation at room temperature; the plates were read at an absorbance of 605 nm. Cells from positive wells were expanded into 24-well plates in HT media (DMEM+20% FBS, Pen/Strep/Glu, 1×NEAA, 1×HT, 0.5×HFCS).

Antibody Purification

Supernatant containing antibodies were purified using protein G (Upstate #16-266 (Billerica, Mass.)). Prior to loading the supernatant, the resin was equilibrated with 10 column volumes of PBS. Following binding of the sample, the column was washed with 10 column volumes of PBS, and the antibody was then eluted with 5 column volumes of 0.1 M Glycine, pH 2.0. Column fractions were immediately neutralized with 1/10th volume of Tris HCl, pH 9.0. The OD280 of the fractions was measured, and positive fractions were pooled and dialyzed overnight against PBS, pH 7.2.

Humanization and Affinity Maturation of Anti-P-Cadherin Antibodies

VH and VL sequences of hybridoma derived anti-P-cadherin antibodies were humanized and affinity matured as follows.

Generation of Humanized Sequences

DNA sequences coding for humanized VL and VH domains were ordered at GeneArt (Life Technologies Inc. Regensburg, Germany) including codon optimization for *homo sapiens*. Sequences coding for VL and VH domains were subcloned by cut and paste from the GeneArt derived vectors into expression vectors suitable for secretion in mammalian cells. The heavy and light chains were cloned into individual expression vectors to allow co-transfection. Elements of the expression vector include a promoter (Cytomegalovirus (CMV) enhancer-promoter), a signal sequence to facilitate secretion, a polyadenylation signal and transcription terminator (Bovine Growth Hormone (BGH) gene), an element allowing episomal replication and replication in prokaryotes (e.g. SV40 origin and ColE1 or others known in the art) and elements to allow selection (ampicillin resistance gene and zeocin marker).

Expression and Purification of Humanized Antibodies

Human Embryonic Kidney cells constitutively expressing the SV40 large T antigen (HEK293-T ATCC11268) are one of the preferred host cell lines for transient expression of humanized and/or optimized IgG proteins. Transfection is performed using PEI (Polyethylenimine, MW 25.000 linear, Polysciences, USA Cat. No. 23966) as transfection reagent. The PEI stock solution is prepared by carefully dissolving 1 g of PEI in 900 ml cell culture grade water at room temperature (RT). To facilitate dissolution of PEI, the solution is acidified by addition of HCl to pH 3-5, followed by neutralization with NaOH to a final pH of 7.05. Finally, the volume is adjusted to 1 L and the solution is filtered through a 0.22 µm filter, aliquotted and frozen at −80° C. until further use. Once thawed, an aliquot can be re-frozen up to 3 times at −20° C. but should not be stored long term at −20° C.

HEK 293T cells are cultivated using serum-free culture medium for transfection and propagation of the cells, and ExCell VPRO serum-free culture medium (SAFC Biosciences, USA, Cat. No. 24561C) as production/feed medium. Cells prepared for transient transfections are cultivated in suspension culture. For small scale (<5 L) transfections, cells are grown in Corning shake flasks (Corning, Tewksbury, Mass.) on an orbital shaker (100-120 rpm) in a humidified incubator at 5% CO2 (seed flasks). Cells in the seed cultures should be maintained in the exponential growth phase (cell densities between $5\times10^5$ and $3\times10^6$/mL) and display a viability of >90% for transfection. Cell densities outside of this range will result in either a lag phase after dilution or reduced transfection efficiency. For small scale (<5 L) transfection an aliquot of cells is taken out of the seed cultures and adjusted to $1.4\times10^6$ cells/mL in 36% of the final volume with Novartis serum-free culture medium. The DNA solution (Solution 1: 0.5 mg of heavy chain and 0.5 mg of light chain expression plasmid for a 1 L transfection) is prepared by diluting the DNA to 1 mg/L (final volume) in 7% of the final culture volume followed by gentle mixing. To prevent bacterial contamination, this solution is filtered using a 0.22 µm filter (e.g. Millipore Stericup). Then 3 mg/L (final volume) of PEI solution is also diluted in 7% of final culture volume and mixed gently (Solution 2). Both solutions are incubated for 5-10 min at room temperature (RT). Thereafter solution 2 is added to solution 1 with gentle mixing and incubated for another 5-15 minutes at room temperature. The transfection mix is then added to the cells and the cultivation of cells is continued for 4 to 6 hours. Finally, the remaining 50% of total production volume are achieved by addition of ExCell® VPRO serum-free culture medium. The cell cultivation is continued for eleven days post transfection. The culture is harvested by centrifugation at 4500 rpm for 20 minutes at 4° C. (Heraeus®, Multifuge 3 S-R, Thermo Scientific, Rockford, Ill.). The cell supernatant recovered is sterile filtered through a stericup filter (0.22 µm) and stored at 4° C. until further processing.

Purification was performed on an "ÄKTA 100 explorer Air" chromatography system at 4° C. in a cooling cabinet, using a freshly sanitized (0.25 M NaOH) HiTrap ProtA MabSelect® SuRe, 5 ml column. The column was equilibrated with 5 CV of PBS (Gibco, Life Technologies, Carlsbad, Calif.), and then the sterile filtered supernatant (2 L) was loaded at 4.0 ml/min. The column was washed with 8 CV of PBS to elute the unbound sample and again washed with 5 CV of PBS. Antibody was eluted with 5 CV of 50 mM citrate, 70 mM NaCl pH 3.2. The eluate was collected in 3 ml fractions; fractions were pooled and adjusted at pH 7 with 1 M Tris HCl pH10. The pools were pooled and sterile filtered (Millipore Steriflip, 0.22 um), the OD 280 nm was measured in a Spectrophotometer ND-1000 (NanoDrop), and the protein concentration was calculated based on the sequence data. The eluate was tested for aggregation (SEC-MALS) and purity (SDS-PAGE, LAL and MS). For the second purification step, if needed, pools from the first purification were loaded into a freshly sanitized (0.5 M NaOH) SPX (Hi Load 16/60 Superdex 200 grade 120 mL (GE-Healthcare). The column was equilibrated with PBS and the run was done with PBS buffer at 1 ml/min, the eluate was collected in 1.2 ml fractions and analyzed as described for the first purification step.

Antibodies from Morphosys HuCAL PLATINUM® Phage Library Pannings

For the selection of antibodies recognizing human P-cadherin, multiple panning strategies were utilized. Therapeutic antibodies against human P-cadherin protein were generated by the selection of clones that bound to P-cadherin using as a source of antibody variant proteins a commercially available phage display library, the Morphosys HuCAL PLATINUM® library. The phagemid library is based on the HuCAL® concept (Knappik et al., 2000, J Mol Biol 296: 57-86) and employs the CysDisplay™ technology for displaying the Fab on the phage surface (WO01/05950).

For the isolation of anti-P-cadherin antibodies solid phase, liquid phase, and cell based panning strategies were employed.

Solid Phase Panning on Recombinant P-Cadherin

Prior to the antigen selection process a coating check ELISA was performed to determine the optimal coating concentration for the antigen. Recombinant P-cadherin protein with His tag was used in the solid phase panning approach by coating on Maxisorp™ plates (Nunc) via passive adsorption. An appropriate number (dependent on the number of sub-library pools) of wells of a 96-well Maxisorp™ plate (Nunc) were coated with 125 nM antigen overnight at 4° C. The coated wells were blocked with PBS (phosphate buffered saline)/5% milk powder/5% BSA (bovine serum albumin)/0.1% Tween 20/1 mM $CaCl_2$. For each panning, about 50 uL HuCAL PLATINUM® phage-antibodies were blocked in solution for 2 h at room temperature (RT). After the blocking procedure, pre-blocked phage mix was added to each antigen coated and blocked well and incubated for 2 hours (h) at RT on a microtiter plate (MTP) shaker. Afterwards, unspecific bound phage was washed off by several washing steps with PBS. For elution of specifically bound phage, 25 mM DTT (Dithiothreitol) was added for 10 minutes (min) at RT. The DTT eluates were used for infection of E. coli (Escherichia coli) TG-F$^+$ cells. After infection, the bacteria were plated on LB (lysogeny broth)/Cam (chloramphenicol) agar plates and incubated overnight at 30° C. Colonies were scraped off the plates and were used for phage rescue, polyclonal amplification of selected clones, and phage production. With purified phage the next panning round was started.

The second and third round of solid phase panning was performed according to the protocol of the first round except for more stringent washing conditions.

Subcloning and Microexpression of Selected Fab Fragments

To facilitate rapid expression of soluble Fab, the Fab encoding inserts of the selected HuCAL PLATINUM® phage were subcloned from pMORPH®30 display vector into pMORPH® x11 expression vector pMORPH® x11_FH.

For initial screening and characterization an overnight culture of individual Fab-expressing E. coli clones were lysed using 0.5 mg/mL lysozyme, 0.8 mM EDTA and 4 U/µl Benzonase. Fab containing E. coli lysates were used for ELISA and FACS screening.

ELISA Screening

Using ELISA screening, single Fab clones were identified from panning output for binding to the target antigen. Fabs are tested using Fab containing crude E. coli lysates.

For verification of Fab expression in the prepared E. coli lysates, Maxisorp™ (Nunc) 384 well plates were coated with Fd fragment specific sheep anti-human IgG diluted 1:1000 in PBS. After blocking of plates with 5% skim milk powder in PBS, Fab-containing E. coli lysates were added. Binding of Fabs was detected by $F(ab)_2$ specific goat anti-human IgG conjugated to alkaline phosphatase (diluted 1:5000) using Attophos fluorescence substrate (Roche, catalog #11681982001). Fluorescence emission at 535 nm was recorded with excitation at 430 nm.

For identification P-cadherin antigen binding Fab fragments Maxisorp™ (Nunc) 384 well plates were coated with 25 nM human P-cadherin antigen via passive adsorption in PBS. After blocking of plates with 5% skim milk powder in PBS, Fab-containing E. coli lysates were added. Binding of Fabs was detected by F(ab)$_2$ specific goat anti-human IgG conjugated to alkaline phosphatase (diluted 1:5000) using Attophos fluorescence substrate (Roche, catalog #11681982001). Fluorescence emission at 535 nm was recorded with excitation at 430 nm.

FACS Screening (Fluorescence Activated Cell Sorting)

In FACS screening, single Fab clones binding to cell surface expressed antigen are identified from the panning output. Fabs are tested for cell binding using Fab containing crude E. coli lysates.

50 μl of cell-suspension was transferred into a fresh 96-well plate (resulting in 1×10$^5$ cells/well) and mixed with 50 μl of Fab containing bacterial extracts.

The cell-antibody suspensions were then incubated on ice for 1 hour on a shaker. Following incubation, cells were spun down and washed two times with ice cold FACS buffer. After each washing step, cells were centrifuged and carefully re-suspended.

Secondary detection antibody (PE conjugated goat anti human IgG; Dianova) was added and samples were incubate on ice and subsequently washed according to Fab incubation Fluorescence intensity was determined in a FACSCalibur™ instrument.

Expression and Purification of HuCAL® Fab Fragments

Expression of Fab fragments was performed in E. coli TG1 F-cells. Cultures were shaken at 30° C. for 18 h. Cells were harvested and disrupted. His$_6$-tagged Fab fragments ("His$_6$" disclosed as SEQ ID NO: 130) were isolated via IMAC and gel filtration and protein concentrations were determined by UV-spectrophotometry at 280 nm.

The identity and purity of Fab preparations was determined in native state by mass spectrometry (MS).

Cross-Reactivity Analysis

Purified Fabs were tested in ELISA for binding to human, cyno, rat and mouse P-cadherin ECD proteins. For this purpose Maxisorp™ (Nunc) 384 well plates were coated with antigen at a concentration of 10 ug/mL in PBS overnight at 4° C. Binding of Fabs was detected by F(ab)$_2$ specific goat anti-human IgG conjugated to alkaline phosphatase (diluted 1:5000) using Attophos fluorescence substrate (Roche, catalog #11681982001). Fluorescence emission at 535 nm was recorded with excitation at 430 nm.

Conversion to IgG and IgG Expression

In order to express full length IgG in HEK cells, variable domain fragments of heavy (VH) and light chains (VL) were subcloned from Fab expression vectors into appropriate pMorph®_hIg vectors for human IgG1. The cell culture supernatant was harvested 10 days post transfection. After sterile filtration, the solution was subjected to Protein A affinity chromatography using a liquid handling station. Buffer exchange was performed to 1×Dulbecco's PBS (pH 7.2, Invitrogen) and samples were sterile filtered (0.2 μm pore size). Protein concentrations were determined by UV-spectrophotometry at 280 nm and purity of IgGs was analyzed under denaturing, reducing conditions in SDS-PAGE.

Bioassay

Anti-P-cadherin antibodies obtained following the panning processes described above were evaluated in the assay exemplified below:

HCC1954 Cell Internalization Assay

To determine the capacity of anti-P-cadherin antibodies to undergo target mediated cell internalization a microscopy based internalization assay was established using the P-cadherin expressing HCC1954 tumor cell line.

Cells were re-suspended in full-growth medium (RPMI-1640+10% FCS and seeded into flat-bottomed microscopic 96-well assay plates (ViewPlate®-96 F TC, Perkin Elmer, #6005225) at a cell density of 5×10$^3$ cells/well in 100 μl and incubated at 37° C. and 5% CO$_2$ for 2 days.

After two days, the HuCAL® antibodies (IgG) were diluted in PBS to the desired concentrations. 100 μl of the antibody solutions were added to the seeded cells and incubated for 2 h. After that, cells were washed twice with PBS, fixed with 1× CellFIX reagent (CellFIX™ BD Biosciences, #340181), washed again twice with PBS and permeabilized with 0.1% Triton X-100. Cells were then blocked with 1× Odyssey buffer (Li-Cor, No. 927-40000) for 1 h. After aspiration, cells were stained for 1 h with Hoechst (bisBenzimide H 33342 trichloride, #B2261, Sigma) and Alexa Fluor® 488 goat anti-human IgG (Invitrogen, #A-11013). After staining, cells were washed three times with PBS and analyzed using a Cellomics ArrayScan VTI HCS Reader (Thermo Fischer Scientific. To assess the half maximal internalization concentration (IC$_{50}$ values), IgG titration was performed covering a 10 nM to 2.4 pM range in 4 fold dilution steps.

Removal of Post-Translational Modification (PTM) Site

One antibody, NOV169, which was identified in the internalization assay described above and found to efficiently internalize into P-cadherin expressing tumor cells HCC1954, was found to contain a single N31S PTM site in HCDR1. To prevent deamidation this site was converted into a N31Q site by single point Kunkel mutagenesis, resulting into antibody NOV169N31Q. Equivalent binding strength to recombinant human P-cadherin by NOV169N31Q in comparison to parental NOV169 was confirmed by forteBIO KD determination.

Summary of Antibodies

Table 1 sets forth the relevant sequence information for anti-P-cadherin antibodies isolated from the Morphosys HuCAL PLATINUM® phage library and humanized anti-P-cadherin antibodies derived from murine hybridomas.

Example 2: X-Ray Crystallographic Structure Determination of the Human P-Cadherin EC1_EC2 and of its Complex with the NOV169N31Q Fab The three dimensional structure of human P-cadherin was hitherto unknown. The crystal structure of a human P-cadherin ECD (extracellular domain) fragment (first two N-terminal cadherin-repeat domains, or EC1_EC2, amino acids 108 to 324, SEQ ID NO: 2, Table 1) as well as its complex with the Fab fragment of NOV169N31Q (Table 1) was determined. As detailed below, human P-cadherin EC1_EC2 was expressed, refolded, purified and crystallized. In addition, purified human P-cadherin EC1_EC2 was mixed with the NOV169N31Q Fab to form a complex which was also subsequently purified and crystallized. Protein crystallography was then employed to generate atomic resolution data for human P-cadherin EC1_EC2 in the free state and bound to the NOV169N31Q Fab to define the epitope.

Protein Production of Human P-Cadherin EC1_EC2 and NOV169N31Q Fab for Crystallography The amino acid sequences of human P-cadherin EC1_EC2 and NOV169N31Q Fab produced for crystallography are shown in Table 3. The construct of human P-cadherin EC1_EC2 comprised residues 108 to 324 (underlined) of human P-cadherin (UniProt identifier P22223, SEQ ID NO:126), along with N-terminal residues from the recombinant expression vector (shown in lower case letters, SEQ ID NO:127). For the NOV169N31Q Fab, the amino acid sequences of the heavy and light chains are shown, along with C-terminal identification/purification tags (shown in lower case letters, SEQ ID NOs: 128 and 129, respectively).

TABLE 3

Proteins used for crystal structure determination

| Construct | Amino acid sequence in one letter code | SEQ ID NO |
|---|---|---|
| Human P-cadherin (P22223) | MGLPRGPLASLLLLQVCWLQCAASEPCRAVFREAEVTLEAGGA EQEPGQALGKVFMGCPGQEPALFSTDNDDFTVRNGETVQERRS LKERNPLKIFPSKRILRRHKRDWVVAPISVPENGKGPFPQRLN QLKSNKDRDTKIFYSITGPGADSPPEGVFAVEKETGWLLLNKP LDREEIAKYELFGHAVSENGASVEDPMNISIIVTDQNDHKPKF TQDTFRGSVLEGVLPGTSVMQVTATDEDDAIYTYNGVVAYSIH SQEPKDPHDLMFTIHRSTGTISVISSGLDREKVPEYTLTIQAT DMDGDGSTTTAVAVVEILDANDNAPMFDPQKYEAHVPENAVGH EVQRLTVTDLDAPNSPAWRATYLIMGGDDGDHFTITTHPESNQ GILTTRKGLDFEAKNQHTLYVEVTNEAPFVLKLPTSTATIVVH VEDVNEAPVFVPPSKVVEVQEGIPTGEPVCVYTAEDPDKENQK ISYRILRDPAGWLAMDPDSGQVTAVGTLDREDEQFVRNNIYEV MVLAMDNGSPPTTGTGTLLLTLIDVNDHGPVPEPRQITICNQS PVRQVLNITDKDLSPHTSPFQAQLTDDSDIYWTAEVNEEGDTV VLSLKKFLKQDTYDVHLSLSDHGNKEQLTVIRATVCDCHGHVE TCPGPWKGGFILPVLGAVLALLFLLLVLLLLVRKKRKIKEPLL LPEDDTRDNVFYYGEEGGGEEDQDYDITQLHRGLEARPEVVLR NDVAPTIIPTPMYRPRPANPDEIGNFIIENLKAANTDPTAPPY DTLLVFDYEGSGSDAASLSSLTSSASDQDQDYDYLNEWGSRFK KLADMYGGGEDD | 126 |
| Human P-cadherin EC1_EC2 | gpDWVVAPISVPENGKGPFPQRLNQLKSNKDRDTKIFYSITGP GADSPPEGVFAVEKETGWLLLNKPLDREEIAKYELFGHAVSEN GASVEDPMNISIIVTDQNDHKPKFTQDTFRGSVLEGVLPGTSV MQVTATDEDDAIYTYNGVVAYSIHSQEPKDPHDLMFTIHRSTG TISVISSGLDREKVPEYTLTIQATDMDGDGSTTTAVAVVEILD ANDN | 127 |
| NOV169N31Q Fab heavy chain | QVQLQQSGPGLVKPSQTLSLTCAISGDSVSSQSAAWNWIRQSP SRGLEWLGRIYYRSKWYNDYALSVKSRITINPDTSKNQFSLQL NSVTPEDTAVYYCARGEGYGREGFAIWGQGTLVTVSSASTKGP SVFPLAPSSKSTSGGTAALGCLVKDYFPEPVTVSWNSGALTSG VHTFPAVLQSSGLYSLSSVVTVPSSSLGTQTYICNVNH KPSNTKVDKKVEPKSEFdykddddkgaphhhhhh | 128 |
| NOV169N31Q Fab light chain | DIQMTQSPSSLSASVGDRVTITCRASQTISNTLAWYQQKPGKA PKLLIYAASNLQSGVPSRFSGSGSGTDFTLTISSLQPEDFATY YCQQYLSWFTFGQGTKVEIKRTVAAPSVFIFPPSDEQLKSGTA SVVCLLNNFYPREAKVQWKVDNALQSGNSQESVTEQDSKDSTY SLSSTLTLSKADYEKHKVYACEVTHQGLSSPVTKSFNRGEA | 129 |

Human P-cadherin EC1_EC2 with an N-terminal hexa-histidine tag (SEQ ID NO: 130) followed by a PreScission cleavage site was cloned and expressed in E. coli BL21 (DE3) Star (Invitrogen) with a pET28 vector. Following overnight induction with IPTG at 18° C., cells (67 g) were harvested and lysed with a French press in 700 ml of 50 mM TRIS pH 8.0, 500 mM NaCl, 10% glycerol, 2 mM TCEP, and 14 tablets of EDTA-free cOmplete protease inhibitor cocktail (Roche). After centrifugation (35 min at 18,000 rpm with SS34 rotor), the supernatant was sterile filtered (0.45 µm) and loaded onto a Crude FF metal chelation chromatography column (5 ml, GE Healthcare) pre-equilibrated with Buffer A (50 mM TRIS pH 8.0, 500 mM NaCl, 10% glycerol). The column was first washed with the equilibration buffer and then with buffer A including 25 mM imidazole, followed by elution with a 25 mM to 500 mM imidazole gradient. The eluted protein (36 mg) was then cleaved using PreScission protease (10 µg per mg) during overnight dialysis against 50 mM TRIS pH 8.0. After filtration (0.22 µm), the sample was loaded onto a MonoQ anion exchange chromatography column (GE Healthcare) pre-equilibrated with 50 mM TRIS pH 8.0, and eluted with a 0.0 M to 1.0 M NaCl gradient. The major peak containing P-cadherin EC1_EC2 (25.6 mg) was collected and analyzed by SDS-PAGE and HPLC. The fraction pool was then re-loaded onto the Crude FF metal chelation chromatography column (5 ml, GE Healthcare) pre-equilibrated with 50 mM TRIS pH 8.0, 500 mM NaCl, 10% glycerol as before. The P-cadherin EC1_EC2 protein was recovered in the flow-through, and analyzed by HPLC and LC-MS. LC-MS analyses showed the expected molecular weight (23,837 Da).

The NOV169N31Q Fab was expressed at 1 liter scale in E. coli. First, the plasmid encoding the Fab fragment was transformed into chemically competent TG1F⁻ E. coli cells. After overnight growth of the bacteria on LB/Agar/1% Glucose/34 µg/ml chloramphenicol plate at 37° C., one colony was used to inoculate a 6 ml pre-culture (2×YT/1.0% Glucose/34 µg/ml chloramphenicol). The culture was incubated overnight at 30° C., shaking at 220 rpm. Next day, the pre-culture was transferred to 1 liter expression culture (2×YT/0.1% Glucose/34 µg/ml chloramphenicol). The expression culture was incubated at 30° C., shaking at 220 rpm until an $OD_{600\ nm}$ of 0.6-0.8 was reached. Expression was induced by adding IPTG to a final concentration of 0.5 mM. The expression was carried on overnight at 25° C. and 220 rpm. Next day, cells were pelleted and frozen at −80° C.

The Fab fragment was purified in 2 steps using an automated protocol on the AEKTA Express system (software: Unicorn_v5.11). Bacteria pellet was first resuspended in 40 ml lysis buffer (200 mM Na phosphate pH 7.4, 0.5M NaCl, 0.1% lysozyme, 2 mM $MgCl_2$, 10 U/ml benzonase, 1 tablet/50 ml of cOmplete EDTA-free protease inhibitor) and incubated at room temperature for 1 hour under shaking. The cell debris was removed by centrifugation at 16,000 g for 30 min. The Fab containing supernatant was passed through 0.2 µM syringe filters (Pall, #PN4525) and loaded onto the system pre-equilibrated with running buffer (20 mM Na phosphate, 0.5M NaCl, 10 mM imidazole, pH 7.4). The first purification step was performed over a 1 ml HiTrap HP column (GE Healthcare). The column was washed with running buffer and $His_6$-tagged Fab fragments ("$His_6$" disclosed as SEQ ID NO: 130) were eluted with the elution buffer (20 mM Na phosphate, 0.5M NaCl, 250 mM imidazole, pH 7.4). The peak fraction was automatically applied on the gel filtration column (HiLoad 16/60 Superdex 75; GE Healthcare). The purified Fab fragment was eluted in PBS. The concentration of the Fab fragment was determined by $UV_{280\ nm}$ measurements and by applying the Lambert-Beer equation, using the extinction coefficient estimated from the amino acid sequence.

Crystallization and Structure Determination of the Human P-Cadherin EC1_EC2

Human P-cadherin EC1_EC2 was dialyzed against 10 mM Tris-HCl pH 7.4, 25 mM NaCl, concentrated to 15 mg/ml and screened for crystallization at 20° C.

Crystals were grown in 96-well SD2 plates by sitting drop vapor diffusion. In detail, 0.2 µl of protein was mixed with 0.2 µl of reservoir solution, and the drop was equilibrated against 80 µl of the same reservoir solution at 20° C. Crystals suitable for X-ray diffraction analysis were obtained with a reservoir solution made of 0.085M HEPES pH 7.5, 3,655M NaCl, 15% glycerol.

For data collection, one human P-cadherin EC1_EC2 crystal was mounted in a cryo-loop and directly flash cooled in liquid nitrogen. Diffraction data were collected at beamline X10SA (PX-II) of the Swiss Light Source (Paul Scherrer Institute, Switzerland), with a Pilatus pixel detector and X-rays of 0.99999 Å wavelength. In total, 720 images of 0.25 deg oscillation each were recorded at a crystal to detector distance of 200 mm. Data were processed and scaled at 1.40 Å resolution using XDS (Kabsch (1993) J. Appl. Crystallogr. 26:795-800) as implemented in APRV-INDEX (Kroemer, Dreyer, Wendt (2004) Acta Crystallogr. Sect. D: Biol. Crystallogr. 60:1679-1682). The crystal was in space group C2 with cell dimensions a=120.89 Å, b=76.52 Å, c=46.21 Å, alpha=90°, beta=107.79°, gamma=90°. The human P-cadherin EC1_EC2 structure was solved by molecular replacement using the program Phaser (McCoy et al., (2007) J. Appl. Cryst. 40:658-674) and PDB entry 1L3W (*X. Laevis* C-cadherin, 3.08 Å, 55% sequence identity). The final model was built in COOT (Emsley et al., (2010) Acta Crystallogr. Sect. D: Biol. Crystallogr. 66:486-501) and refined with Buster (Global Phasing, LTD) to $R_{work}$ and $R_{free}$ values of 19.8% and 21.3%, respectively, with a rmsd of 0.010 Å and 1.13° for bond lengths and bond angles, respectively.

Human P-Cadherin EC1_EC2 Structure

The crystal structure of human P-cadherin EC1_EC2 (amino acid residues 108 to 322) is shown in FIG. 1. Both cadherin domains had well-defined electron-density and showed the expected overall fold. Three calcium ions were observed at the domain interface.

The ECD domain of cadherins has been proposed to play a role in the extracellular architecture of adherens junctions, which control intercellular adhesion. Junction assembly involves both trans and cis homotypic interactions between the ectodomains of cadherin clusters (Boggon et al., (2002) Science 296:1308-1313; Harrison et al., (2011) Structure 19:244-256). Trans homotypic interaction involves N-terminal Trp exchange ("strand swapped dimer") between the EC1 domains of two cadherin molecules in opposite orientation (presented by two different cells). In contrast, cis homotypic interaction involves the N-terminal extracellular cadherin (EC1) domain of one molecule and the second (EC2) domain of another molecule in the same orientation. Trans interactions are thought to be much stronger than cis interactions. While trans interactions form the molecular basis of intercellular adhesion, cis interactions are believed to promote cell adhesion via molecular clustering.

The crystal structure of the human P-cadherin EC1_EC2 fragment showed that the N-terminal segment involved in trans homotypic interactions via Trp exchange was not taking part in such interactions in the crystal and was bound to its own domain. Furthermore, an analysis of the crystal packing revealed that one of the symmetry-related P-cadherin EC1_EC2 molecule was making cis homotypic interactions highly similar to those already reported for other cadherins, showing that crystallization was, in this case, driven by cis homotypic interactions.

Crystallization and Structure Determination of the NOV169N31Q Fab Complex

The complex of human P-cadherin EC1_EC2 with the NOV169N31Q Fab was prepared by mixing the purified human P-cadherin EC1_EC2 and the NOV169N31Q Fab at a 1.5:1.0 molar ratio (concentration measured by HPLC) and purifying the complex on a Superdex 200 (GE Healthcare) size exclusion chromatography equilibrated in 10 mM Tris-HCl pH 7.5, 150 mM NaCl, with 2 tablets of EDTA-free cOmplete protease inhibitor cocktail (Roche). Peak fractions were analyzed by SDS-PAGE and LCMS. Fractions containing the human P-cadherin EC1_EC2/NOV169N31Q Fab complex were concentrated to about 12 mg/ml, $CaCl_2$ was added to a final concentration of 5 mM and the sample was screened for crystallization at 20° C.

Crystals were grown in 96-well SD2 plates by sitting drop vapor diffusion. In detail, 0.2 µl of protein was mixed with 0.2 µl of reservoir solution, and the drop was equilibrated against 80 µl of the same reservoir solution at 20° C. Crystals suitable for X-ray diffraction analysis were obtained with a reservoir solution made of 0.2M calcium acetate, 10% (w/v) PEG 8,000, 0.1M MES pH 6.5.

Before data collection, one human P-cadherin EC1_EC2/NOV169N31Q Fab crystal was briefly transferred into a 1:1 mix of the reservoir solution with 20% PEG 8,000, 30% glycerol, and flash cooled in liquid nitrogen.

Diffraction data were collected at beamline X10SA (PX-II) of the Swiss Light Source (Paul Scherrer Institute, Switzerland), with a Pilatus pixel detector and X-rays of 0.99999 Å wavelength. In total, 720 images of 0.25 deg oscillation each were recorded at a crystal to detector distance of 340 mm. Data were processed and scaled at 2.10 Å resolution using XDS (Kabsch (1993) J. Appl. Crystallogr. 26:795-800) as implemented in APRV-INDEX (Kroemer, Dreyer, Wendt (2004) Acta Crystallogr. Sect. D: Biol. Crystallogr. 60:1679-1682). The crystal was in space group $P2_12_12$ with cell dimensions a=172.69 Å, b=77.79 Å, c=133.41 Å, alpha=90°, beta=90.0°, gamma=90°. The human P-cadherin EC1_EC2/NOV169N31Q Fab complex structure was solved by molecular replacement using Phaser (McCoy et al., (2007) J. Appl. Cryst. 40:658-674). The final model was built in COOT (Emsley et al., (2010) Acta Crystallogr. Sect. D: Biol. Crystallogr. 66:486-501) and refined with Buster (Global Phasing, LTD) to $R_{work}$ and $R_{free}$ values of 19.2% and 22.1%, respectively, with a rmsd of 0.010 Å and 1.18° for bond lengths and bond angles, respectively. Residues of human P-cadherin EC1_EC2 that contain atoms within 4.0 Å of any atom in NOV169N31Q Fab were identified by the program Ncont of the CCP4 program suite (Collaborative Computing Project, Number 4 (1994) Acta Crystallogr. Sect. D: Biol. Crystallogr. 50:760-763) and listed in Tables 4 and 5. Residues of human P-cadherin EC1_EC2 that become less accessible to solvent upon binding of the NOV169N31Q antibody were identified by the program AREAIMOL of the CCP4 program suite.

P-Cadherin EC1_EC2 Epitope for NOV169N31Q

Figure 2:
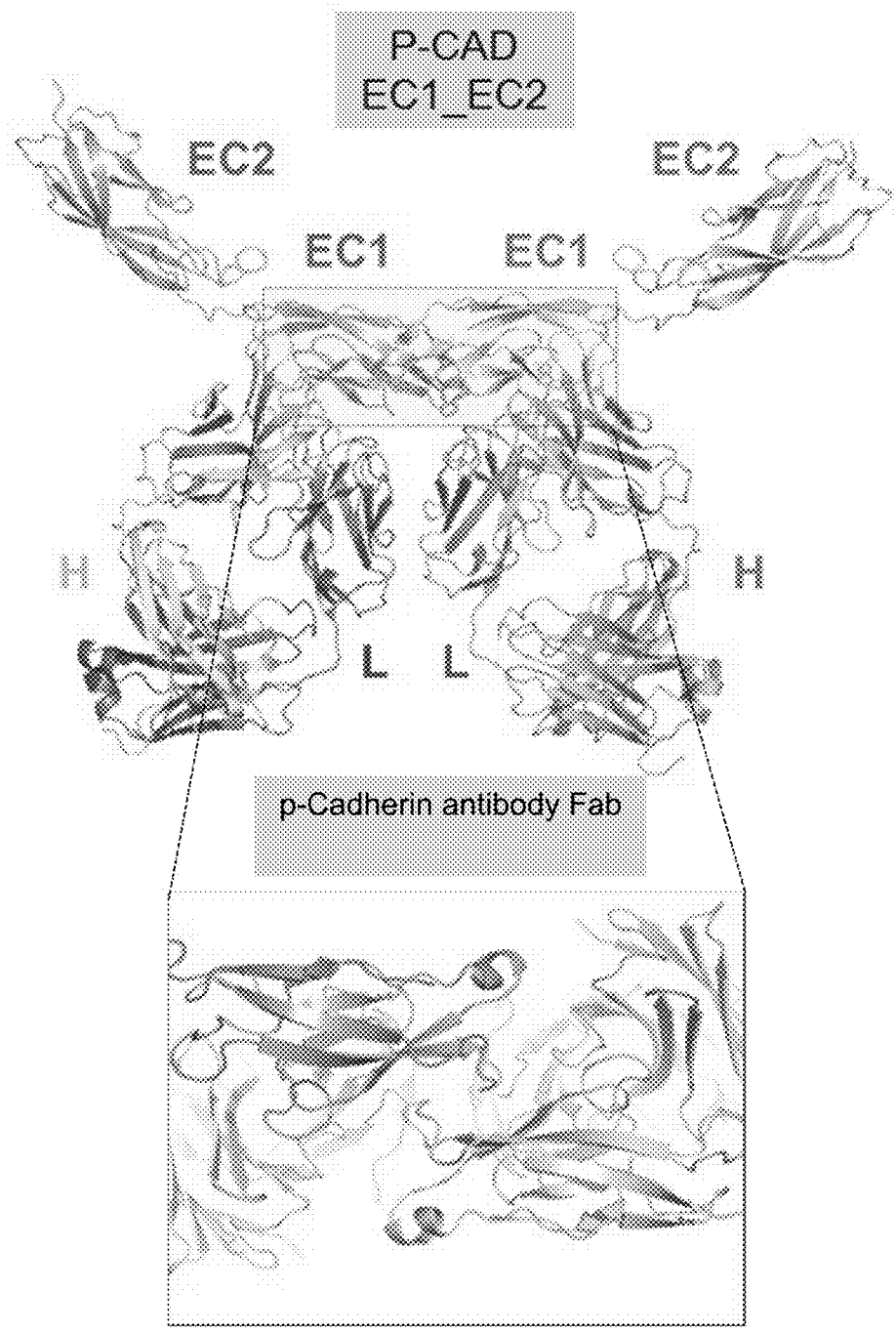
FIG. 2 depicts the overall view of the crystal structure of two P-cadherin antibody Fabs complexed with two human P-cadherin proteins, forming the asymmetric unit of the crystal. The inset is a close-up view of the contact region involving the EC1 domain of the two P-cadherin molecules. There are only a few crystal contacts between the two complexes.

The crystal structure of the P-cadherin EC1_EC2/ NOV169N31Q Fab complex was used to identify the P-cadherin EC1_EC2 epitope for NOV169N31Q. The X-ray analysis shows that NOV169N31Q binds to the EC1 domain (N-terminal cadherin-repeat domain) of human P-cadherin (FIG. 2). There are two copies of the NOV169N31Q Fab-human P-cadherin EC1_EC2 complex in the asymmetric unit of the crystal (an asymmetric unit contains all the structural information which is needed to reproduce the whole crystal by applying crystallographic symmetry operators). Both copies share almost identical residues in contact with NOV169N31Q Fab except for small variations due to crystal packing.

Figure 3:
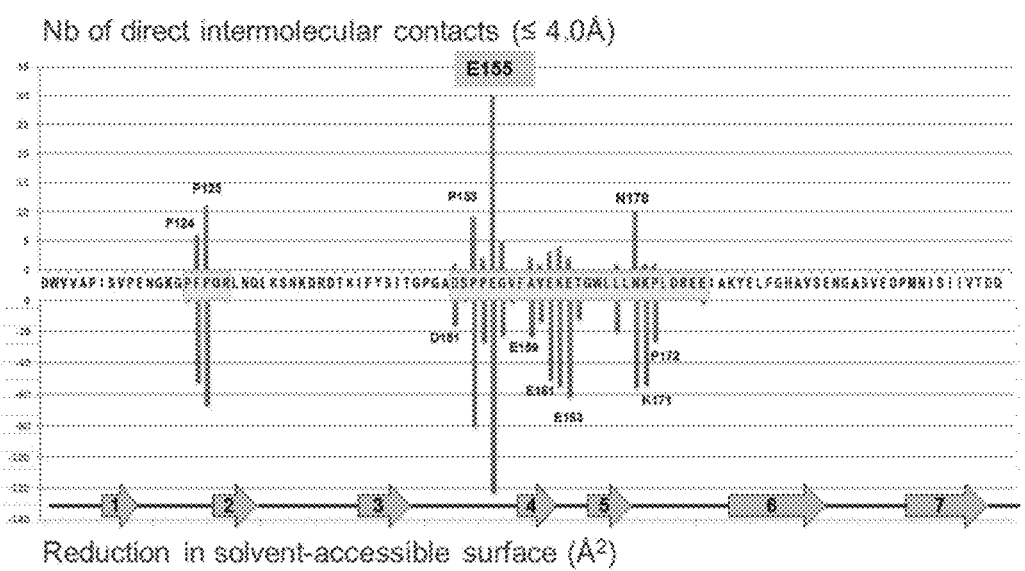
FIG. 3 is a graph depicting human P-cadherin epitope residues (SEQ ID NO: 133) that contact residues of the Fab of P-cadherin antibody NOV169N31Q. The amino acid sequence of the human P-cadherin EC1 domain is listed on the horizontal axis. The upper part of the graph shows the number of direct intermolecular contacts between the protein antigen and the antibody, as identified by the program NCONT using a cut-off distance of 4.0 Å between non-hydrogen atoms. The lower part of the graph shows the reduction in solvent-accessible surface (in Å2) incurred by P-cadherin residues upon antibody binding, as calculated by the program AREAIMOL. The β-barrel structure of the EC1 domain is schematically shown as a string of arrows with labels corresponding to the numbering of the β-strands.
Figure 4:
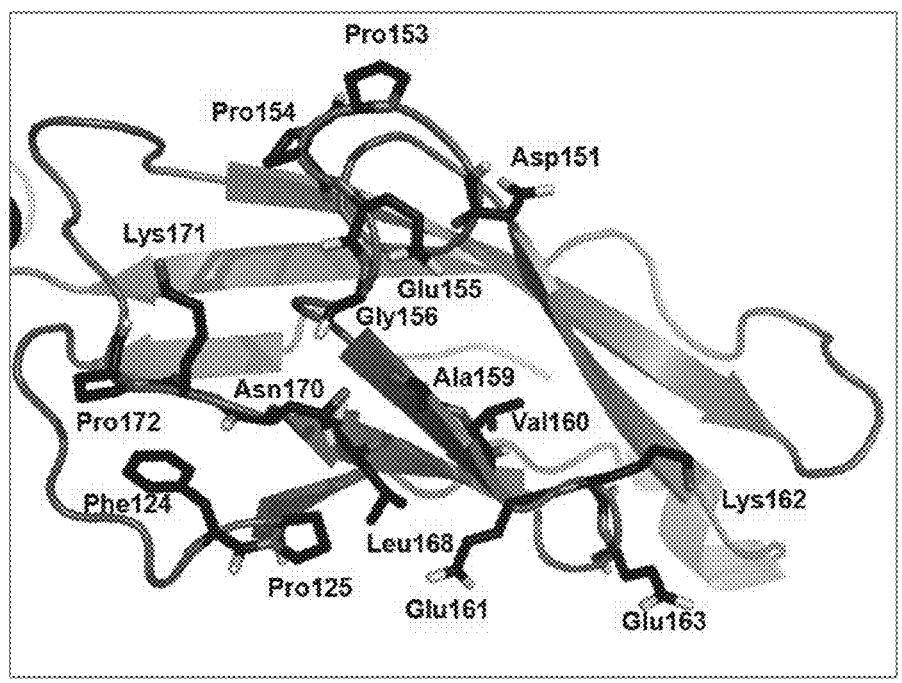
FIG. 4 depicts a close-up view of the crystal structure of N-terminal cadherin-repeat (EC1) domain of human P-cadherin (grey cartoon) with all amino acid residues interacting with the antibody (4.0 Å cut-off distance) shown in black stick (antibody view).

The interaction surface on human P-cadherin EC1_EC2 by the NOV169N31Q Fab is formed by two discontinuous (i.e., noncontiguous) sequences, entirely comprised within the EC1 domain of P-cadherin and encompassing residues 123 through 127, and residues 151 through 177 (FIG. 3). Among those, residues 124 and 125, and residues 151 through 172 are contributing direct intermolecular contacts shorter than 4.0 Å (between non-hydrogen atoms), as detailed in Tables 4 and 5 and shown in FIG. 3. These residues form the three-dimensional surface that is recognized by the NOV169N31Q Fab (FIG. 4).

TABLE 4

Interactions between human P-cadherin EC1_EC2 and the NOV169N31Q Fab heavy chain (H). P-cadherin residues are numbered based upon P22223 (SEQ ID NO: 126). Fab heavy chain residues are numbered based upon their linear amino acid sequence (SEQ ID NO: 128). P-cadherin residues shown have at least one atom within 4.0 Å of an atom in the NOV169N31Q Fab.

| Human P-cadherin Residues (SEQ ID NO: 126) | | NOV169N31Q Fab Residues (SEQ ID NO: 128) | | |
|---|---|---|---|---|
| Amino acid | Number | Amino acid | Number | Chain |
| Phe | 124 | Leu | 65 | H |
| Asp | 151 | Tyr | 105 | H |
| Pro | 153 | Tyr | 54 | H |
| | | Arg | 56 | H |
| | | Tyr | 60 | H |
| | | Tyr | 105 | H |
| Pro | 154 | Tyr | 54 | H |
| Glu | 155 | Arg | 52 | H |
| | | Tyr | 54 | H |
| | | Tyr | 105 | H |
| | | Arg | 107 | H |
| Gly | 156 | Arg | 107 | H |
| Pro | 172 | Leu | 65 | H |

TABLE 5

Interactions between human P-cadherin EC1_EC2 and the NOV169N31Q Fab light chain (L). P-cadherin residues are numbered based upon P22223 (SEQ ID NO: 126). Fab light chain residues are numbered based upon their linear amino acid sequence (SEQ ID NO: 129). P-cadherin residues shown have at least one atom within 4.0 Å of an atom in the NOV169N31Q Fab.

| Human P-cadherin Residues (SEQ ID NO: 126) | | NOV169N31Q Fab Residues (SEQ ID NO: 129) | | |
|---|---|---|---|---|
| Residue | Number | Residue | Number | Chain |
| Phe | 124 | Asp | 1 | L |
| Pro | 125 | Ile | 2 | L |
| | | Gln | 27 | L |
| | | Ser | 93 | L |
| Glu | 155 | Trp | 94 | L |
| Gly | 156 | Trp | 94 | L |
| Ala | 159 | Leu | 92 | L |
| Val | 160 | Leu | 92 | L |
| Glu | 161 | Gln | 27 | L |
| | | Thr | 28 | L |
| Lys | 162 | Ser | 30 | L |
| Glu | 163 | Gly | 68 | L |
| Leu | 168 | Leu | 92 | L |
| Asn | 170 | Ser | 93 | L |
| | | Trp | 94 | L |
| Lys | 171 | Trp | 94 | L |

In contrast to the other extracellular cadherin-repeat domains of human P-cadherin, the EC1 domain does not harbor any known N-linked or O-linked glycosylation sites. NOV169N31Q binding to P-cadherin is thus independent of glycosylation. Also worth of note, the amino acid sequence of the human P-cadherin EC1 domain is fully conserved in cynomolgus (*Macaca fascicularis*) P-cadherin (FIG. 5). Therefore, the P-cadherin epitope recognized by NOV169N31Q is fully conserved in this monkey species used in toxicological studies.

Figure 6:
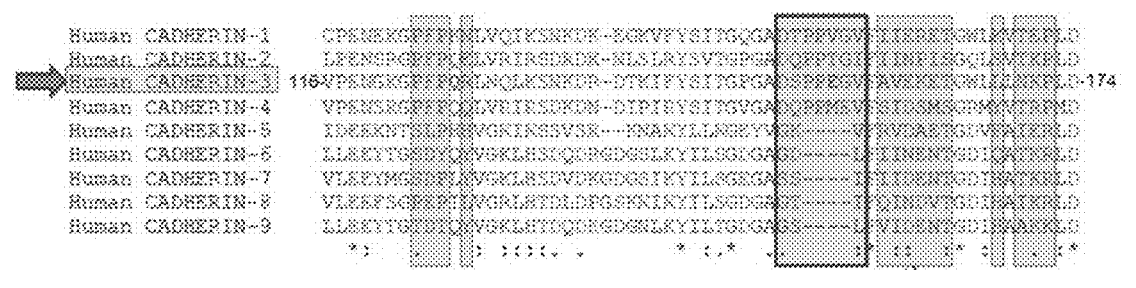

Glu155 of human P-cadherin EC1_EC2 is the epitope residue making most contacts with the NOV169N31Q Fab (see FIG. 3). Interestingly, Glu155 is located within a non-conserved insertion found in human cadherins 1 to 4 only, as shown by a multiple sequence alignment of all human cadherins (FIG. 6). As Glu155 itself is not conserved in human cadherins 1, 2 and 4, NOV169N31Q is expected to display high selectivity towards human cadherin-3 (aka human P-cadherin).

As already mentioned above, cadherins plays an important role in the molecular mechanism of intercellular adhesion, which involves both strong trans and weak cis homotypic interactions between the ectodomains of cadherin clusters. (Boggon et al., (2002) Science 296:1308-1313; Harrison et al., (2011) Structure 19:244-256). Based on the crystal structure of the human P-cadherin EC1_EC2/ NOV169N31Q Fab complex, it appears that the binding epitope for NOV169N31Q partially overlaps with the surface region of the EC1 domain involved in cis homotypic interactions, but not with the N-terminal region involved in trans (intercellular) homotypic interactions. As a consequence, NOV169N31Q does not compete with strong trans interactions for cadherin binding, and therefore is more likely to have easier access to its binding epitope. Moreover, the binding of this antibody to its target antigen is not expected to disrupt intercellular adhesion fully, as trans homotypic interactions are preserved.

Example 3: Generation and Characterization of P-Cadherin Antibody Drug Conjugates Preparation of the DM1 Conjugates by One-Step Process Antibodies to P-cadherin were diafiltered into a reaction buffer (15 mM potassium phosphate, 2 mM EDTA, pH 7.6) via Tangential Flow Filtration (TFF#1) prior to the start of the conjugation reaction. Subsequently, antibodies (5.0 mg/mL) were mixed with DM1 (5.6-fold molar excess relative to the amount of antibody) and then with SMCC (4.7 fold excess relative to the amount of antibody). The reaction was performed at 20° C. in 15 mM potassium phosphate buffer (pH 7.6) containing 2 mM EDTA and 10% DMA for approximately 16 hours. The reaction was quenched by adding 1 M acetic acid to adjust the pH to 5.50. After pH adjustment, the reaction mixture was filtered through a multi-layer (0.45/0.22 µm) PVDF filter and purified and diafiltered into a 20 mM histidine buffer (pH 5.6) containing 8.22% sucrose using Tangential Flow Filtration (TFF#2). The instrument parameters for the Tangential Flow Filtration are listed in Table 6 below.

TABLE 6

Instrument parameters for the Tangential Flow Filtration

| TFF Parameter | TFF#1 Set Point | TFF#2 Set Point |
| --- | --- | --- |
| Bulk Concentration (Cb-g/L) | 20 | 20 |
| TMP (psi) | 12-18 | 12-18 |
| Feed Flow rate (LMH) | 324 | 324 |
| Membrane Load (g/m2) | 110-150 | 110-150 |
| Diavolumes | 10 | 14 |
| Diafiltration Buffer | 15 mM potassium phosphate, 2 mM EDTA, pH 7.6 | 20 mM histidine, 8.22% Sucrose, pH 5.6 |
| Temperature (° C.) | RT (20-25) | RT (20-25) |

Conjugates obtained from the process described above were analyzed by: UV spectroscopy for cytotoxic agent loading (Maytansinoid to Antibody Ratio, MAR); SEC-HPLC for determination of conjugate monomer; and reverse-phase HPLC or hydrophobic shielded phase (Hisep)-HPLC for free maytansinoid percentage. The data is shown in Table 7.

TABLE 7

Properties of P-cadherin ADC Prepared Using One-Step Process

| Sample | MAR | Monomer (%) | Total Free Maytansinoid (%) |
| --- | --- | --- | --- |
| NOV169N31Q-MCC-DM1 | 3.7 | 99.1 | 0.6 |

Preparation of DM1 Conjugates by In Situ Process

The conjugates of the present invention can also be prepared by in situ process according to the following procedures. P-cadherin antibodies were conjugated to DM1 using the sulfosuccinimidyl 4-(N-maleimidomethyl)cyclohexane-1-carboxylate (sulfo-SMCC) linker. Stock solutions of DM1 and sulfo-SMCC heterobifunctional linker were prepared in DMA. Sulfo-SMCC and DM1 thiol were mixed together to react for 10 minutes at 25° C. in DMA containing 40% v/v of aqueous 50 mM succinate buffer, 2 mM EDTA, pH 5.0, at the ratio of DM1 to linker of 1.3:1 mole equivalent and a final concentration of DM1 of 1.95 mM. The antibody was then reacted with an aliquot of the reaction to give a mole equivalent ratio of SMCC to Ab of around 6.5:1 under final conjugation conditions of 2.5 mg/mL of Ab in 50 mM EPPS, pH 8.0 and 10% DMA (v/v). After approximately 18 hours at 25° C., the conjugation reaction mixture was purified using a SEPHADEX™ G25 column equilibrated with 10 mM succinate, 250 mM glycine, 0.5% sucrose, 0.01% Tween 20, pH 5.5.

TABLE 8

Properties of DM1-conjugated antibodies

| Clone name | Linker excess | MAR | Monomer (%) | Yield (%) | Free drug (%) |
| --- | --- | --- | --- | --- | --- |
| NOV169N31Q | 7.0 | 3.15 | 99.0 | 76 | <2 |
| NEG0012 | 6.8 | 4.07 | 97.8 | 56 | <2 |
| NEG0013 | 5.5 | 3.29 | 94.6 | 70 | <2 |
| NEG0016 | 6.8 | 3.44 | 97.3 | 70 | <2 |
| NEG0064 | 5.3 | 3.91 | 98.0 | 76 | <2 |
| NEG0067 | 5.1 | 3.63 | 97.8 | 79 | <2 |

Preparation of ADCs with the SPDB Linker

P-cadherin antibodies (8 mg/ml) were modified with N-succinimidyl 4-(2-pyridyldithio)butanoate (SPDB, 4.0-4.1-fold molar excess) for 120 minutes at 25° C. in 60 mM EPPS buffer (pH 8.5) containing 50 mM potassium phosphate, 50 mM NaCl, 2 mM EDTA, and 5% DMA. The modified Ab without purification was subsequently conjugated to DM4 (1.5 fold molar excess over the unbound linker) at a final modified antibody concentration of 4 mg/mL in 60 mM EPPS buffer (pH 8.5) containing 50 mM potassium phosphate, 50 mM NaCl, 2 mM EDTA, and 5% DMA for 18 hours at 25° C. The conjugation reaction mixture was purified using a SEPHADEX™ G25 column equilibrated and eluted with 10 mM succinate, 250 mM glycine, 0.5% sucrose, 0.01% Tween 20, pH 5.5.

TABLE 9

Properties of DM4-conjugated antibodies

| Clone name | Linker excess | MAR | Monomer (%) | Yield (%) | Free drug (%) |
| --- | --- | --- | --- | --- | --- |
| 2P10 | 4.0 | 3.18 | 95.6 | 93 | <0.5% |
| 1G12 | 4.1 | 3.60 | 96.8 | 95 | <0.5% |
| 3D21 | 4.0 | 3.42 | 97.0 | 96 | <0.5% |

Preparation of ADCs with the CX1-1 Linker

Antibody NEG0067 (5.0 mg/mL) was mixed with DM1 (7.4 fold molar excess relative to the amount of antibody) and then with CX1-1 (5.7-fold excess relative to the amount of antibody). The reaction was performed at 25° C. in 50 mM EPPS [4-(2-Hydroxyethyl)-1-piperazinepropanesulfonic acid] buffer (pH 8.0) containing 2 mM EDTA and 5% DMA for approximately 16 hours. The reaction mixture was then purified using a SEPHADEX™ G25 column equilibrated and eluted in 10 mM succinate, 250 mM glycine, 0.5% sucrose, 0.01% Tween 20, pH 5.5

TABLE 10

Properties of CX1-1/DM1 conjugated NEG0067

| Clone name | Linker excess | MAR | Monomer (%) | Yield (%) | Free drug (%) |
| --- | --- | --- | --- | --- | --- |
| NEG0067 | 5.7 | 3.47 | 99.4 | 79 | 0.7 |

Example 4: Affinity of P-Cadherin Antibodies and ADCs to P-Cadherin

The affinity of various antibodies and antibody drug conjugates (in Ab-MCC-DM1 format) to P-cadherin and its species orthologues was determined using SPR technology using a Biacore® T100 instrument (GE Healthcare, Pittsburgh, Pa.) or a Biacore® 2000 instrument (GE Healthcare, Pittsburgh, Pa.) using CM5 sensor chips.

Briefly, HBS-P+ (0.01 M HEPES, pH 7.4, 0.15 M NaCl, 0.05% Surfactant P20) supplemented with 2% Odyssey® blocking buffer (Li-Cor Biosciences, Lincoln, Nebr.) was used as the running buffer for all the experiments on the Biacore® T100 instrument. HBS-P (0.01 M HEPES, pH 7.4, 0.15 M NaCl, 0.005% Surfactant P20) supplemented with 2% Odyssey® blocking buffer was used as the running buffer for all the experiments on the Biacore® 2000 instrument. The immobilization level and analyte interactions were measured by response unit (RU). Pilot experiments were performed to test and confirm the feasibility of the immobilization of Protein A (GE Healthcare, Pittsburgh, Pa.) and the capture of the test antibodies.

For kinetic measurements, experiments were performed in which the antibodies were captured to the sensor chip surface via the immobilized Protein A and the ability of the P-cadherin proteins to bind in free solution was determined. Briefly, 28 μg/ml of Protein A at pH 4.5 was immobilized on a CM5 sensor chip through amine coupling at flow rate of 10 μl/minute on two flow cells to reach 2300-3300 RUs. 0.01-0.25 μg/ml of test antibodies was then injected at 5 μl/min for 3 minute. Captured levels of the antibodies were generally kept below 400 RUs. Subsequently, 6.25-100 nM of P-cadherin ECD was diluted in a 2-fold series and injected at a flow rate of 40 μl/min for 2-4 min over both reference and test flow cells. Table 11 of tested ECDs is listed below. Dissociation of the binding was followed for 5 min. After each injection cycle, the chip surface was regenerated with PBS/6 M Guanidine HCl, pH 7.4 at 100 μl/min for 45 seconds. All experiments were performed at 25° C. and the response data were globally fitted with a simple 1:1 interaction model using Biacore T100 Evaluation Software version 2.0.3 (GE Healthcare) to obtain estimates of on rate ($k_a$), off-rate ($k_d$) and affinity ($K_D$) on the Biacore® T100 instrument. Experiments that were ran on the Biacore® 2000 instrument were globally fitted with a simple 1:1 interaction model using Scrubber 2 ® software version 2.0b (BioLogic Software) to obtain estimates of on rate ($k_a$), off-rate ($k_d$) and affinity ($K_D$)

TABLE 11

P-cadherin ECD isotype and source used in Affinity Assay

| ECD Isotype | Tag | Source |
|---|---|---|
| Human | C-terminal 6x His (SEQ ID NO: 130) | NVS |
| Cyno_1 | C-terminal 6x His (SEQ ID NO: 130) | NVS |
| Cyno_2 | C-terminal 6x His (SEQ ID NO: 130) | NVS |
| Mouse | C-terminal 6x His (SEQ ID NO: 130) | NVS |
| Rat | C-terminal 6x His (SEQ ID NO: 130) | NVS |

Table 12 lists the domain binding and affinity of various P-cadherin antibodies disclosed in Table 1. As shown in the Table, the antibodies NOV169N31Q, NEG0012, NEG0013, NEG0016, NEG0064, and NEG0067 all reacted with the human P-cadherin at the nanomolar level, and have similar affinities for those tested against cynomolgus monkey P-cadherin ECD. All the antibodies cross reacted with the rat except NOV169N31Q.

TABLE 12

Affinity estimates of anti-P-cadherin antibodies and ADCs obtained against human P-cadherin and species orthologues

| | | Affinity estimate ($K_D$) | | | |
|---|---|---|---|---|---|
| Antibody ID | | Human P-cad (nM) | Cyno_1 P-cad (nM) | Cyno_2 P-cad (nM) | Rat P-cad (nM) |
| NOV169N31Q | Naked | 33.3 | 36.8 | 44.5 | No Binding |
| | ADC | 27 | 27.5 | 47.1 | ND |
| NEG0012 | Naked | 44.8 | 30.2 | 23 | 44.5 |
| | ADC | 31.3 | 39 | 37.1 | ND |
| NEG0013 | Naked | 37.3 | 21.1 | 17.2 | 37 |
| | ADC | 36 | ND | ND | ND |
| NEG0016 | Naked | 60 | 26.9 | 33.6 | 60.1 |
| | ADC | 54 | ND | ND | ND |
| NEG0064 | Naked | 3.66 | 3.46 | 2.9 | 8.99 |
| | ADC | 4.4 | 6 | 6.4 | 13.3 |
| NEG0067 | Naked | 3.21 | 3.27 | 3.53 | 10.3 |
| | ADC | 6 | ND | ND | ND |

ND = Not Determined

Example 5:
NOV169N31Q-MCC-DM1/NOV169N31Q Selectivity in Biochemical Assays

To examine the potential for off-target cross-reactivity of NOV169N31Q-MCC-DM1, NOV169N31Q was evaluated for binding to two closely related classical cadherin family members with the highest degree of amino acid sequence identity in their corresponding ECDs: E-cadherin (CDH1) or N-cadherin (CDH2).

To assess specificity of binding to P-cadherin vs E-cadherin and N-cadherin, Maxisorp 384-well plates were o/n at 4° C. with recombinant human E-cadherin or N-cadherin ECD and Fab fragments were assayed using an enzyme-linked immunosorbent assay (ELISA) format. After washing, plates were blocked for 2 h with 5% skim milk in 1×PBST. Fab-containing E. coli lysates were added and binding allowed for 1 h at room temperature (RT). To detect bound Fab fragments, plates were washed 5× with TBST and AP-anti human IgG F(ab')2 was added in a 1/2500 dilution. After 1 h at RT, plates were washed 5× with TBST and AttoPhos substrate was added according to the manufacturers specifications. Plates were read in an ELISA reader 5 minutes after adding the substrate.

Utilizing ELISA methodology, no significant binding to human E-cadherin or N-cadherin was detected for the anti-P-cadherin antibody candidate NOV169N31Q.

Example 6:
NOV169N31Q-MCC-DM1/NOV169N31Q Selectivity in Biochemical Assays

To examine the potential for off-target cross-reactivity of NOV169N31Q-MCC-DM1, NOV169N31Q was evaluated for binding to two closely related classical cadherin family members with the highest degree of amino acid sequence identity in their corresponding ECDs: E-cadherin (CDH1) or N-cadherin (CDH2).

To assess specificity of binding to P-cadherin vs E-cadherin and N-cadherin, Maxisorp 384-well plates were o/n at 4° C. with recombinant human E-cadherin or N-cadherin ECD and Fab fragments were assayed using an enzyme-linked immunosorbent assay (ELISA) format. After washing, plates were blocked for 2 h with 5% skim milk in 1×PBST. Fab-containing *E. coli* lysates were added and binding allowed for 1 h at room temperature (RT). To detect bound Fab fragments, plates were washed 5× with TBST and AP-anti human IgG F(ab')$_2$ was added in a 1/2500 dilution. After 1 h at RT, plates were washed 5× with TBST and AttoPhos substrate was added according to the manufacturers specifications. Plates were read in an ELISA reader 5 minutes after adding the substrate.

Utilizing ELISA methodology, no significant binding to human E-cadherin or N-cadherin was detected for the anti-P-cadherin antibody candidate NOV169N31Q.

Example 7: Assessment of NOV169N31Q Impact on P-Cadherin Function

A study was performed to assess the ability of anti-P-cadherin antibody NOV169N31Q (a component of the antibody drug conjugate NOV169N31Q-MCC-DM1) to exert a functional effect on P-cadherin in a cellular assay. P-cadherin is a homotypic cell adhesion molecule expressed on the cell surface of cancer cells, thus a spheroid integrity assay using P-cadherin positive HCT116 cells and P-cadherin negative HT-29 cells was employed to assess potential antagonistic properties of the antibody. The read-out of this assay is shape and tightness of the spheroid, as determined by brightfield microscopy and 7-AAD fluorescence detection of cellular DNA.

HCT116 cells (P-cadherin positive) or HT29 cells (P-cadherin negative) were seeded at a density of 6,000 cells per well in 96-well round bottom ultra-low attachment plates (Corning Cat.#7007), with or without human IgG1 isotype control Ab (10 µg/mL) or NOV169N31Q (10 µg/mL). Cells were placed on an orbital shaker (60 rpm) at 37° C., 5% CO2. 7-Aminoactinomycin D (7-AAD; BD Pharmingen, Cat. #559925) was added 116 hours after cells were plated to label cellular DNA. 7-AAD imaging was performed on a GE IN Cell Analyzer 2000 using the Texas Red filter 132 hours after cells were plated. 7-9 "z" image stacks were taken of each well and the image stacks were collapsed using the IN Cell Developer Toolbox 1.8 program.

Figure 7:
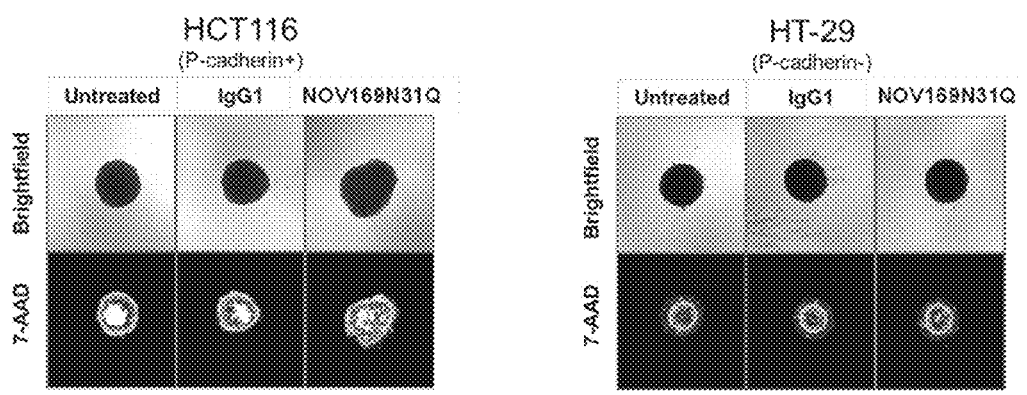
FIG. 7 depicts micrographs that illustrate the effect of P-cadherin antibody NOV169N31Q on P-cadherin mediated cellular adhesion. Cells were pre-treated with NOV169N31Q or a non-specific human IgG1 antibody prior to induction of spheroid formation. Spheroid shapes and densities were assessed by microscopy after a 132 hr incubation period.

In FIG. 7, NOV169N31Q showed a small, but discernable effect on P-cadherin-mediated cellular adhesion in P-cadherin expressing HCT116 cells, but not in P-cadherin negative HT29 cells, as evidenced by bright field microscopy and spheroid density analysis determined by 7-AAD (DNA-based) imaging. In contrast, a non-specific control human IgG1 antibody had no impact on the integrity of multicellular spheroids. Thus, NOV169N31Q may be a partial antagonist of P-cadherin function in vitro and/or in vivo.

Example 8: NOV169N31Q-MCC-DM1 Inhibition of Cell Proliferation and Survival

The ability of NOV169N31Q-MCC-DM1 to inhibit cell proliferation and survival was assessed using the CellTiter-Glo® proliferation assay.

The cell lines were cultured in media that is optimal for their growth at 5% CO$_2$, 37° C. in a tissue culture incubator. Prior to seeding for the proliferation assay, the cells were split at least 2 days before the assay to ensure optimal growth density. On the day of seeding, cells were lifted off tissue culture flasks using 0.25% trypsin. Cell viability and cell density were determined using a cell counter (Vi-Cell XR Cell Viability Analyzer, Beckman Coulter). Cells with higher than 85% viability were seeded in black-walled clear bottom 96-well plates (Corning cat #3904) at a density of 2,500 cells per well in 50 µL of standard growth media. Wells bordering the edge of plates were filled with PBS in order to minimize the effects of evaporation on well volumes. Plates were incubated at 37° C. overnight in a tissue culture incubator. The next day, free maytansine (L-DM1-Me), NOV169N31Q-MCC-DM1 and the non-targeting ADC control (IgG1-SMCC-DM1) were prepared at 2× in standard growth media. The prepared drug treatments were then added to the cells resulting in final concentrations ranging from 0-100 nM and a final volume of 100 µL, per well. Each drug concentration was tested in triplicate. Plates were incubated at 37° C. overnight or for 5 days in a tissue culture incubator, after which cell viability was assessed through the addition of 100 µL of CellTiter Glo® (Promega, cat# G7573), a reagent which lyses cells and measures total adenosine triphosphate (ATP) content. The plates were incubated in the dark at room temperature on an orbital shaker at a speed that provides adequate mixing for 3 minutes to induce cell lysis. Plates were incubated at room temperature for 10 minutes to stabilize luminescent signals prior to reading using a luminescence counter (Wallac 1450 Micro-Beta TriLux, Perkin Elmer). Luminescent counts of untreated cells were taken the day after seeding (Day 0 readings), and after 5 days of drug exposure (Day 5 readings). As an assay specification, the Day 5 readings of the untreated cells were compared to the Day 0 readings. Assays with at least one cell doubling during the incubation period were considered valid. To evaluate the effect of the drug treatments, luminescent counts from wells containing untreated cells (100% viability) were used to normalize treated samples. IC$_{50}$ values were calculated using Graph Pad Prism 6 software. Each cell line was evaluated at least 3 times and representative IC50 values are shown.

Figure 8:
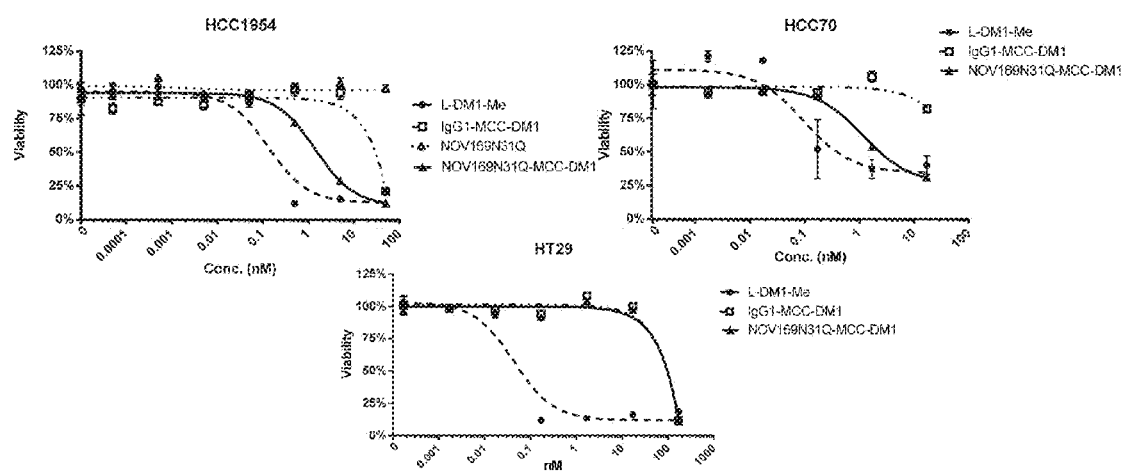
FIG. 8 depicts graphs illustrating the in vitro cytotoxic potency of NOV169N31Q-MCC-DM1 in P-cadherin positive (HCC70 and HCC1954) and negative (HT29) cell lines. In vitro dose-response of NOV169N31Q-MCC-DM1 in (A) HCC1954 (P-cadherin+), (B) HCC70 (P-cadherin+) and (C) HT29 (P-cadherin−) cells. Viability was measured after 5 days of treatment with free maytansine (L-DM1-Me; filled circle), isotype control ADC (IgG1-MCC-DM1; open square), antibody component of NOV169N31Q-MCC-DM1 (NOV169N31Q; open triangle) and NOV169N31Q-MCC-DM1 (filled triangle).

NOV169N31Q-MCC-DM1 has a target average of 3.8 molecules of DM1 bound to each antibody (Drug to Antibody Ratio, or DAR, of 3.8). The dose-response curves of 3 representative cell lines are shown (FIG. 8). The concentrations of treatment required to inhibit 50% of cell growth or survival (IC$_{50}$) were calculated, with representative IC$_{50}$ values of the cell lines tested summarized in Table 13.

The unconjugated antibody NOV169N31Q was demonstrated to be neither cytotoxic nor proliferative, while NOV169N31Q-MCC-DM1 potently inhibited proliferation and survival in P-cadherin-expressing cell lines. Neither molecule was active in the P-cadherin negative cell line HT29 (FIG. 8). In contrast, NOV169N31Q-MCC-DM1 potently inhibited growth of two breast cancer cell lines HCC1954 and HCC70. Table 13 summarizes the activity of NOV169N31Q-MCC-DM1 in a panel of cell lines. Compared with the isotype matched non-targeting control ADC (IgG1-MCC-DM1), NOV169N31Q-MCC-DM1 often showed cytotoxic activities toward cell lines that express more than >50,000 cell surface copies of P-cadherin per cell. These studies indicate that the cytotoxic effect of NOV169N31Q-MCC-DM1 is due to the internalized maytansine component of the ADC and that NOV169N31Q-MCC-DM1 specifically targets cells overexpressing P-cadherin.

TABLE 13

P-cadherin expression and NOV169N31Q-MCC-DM1 activity in a panel of human cancer cell lines. IC$_{50}$ (nM) values of NOV169N31Q-MCC-DM1 in comparison with free maytansine (L-DM1-Me) and isotype control ADC (IgG1-MCC-DM1) in the panel of cell lines. The maximum cell kill values for NOV169N31Q-MCC-DM1 are reported. The values reported here are values from individual assays which are representative of multiple replicates.

| Cell Line | Origin | Antigen Density (×1000) | IC50 (nM) NOV169N31Q-MCC-DM1 | L-DM1-Me | IgG1-MCC-DM1 | Maximum cell kill (%) NOV169N31Q-MCC-DM1 |
|---|---|---|---|---|---|---|
| scaBER | Bladder | 63 | 4.06 | 0.07 | 27.77 | 89 |
| HCC1954 | Breast | 80 | 2.28 | 0.17 | 26.68 | 88 |
| HCC38 | Breast | 95 | 5.29 | 0.09 | 35.10 | 81 |
| HCC70 | Breast | 86 | 3.23 | 0.23 | 92.58 | 69 |
| HCC1806 | Breast | 68 | 11.45 | 0.07 | 10.54 | 84 |
| BICR6 | Head and Neck | 70 | 9.62 | 0.16 | 25.34 | 71 |
| A431 | Skin | 81 | 21.76 | 0.06 | 27.28 | 83 |
| HT29 | Colon | 0.2 | 62.94 | 0.06 | 64.32 | 89 |

Example 9: In Vitro Assessment of NOV169N31Q and NOV169N31Q-MCC-DM1 Induced ADCC Activity In addition to its impact on proliferation, NOV169N31Q and NOV169N31Q-MCC-DM1 were also evaluated for their ability to mediate antibody dependent cellular cytotoxicity (ADCC).

Effector cells were untouched human natural killer (NK) cells obtained from AllCells, LLC (catalog # PB012: Fresh/Untouched Normal PB CD56+NK Cells). Target cells were obtained from American Type Culture Collection (P-cadherin positive HCC1954, P-cadherin negative HT-29) via Novartis Cell Services (NCS). HCC1954 and HT-29 target cells were lifted from tissue culture vessels using a trypsin-free cell dissociation buffer ("Cell Dissociation Buffer" from Gibco, Cat. #13151-014), washed 2-3 times with PBS, and resuspended in culture medium. Cells were counted manually or using an automated cell counter. Cells at >90% viability were suspended at 1×10$^5$ cells/mL in culture medium. Human NK cells were washed and counted in same manner as target cell lines. Effector cells were then suspended at 1-2×10$^6$ cells/mL in cell culture medium.

Treatments include NOV169N31Q antibody, matched isotype control antibody (IgG1 control), as well as antibody drug conjugates NOV169N31Q-MCC-DM1 and IgG1-SMCC-DM1. 5000 target cells in 50 µL of media were seeded in 96-well flat bottom plates (Corning #3603). Test and control antibodies were then added at 4× final concentration (final concentration range 50-0.0001 µg/mL, in addition to no treatment controls) in 25 µL media for 20 minutes at 37° C. Effector cells were then added at an effector to target cell ratio (E:T) of 5:1 in 25 µL of media (e.g., 25000 effector cells per well for 5:1 ratio). Treatments and controls (target cells only, effector cells only, no cells) were run in triplicate. Plates were then spun at 500 RPM (with no brake) in a centrifuge to concentrate cells at the bottom of plate. Plates were then incubated under normal cell culture conditions (37° C., 5% CO$_2$) for 24 hrs.

After the incubation period, media was removed from plates and wells were washed with PBS 2-3 times to remove non-adherent effector cells. 100 µL of Cell Titer Glo (Promega Cat# G7570) was added to each well, plates were shielded from light and placed on an orbital shaker for 2 minutes. Plates were then read on a luminescence counter (Wallac Trilux MicroBeta 1450). The signal detected by the luminescence counter is directly proportional to the amount of ATP or number of cells remaining in the wells. Using the control wells as a baseline, the viable cell number for each treatment can be determined as a percent of untreated control.

Figure 9:
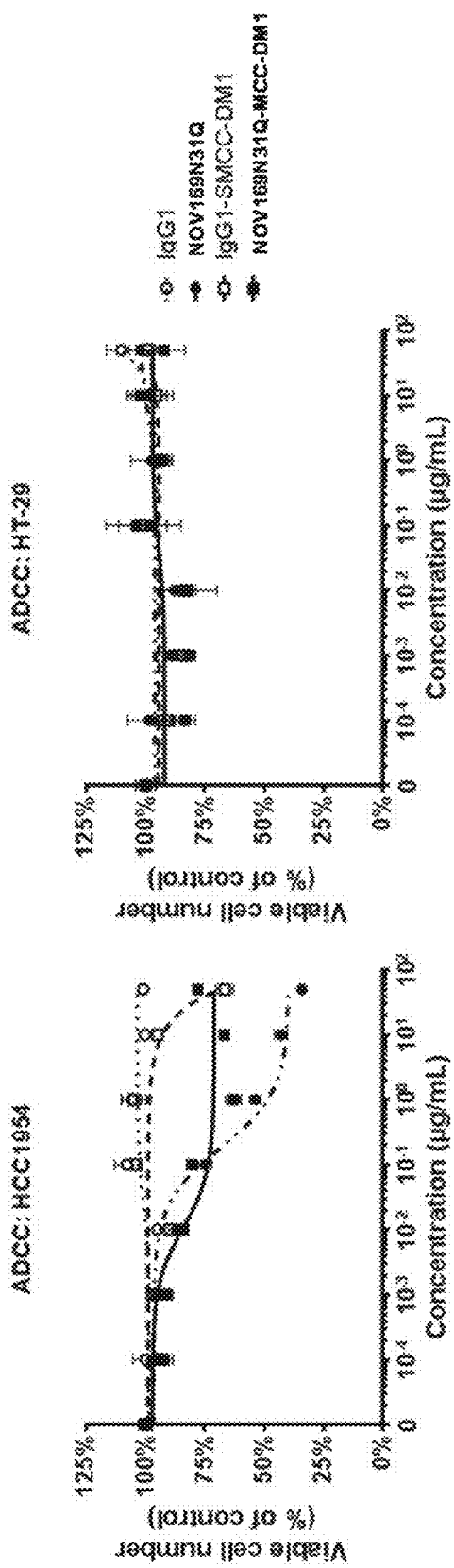
FIG. 9 depicts graphs illustrating the ADCC activity of NOV169N31Q and NOV169N31Q-MCC-DM1. Target cells were incubated with a fixed number of fresh human NK effector cells (5:1 effector to target cell ratio) and increasing amounts of NOV169N31Q (closed circles), IgG1 control antibody (open circles), NOV169N31Q-MCC-DM1 (closed squares) or IgG1-SMCC-DM1 (open squares). All samples were run in triplicate; cell viability was assessed after 24 hrs.

NOV169N31Q-MCC-DM1 and NOV169N31Q both demonstrated an ability to mediate ADCC activity against P-cadherin overexpressing cells in the presence of human natural killer (NK) cells in vitro in a dose-dependent manner (FIG. 9). This activity was found to be P-cadherin specific as a matched isotype control for both the antibody and ADC demonstrated no significant cell killing. Neither NOV169N31Q nor NOV169N31Q-MCC-DM1 show any induction of ADCC on the P-cadherin negative cell line HT-29, also indicating a specific effect of the antibody and antibody drug conjugate. Thus, in addition to the delivery of cytotoxic payload to tumor cells, ADCC represents another potential mechanism of NOV169N31Q-MCC-DM1 action for killing tumor cells in vivo.

Example 10: In Vivo on-Target Pharmacodynamic Marker Modulation by Anti-P-Cadherin ADCs A study was conducted to assess the ability of the P-cadherin ADC NOV169N31Q-MCC-DM1 to modulate a pharmacodynamic marker of G2/M arrest [accumulation of cells with phospho-histone H3 (pHH3)] in vivo. The goal was to evaluate the degree and duration of G2/M cell cycle arrest in tumors from mice treated with NOV169N31Q-MCC-DM1, an isotype control ADC or vehicle alone.

To measure the accumulation of pHH3 positive nuclei, as assessed by immunohistochemistry, a rabbit polyclonal antibody produced by immunizing animals with a synthetic phosphopeptide corresponding to residues surrounding phosphorylated Ser10 of human histone H3 (pHH3) was obtained from Cell Signaling Technology (Danvers, Mass., Cat#9701). Briefly, the IHC protocol included heat and standard exposure to Ventana Cell Conditioning #1 antigen retrieval reagent. The primary antibody was diluted to 1:50 and incubated for 60 minutes at room temperature. Subsequently, incubation with Jackson ImmunoResearch Laboratories goat anti-rabbit biotinylated secondary antibody (Cat#111-065-144, West Grove, Pa.) was performed for 32 minutes.

To assess anti-P-cadherin ADC induced PD marker changes in the HCC70 triple negative breast cancer model in a subcutaneous tumor xenograft model, female SCID-beige mice were implanted subcutaneously with 10×10⁶ cells in a suspension containing 50% Matrigel™ (BD Biosciences) in Hank's balanced salt solution.

The total injection volume containing cells in suspension was 200 µl. Mice were randomly assigned to receive a single intravenous (IV) dose of either NOV169N31Q-MCC-DM1 (10 mg/kg), non-specific IgG1-MCC-DM1 isotype control (10 mg/kg) or empty vehicle control (20 mM histidine, 8.22% sucrose, 0.02% PS-20, pH 5.6) once tumors averaged ~130 mm³ (n=3/group). Tumors were collected at time points up to 21 days post-dose. As a measure of PD response, a qualitative assessment of phospho-histone H3 (pHH3) levels was conducted by immunohistochemical staining described above.

Figure 10:
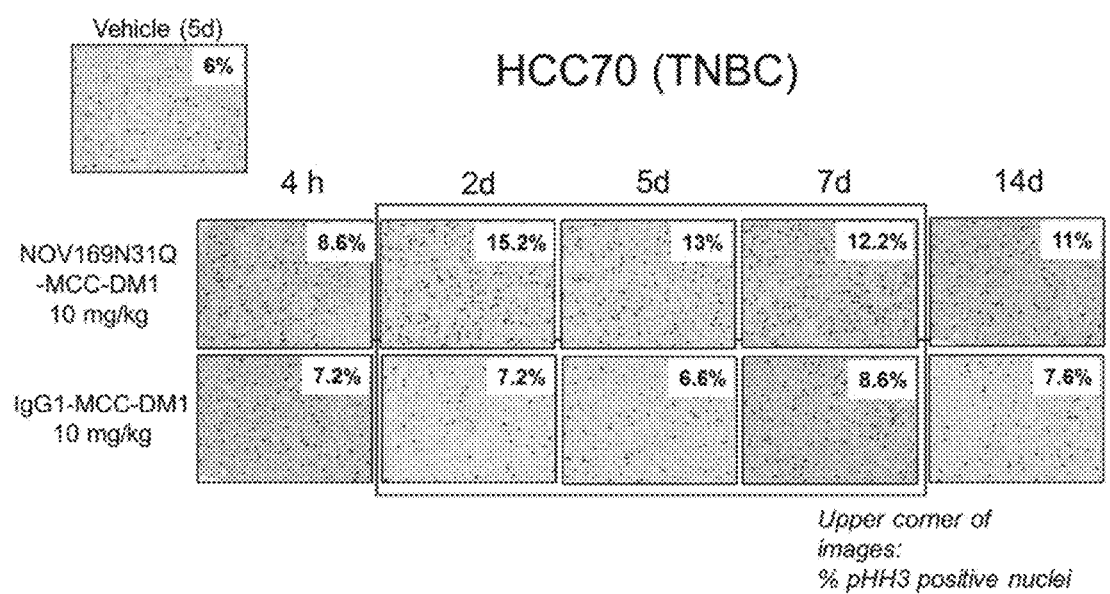
FIG. 10 depicts a series of IHC images to illustrate the activity of NOV169N31Q-MCC-DM1 ADC in the HCC70 triple negative breast cancer subcutaneous tumor xenograft model. The images illustrate mitotic arrest (p-histone H3) after single dose of NOV169N31Q-MC-DM1.

In FIG. 10, consistent with the expected mechanism of action of the maytansinoid payload, while some baseline phospho-histone H3 immunostaining staining was detected in the vehicle treated tumors, these levels were elevated following NOV169N31Q-MCC-DM1 treatment, particularly between days 2-7 post-dose. These data demonstrate that NOV169N31Q-MCC-DM1 is capable of eliciting a robust cellular PD response in tumor xenografts, consistent with the mechanism of action of the maytansinoid payload.

Example 11: In Vivo Efficacy of Anti-P-Cadherin ADCs Against the HCC70 Triple Negative Breast Cancer (TNBC) Model in Mice (ADC Efficacy Screening)

Figure 11A:
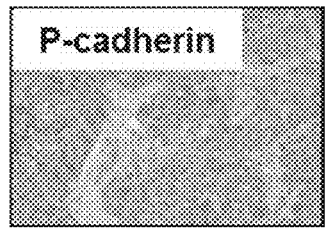
FIG. 11A depicts a representative image of IHC for P-cadherin on HCC70 tumor tissue to show expression of P-cadherin.

In breast cancers, P-cadherin is frequently highly expressed, which was exemplified by the HCC70 cell line with approximately 66,000 receptors on the surface of each cell. A representative photo of P-cadherin immunostaining on HCC70 tumors is shown to visualize the staining pattern in this xenograft model (FIG. 11A). IHC was performed using a Ventana Discovery XT autostainer. Sections of formalin fixed, paraffin embedded tumors were deparaffinized, treated with the Ventana Cell Conditioning #1 (CCIS) antigen retrieval reagent and then incubated for 60 minutes at room temperature in the primary antibody [mouse monoclonal anti-human P-cad antibody from BD Transduction Lab (Cat#610228, Lot 09934)] at a concentration of 10 ug/ml. This was followed by incubation with a biotinylated goat anti-mouse (Jackson Laboratories, cat#115-066-072, Lot#63620) used at working concentration of 1:250 was performed. Detection was performed using DAB Map Kit (Ventana Medical, cat#760-124). A non-specific mouse IgG antibody (Vector Laboratories Cat#1-2000, Lot# V0610) was used as a control to ensure that staining observed with the P-cadherin antibody was specific.

When tumors reached ~215 mm³, mice were randomized according to tumor volume into treatment groups (n=8/group) and dosed with a single IV administration of vehicle or 7 mg/kg of ADC. The 7 mg/kg dose level was selected as it was expected to provide a window to discern difference among ADC candidates in this model. Doses were adjusted to individual mouse body weights. The IV dose volume was 8 ml/kg.

Figure 11B:
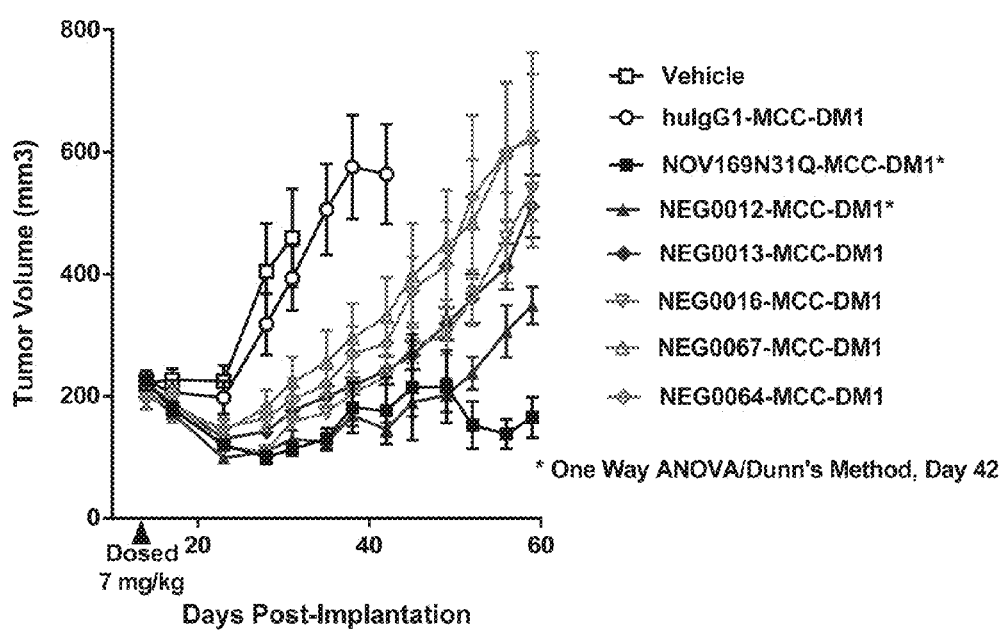
FIG. 11B depicts a graph illustrating efficacy of various P-cadherin ADCs in a HCC70 breast cancer xenograft model.

The mean tumor volumes in NEG0012-MCC-DM1 and NOV169N31Q-MCC-DM1 treated groups were significantly different from the isotype-matched huIgG1-MCC-DM1 control group on day 42 (One way ANOVA; Dunn's Method, p≤0.05). The other groups treated with ADC candidates did not show statistically different tumor volumes compared to the controls (FIG. 11B). This singled out NEG0012-MCC-DM1 and NOV169N31Q-MCC-DM1 as lead ADC candidates. No significant body weight loss was observed in any group.

Example 12: Dose Dependent In Vivo Efficacy of NOV169N31Q-MCC-DM1 Against the HCC70 Triple Negative Breast Cancer (TNBC) Model in Mice The HCC70 cell line with approximately 66,000 receptors on the surface of each cell, was shown to be sensitive to NOV169N31Q-MCC-DM1 in vitro. To demonstrate targeted anti-tumor activity by NOV169N31Q-MCC-DM1 in the HCC70 model, a single IV treatment of 2.5, 5, 10 and 15 mg/kg or 10 mg/kg of NOV169N31Q-MCC-DM1 or non-specific isotype control IgG1-MCC-DM1 was administered. HCC70 tumors were established in female SCID mice by subcutaneous injection of 10×10⁶ cells into the right flank of each mouse. When tumors reached ~143 mm³, mice were randomized according to tumor volume into treatment groups (n=9). All test agents were administered at the dose levels and schedules indicated, and doses were adjusted individual mouse body weights. The IV dose volume was 5 ml/kg.

NOV169N31Q-MCC-DM1 treatment resulted in dose proportional anti-tumor efficacy, with %ΔT/ΔC values of 48% (2.5 mg/kg), 1% (5 mg/kg), while doses of 10 and 15 mg/kg resulted in mean regression of 64% and 61%, respectively. Maximal efficacy was achieved at 10 mg/kg. The 5, 10 and 15 mg/kg groups tested statistically different from vehicle treatment (P<0.05, ANOVA on Ranks/Dunn's Method, day 59). Dose levels of 10 and 15 mg/kg elicited durable tumor regressions in mice that lasted up to 86 days post-treatment, when the study was terminated.

Figure 12:
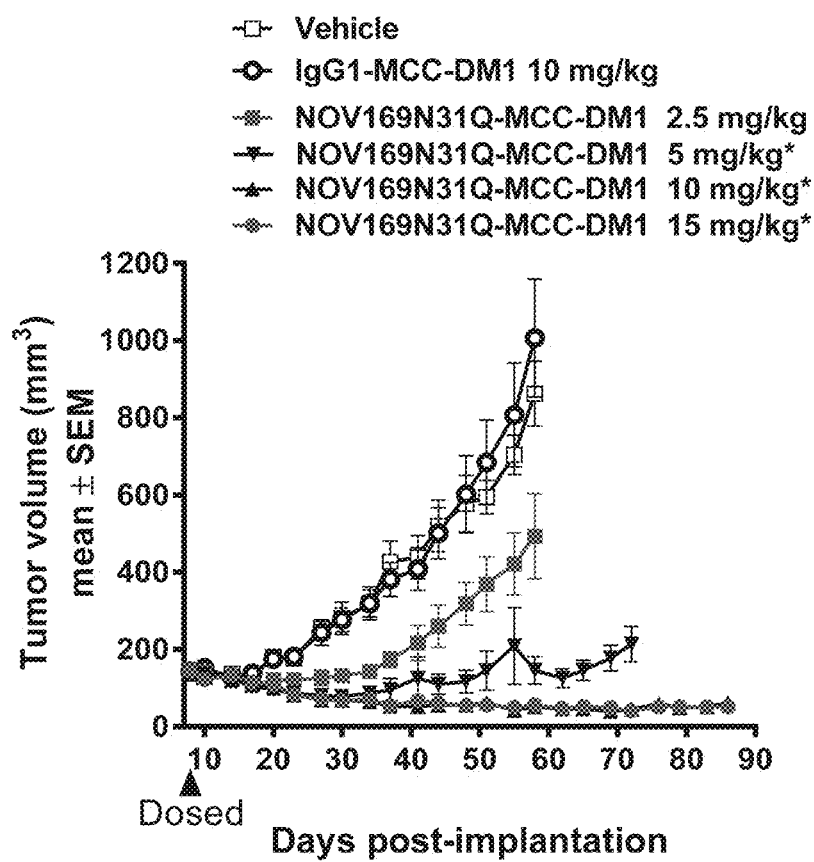
FIG. 12 depicts a graph illustrating dose response efficacy of NOV169N31Q-MCC-DM1 against a HCC70 breast cancer xenograft model.

All test agents were tolerated on study and no overt clinical symptoms of toxicities were observed in any of the treatment groups, as expected for an ADC that does not bind mouse P-cadherin. In all groups, body weight gain was observed compared to the mean body weights at randomization, and was similar to that of vehicle-treated mice, as expected for an ADC that does not bind mouse P-cadherin (FIG. 12 and Table 14).

TABLE 14

NOV169N31Q-MCC-DM1 dose response efficacy in HCC70 breast cancer xenograft model on Day 59. The effect of the treatment on tumor volumes and body weights are presented as means ± SEM. The experiment was evaluated on treatment day 59.

| | | Tumor response | | Host response | |
|---|---|---|---|---|---|
| Compound | Dose, schedule | ΔT/ΔC (%) | Regression (%) | Δ body weight (%) | Survival (alive/total) |
| Vehicle | None, Single Dose | 100 | — | 11.1 ± 1.6 | 9/9 |

TABLE 14-continued

NOV169N31Q-MCC-DM1 dose response efficacy in HCC70 breast cancer xenograft model on Day 59. The effect of the treatment on tumor volumes and body weights are presented as means ± SEM. The experiment was evaluated on treatment day 59.

| Compound | Dose, schedule | Tumor response | | Host response | |
|---|---|---|---|---|---|
| | | ΔT/ΔC (%) | Regression (%) | Δ body weight (%) | Survival (alive/total) |
| IgG1-MCC-DM1 | 10 mg/kg, Single Dose | 119 | — | 10.9 ± 1.7 | 9/9 |
| NOV169N31Q-MCC-DM1 | 2.5 mg/kg, Single Dose | 48 | — | 10.2 ± 2.5 | 9/9 |
| NOV169N31Q-MCC-DM1 | 5 mg/kg, Single Dose | 1* | — | 12.0 ± 2.4 | 8/9 |
| NOV169N31Q-MCC-DM1 | 10 mg/kg, Single Dose | — | −64* | 9.9 ± 2.3 | 9/9 |
| NOV169N31Q-MCC-DM1 | 15 mg/kg, Single Dose | — | −61* | 8.8 ± 1.9 | 9/9 |

*p < 0.001 versus vehicle (Kruskal-Wallis One Way ANOVA on Ranks/Dunn's Method).
% ΔT/ΔC = 100 ΔT/ΔC where: ΔT = mean tumor volume of the drug-treated group on Day 21 of study − mean tumor volume of the drug-treated group on initial day of dosing;
ΔC = mean tumor volume of the control group on Day 21 of study − mean tumor volume of the control group on initial day of dosing.
% Regression = (1 − Tfinal/Tinitial) × 100

Figure 13A:
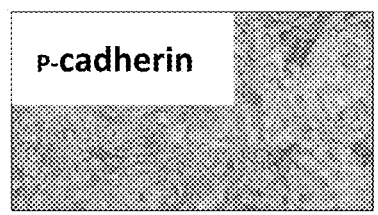
FIG. 13A depicts a representative image of IHC for P-cadherin on HCC1954 tumor tissue to show expression of P-cadherin.

Example 13: In Vivo Efficacy of NOV169N31Q-MCC-DM1 Against the HCC1954 Breast Cancer Model in Mice To demonstrate efficacy in an additional breast cancer model, NOV169N31Q-MCC-DM1 activity was evaluated in the HCC1954 basal-like (Her2+) breast cancer xenograft model in SCID-beige mice. The HCC1954 model was selected based on P-cadherin expression (84,000 receptors/cell) and sensitivity to NOV169N31Q-MCC-DM1 in vitro. Immunohistochemistry was performed to confirm the tumor P-cadherin protein levels in HCC70 tumors as described previously (FIG. 13A).

When tumors reached ~150 mm$^3$, mice were randomized according to tumor volume into treatment groups (n=9/group) and dosed with a single IV administration of vehicle or 10 mg/kg of either IgG1-MCC-DM1 or NOV169N31Q-MCC-DM1. Doses were adjusted to individual mouse body weights. The IV dose volume was 5 ml/kg.

Figure 13B:
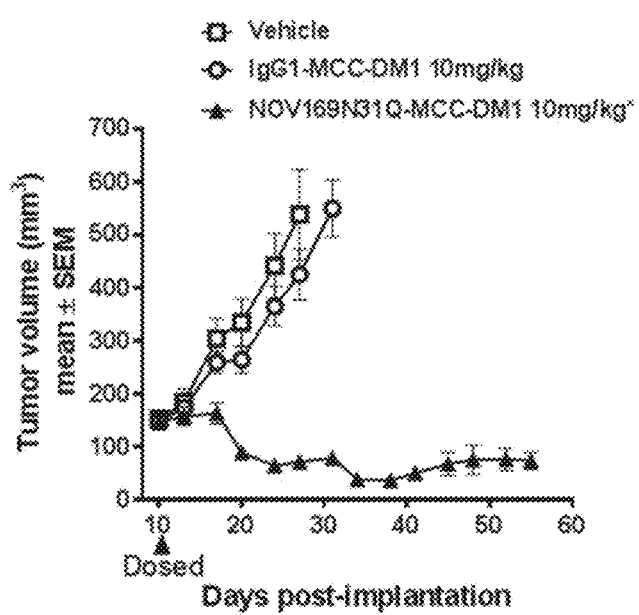
FIG. 13B is a graph illustrating efficacy of NOV169N31Q-MCC-DM1 in a HCC1954 breast cancer xenograft model.

NOV169N31Q-MCC-DM1 treatment resulted in a 56% regression of HCC1954 tumors, which was durable to day 55 (versus vehicle or IgG1-MCC-DM1, p<0.05, Kruskal-Wallis One Way ANOVA on Ranks/Dunn's Method). The efficacy of IgG1-MCC-DM1 was % ΔT/ΔC of 75% and was not significantly different from vehicle (p>0.05). All test agents were tolerated on study and no overt clinical symptoms of toxicities were observed in any of the treatment groups (FIG. 13B and Table 15A).

TABLE 15A

NOV169N31Q-MCC-DM1 efficacy in the HCC1954 breast cancer xenograft model on Day 31. The effect of the treatment on tumor volumes and body weights are presented as means ± SEM. The experiment was evaluated on treatment day 31.

| Test agent | Dose, schedule | Tumor response | | | Host response | |
|---|---|---|---|---|---|---|
| | | ΔT/ΔC (%) | Regression (%) | ΔTumor volume (mm$^3$) | Δbody weight (%) | Survival (alive/total) |
| Vehicle | None, Single Dose | 100 | — | 289 ± 49 | 4.1 ± 1.6 | 9/9 |
| IgG1-MCC-DM1 | 10 mg/kg, Single Dose | 75 | — | 218 ± 36 | 4.3 ± 1.5 | 9/9 |
| NOV169N31Q-MCC-DM1 | 10 mg/kg, Single Dose | — | −55.8* | −82 ± 10 | 4.8 ± 1.7 | 9/9 |

*p < 0.001 versus vehicle (Kruskal-Wallis One Way ANOVA on Ranks/Dunn's Method).

Figure 13C:
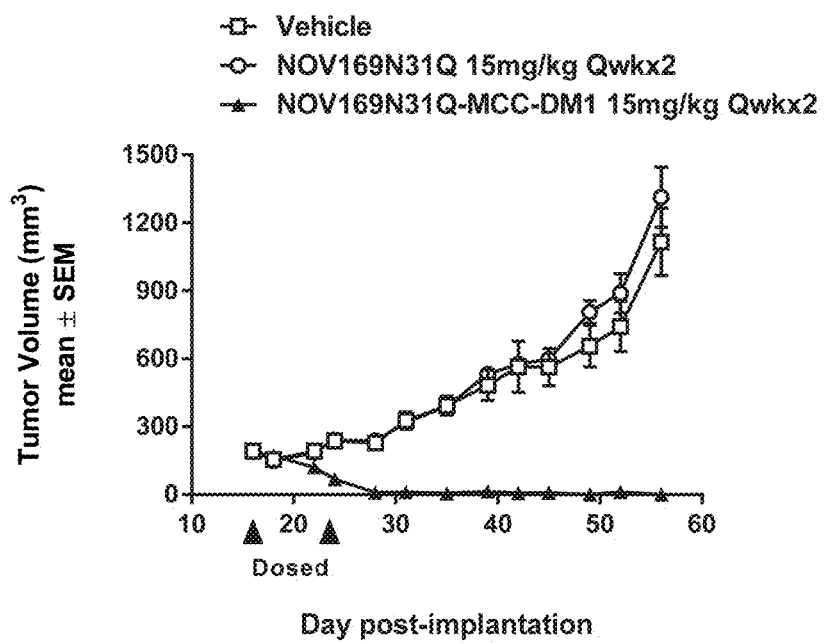
FIG. 13C is a graph illustrating efficacy of NOV169N31Q-MCC-DM1 in a HCC1954 breast cancer xenograft model.
Figure 13D:
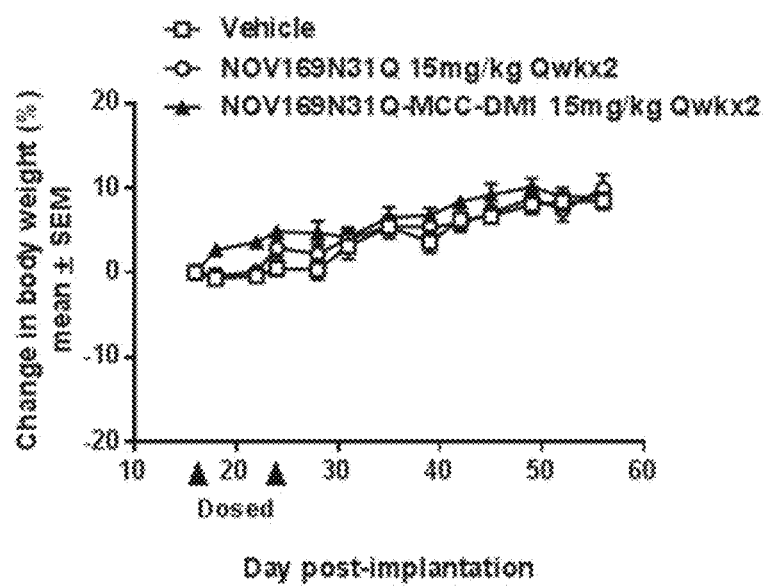
FIG. 13D is a graph depicting change in body weight of HCC1954 breast cancer xenograft mice in response to treatment using NOV169N31Q-MCC-DM1.

In another example, NOV169N31Q-MCC-DM1 activity was evaluated in the HCC1954 basal-like (Her2+) breast cancer xenograft model in SCID mice. The HCC1954 model was selected based on P-cadherin expression (84,000 receptors/cell) and sensitivity to NOV169N31Q-MCC-DM1 in vitro. When tumors reached ~190 mm$^3$, mice were randomized according to tumor volume into treatment groups (n=5/group) and dosed with two (given on Day 0 and Day 7) IV administration of vehicle, 15 mg/kg of NOV169N31Q or 15 mg/kg of NOV169N31Q-MCC-DM1. Doses were adjusted to individual mouse body weights. The IV dose volume was 10 ml/kg. NOV169N31Q-MCC-DM1 treatment resulted in a 100% regression of HCC1954 tumors, which was durable to the end of the study on day 56 (versus vehicle, p<0.05, Kruskal-Wallis One Way ANOVA on Ranks/Dunn's Method, FIG. 13C). The efficacy of NOV169N31Q was %ΔT/ΔC of 121.4% and was not significantly different from vehicle (p>0.05). All test agents were tolerated on study and no overt clinical symptoms of toxicities were observed in any of the treatment groups (FIG. 13D and Table 15B).

TABLE 15B

NOV169N31Q-MCC-DM1 efficacy in the HCC1954 breast cancer xenograft model on Day 56. The effect of the treatment on tumor volumes and body weights are presented as means ± SEM. The experiment was evaluated on treatment day 56.

| | | Tumor response | | | Host response | |
|---|---|---|---|---|---|---|
| Test agent | Dose, schedule | ΔT/ΔC (%) | Regression (%) | ΔTumor volume (mm$^3$) | Δbody weight (%) | Survival (alive/total) |
| Vehicle | None, Day 0 and 7 | 100 | — | 925 ± 147 | 8.4 ± 1.0 | 5/5 |
| NOV169N31Q | 15 mg/kg, Day 0 and 7 | 121.4 | — | 1123 ± 134 | 9.9 ± 1.7 | 5/5 |
| NOV169N31Q-MCC-DM1 | 15 mg/kg, Day 0 and 7 | −20.8 | −100* | −192 ± 9 | 9.0 ± 0.7 | 5/5 |

*p < 0.05 versus vehicle (Kruskal-Wallis One Way ANOVA on Ranks/Dunn's Method).

Figure 14A:
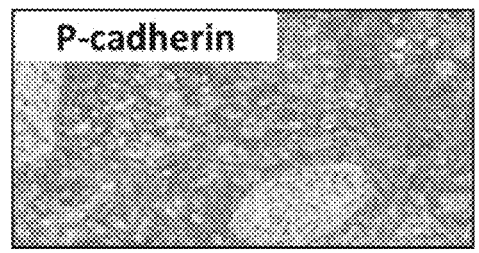
FIG. 14A depicts a representative image of IHC for P-cadherin on BICR6 tumor tissue to show expression of P-cadherin.

Example 14: In Vivo Efficacy of NOV169N31Q-MCC-DM1 Against the BICR6 Head and Neck (Hypopharynx Squamous Cell Carcinoma) Cancer Model in Mice An efficacy evaluation of NOV169N31Q-MCC-DM1 was conducted in the BICR6 cell line based on its P-cadherin expression of 70,000 receptors/cell and sensitivity to NOV169N31Q-MCC-DM1 in vitro. Immunohistochemistry was performed to confirm the tumor P-cadherin levels in BICR6 tumors as described previously, where 82% of the tumor cells stain at least 2+ for P-cadherin (FIG. 14A).

BICR6 tumors were established in female SCID-beige mice by subcutaneous engraftment of 5×10$^6$ tumor cells into the right flank of each mouse. When tumors reached ~130 mm$^3$, mice were randomized according to tumor volume into treatment groups (n=10/group) and dosed with an IV administration of vehicle or 10 mg/kg of either IgG1-MCC-DM1 or NOV169N31Q-MCC-DM1 given over a q7d schedule (q7d×2). Doses were adjusted to individual mouse body weights. The IV dose volume was 5 ml/kg.

Figure 14B:
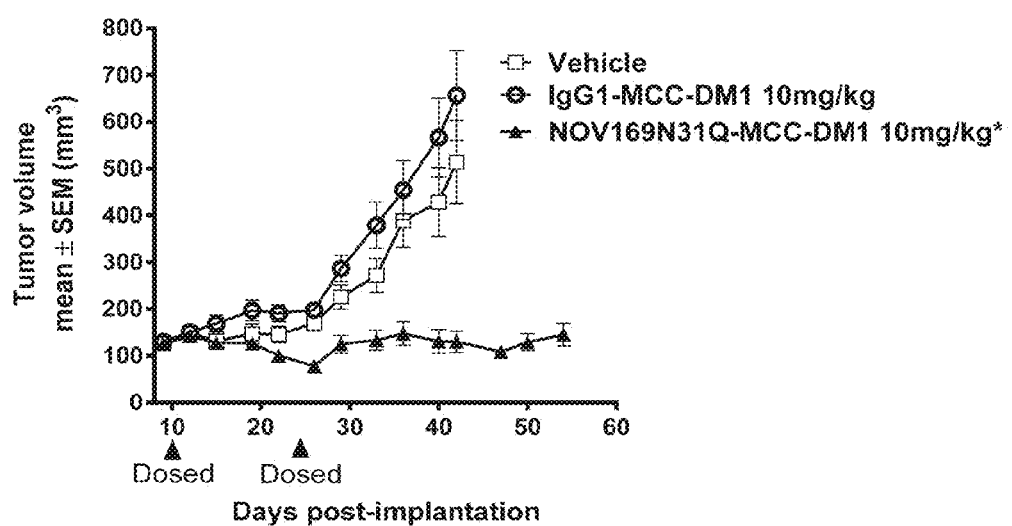
FIG. 14B depicts a graph illustrating efficacy of NOV169N31Q-MCC-DM1 in a BICR6 head and neck cancer xenograft model.

NOV169N31Q-MCC-DM1 treatment resulted in a maximal 37% tumor regression (on day 26 of study). Overall, a tumor response of stasis was durable with NOV169N31Q-MCC-DM1 (ΔT/ΔC 1%, p<0.05, Kruskal-Wallis One Way ANOVA on Ranks/Tukey's Test) for up to 42 days post-dosing. All test agents were tolerated on study and no overt clinical symptoms of toxicities were observed in any of the treatment groups (FIG. 14B and Table 16).

TABLE 16

NOV169N31Q-MCC-DM1 efficacy in the BICR6 human squamous cell carcinoma of the hypopharynx (head and neck) xenograft model on Day 42. The effect of the treatment on tumor volumes and body weights are presented as means ± SEM. The experiment was evaluated on treatment day 42.

| Test agent | Dose, schedule | Tumor response | | | Host response | |
|---|---|---|---|---|---|---|
| | | ΔT/ΔC (%) | Regression (%) | ΔTumor volume (mm$^3$) | Δbody weight (%) | Survival (alive/total) |
| Vehicle | None, Q2W × 2 | 100 | — | 386 ± 90 | 7.6 ± 1.4 | 10/10 |
| IgG1-MCC-DM1 | 10 mg/kg, Q2W × 2 | 136 | — | 526 ± 96 | 8.9 ± 1.1 | 10/10 |
| NOV169N31Q-MCC-DM1 | 10 mg/kg, Q2W × 2 | 1* | — | 5 ± 20 | 7.4 ± 2.3 | 10/10 |

*p < 0.05 versus vehicle (Kruskal-Wallis One Way ANOVA on Ranks/Tukey's Test).

Figure 15A:
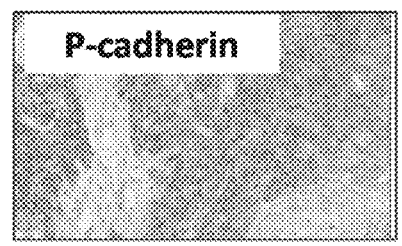
FIG. 15A depicts a representative image of IHC for P-cadherin on scaBER tumor tissue to show expression of P-cadherin.

Example 15: In Vivo Efficacy of NOV169N31Q-MCC-DM1 Against the scaBER Bladder Cancer Model in Mice The anti-tumor activity of the NOV169N31Q-MCC-DM1 was evaluated in a scaBER urinary bladder cancer xenograft model, selected based on its P-cadherin expression of 63,000 receptors/cell and sensitivity to NOV169N31Q-MCC-DM1 in vitro. Immunohistochemistry was performed to confirm the tumor P-cadherin levels in scaBER tumors, showing approximately 52% tumor cells stained at least 2+. (FIG. 15A).

scaBER tumors were established in female SCID-beige mice by subcutaneous engraftment of tumor fragments into the right flank of each mouse. When tumors reached ~130 mm$^3$, mice were randomized according to tumor volume into treatment groups (n=10/group) and dosed with an IV administration of vehicle or 10 mg/kg of either IgG1-MCC-DM1 or NOV169N31Q-MCC-DM1 given twice, two weeks apart (Q2W×2). Doses were adjusted to individual mouse body weights. The IV dose volume was 5 ml/kg.

Figure 15B:
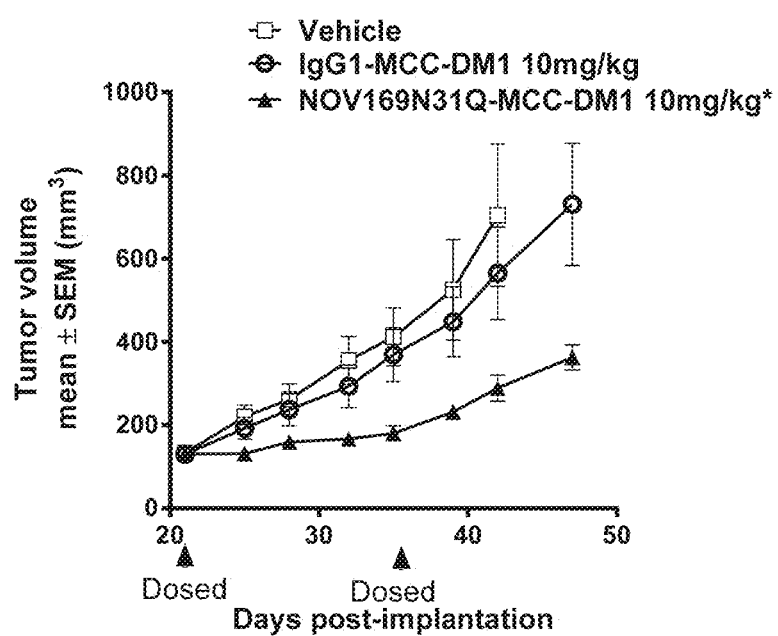
FIG. 15B depicts a graph illustrating efficacy of NOV169N31Q-MCC-DM1 in a scaBER bladder cancer xenograft model.

NOV169N31Q-MCC-DM1 treatment resulted in ΔT/ΔC of 18% (versus vehicle or IgG1-MCC-DM1, p<0.05, ANOVA/Tukey's Test, day 35). The efficacy of IgG1-MCC-DM1 was ΔT/ΔC of 86% and was not significantly different from vehicle (p>0.05). All test agents were tolerated on study and no overt clinical symptoms of toxicities were observed in any of the treatment groups (FIG. 15B and Table 17).

Example 16: In Vivo Efficacy of NOV169N31Q-MCC-DM1 Against the HuPrime® ES2267 Esophageal Cancer Model in Mice The anti-tumor activity of NOV169N31Q-MCC-DM1 was evaluated in the P-cadherin expressing ES2267 esophageal cancer xenograft model. Female BALB/c nude mice were implanted subcutaneously with tumor fragments in the right flank of each mouse. When tumors reached ~154 mm$^3$, mice were randomized according into treatment groups (n=5). NOV169N31Q-MCC-DM1 or the humanized non-specific isotype control 3207-MCC-DM1 dosed at 10 mg/kg were administered IV on Days 0 and 13 post randomization. Doses were adjusted to individual mouse body weights. The IV dose volume was 10 ml/kg.

Figure 16:
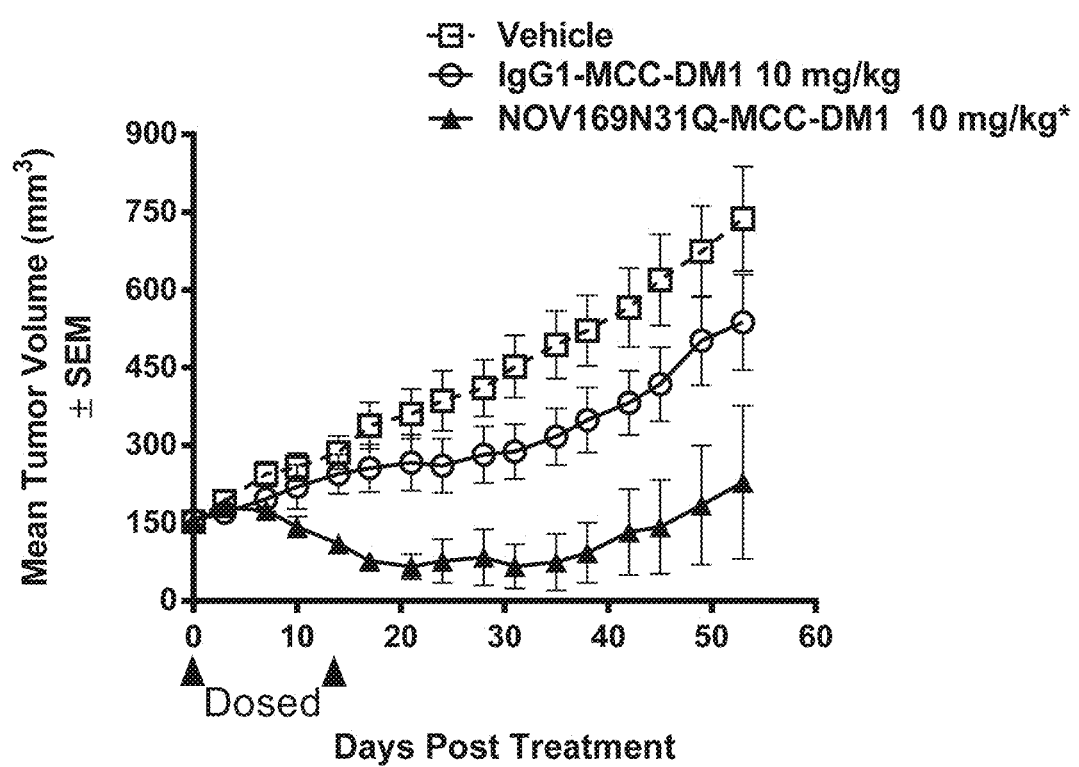
FIG. 16 depicts a graph illustrating efficacy of NOV169N31Q-MCC-DM1 in a HuPrime ED2267 esophageal cancer xenograft model.

Treatment with NOV169N31Q-MCC-DM1 at 10 mg/kg resulted in anti-tumor efficacy when compared with the vehicle with a 58% mean regression at Day 21. Moreover, no significant anti-tumor efficacy was observed after treatment with the non-specific isotype control IgG1-MCC-DM1 at 10 mg/kg. On Day 21, and on the last day of the study (Day 53), NOV169N31Q-MCC-DM1 tested statistically different from the vehicle and isotype control IgG1-MCC-DM1 treated groups (P<0.05, ANOVA/Holm-Sidak Method, Day 21). All test agents were well tolerated and no body weight loss was observed in any of the treatment groups, as expected for an ADC that does not bind mouse P-cadherin (FIG. 16 and Table 18).

TABLE 17

NOV169N31Q-MCC-DM1 efficacy in the scaBER human urinary bladder squamous carcinoma xenograft model on Day 42. The effect of the treatment on tumor volumes and body weights are presented as means ± SEM. The experiment was evaluated on treatment day 42.

| Test agent | Dose, schedule | Tumor response | | | Host response | |
|---|---|---|---|---|---|---|
| | | ΔT/ΔC (%) | Regression (%) | ΔTumor volume (mm$^3$) | Δbody weight (%) | Survival (alive/total) |
| Vehicle | None, Q2W × 2 | 100 | — | 279 ± 67 | 5.6 ± 1.9 | 10/10 |
| IgG1-MCC-DM1 | 10 mg/kg, Q2W × 2 | 86 | — | 239 ± 56 | 4.9 ± 1.8 | 10/10 |
| NOV169N31Q-MCC-DM1 | 10 mg/kg, Q2W × 2 | 18* | — | 50 ± 15 | 2.1 ± 1.5 | 10/10 |

*p < 0.001 versus vehicle (Kruskal-Wallis One Way ANOVA on Ranks/Tukey's Test).

TABLE 18

NOV169N31Q-MCC-DM1 efficacy in the HuPrime ® ES2267 esophageal cancer xenograft model on day 21 (maximal tumor regression post-dose). The effect of the treatment on tumor volumes and body weights are presented as means ± SEM. The experiment was evaluated on treatment day 21, when NOV169N31Q-MCC-DM1tumors reached their maximum regression post-treatment.

| Compound | Dose, route, schedule | Tumor response | | | Host response |
| --- | --- | --- | --- | --- | --- |
| | | Tumor Size (mm³ +/− SEM) | ΔT/ΔC (%) | Regression (%) | Survival (alive/total) |
| Vehicle | 0 mg/kg, IV, Days 0 and 13 | 361 ± 48 | 100 | — | 5/5 |
| NOV169N31Q-MCC-DM1 | 10 mg/kg, IV, Days 0 and 13 | 66 ± 24 | 43 | 58* | 5/5 |
| IgG1-MCC-DM1 | 10 mg/kg, IV, Days 0 and 13 | 267 ± 54 | 55 | — | 5/5 |

*p = 0.014 versus vehicle (One-Way ANOVA on Ranks/Holm-Sidak Method).

Example 17: Efficacy Comparison of NEG0067 Conjugated to DM1 Using Two Linkers (MCC and CX1-1) in the HCC70 Breast Cancer Xenograft Model The HCC70 breast cancer xenograft model was use to compare the anti-tumor efficacy of an anti-P-cadherin antibody NEG0067 conjugated to DM1 using the MCC versus CX-1-1 linkers. When tumors reached ~215 mm³, mice were randomized according to tumor volume into treatment groups (n=8/group) and dosed with a single IV administration of vehicle or 7 mg/kg of ADC. Doses were adjusted to individual mouse body weights. The IV dose volume was 8 ml/kg.

Figure 17:
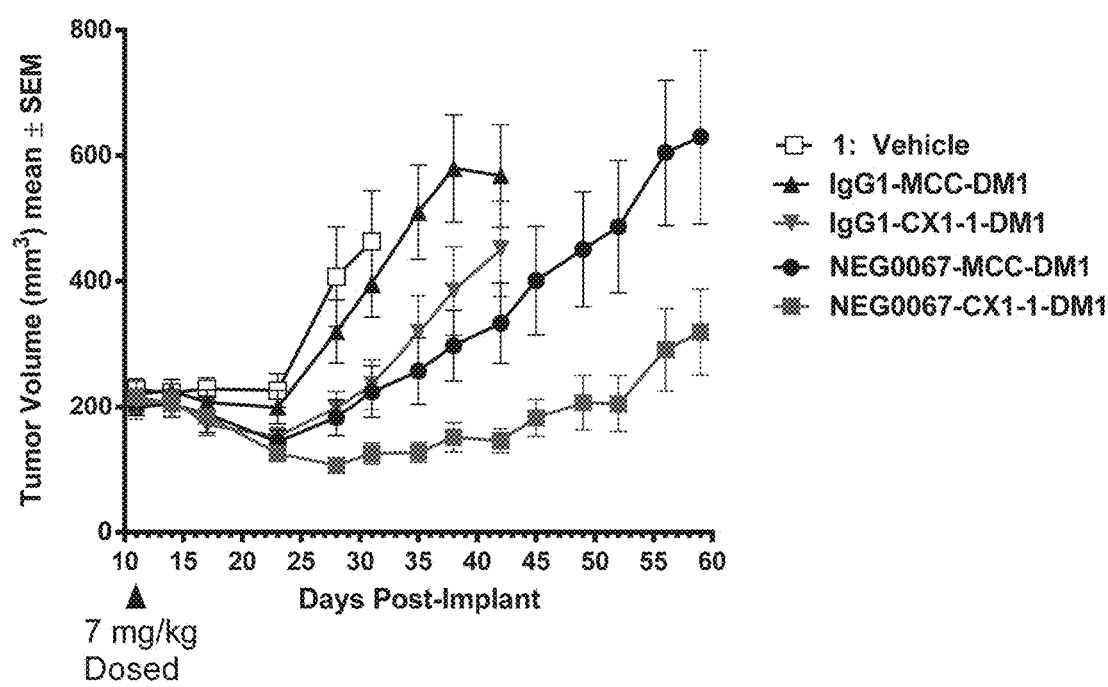
FIG. 17 depicts a graph comparing efficacy of anti-P-cadherin NEG0067 antibody conjugated to DM1 using two different linkers (MCC versus CX1-1) in the HCC70 breast cancer xenograft model.

The mean tumor volume in the NEG0067-CX1-1-DM1 group was significantly different than the control IgG1-CX1-1-DM1 group (One way ANOVA; Dunn's Method, p≤0.05), while NEG0067-MCC-DM1 was not statistically different from IgG1-MCC-DM1. However, there was a trend towards increased activity in the IgG1-CX1-1-DM1 treated group compared with the huIgG1-MCC-DM1 treated group (FIG. 17).

Example 18: Efficacy Assessment of Murine Hybridoma-Derived Anti-P-Cadherin ADCs Conjugated Using the SPDB-DM4 Linker-Payload (Cleavable Linker) in the HCC70 Breast Cancer Xenograft Model The HCC70 breast cancer xenograft model was use to compare the anti-tumor efficacy of 3 murine hybridoma-derived ADCs using the SBDB-DM4 linker-payload. When tumors reached ~150 mm³, mice were randomized according to tumor volume into treatment groups (n=10/group) and dosed with a single IV administration of vehicle or 5 mg/kg of ADC. Doses were adjusted to individual mouse body weights.

Figure 18:
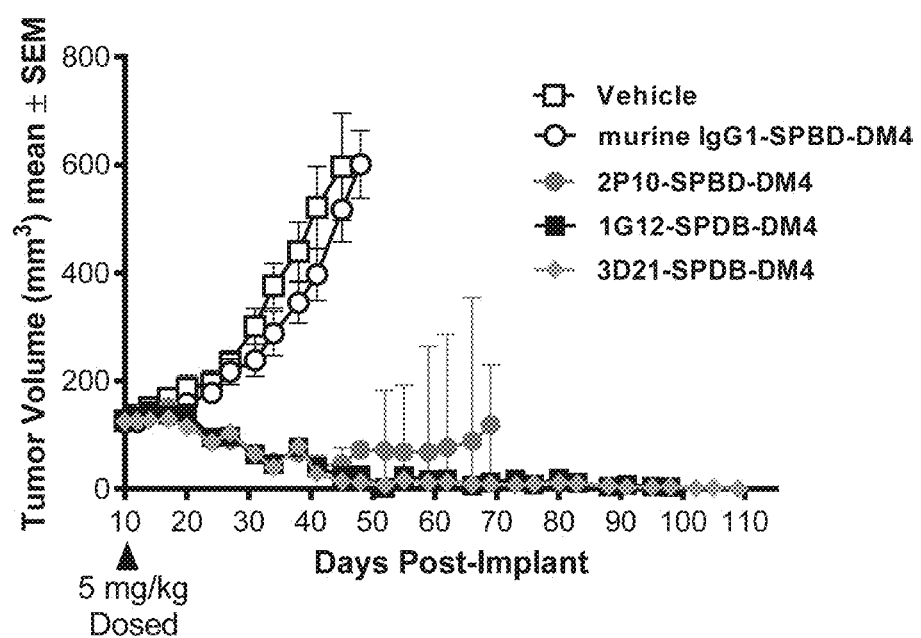
FIG. 18 depicts a graph comparing efficacy of 3 murine hybridoma-derived anti-P-cadherin ADCs conjugated using the SPDB-DM4 linker-payload in the HCC70 breast cancer xenograft model.

A single 5 mg/kg dose of all three SPDB-DM4 linked ADCs significantly induced durable tumor regressions (p≤0.05), with some tumor regrowth in the 2P10-SPDB-DM4 treated group. Tumors remained fully regressed in groups treated with 1G12-SPDB-DM4 or 3D21-SPDB-DM4 (FIG. 18).

Example 19: ADC Formulation

The clinical service form (CSF) of the ADC NOV169N31Q-MCC-DM1 is a lyophilisate in vial containing 50 mg NOV169N31Q-MCC-DM1. After reconstitution of the lyophilizate with 5 mL water for injection, a solution containing 10 mg/mL NOV169N31Q-MCC-DM1, 20 mM L-histidine/L-Histidine hydrochloride monohydrate, 240 mM sucrose and 0.02% polysorbate 20 at a pH of 5.3 is obtained.

For subsequent intravenous administration, the obtained solution will usually be further diluted into a carrier solution to the ready-to-use ADC solution for infusion.

For the CSF, an ADC concentration of 10 mg/mL was chosen. A sucrose concentration of 240 mM was selected in order to create an isotonic formulation, to maintain an amorphous lyophilizate cake structure, and to afford protein stabilization.

Important stability-indicating analytical methods to select the most stable formulation encompassed, amongst others, size-exclusion chromatography to determine aggregation levels, subvisible particulate matter testing, free Toxin determination and potency testing. The pre-screening study showed that polysorbate 20 at a concentration of 0.02% provides sufficient stabilization against mechanical stress. The liquid and lyophilized stability studies at real-time and accelerated stability conditions (25° C. and 40° C.) demonstrated that a histidine-based formulation at a pH-value between 5.0 and 5.5 provides the overall best storage stability. Notably in this range the balances of all tested formulations between aggregation and release of the free Toxin could be met. A two-month stability study at 25° C. and 40° C. demonstrated very low levels of aggregation and degradation products.

It is understood that the examples and embodiments described herein are for illustrative purposes only and that various modifications or changes in light thereof will be suggested to persons skilled in the art and are to be included within the spirit and purview of this application and the scope of the appended claims.

We claim:

1. An antibody or antigen binding fragment thereof that binds P-cadherin comprising:
   a. a heavy chain variable region (VH) that comprises a VH CDR1 of SEQ ID NO: 1, a VH CDR2 of SEQ ID NO: 2, and a VH CDR3 of SEQ ID NO: 3, wherein the CDR is defined in accordance with the Kabat definition; and a light chain variable region (VL) that comprises a VL CDR1 of SEQ ID NO: 11, a VL CDR2 of SEQ ID NO: 12, and a VL CDR3 of SEQ ID NO: 13, wherein the CDR is defined in accordance with the Kabat definition.

2. An antibody or antigen binding fragment thereof that binds P-cadherin comprising:
   a. A heavy chain variable region (VH) comprising the amino acid sequence of SEQ ID NO:7, and a light chain variable region (VL) comprising the amino acid sequence of SEQ ID NO:17.

3. An antibody or antigen binding fragment thereof that binds P-cadherin comprising:
   a. A heavy chain comprising the amino acid sequence of SEQ ID NO:9, and a light chain comprising the amino acid sequence of SEQ ID NO:19.

4. An antibody drug conjugate comprising the formula

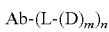

or a pharmaceutically acceptable salt thereof; wherein
   Ab is an antibody or antigen binding antigen binding fragment thereof according to claim 1;
   L is a linker;
   D is a drug moiety;
   m is an integer from 1 to 8; and
   n is an integer from 1 to 10.

5. The antibody drug conjugate of claim 4, wherein said m is 1.

6. The antibody drug conjugate of claim 4, wherein said n is 3 or 4.

7. The antibody drug conjugate of claim 4, wherein the antibody or antigen binding fragment thereof (Ab) comprises a VH region comprising the amino acid sequence of SEQ ID NO:7 and a VL region comprising the amino acid sequence of SEQ ID NO:17.

8. The antibody drug conjugate of claim 4, wherein said antibody or antigen binding fragment thereof comprises a heavy chain of SEQ ID NO: 9 and a light chain of SEQ ID NO: 19.

9. The antibody drug conjugate of claim 4, wherein said linker (L) is derived from cross-linking reagents selected from the group consisting of N-succinimidyl 4-(maleimidomethyl) cyclohexanecarboxylate (SMCC), N-succinimidyl 4-(2-pyridyldithio)butanoate (SPDB), and 2,5-dioxopyrrolidin-1-yl 17-(2,5-dioxo-2,5-dihydro-1H-pyrrol-1-yl)-5,8,11,14-tetraoxo-4,7,10,13-tetraazaheptadecan-1-oate (CX1-1).

10. The antibody drug conjugate of claim 4, wherein the drug moiety (D) is a maytansinoid.

11. The antibody drug conjugate of claim 10, wherein the maytansinoid is N(2')-deacetyl-N(2')-(3-mercapto-1-oxopropyl)-maytansine (DM1) or N(2')-deacetyl-N2-(4-mercapto-4-methyl-1-oxopentyl)-maytansine (DM4).

12. The antibody drug conjugate of claim 4 comprising the following formula:

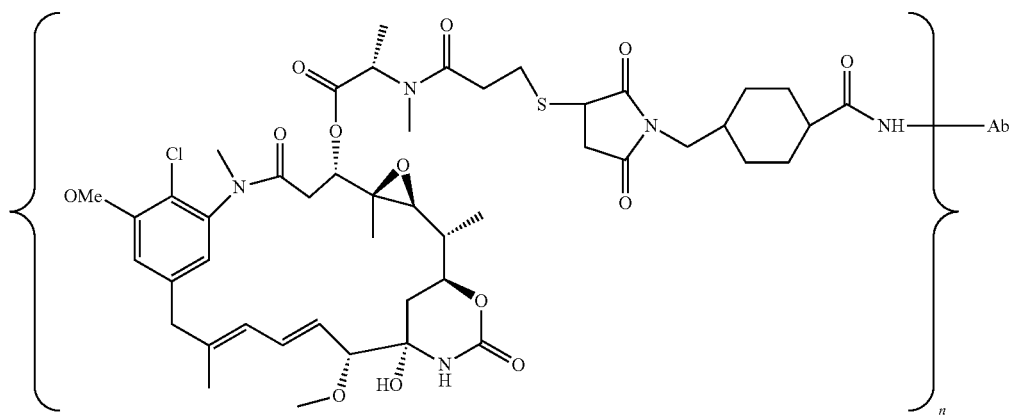

wherein Ab is an antibody or antigen binding fragment thereof that binds P-cadherin comprising a VH CDR1 of SEQ ID NO: 1, a VH CDR2 of SEQ ID NO: 2, and a VH CDR3 of SEQ ID NO: 3, and a VL CDR1 of SEQ ID NO: 11, a VL CDR2 of SEQ ID NO: 12, and a VL CDR3 of SEQ ID NO: 13, wherein the CDR is defined in accordance with the Kabat definition; and n is an integer from 1 to 10; or a pharmaceutically acceptable salt thereof.

13. A pharmaceutical composition comprising the antibody, or antigen binding fragment thereof, of claim 1 and a pharmaceutically acceptable carrier.

14. A pharmaceutical composition comprising the antibody drug conjugate of claim 4 and a pharmaceutically acceptable carrier.

15. The pharmaceutical composition of claim 14 wherein said composition is prepared as a lyophilisate.

16. The pharmaceutical composition of claim 15 wherein said lyophilisate comprises the antibody drug conjugate, histidine, sucrose, and polysorbate 20.

17. The pharmaceutical composition of claim 16 wherein the composition comprises about 10 mg/mL of the antibody drug conjugate, 20 mM histidine, 240 mM sucrose, and 0.02% polysorbate 20.

18. The antibody or antigen binding fragment of claim 1, wherein said antibody is a human or humanized antibody.

19. The antibody or antigen binding fragment of claim 1, wherein said antibody is a monoclonal antibody.

20. The antibody or antigen binding fragment of claim 1, wherein said antibody or antigen binding fragment is a single chain antibody (scFv).

21. A diagnostic reagent comprising the antibody or antigen binding fragment thereof according to claim 1.

22. The diagnostic reagent of claim 21, wherein the antibody or antigen binding fragment thereof is labeled with a radiolabel, a fluorophore, a chromophore, an imaging agent, or a metal ion.

\* \* \* \* \*

SEQUENCE LISTING

<160> NUMBER OF SEQ ID NOS: 143

<210> SEQ ID NO 1
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ser Gln Ser Ala Ala Trp Asn
1               5

<210> SEQ ID NO 2
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Arg Ile Tyr Tyr Arg Ser Lys Trp Tyr Asn Asp Tyr Ala Leu Ser Val
1               5                   10                  15

Lys Ser

<210> SEQ ID NO 3
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly Glu Gly Tyr Gly Arg Glu Gly Phe Ala Ile
1               5                   10

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Asp Ser Val Ser Ser Gln Ser Ala
1               5

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Tyr Tyr Arg Ser Lys Trp Tyr
1               5

<210> SEQ ID NO 6
<211> LENGTH: 11
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 6

Gly Glu Gly Tyr Gly Arg Glu Gly Phe Ala Ile
1               5                   10

<210> SEQ ID NO 7
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Gln
            20                  25                  30

Ser Ala Ala Trp Asn Trp Ile Arg Gln Ser Pro Ser Arg Gly Leu Glu
        35                  40                  45

Trp Leu Gly Arg Ile Tyr Tyr Arg Ser Lys Trp Tyr Asn Asp Tyr Ala
    50                  55                  60

Leu Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Gly Glu Gly Tyr Gly Arg Glu Gly Phe Ala Ile
            100                 105                 110

Trp Gly Gln Gly Thr Leu Val Thr Val Ser Ser
        115                 120

<210> SEQ ID NO 8
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8
caggtgcagc tgcagcagtc aggccctggc ctggtcaagc ctagtcagac cctgagcctg    60
acctgcgcta ttagcggcga tagtgtgtct agtcagtcag ccgcctggaa ctggattaga   120
cagtcaccct ctaggggcct ggagtggctg ggtagaatct actataggtc taagtggtat   180
aacgactacg ccctgagcgt gaagtctagg atcactatta accccgacac ctctaagaat   240
cagtttagcc tgcagctgaa tagcgtgacc cccgaggaca ccgccgtcta ctactgcgct   300
agaggcgagg gctacggtag agagggcttc gctatctggg gtcagggcac cctggtcacc   360
gtgtctagc                                                          369

<210> SEQ ID NO 9
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9
```

```
Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Gln
            20                  25                  30

Ser Ala Ala Trp Asn Trp Ile Arg Gln Ser Pro Ser Arg Gly Leu Glu
        35                  40                  45

Trp Leu Gly Arg Ile Tyr Tyr Arg Ser Lys Trp Tyr Asn Asp Tyr Ala
    50                  55                  60

Leu Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
            85                  90                  95

Tyr Tyr Cys Ala Arg Gly Glu Gly Tyr Gly Arg Glu Gly Phe Ala Ile
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
            165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
            195                 200                 205

Asn His Lys Pro Ser Asn Thr Lys Val Asp Lys Arg Val Glu Pro Lys
            210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
            275                 280                 285

Glu Val His Asn Ala Lys Thr Lys Pro Arg Glu Glu Gln Tyr Asn Ser
            290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
            355                 360                 365

Val Ser Leu Thr Cys Leu Val Lys Gly Phe Tyr Pro Ser Asp Ile Ala
            370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415
```

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 10
<211> LENGTH: 1359
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10
caggtgcagc tgcagcagtc aggccctggc ctggtcaagc ctagtcagac cctgagcctg      60
acctgcgcta ttagcggcga tagtgtgtct agtcagtcag ccgcctggaa ctggattaga     120
cagtcaccct ctaggggcct ggagtggctg gtagaatct actataggtc taagtggtat      180
aacgactacg ccctgagcgt gaagtctagg atcactatta accccgacac ctctaagaat    240
cagtttagcc tgcagctgaa tagcgtgacc cccgaggaca ccgccgtcta ctactgcgct    300
agaggcgagg gctacggtag agagggcttc gctatctggg gtcagggcac cctggtcacc    360
gtgtctagcg ctagcactaa gggcccaagt gtgtttcccc tggcccccag cagcaagtct    420
acttccggcg aactgctgc cctgggttgc ctggtgaagg actacttccc cgagcccgtg      480
acagtgtcct ggaactctgg ggctctgact tccggcgtgc acaccttccc cgccgtgctg    540
cagagcagcg gcctgtacag cctgagcagc gtggtgacag tgccctccag ctctctggga    600
acccagacct atatctgcaa cgtgaaccac aagcccagca acaccaaggt ggacaagaga    660
gtggagccca gagctgcga caagacccac acctgccccc cctgcccagc tccagaactg      720
ctgggagggc cttccgtgtt cctgttcccc ccaagcccca aggacaccct gatgatcagc    780 aggaccccg aggtgacctg cgtggtggtg gacgtgtccc acgaggaccc agaggtgaag      840
ttcaactggt acgtggacgg cgtggaggtg cacaacgcca agaccaagcc cagagaggag    900
cagtacaaca gcacctacag ggtggtgtcc gtgctgaccg tgctgcacca ggactggctg    960
aacggcaaag aatacaagtg caaagtctcc aacaaggccc tgccagcccc aatcgaaaag    1020
acaatcagca aggccaaggg ccagccacgg gagccccagg tgtacaccct gcccccagc    1080 cgggaggaga tgaccaagaa ccaggtgtcc ctgacctgtc tggtgaaggg cttctacccc    1140
agcgatatcg ccgtggagtg ggagagcaac ggccagcccg agaacaacta caagaccacc    1200
cccccagtgc tggacagcga cggcagcttc ttcctgtaca gcaagctgac cgtggacaag    1260
tccaggtggc agcagggcaa cgtgttcagc tgcagcgtga tgcacgaggc cctgcacaac    1320
cactacaccc agaagtccct gagcctgagc cccggcaag                            1359

<210> SEQ ID NO 11
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Arg Ala Ser Gln Thr Ile Ser Asn Thr Leu Ala
1               5                   10

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Ala Ala Ser Asn Leu Gln Ser
1               5

<210> SEQ ID NO 13
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gln Gln Tyr Leu Ser Trp Phe Thr
1               5

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ser Gln Thr Ile Ser Asn Thr
1               5

<210> SEQ ID NO 15
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Ala Ala Ser
1

<210> SEQ ID NO 16
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Tyr Leu Ser Trp Phe
1               5

<210> SEQ ID NO 17
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Thr Ile Ser Asn Thr
            20                  25                  30

Leu Ala Trp Tyr Gln Gln Lys Pro Gly Lys Ala Pro Lys Leu Leu Ile
        35                  40                  45

Tyr Ala Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Ser Trp Phe Thr
                85                  90                  95

Phe Gly Gln Gly Thr Lys Val Glu Ile Lys
            100                 105

<210> SEQ ID NO 18
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18
gatattcaga tgactcagtc acctagtagc ctgagcgcta gtgtgggcga tagagtgact      60
atcacctgta gagcctctca gactatctct aacaccctgg cctggtatca gcagaagccc     120
ggtaaagccc ctaagctgct gatctacgcc gcctctaacc tgcagtcagg cgtgccctct     180
aggtttagcg gtagcggtag tggcaccgac ttcaccctga ctattagtag cctgcagccc     240
gaggacttcg ctacctacta ctgtcagcag tacctgagct ggttcacctt cggtcagggc     300
actaaggtcg agattaag                                                   318

<210> SEQ ID NO 19
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Thr Ile Ser Asn Thr
            20                  25                  30

Leu Ala Trp Tyr Gln Gln Lys Pro Gly Lys Ala Pro Lys Leu Leu Ile
        35                  40                  45

Tyr Ala Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Ser Trp Phe Thr
                85                  90                  95

Phe Gly Gln Gly Thr Lys Val Glu Ile Lys Arg Thr Val Ala Ala Pro
            100                 105                 110

```
Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
            195                 200                 205

Asn Arg Gly Glu Cys
    210

<210> SEQ ID NO 20
<211> LENGTH: 639
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20
gatattcaga tgactcagtc acctagtagc ctgagcgcta gtgtgggcga tagagtgact      60
atcacctgta gagcctctca gactatctct aacaccctgg cctggtatca gcagaagccc     120
ggtaaagccc ctaagctgct gatctacgcc gcctctaacc tgcagtcagg cgtgccctct     180
aggtttagcg gtagcggtag tggcaccgac ttcaccctga ctattagtag cctgcagccc     240
gaggacttcg ctacctacta ctgtcagcag tacctgagct ggttcacctt cggtcagggc     300
actaaggtcg agattaagcg tacggtggcc gctcccagcg tgttcatctt cccccccagc     360
gacgagcagc tgaagagcgg caccgccagc gtggtgtgcc tgctgaacaa cttctacccc     420
cgggaggcca aggtgcagtg gaaggtggac aacgccctgc agagcggcaa cagccaggag     480
agcgtcaccg agcaggacag caaggactcc acctacagcc tgagcagcac cctgaccctg     540
agcaaggccg actacgagaa gcataaggtg tacgcctgcg aggtgaccca ccagggcctg     600
tccagccccg tgaccaagag cttcaacagg ggcgagtgc                            639

<210> SEQ ID NO 21
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Asp His Thr Ile His
1               5

<210> SEQ ID NO 22
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22
```

Tyr Ile Tyr Pro Arg Ser Gly Ser Ile Asn Tyr Asn Glu Lys Phe Lys
1               5                   10                  15

Gly

<210> SEQ ID NO 23
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Arg Asn Leu Phe Leu Pro Met Glu Tyr
1               5

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Gly Tyr Thr Phe Thr Asp His
1               5

<210> SEQ ID NO 25
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Tyr Pro Arg Ser Gly Ser
1               5

<210> SEQ ID NO 26
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Arg Asn Leu Phe Leu Pro Met Glu Tyr
1               5

<210> SEQ ID NO 27
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Glu Val Gln Leu Val Gln Ser Gly Ala Glu Val Lys Lys Pro Gly Glu
1               5                   10                  15

Ser Leu Lys Ile Ser Cys Lys Val Ser Gly Tyr Thr Phe Thr Asp His
            20                  25                  30

Thr Ile His Trp Met Arg Gln Met Pro Gly Lys Gly Leu Glu Trp Met

```
                35                  40                  45
Gly Tyr Ile Tyr Pro Arg Ser Gly Ser Ile Asn Tyr Asn Glu Lys Phe
        50                  55                  60

Lys Gly Gln Val Thr Ile Ser Ala Asp Lys Ser Ser Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Arg Asn Leu Phe Leu Pro Met Glu Tyr Trp Gly Gln Gly Thr
            100                 105                 110

Leu Val Thr Val Ser Ser
            115

<210> SEQ ID NO 28
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 28
gaggtgcagc tggtgcagtc aggcgccgaa gtgaagaagc ccggcgagtc actgaagatt      60
agctgtaaag tctcaggcta caccttcacc gatcacacta ttcactggat gagacagatg     120
cccggtaaag gcctggagtg gatgggctat atctacccta gatcaggctc tattaactat     180
aacgagaagt ttaagggtca ggtcacaatt agcgccgata agtctagctc taccgcctac     240
ctgcagtggt ctagcctgaa ggctagtgac accgctatgt actactgcgc tagacgtaac     300
ctgttcctgc ctatggaata ctggggtcag ggcaccctgg tcaccgtgtc tagc          354

<210> SEQ ID NO 29
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Glu Val Gln Leu Val Gln Ser Gly Ala Glu Val Lys Lys Pro Gly Glu
1               5                   10                  15

Ser Leu Lys Ile Ser Cys Lys Val Ser Gly Tyr Thr Phe Thr Asp His
            20                  25                  30

Thr Ile His Trp Met Arg Gln Met Pro Gly Lys Gly Leu Glu Trp Met
        35                  40                  45

Gly Tyr Ile Tyr Pro Arg Ser Gly Ser Ile Asn Tyr Asn Glu Lys Phe
        50                  55                  60

Lys Gly Gln Val Thr Ile Ser Ala Asp Lys Ser Ser Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Arg Asn Leu Phe Leu Pro Met Glu Tyr Trp Gly Gln Gly Thr
            100                 105                 110

Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
```

| | | | | | | | | | | | |
|---|---|---|---|---|---|---|---|---|---|---|---|
| | 145 | | | | 150 | | | | 155 | | 160 |
| Ser | Gly | Ala | Leu | Thr | Ser | Gly | Val | His | Thr | Phe | Pro | Ala | Val | Leu | Gln |

Ser Gly Ala Leu Thr Ser Gly Val His Thr Phe Pro Ala Val Leu Gln
                 165                    170                 175

Ser Ser Gly Leu Tyr Ser Leu Ser Ser Val Val Thr Val Pro Ser Ser
                 180                    185                 190

Ser Leu Gly Thr Gln Thr Tyr Ile Cys Asn Val Asn His Lys Pro Ser
                 195                    200                 205

Asn Thr Lys Val Asp Lys Arg Val Glu Pro Lys Ser Cys Asp Lys Thr
210                    215                    220

His Thr Cys Pro Pro Cys Pro Ala Pro Glu Leu Leu Gly Gly Pro Ser
225                    230                    235                 240

Val Phe Leu Phe Pro Pro Lys Pro Lys Asp Thr Leu Met Ile Ser Arg
                 245                    250                 255

Thr Pro Glu Val Thr Cys Val Val Val Asp Val Ser His Glu Asp Pro
                 260                    265                 270

Glu Val Lys Phe Asn Trp Tyr Val Asp Gly Val Glu Val His Asn Ala
                 275                    280                 285

Lys Thr Lys Pro Arg Glu Glu Gln Tyr Asn Ser Thr Tyr Arg Val Val
                 290                    295                 300

Ser Val Leu Thr Val Leu His Gln Asp Trp Leu Asn Gly Lys Glu Tyr
305                    310                    315                 320

Lys Cys Lys Val Ser Asn Lys Ala Leu Pro Ala Pro Ile Glu Lys Thr
                 325                    330                 335

Ile Ser Lys Ala Lys Gly Gln Pro Arg Glu Pro Gln Val Tyr Thr Leu
                 340                    345                 350

Pro Pro Ser Arg Glu Glu Met Thr Lys Asn Gln Val Ser Leu Thr Cys
                 355                    360                 365

Leu Val Lys Gly Phe Tyr Pro Ser Asp Ile Ala Val Glu Trp Glu Ser
                 370                    375                 380

Asn Gly Gln Pro Glu Asn Asn Tyr Lys Thr Thr Pro Pro Val Leu Asp
385                    390                    395                 400

Ser Asp Gly Ser Phe Phe Leu Tyr Ser Lys Leu Thr Val Asp Lys Ser
                 405                    410                 415

Arg Trp Gln Gln Gly Asn Val Phe Ser Cys Ser Val Met His Glu Ala
                 420                    425                 430

Leu His Asn His Tyr Thr Gln Lys Ser Leu Ser Leu Ser Pro Gly Lys
                 435                    440                 445

<210> SEQ ID NO 30
<211> LENGTH: 1344
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 30

```
gaggtgcagc tggtgcagtc aggcgccgaa gtgaagaagc ccggcgagtc actgaagatt      60
agctgtaaag tctcaggcta cacccttcacc gatcacacta ttcactggat gagacagatg     120
cccggtaaag gcctggagtg gatgggctat atctacccta gatcaggctc tattaactat     180
aacgagaagt ttaagggtca ggtcacaatt agcgccgata agtctagctc taccgcctac     240
ctgcagtggt ctagcctgaa ggctagtgac accgctatgt actactgcgc tagacgtaac     300
ctgttcctgc ctatggaata ctgggggtcag ggcacccctgg tcaccgtgtc tagcgctagc     360
```

```
actaagggcc caagtgtgtt tcccctggcc cccagcagca agtctacttc cggcggaact    420
gctgccctgg gttgcctggt gaaggactac ttccccgagc ccgtgacagt gtcctggaac    480 tctgggctc tgacttccgg cgtgcacacc ttccccgccg tgctgcagag cagcggcctg    540
tacagcctga gcagcgtggt gacagtgccc tccagctctc tgggaaccca gacctatatc    600
tgcaacgtga accacaagcc cagcaacacc aaggtggaca gagagtgga gcccaagagc    660 tgcgacaaga cccacacctg cccccccctgc ccagctccag aactgctggg agggccttcc    720
gtgttcctgt tcccccccaa gcccaaggac accctgatga tcagcaggac ccccgaggtg    780
acctgcgtgg tggtggacgt gtcccacgag acccagagg tgaagttcaa ctggtacgtg    840
gacggcgtgg aggtgcacaa cgccaagacc aagcccagag aggagcagta caacagcacc    900
tacagggtgg tgtccgtgct gaccgtgctg caccaggact ggctgaacgg caaagaatac    960
aagtgcaaag tctccaacaa ggccctgcca gccccaatcg aaaagacaat cagcaaggcc   1020
aagggccagc cacgggagcc ccaggtgtac accctgcccc cagccggga ggagatgacc   1080 aagaaccagg tgtccctgac ctgtctggtg aagggcttct accccagcga tatcgccgtg   1140
gagtgggaga gcaacggcca gcccgagaac aactacaaga ccaccccccc agtgctggac   1200
agcgacggca gcttcttcct gtacagcaag ctgaccgtgg acaagtccag gtggcagcag   1260
ggcaacgtgt tcagctgcag cgtgatgcac gaggccctgc acaaccacta cacccagaag   1320
tccctgagcc tgagccccgg caag                                          1344
```

<210> SEQ ID NO 31
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Arg Ser Ser Gln Ser Leu Leu Ser Ser Gly Asp Gln Lys Asn Tyr Leu
1               5                   10                  15

Thr

<210> SEQ ID NO 32
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Trp Ala Ser Thr Arg Glu Ser
1               5

<210> SEQ ID NO 33
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Gln Asn Asp Tyr Arg Tyr Pro Leu Thr
1               5

```
<210> SEQ ID NO 34
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Ser Gln Ser Leu Leu Ser Ser Gly Asp Gln Lys Asn Tyr
1               5                   10

<210> SEQ ID NO 35
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Trp Ala Ser
1

<210> SEQ ID NO 36
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Asp Tyr Arg Tyr Pro Leu
1               5

<210> SEQ ID NO 37
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Leu Ser Ser
                20                  25                  30

Gly Asp Gln Lys Asn Tyr Leu Thr Trp Tyr Leu Gln Lys Pro Gly Gln
            35                  40                  45

Ser Pro Gln Leu Leu Ile Tyr Trp Ala Ser Thr Arg Glu Ser Gly Val
        50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Gln Asn
                85                  90                  95

Asp Tyr Arg Tyr Pro Leu Thr Phe Gly Gln Gly Thr Lys Leu Glu Ile
            100                 105                 110

Lys

<210> SEQ ID NO 38
<211> LENGTH: 339
<212> TYPE: DNA
```

<213> ORGANISM: Artificial Sequence
<220> FEATURE:
<223> OTHER INFORMATION: Description of Artificial Sequence: Synthetic polynucleotide

<400> SEQUENCE: 38

```
gatatcgtga tgactcagac ccccctgagc ctgcccgtga cccctggcga gcctgcctct      60
attagctgta gatctagtca gtcactgctg tctagcggcg atcagaagaa ctacctgacc     120
tggtatctgc agaagcccgg tcagtcacct cagctgctga tctactgggc ctctactaga     180
gaatcaggcg tgcccgatag gtttagcggt agcggtagtg gcaccgactt caccctgaag     240
atctctaggg tggaagccga ggacgtgggc gtctactact gtcagaacga ctatagatac     300
cccctgacct tcggtcaggg cactaagctg gagattaag                            339
```

<210> SEQ ID NO 39
<211> LENGTH: 220
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 39

```
Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Leu Ser Ser
            20                  25                  30

Gly Asp Gln Lys Asn Tyr Leu Thr Trp Tyr Leu Gln Lys Pro Gly Gln
        35                  40                  45

Ser Pro Gln Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Gln Asn
                85                  90                  95

Asp Tyr Arg Tyr Pro Leu Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220
```

<210> SEQ ID NO 40
<211> LENGTH: 660
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 40

```
gatatcgtga tgactcagac cccctgagc ctgcccgtga cccctggcga gcctgcctct    60
attagctgta gatctagtca gtcactgctg tctagcggcg atcagaagaa ctacctgacc   120
tggtatctgc agaagcccgg tcagtcacct cagctgctga tctactgggc ctctactaga   180
gaatcaggcg tgcccgatag gtttagcggt agcggtagtg gcaccgactt caccctgaag   240
atctctaggg tggaagccga ggacgtgggc gtctactact gtcagaacga ctatagatac   300
cccctgacct tcggtcaggg cactaagctg gagattaagc gtacggtggc cgctcccagc   360
gtgttcatct cccccccag cgacgagcag ctgaagagcg gcaccgccag cgtggtgtgc   420
ctgctgaaca acttctaccc ccgggaggcc aaggtgcagt ggaaggtgga caacgccctg   480
cagagcggca cagccagga gagcgtcacc gagcaggaca gcaaggactc cacctacagc   540
ctgagcagca ccctgaccct gagcaaggcc gactacgaga agcataaggt gtacgcctgc   600
gaggtgaccc ccagggcct gtccagcccc gtgaccaaga gcttcaacag gggcgagtgc   660
```

<210> SEQ ID NO 41
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Asp His Thr Ile His
1               5

<210> SEQ ID NO 42
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Tyr Ile Tyr Pro Arg Ser Gly Ser Ile Asn Tyr Asn Glu Lys Phe Lys
1               5                   10                  15

Gly

<210> SEQ ID NO 43
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Arg Asn Leu Phe Leu Pro Met Glu Tyr
1               5

<210> SEQ ID NO 44
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Gly Tyr Thr Phe Thr Asp His
1               5

<210> SEQ ID NO 45
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Tyr Pro Arg Ser Gly Ser
1               5

<210> SEQ ID NO 46
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Arg Asn Leu Phe Leu Pro Met Glu Tyr
1               5

<210> SEQ ID NO 47
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Glu Val Gln Leu Val Gln Ser Gly Ala Glu Val Lys Lys Pro Gly Glu
1               5                   10                  15

Ser Leu Lys Ile Ser Cys Lys Val Ser Gly Tyr Thr Phe Thr Asp His
            20                  25                  30

Thr Ile His Trp Met Arg Gln Met Pro Gly Lys Gly Leu Glu Trp Met
        35                  40                  45

Gly Tyr Ile Tyr Pro Arg Ser Gly Ser Ile Asn Tyr Asn Glu Lys Phe
    50                  55                  60

Lys Gly Gln Val Thr Ile Ser Ala Asp Lys Ser Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Arg Asn Leu Phe Leu Pro Met Glu Tyr Trp Gly Gln Gly Thr
            100                 105                 110

Leu Val Thr Val Ser Ser
        115

<210> SEQ ID NO 48
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 48

```
gaggtgcagc tggtgcagtc aggcgccgaa gtgaagaagc ccggcgagtc actgaagatt    60
agctgtaaag tctcaggcta caccttcacc gatcacacta ttcactggat gagacagatg   120
cccggtaaag gcctggagtg gatgggctat atctacccta gatcaggctc tattaactat   180
aacgagaagt ttaagggtca ggtcacaatt agcgccgata gtctagctc taccgcctac    240 ctgcagtggt ctagcctgaa ggctagtgac accgctatgt actactgcgc tagacgtaac   300
ctgttcctgc ctatggaata ctggggtcag ggcaccctgg tcaccgtgtc tagc         354
```

```
<210> SEQ ID NO 49
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49
```

```
Glu Val Gln Leu Val Gln Ser Gly Ala Glu Val Lys Lys Pro Gly Glu
1               5                   10                  15

Ser Leu Lys Ile Ser Cys Lys Val Ser Gly Tyr Thr Phe Thr Asp His
            20                  25                  30

Thr Ile His Trp Met Arg Gln Met Pro Gly Lys Gly Leu Glu Trp Met
        35                  40                  45

Gly Tyr Ile Tyr Pro Arg Ser Gly Ser Ile Asn Tyr Asn Glu Lys Phe
    50                  55                  60

Lys Gly Gln Val Thr Ile Ser Ala Asp Lys Ser Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Arg Asn Leu Phe Leu Pro Met Glu Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300
```

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 50
<211> LENGTH: 1344
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 50
gaggtgcagc tggtgcagtc aggcgccgaa gtgaagaagc ccggcgagtc actgaagatt      60
agctgtaaag tctcaggcta caccttcacc gatcacacta ttcactggat gagacagatg     120
cccggtaaag gcctggagtg gatgggctat atctacccta gatcaggctc tattaactat     180
aacgagaagt ttaagggtca ggtcacaatt agcgccgata gtctagctc taccgcctac      240 ctgcagtggt ctagcctgaa ggctagtgac accgctatgt actactgcgc tagacgtaac     300
ctgttcctgc ctatggaata ctggggtcag ggcaccctgg tcaccgtgtc tagcgctagc     360
actaagggcc caagtgtgtt tcccctggcc ccagcagca agtctacttc cggcggaact      420
gctgccctgg gttgcctggt gaaggactac ttccccgagc ccgtgacagt gtcctggaac     480
tctggggctc tgacttccgg cgtgcacacc ttccccgccg tgctgcagag cagcggcctg     540
tacagcctga gcagcgtggt gacagtgccc tccagctctc tgggaaccca gacctatatc     600
tgcaacgtga accacaagcc cagcaacacc aaggtggaca gagagtgga gcccaagagc     660 tgcgacaaga cccacacctg ccccccctgc ccagctccag aactgctggg agggccttcc     720
gtgttcctgt tcccccccaa gcccaaggac accctgatga tcagcaggac ccccgaggtg     780
acctgcgtgg tggtggacgt gtcccacgag acccagagg tgaagttcaa ctggtacgtg     840
gacggcgtgg aggtgcacaa cgccaagacc aagcccagag aggagcagta caacagcacc     900
tacagggtgg tgtccgtgct gaccgtgctg caccaggact ggctgaacgg caaagaatac     960
aagtgcaaag tctccaacaa ggccctgcca gccccaatcg aaaagacaat cagcaaggcc    1020
aagggccagc cacgggagcc ccaggtgtac accctgcccc cagccgggga ggagatgacc    1080
aagaaccagg tgtccctgac ctgtctggtg aagggcttct accccagcga tatcgccgtg    1140
gagtgggaga gcaacggcca gcccgagaac aactacaaga ccaccccccc agtgctggac    1200

```
agcgacggca gcttcttcct gtacagcaag ctgaccgtgg acaagtccag gtggcagcag    1260
ggcaacgtgt tcagctgcag cgtgatgcac gaggccctgc acaaccacta cacccagaag    1320
tccctgagcc tgagccccgg caag                                            1344
```

<210> SEQ ID NO 51
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

```
Arg Ser Ser Gln Ser Leu Leu Ser Ser Gly Asn Gln Lys Asn Tyr Leu
1               5                   10                  15

Thr
```

<210> SEQ ID NO 52
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

```
Trp Ala Ser Thr Arg Glu Ser
1               5
```

<210> SEQ ID NO 53
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

```
Gln Asn Asp Tyr Ser Tyr Pro Leu Thr
1               5
```

<210> SEQ ID NO 54
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

```
Ser Gln Ser Leu Leu Ser Ser Gly Asn Gln Lys Asn Tyr
1               5                   10
```

<210> SEQ ID NO 55
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

```
Trp Ala Ser
1
```

<210> SEQ ID NO 56
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Asp Tyr Ser Tyr Pro Leu
1               5

<210> SEQ ID NO 57
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Leu Ser Ser
            20                  25                  30

Gly Asn Gln Lys Asn Tyr Leu Thr Trp Tyr Leu Gln Lys Pro Gly Gln
        35                  40                  45

Ser Pro Gln Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Gln Asn
                85                  90                  95

Asp Tyr Ser Tyr Pro Leu Thr Phe Gly Gln Gly Thr Lys Leu Glu Ile
            100                 105                 110

Lys

<210> SEQ ID NO 58
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 58
gatatcgtga tgactcagac ccccctgagc ctgcccgtga cccctggcga gcctgcctct      60
attagctgta gatctagtca gtcactgctg tctagcggta atcagaagaa ctacctgacc     120
tggtatctgc agaagcccgg tcagtcacct cagctgctga tctactgggc ctctactaga     180
gaatcaggcg tgcccgatag gtttagcggt agcggtagtg gcaccgactt caccctgaag     240
atctctaggg tggaagccga ggacgtgggc gtctactact gtcagaacga ctatagctac     300
cccctgacct tcggtcaggg cactaagctg gagattaag                             339

<210> SEQ ID NO 59
<211> LENGTH: 220
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

```
Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Leu Ser Ser
            20                  25                  30

Gly Asn Gln Lys Asn Tyr Leu Thr Trp Tyr Leu Gln Lys Pro Gly Gln
        35                  40                  45

Ser Pro Gln Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Gln Asn
                85                  90                  95

Asp Tyr Ser Tyr Pro Leu Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220
```

<210> SEQ ID NO 60
<211> LENGTH: 660
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 60

```
gatatcgtga tgactcagac cccctgagc ctgcccgtga ccctggcga gcctgcctct    60
attagctgta gatctagtca gtcactgctg tctagcggta atcagaagaa ctacctgacc   120
tggtatctgc agaagcccgg tcagtcacct cagctgctga tctactgggc ctctactaga   180
gaatcaggcg tgcccgatag gtttagcggt agcggtagtg gcaccgactt caccctgaag   240
atctctaggg tggaagccga ggacgtgggc gtctactact gtcagaacga ctatagctac   300
cccctgacct tcggtcaggg cactaagctg gagattaagc gtacggtggc cgctcccagc   360
gtgttcatct tccccccag cgacgagcag ctgaagagcg gcaccgccag cgtggtgtgc   420
ctgctgaaca acttctaccc ccgggaggcc aaggtgcagt ggaaggtgga caacgccctg   480
cagagcggca cagccagga gagcgtcacc gagcaggaca gcaaggactc cacctacagc   540
ctgagcagca ccctgaccct gagcaaggcc gactacgaga agcataaggt gtacgcctgc   600
gaggtgaccc accagggcct gtccagcccc gtgaccaaga gcttcaacag gggcgagtgc   660
```

<210> SEQ ID NO 61

```
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Asp His Thr Leu His
1               5

<210> SEQ ID NO 62
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Tyr Ile Tyr Pro Arg Ser Gly Ser Thr Lys Tyr Asn Glu Asn Phe Arg
1               5                   10                  15

Gly

<210> SEQ ID NO 63
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Arg Leu Leu Phe Leu Pro Leu Asp Tyr
1               5

<210> SEQ ID NO 64
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Gly Tyr Thr Phe Thr Asp His
1               5

<210> SEQ ID NO 65
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Tyr Pro Arg Ser Gly Ser
1               5

<210> SEQ ID NO 66
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 66

Arg Leu Leu Phe Leu Pro Leu Asp Tyr
1               5

<210> SEQ ID NO 67
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Gln Ile Gln Leu Val Gln Ser Gly Ala Glu Val Lys Lys Pro Gly Ser
1               5                   10                  15

Ser Val Lys Val Ser Cys Lys Val Ser Gly Tyr Thr Phe Thr Asp His
            20                  25                  30

Thr Leu His Trp Met Arg Gln Ala Pro Gly Gln Gly Leu Glu Trp Met
        35                  40                  45

Gly Tyr Ile Tyr Pro Arg Ser Gly Ser Thr Lys Tyr Asn Glu Asn Phe
    50                  55                  60

Arg Gly Arg Val Thr Ile Thr Ala Asp Thr Ser Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Leu Leu Phe Leu Pro Leu Asp Tyr Trp Gly Gln Gly Thr
            100                 105                 110

Leu Val Thr Val Ser Ser
        115

<210> SEQ ID NO 68
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 68
cagattcagc tggtgcagtc aggcgccgaa gtgaagaaac ccggctctag cgtgaaagtc       60
agctgtaaag tctcaggcta caccttcacc gatcacaccc tgcactggat gagacaggcc      120
ccaggtcagg gcctggagtg gatgggctat atctacccta gatcaggctc tactaagtat      180
aacgagaact ttaggggtag agtgactatc accgccgaca ctagctctag caccgcctat      240
atggaactgt ctagcctgag atcagaggac accgccgtct actactgcgc tagacggctg      300
ctgttcctgc ccctggacta ctggggtcag ggcacccctgg tcaccgtgtc tagc           354

<210> SEQ ID NO 69
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Gln Ile Gln Leu Val Gln Ser Gly Ala Glu Val Lys Lys Pro Gly Ser
1               5                   10                  15

Ser Val Lys Val Ser Cys Lys Val Ser Gly Tyr Thr Phe Thr Asp His
            20                  25                  30
```

```
Thr Leu His Trp Met Arg Gln Ala Pro Gly Gln Gly Leu Glu Trp Met
         35                  40                  45

Gly Tyr Ile Tyr Pro Arg Ser Gly Ser Thr Lys Tyr Asn Glu Asn Phe
 50                  55                  60

Arg Gly Arg Val Thr Ile Thr Ala Asp Thr Ser Ser Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Arg Leu Leu Phe Leu Pro Leu Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445
```

<210> SEQ ID NO 70
<211> LENGTH: 1344
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 70

```
cagattcagc tggtgcagtc aggcgccgaa gtgaagaaac ccggctctag cgtgaaagtc      60
agctgtaaag tctcaggcta caccttcacc gatcacaccc tgcactggat gagacaggcc     120
ccaggtcagg gcctggagtg gatgggctat atctacccta gatcaggctc tactaagtat     180
aacgagaact ttaggggtag agtgactatc accgccgaca ctagctctag caccgcctat     240
atggaactgt ctagcctgag atcagaggac accgccgtct actactgcgc tagacggctg     300
ctgttcctgc ccctggacta ctggggtcag ggcaccctgg tcaccgtgtc tagcgctagc     360
actaagggcc caagtgtgtt tcccctggcc ccagcagca agtctacttc ggcggaact      420
gctgccctgg gttgcctggt gaaggactac ttccccgagc ccgtgacagt gtcctggaac     480
tctgggctc tgacttccgg cgtgcacacc ttccccgccg tgctgcagag cagcggcctg     540
tacagcctga gcagcgtggt gacagtgccc tccagctctc tgggaaccca gacctatatc     600
tgcaacgtga accacaagcc cagcaacacc aaggtggaca gagagtggac gcccaagagc     660
tgcgacaaga cccacacctg ccccccctgc ccagctccag aactgctggg agggccttcc     720
gtgttcctgt tccccccaa gcccaaggac accctgatga tcagcaggac ccccgaggtg     780
acctgcgtgg tggtggacgt gtcccacgag gacccagagg tgaagttcaa ctggtacgtg     840
gacggcgtgg aggtgcacaa cgccaagacc aagcccagag aggagcagta caacagcacc     900
tacagggtgg tgtccgtgct gaccgtgctg caccaggact ggctgaacgg caaagaatac     960
aagtgcaaag tctccaacaa ggcccctgcca gccccaatcg aaaagacaat cagcaaggcc    1020
aagggccagc cacgggagcc ccaggtgtac accctgcccc cagccggga ggagatgacc     1080
aagaaccagg tgtccctgac ctgtctggtg aagggcttct accccagcga tatcgccgtg    1140
gagtgggaga gcaacggcca gcccgagaac aactacaaga ccaccccccc agtgctggac    1200
agcgacggca gcttcttcct gtacagcaag ctgaccgtgg acaagtccag gtggcagcag    1260
ggcaacgtgt tcagctgcag cgtgatgcac gaggccctgc acaaccacta cacccagaag    1320
tccctgagcc tgagccccgg caag                                           1344
```

<210> SEQ ID NO 71
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 71

Arg Ser Ser Gln Ser Leu Leu Ser Ser Gly Asn Gln Lys Ser Tyr Leu
1               5                   10                  15

Thr

<210> SEQ ID NO 72
<211> LENGTH: 7
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 72

Trp Ala Ser Thr Arg Glu Ser
1               5

<210> SEQ ID NO 73
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Gln Asn Asp Tyr Ser Tyr Pro Phe Thr
1               5

<210> SEQ ID NO 74
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Ser Gln Ser Leu Leu Ser Ser Gly Asn Gln Lys Ser Tyr
1               5                   10

<210> SEQ ID NO 75
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Trp Ala Ser
1

<210> SEQ ID NO 76
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Asp Tyr Ser Tyr Pro Phe
1               5

<210> SEQ ID NO 77
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Glu Ile Val Met Thr Gln Ser Pro Ala Thr Leu Ser Leu Ser Pro Gly
1               5                   10                  15

Glu Arg Ala Thr Leu Ser Cys Arg Ser Ser Gln Ser Leu Leu Ser Ser
```

```
            20                  25                  30
Gly Asn Gln Lys Ser Tyr Leu Thr Trp Tyr Gln Gln Lys Pro Gly Gln
            35                  40                  45

Ala Pro Arg Leu Leu Ile Tyr Trp Ala Ser Thr Arg Glu Ser Gly Ile
        50                  55                  60

Pro Ala Arg Phe Ser Gly Ser Gly Ser Gly Thr Asp Phe Thr Leu Thr
65                  70                  75                  80

Ile Ser Ser Leu Gln Pro Glu Asp Phe Ala Val Tyr Tyr Cys Gln Asn
                85                  90                  95

Asp Tyr Ser Tyr Pro Phe Thr Phe Gly Gln Gly Thr Lys Leu Glu Ile
            100                 105                 110

Lys

<210> SEQ ID NO 78
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 78
gagatcgtga tgactcagtc acccgctacc ctgagcctga gccctggcga gagagctaca    60
ctgagctgta gatctagtca gtcactgctg tctagcggta atcagaagtc ctacctgacc   120
tggtatcagc agaagcccgg tcaggcccct agactgctga tctactgggc tctactaga    180 gagtcaggga tccccgctag gtttagcggt agcggtagtg gcaccgactt caccctgact   240
atctctagcc tgcagcccga ggacttcgcc gtctactact gtcagaacga ctatagctac   300
cccttcacct tcggtcaggg cactaagctg gagattaag                          339

<210> SEQ ID NO 79
<211> LENGTH: 220
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Glu Ile Val Met Thr Gln Ser Pro Ala Thr Leu Ser Leu Ser Pro Gly
1               5                   10                  15

Glu Arg Ala Thr Leu Ser Cys Arg Ser Ser Gln Ser Leu Leu Ser Ser
            20                  25                  30

Gly Asn Gln Lys Ser Tyr Leu Thr Trp Tyr Gln Gln Lys Pro Gly Gln
            35                  40                  45

Ala Pro Arg Leu Leu Ile Tyr Trp Ala Ser Thr Arg Glu Ser Gly Ile
        50                  55                  60

Pro Ala Arg Phe Ser Gly Ser Gly Ser Gly Thr Asp Phe Thr Leu Thr
65                  70                  75                  80

Ile Ser Ser Leu Gln Pro Glu Asp Phe Ala Val Tyr Tyr Cys Gln Asn
                85                  90                  95

Asp Tyr Ser Tyr Pro Phe Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140
```

```
Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
        210                 215                 220

<210> SEQ ID NO 80
<211> LENGTH: 660
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 80
gagatcgtga tgactcagtc acccgctacc ctgagcctga gccctggcga gagagctaca    60
ctgagctgta gatctagtca gtcactgctg tctagcggta atcagaagtc ctacctgacc   120
tggtatcagc agaagcccgg tcaggcccct agactgctga tctactgggc ctctactaga   180
gagtcaggga tccccgctag gtttagcggt agcggtagtg gcaccgactt caccctgact   240
atctctagcc tgcagcccga ggacttcgcc gtctactact gtcagaacga ctatagctac   300
cccttcacct tcggtcaggg cactaagctg gagattaagc gtacggtggc cgctcccagc   360
gtgttcatct cccccccag cgacgagcag ctgaagagcg gcaccgccag cgtggtgtgc    420
ctgctgaaca acttctaccc ccgggaggcc aaggtgcagt ggaaggtgga caacgccctg   480
cagagcggca acagccagga gagcgtcacc gagcaggaca gcaaggactc cacctacagc   540
ctgagcagca ccctgaccct gagcaaggcc gactacgaga agcataaggt gtacgcctgc   600
gaggtgaccc accagggcct gtccagcccc gtgaccaaga gcttcaacag gggcgagtgc   660

<210> SEQ ID NO 81
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Asp His Thr Leu His
1               5

<210> SEQ ID NO 82
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Tyr Ile Tyr Pro Arg Ser Gly Ser Thr Lys Tyr Asn Glu Asn Phe Arg
1               5                   10                  15

Gly
```

<210> SEQ ID NO 83
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Arg Leu Leu Phe Leu Pro Leu Asp Tyr
1               5

<210> SEQ ID NO 84
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Gly Tyr Thr Phe Thr Asp His
1               5

<210> SEQ ID NO 85
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Tyr Pro Arg Ser Gly Ser
1               5

<210> SEQ ID NO 86
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Arg Leu Leu Phe Leu Pro Leu Asp Tyr
1               5

<210> SEQ ID NO 87
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Gln Ile Gln Leu Val Gln Ser Gly Ala Glu Val Lys Lys Pro Gly Ser
1               5                   10                  15

Ser Val Lys Val Ser Cys Lys Val Ser Gly Tyr Thr Phe Thr Asp His
            20                  25                  30

Thr Leu His Trp Met Arg Gln Ala Pro Gly Gln Gly Leu Glu Trp Met
        35                  40                  45

Gly Tyr Ile Tyr Pro Arg Ser Gly Ser Thr Lys Tyr Asn Glu Asn Phe
    50                  55                  60

Arg Gly Arg Val Thr Ile Thr Ala Asp Thr Ser Ser Thr Ala Tyr
65                  70                  75                  80

Met Glu Leu Ser Ser Leu Arg Ser Glu Asp Thr Ala Val Tyr Tyr Cys
                85                  90                  95

Val Arg Arg Leu Leu Phe Leu Pro Leu Asp Tyr Trp Gly Gln Gly Thr
            100                 105                 110

Leu Val Thr Val Ser Ser
        115

<210> SEQ ID NO 88
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 88
cagattcagc tggtgcagtc aggcgccgaa gtgaagaaac ccggctctag cgtgaaagtc        60
agctgtaaag tctcaggcta caccttcacc gatcacaccc tgcactggat gagacaggcc       120
ccaggtcagg gcctggagtg gatgggctat atctacccta gatcaggctc tactaagtat       180
aacgagaact ttaggggtag agtgactatc accgccgaca ctagctctag caccgcctat       240
atggaactgt ctagcctgag atcagaggac accgccgtct actactgcgt cagacggctg       300
ctgttcctgc ccctggacta ctggggtcag ggcaccctgg tcaccgtgtc tagc             354

<210> SEQ ID NO 89
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Gln Ile Gln Leu Val Gln Ser Gly Ala Glu Val Lys Lys Pro Gly Ser
1               5                   10                  15

Ser Val Lys Val Ser Cys Lys Val Ser Gly Tyr Thr Phe Thr Asp His
            20                  25                  30

Thr Leu His Trp Met Arg Gln Ala Pro Gly Gln Gly Leu Glu Trp Met
        35                  40                  45

Gly Tyr Ile Tyr Pro Arg Ser Gly Ser Thr Lys Tyr Asn Glu Asn Phe
    50                  55                  60

Arg Gly Arg Val Thr Ile Thr Ala Asp Thr Ser Ser Thr Ala Tyr
65                  70                  75                  80

Met Glu Leu Ser Ser Leu Arg Ser Glu Asp Thr Ala Val Tyr Tyr Cys
                85                  90                  95

Val Arg Arg Leu Leu Phe Leu Pro Leu Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

```
Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 90
<211> LENGTH: 1344
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 90
cagattcagc tggtgcagtc aggcgccgaa gtgaagaaac ccggctctag cgtgaaagtc      60
agctgtaaag tctcaggcta caccttcacc gatcacaccc tgcactggat gagacaggcc    120
ccaggtcagg gcctggagtg gatgggctat atctacccta gatcaggctc tactaagtat    180
aacgagaact ttaggggtag agtgactatc accgccgaca ctagctctag caccgcctat    240
atggaactgt ctagcctgag atcagaggac accgccgtct actactgcgt cagacggctg    300
ctgttcctgc ccctggacta ctggggtcag ggcaccctgg tcaccgtgtc tagcgctagc    360
actaagggcc caagtgtgtt tcccctggcc ccagcagca agtctacttc cggcggaact    420
gctgccctgg gttgctggt gaaggactac ttccccgagc cgtgacagt gtcctggaac    480 tctggggctc tgacttccgg cgtgcacacc ttccccgccg tgctgcagag cagcggcctg    540
```

-continued

```
tacagcctga gcagcgtggt gacagtgccc tccagctctc tgggaaccca gacctatatc      600
tgcaacgtga accacaagcc cagcaacacc aaggtggaca agagagtgga gcccaagagc      660
tgcgacaaga cccacacctg ccccccctgc ccagctccag aactgctggg agggccttcc      720
gtgttcctgt tccccccaa gcccaaggac accctgatga tcagcaggac ccccgaggtg       780
acctgcgtgg tggtggacgt gtcccacgag gacccagagg tgaagttcaa ctggtacgtg      840
gacggcgtgg aggtgcacaa cgccaagacc aagcccagag aggagcagta caacagcacc      900
tacagggtgg tgtccgtgct gaccgtgctg caccaggact ggctgaacgg caagaatac       960 aagtgcaaag tctccaacaa ggccctgcca gccccaatcg aaaagacaat cagcaaggcc      1020
aagggccagc cacgggagcc ccaggtgtac accctgcccc cagccgggga ggagatgacc      1080
aagaaccagg tgtccctgac ctgtctggtg aagggcttct accccagcga tatcgccgtg      1140
gagtgggaga gcaacggcca gcccgagaac aactacaaga ccaccccccc agtgctggac      1200
agcgacggca gcttcttcct gtacagcaag ctgaccgtgg acaagtccag gtggcagcag      1260
ggcaacgtgt tcagctgcag cgtgatgcac gaggccctgc acaaccacta cacccagaag      1320
tccctgagcc tgagccccgg caag                                             1344
```

<210> SEQ ID NO 91
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Arg Ser Ser Gln Ser Leu Leu Ser Ser Gly Asn Gln Lys Ser Tyr Leu
1               5                   10                  15

Thr

<210> SEQ ID NO 92
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Trp Ala Ser Thr Arg Glu Ser
1               5

<210> SEQ ID NO 93
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Gln Asn Asp Tyr Ser Tyr Pro Phe Thr
1               5

<210> SEQ ID NO 94
<211> LENGTH: 13
<212> TYPE: PRT
<213> ORGANISM: Artificial Sequence
<220> FEATURE:

<223> OTHER INFORMATION: Description of Artificial Sequence: Synthetic
       peptide

<400> SEQUENCE: 94

Ser Gln Ser Leu Leu Ser Ser Gly Asn Gln Lys Ser Tyr
1               5                   10

<210> SEQ ID NO 95
<211> LENGTH: 3
<212> TYPE: PRT
<213> ORGANISM: Artificial Sequence
<220> FEATURE:
<223> OTHER INFORMATION: Description of Artificial Sequence: Synthetic
       peptide

<400> SEQUENCE: 95

Trp Ala Ser
1

<210> SEQ ID NO 96
<211> LENGTH: 6
<212> TYPE: PRT
<213> ORGANISM: Artificial Sequence
<220> FEATURE:
<223> OTHER INFORMATION: Description of Artificial Sequence: Synthetic
       peptide

<400> SEQUENCE: 96

Asp Tyr Ser Tyr Pro Phe
1               5

<210> SEQ ID NO 97
<211> LENGTH: 113
<212> TYPE: PRT
<213> ORGANISM: Artificial Sequence
<220> FEATURE:
<223> OTHER INFORMATION: Description of Artificial Sequence: Synthetic
       polypeptide

<400> SEQUENCE: 97

Glu Ile Val Met Thr Gln Ser Pro Ala Thr Leu Ser Leu Ser Pro Gly
1               5                   10                  15

Glu Arg Ala Thr Leu Ser Cys Arg Ser Ser Gln Ser Leu Leu Ser Ser
            20                  25                  30

Gly Asn Gln Lys Ser Tyr Leu Thr Trp Tyr Gln Gln Lys Pro Gly Gln
        35                  40                  45

Ala Pro Arg Leu Leu Ile Tyr Trp Ala Ser Thr Arg Glu Ser Gly Ile
    50                  55                  60

Pro Ala Arg Phe Ser Gly Ser Gly Ser Gly Thr Asp Phe Thr Leu Thr
65                  70                  75                  80

Ile Ser Ser Leu Gln Pro Glu Asp Phe Ala Val Tyr Tyr Cys Gln Asn
                85                  90                  95

Asp Tyr Ser Tyr Pro Phe Thr Phe Gly Gln Gly Thr Lys Leu Glu Ile
            100                 105                 110

Lys

<210> SEQ ID NO 98
<211> LENGTH: 339
<212> TYPE: DNA
<213> ORGANISM: Artificial Sequence
<220> FEATURE:
<223> OTHER INFORMATION: Description of Artificial Sequence: Synthetic
       polynucleotide

<400> SEQUENCE: 98

```
gagatcgtga tgactcagtc acccgctacc ctgagcctga gccctggcga gagagctaca      60
ctgagctgta gatctagtca gtcactgctg tctagcggta atcagaagtc ctacctgacc     120
tggtatcagc agaagcccgg tcaggcccct agactgctga tctactgggc ctctactaga     180
gagtcaggga tccccgctag gtttagcggt agcggtagtg gcaccgactt caccctgact     240
atctctagcc tgcagcccga ggacttcgcc gtctactact gtcagaacga ctatagctac     300
cccttcacct tcggtcaggg cactaagctg gagattaag                            339
```

<210> SEQ ID NO 99
<211> LENGTH: 220
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 99

```
Glu Ile Val Met Thr Gln Ser Pro Ala Thr Leu Ser Leu Ser Pro Gly
1               5                   10                  15
Glu Arg Ala Thr Leu Ser Cys Arg Ser Ser Gln Ser Leu Leu Ser Ser
            20                  25                  30
Gly Asn Gln Lys Ser Tyr Leu Thr Trp Tyr Gln Gln Lys Pro Gly Gln
        35                  40                  45
Ala Pro Arg Leu Leu Ile Tyr Trp Ala Ser Thr Arg Glu Ser Gly Ile
    50                  55                  60
Pro Ala Arg Phe Ser Gly Ser Gly Ser Gly Thr Asp Phe Thr Leu Thr
65                  70                  75                  80
Ile Ser Ser Leu Gln Pro Glu Asp Phe Ala Val Tyr Tyr Cys Gln Asn
                85                  90                  95
Asp Tyr Ser Tyr Pro Phe Thr Phe Gly Gln Gly Thr Lys Leu Glu Ile
            100                 105                 110
Lys Arg Thr Val Ala Ala Pro Ser Val Phe Ile Phe Pro Pro Ser Asp
        115                 120                 125
Glu Gln Leu Lys Ser Gly Thr Ala Ser Val Val Cys Leu Leu Asn Asn
    130                 135                 140
Phe Tyr Pro Arg Glu Ala Lys Val Gln Trp Lys Val Asp Asn Ala Leu
145                 150                 155                 160
Gln Ser Gly Asn Ser Gln Glu Ser Val Thr Glu Gln Asp Ser Lys Asp
                165                 170                 175
Ser Thr Tyr Ser Leu Ser Ser Thr Leu Thr Leu Ser Lys Ala Asp Tyr
            180                 185                 190
Glu Lys His Lys Val Tyr Ala Cys Glu Val Thr His Gln Gly Leu Ser
        195                 200                 205
Ser Pro Val Thr Lys Ser Phe Asn Arg Gly Glu Cys
    210                 215                 220
```

<210> SEQ ID NO 100
<211> LENGTH: 660
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 100

```
gagatcgtga tgactcagtc acccgctacc ctgagcctga gccctggcga gagagctaca      60
```

```
ctgagctgta gatctagtca gtcactgctg tctagcggta atcagaagtc ctacctgacc    120
tggtatcagc agaagcccgg tcaggcccct agactgctga tctactgggc ctctactaga    180
gagtcaggga tccccgctag gtttagcggt agcggtagtg gcaccgactt caccctgact    240
atctctagcc tgcagcccga ggacttcgcc gtctactact gtcagaacga ctatagctac    300
cccttcacct tcggtcaggg cactaagctg gagattaagc gtacggtggc cgctcccagc    360
gtgttcatct ccccccccag cgacgagcag ctgaagagcg gcaccgccag cgtggtgtgc    420
ctgctgaaca acttctaccc ccgggaggcc aaggtgcagt ggaaggtgga caacgccctg    480
cagagcggca acagccagga gagcgtcacc gagcaggaca gcaaggactc cacctacagc    540
ctgagcagca ccctgaccct gagcaaggcc gactacgaga agcataaggt gtacgcctgc    600
gaggtgaccc caccagggcct gtccagcccc gtgaccaaga gcttcaacag gggcgagtgc    660
```

<210> SEQ ID NO 101
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Asp His Thr Leu His
1               5

<210> SEQ ID NO 102
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Tyr Ile Tyr Pro Arg Ser Gly Ser Thr Lys Tyr Asn Glu Asn Phe Lys
1               5                   10                  15

Gly

<210> SEQ ID NO 103
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Arg Leu Leu Phe Leu Pro Leu Asp Tyr
1               5

<210> SEQ ID NO 104
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Gly Tyr Thr Phe Thr Asp His
1               5

<210> SEQ ID NO 105
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Tyr Pro Arg Ser Gly Ser
1               5

<210> SEQ ID NO 106
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Arg Leu Leu Phe Leu Pro Leu Asp Tyr
1               5

<210> SEQ ID NO 107
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107

Gln Ile Gln Leu Val Gln Ser Gly Ala Glu Val Lys Lys Pro Gly Ser
1               5                   10                  15

Ser Val Lys Val Ser Cys Lys Val Ser Gly Tyr Thr Phe Thr Asp His
            20                  25                  30

Thr Leu His Trp Met Arg Gln Ala Pro Gly Gln Gly Leu Glu Trp Met
        35                  40                  45

Gly Tyr Ile Tyr Pro Arg Ser Gly Ser Thr Lys Tyr Asn Glu Asn Phe
    50                  55                  60

Lys Gly Arg Val Thr Ile Thr Ala Asp Thr Ser Ser Ser Thr Ala Tyr
65                  70                  75                  80

Met Glu Leu Ser Ser Leu Arg Ser Glu Asp Thr Ala Val Tyr Tyr Cys
                85                  90                  95

Val Arg Arg Leu Leu Phe Leu Pro Leu Asp Tyr Trp Gly Gln Gly Thr
            100                 105                 110

Leu Val Thr Val Ser Ser
        115

<210> SEQ ID NO 108
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 108
cagattcagc tggtgcagtc aggcgccgaa gtgaagaaac ccggctctag cgtgaaagtc      60
agctgtaaag tctcaggcta caccttcacc gatcacaccc tgcactggat gagacaggcc     120
ccaggtcagg gcctggagtg gatgggctat atctacccta gatcaggctc tactaagtat     180

```
aacgagaact ttaagggtag agtgactatc accgccgaca ctagctctag caccgcctat    240
atggaactgt ctagcctgag atcagaggac accgccgtct actactgcgt cagacggctg    300
ctgttcctgc ccctggacta ctggggtcag ggcaccctgg tcaccgtgtc tagc          354
```

<210> SEQ ID NO 109
<211> LENGTH: 448
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 109

```
Gln Ile Gln Leu Val Gln Ser Gly Ala Glu Val Lys Lys Pro Gly Ser
1               5                   10                  15

Ser Val Lys Val Ser Cys Lys Val Ser Gly Tyr Thr Phe Thr Asp His
            20                  25                  30

Thr Leu His Trp Met Arg Gln Ala Pro Gly Gln Gly Leu Glu Trp Met
        35                  40                  45

Gly Tyr Ile Tyr Pro Arg Ser Gly Ser Thr Lys Tyr Asn Glu Asn Phe
    50                  55                  60

Lys Gly Arg Val Thr Ile Thr Ala Asp Thr Ser Ser Ser Thr Ala Tyr
65                  70                  75                  80

Met Glu Leu Ser Ser Leu Arg Ser Glu Asp Thr Ala Val Tyr Tyr Cys
                85                  90                  95

Val Arg Arg Leu Leu Phe Leu Pro Leu Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
```

```
                325                 330                 335
Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
                435                 440                 445

<210> SEQ ID NO 110
<211> LENGTH: 1344
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 110
```

| | | | | | |
|---|---|---|---|---|---|
| cagattcagc | tggtgcagtc | aggcgccgaa | gtgaagaaac | ccggctctag | cgtgaaagtc | 60 |
| agctgtaaag | tctcaggcta | caccttcacc | gatcacaccc | tgcactggat | gagacaggcc | 120 |
| ccaggtcagg | gcctggagtg | gatgggctat | atctacccta | gatcaggctc | tactaagtat | 180 |
| aacgagaact | ttaagggtag | agtgactatc | accgccgaca | ctagtctcag | caccgcctat | 240 |
| atggaactgt | ctagcctgag | atcagaggac | accgccgtct | actactgcgt | cagacggctg | 300 |
| ctgttcctgc | cctggactac | tggggtcag | ggcaccctgg | tcaccgtgtc | tagcgctagc | 360 |
| actaagggcc | caagtgtgtt | tcccctggcc | cccagcagca | agtctacttc | cggcggaact | 420 |
| gctgccctgg | gttgcctggt | gaaggactac | ttccccgagc | ccgtgacagt | gtcctggaac | 480 |
| tctggggctc | tgacttccgg | cgtgcacacc | ttccccgccg | tgctgcagag | cagcggcctg | 540 |
| tacagcctga | gcagcgtggt | gacagtgccc | tccagctctc | tgggaaccca | gacctatatc | 600 |
| tgcaacgtga | accacaagcc | cagcaacacc | aaggtggaca | agagagtgga | gcccaagagc | 660 |
| tgcgacaaga | cccacacctg | cccccccctgc | ccagctccag | aactgctggg | agggccttcc | 720 |
| gtgttcctgt | tccccccaa | gcccaaggac | accctgatga | tcagcaggac | ccccgaggtg | 780 |
| acctgcgtgg | tggtggacgt | gtcccacgag | gacccagagg | tgaagttcaa | ctggtacgtg | 840 |
| gacggcgtgg | aggtgcacaa | cgccaagacc | aagcccagag | aggagcagta | caacagcacc | 900 |
| tacagggtgg | tgtccgtgct | gaccgtgctg | caccaggact | ggctgaacgg | caaagaatac | 960 |
| aagtgcaaag | tctccaacaa | ggcccctgcca | gcccaatcg | aaaagacaat | cagcaaggcc | 1020 |
| aagggccagc | cacgggagcc | ccaggtgtac | accctgcccc | cagccgggga | ggagatgacc | 1080 |
| aagaaccagg | tgtccctgac | ctgtctggtg | aagggcttct | accccagcga | tatcgccgtg | 1140 |
| gagtgggaga | gcaacggcca | gcccgagaac | aactacaaga | ccacccccccc | agtgctggac | 1200 |
| agcgacggca | gcttcttcct | gtacagcaag | ctgaccgtgg | acaagtccag | gtggcagcag | 1260 |
| ggcaacgtgt | tcagctgcag | cgtgatgcac | gaggccctgc | acaaccacta | cacccagaag | 1320 |
| tccctgagcc | tgagccccgg | caag |  |  |  | 1344 |

```
<210> SEQ ID NO 111
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Arg Ser Ser Gln Ser Leu Leu Ser Ser Gly Asn Gln Lys Ser Tyr Leu
1               5                   10                  15
Thr

<210> SEQ ID NO 112
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Trp Ala Ser Thr Arg Glu Ser
1               5

<210> SEQ ID NO 113
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Gln Asn Asp Tyr Ser Tyr Pro Phe Thr
1               5

<210> SEQ ID NO 114
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Ser Gln Ser Leu Leu Ser Ser Gly Asn Gln Lys Ser Tyr
1               5                   10

<210> SEQ ID NO 115
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Trp Ala Ser
1

<210> SEQ ID NO 116
<211> LENGTH: 6
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 116

Asp Tyr Ser Tyr Pro Phe
1               5

<210> SEQ ID NO 117
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 117

Glu Ile Val Met Thr Gln Ser Pro Ala Thr Leu Ser Leu Ser Pro Gly
1               5                   10                  15

Glu Arg Ala Thr Leu Ser Cys Arg Ser Ser Gln Ser Leu Leu Ser Ser
                20                  25                  30

Gly Asn Gln Lys Ser Tyr Leu Thr Trp Tyr Gln Gln Lys Pro Gly Gln
            35                  40                  45

Ala Pro Arg Leu Leu Ile Tyr Trp Ala Ser Thr Arg Glu Ser Gly Ile
        50                  55                  60

Pro Ala Arg Phe Ser Gly Ser Gly Ser Gly Thr Asp Phe Thr Leu Thr
65                  70                  75                  80

Ile Ser Ser Leu Gln Pro Glu Asp Phe Ala Val Tyr Tyr Cys Gln Asn
                85                  90                  95

Asp Tyr Ser Tyr Pro Phe Thr Phe Gly Gln Gly Thr Lys Leu Glu Ile
            100                 105                 110

Lys

<210> SEQ ID NO 118
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 118
gagatcgtga tgactcagtc acccgctacc ctgagcctga gccctggcga gagagctaca      60
ctgagctgta gatctagtca gtcactgctg tctagcggta atcagaagtc ctacctgacc     120
tggtatcagc agaagcccgg tcaggcccct agactgctga tctactgggc ctctactaga     180
gagtcaggga tccccgctag gtttagcggt agcggtagtg gcaccgactt caccctgact     240
atctctagcc tgcagcccga ggacttcgcc gtctactact gtcagaacga ctatagctac     300
cccttcacct tcggtcaggg cactaagctg gagattaag                            339

<210> SEQ ID NO 119
<211> LENGTH: 220
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 119

Glu Ile Val Met Thr Gln Ser Pro Ala Thr Leu Ser Leu Ser Pro Gly
1               5                   10                  15

-continued

```
Glu Arg Ala Thr Leu Ser Cys Arg Ser Ser Gln Ser Leu Leu Ser Ser
             20                  25                  30
Gly Asn Gln Lys Ser Tyr Leu Thr Trp Tyr Gln Lys Pro Gly Gln
         35                  40                  45
Ala Pro Arg Leu Leu Ile Tyr Trp Ala Ser Thr Arg Glu Ser Gly Ile
     50                  55                  60
Pro Ala Arg Phe Ser Gly Ser Gly Ser Gly Thr Asp Phe Thr Leu Thr
 65                  70                  75                  80
Ile Ser Ser Leu Gln Pro Glu Asp Phe Ala Val Tyr Tyr Cys Gln Asn
                 85                  90                  95
Asp Tyr Ser Tyr Pro Phe Thr Phe Gly Gln Gly Thr Lys Leu Glu Ile
            100                 105                 110
Lys Arg Thr Val Ala Ala Pro Ser Val Phe Ile Phe Pro Pro Ser Asp
        115                 120                 125
Glu Gln Leu Lys Ser Gly Thr Ala Ser Val Val Cys Leu Leu Asn Asn
    130                 135                 140
Phe Tyr Pro Arg Glu Ala Lys Val Gln Trp Lys Val Asp Asn Ala Leu
145                 150                 155                 160
Gln Ser Gly Asn Ser Gln Glu Ser Val Thr Glu Gln Asp Ser Lys Asp
                165                 170                 175
Ser Thr Tyr Ser Leu Ser Ser Thr Leu Thr Leu Ser Lys Ala Asp Tyr
            180                 185                 190
Glu Lys His Lys Val Tyr Ala Cys Glu Val Thr His Gln Gly Leu Ser
        195                 200                 205
Ser Pro Val Thr Lys Ser Phe Asn Arg Gly Glu Cys
    210                 215                 220
```

<210> SEQ ID NO 120
<211> LENGTH: 660
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 120

```
gagatcgtga tgactcagtc acccgctacc ctgagcctga gccctggcga gagagctaca    60
ctgagctgta gatctagtca gtcactgctg tctagcggta atcagaagtc ctacctgacc   120
tggtatcagc agaagcccgg tcaggcccct agactgctga tctactgggc ctctactaga   180
gagtcaggga tccccgctag gtttagcggt agcggtagtg gcaccgactt caccctgact   240
atctctagcc tgcagcccga ggacttcgcc gtctactact gtcagaacga ctatagctac   300
cccttcacct tcggtcaggg cactaagctg gagattaagc gtacggtggc cgctcccagc   360
gtgttcatct tcccccccag cgacgagcag ctgaagagcg gcaccgccag cgtggtgtgc   420
ctgctgaaca acttctaccc ccgggaggcc aaggtgcagt ggaaggtgga caacgccctg   480
cagagcggca acagccagga gagcgtcacc gagcaggaca gcaaggactc cacctacagc   540
ctgagcagca ccctgaccct gagcaaggcc gactacgaga agcataaggt gtacgcctgc   600
gaggtgaccc accagggcct gtccagcccc gtgaccaaga gcttcaacag gggcgagtgc   660
```

<210> SEQ ID NO 121
<211> LENGTH: 829
<212> TYPE: PRT
<213> ORGANISM: Homo sapiens

<400> SEQUENCE: 121

```
Met Gly Leu Pro Arg Gly Pro Leu Ala Ser Leu Leu Leu Gln Val
1               5                   10                  15

Cys Trp Leu Gln Cys Ala Ala Ser Glu Pro Cys Arg Ala Val Phe Arg
            20                  25                  30

Glu Ala Glu Val Thr Leu Glu Ala Gly Ala Glu Gln Pro Gly
            35                  40                  45

Gln Ala Leu Gly Lys Val Phe Met Gly Cys Pro Gly Gln Glu Pro Ala
50                  55                  60

Leu Phe Ser Thr Asp Asn Asp Phe Thr Val Arg Asn Gly Glu Thr
65                  70                  75                  80

Val Gln Glu Arg Arg Ser Leu Lys Glu Arg Asn Pro Leu Lys Ile Phe
                85                  90                  95

Pro Ser Lys Arg Ile Leu Arg Arg His Lys Arg Asp Trp Val Val Ala
            100                 105                 110

Pro Ile Ser Val Pro Glu Asn Gly Lys Gly Pro Phe Pro Gln Arg Leu
            115                 120                 125

Asn Gln Leu Lys Ser Asn Lys Asp Arg Asp Thr Lys Ile Phe Tyr Ser
            130                 135                 140

Ile Thr Gly Pro Gly Ala Asp Ser Pro Pro Glu Gly Val Phe Ala Val
145                 150                 155                 160

Glu Lys Glu Thr Gly Trp Leu Leu Leu Asn Lys Pro Leu Asp Arg Glu
                165                 170                 175

Glu Ile Ala Lys Tyr Glu Leu Phe Gly His Ala Val Ser Glu Asn Gly
            180                 185                 190

Ala Ser Val Glu Asp Pro Met Asn Ile Ser Ile Ile Val Thr Asp Gln
            195                 200                 205

Asn Asp His Lys Pro Lys Phe Thr Gln Asp Thr Phe Arg Gly Ser Val
            210                 215                 220

Leu Glu Gly Val Leu Pro Gly Thr Ser Val Met Gln Val Thr Ala Thr
225                 230                 235                 240

Asp Glu Asp Asp Ala Ile Tyr Thr Tyr Asn Gly Val Val Ala Tyr Ser
            245                 250                 255

Ile His Ser Gln Glu Pro Lys Asp Pro His Asp Leu Met Phe Thr Ile
            260                 265                 270

His Arg Ser Thr Gly Thr Ile Ser Val Ile Ser Ser Gly Leu Asp Arg
            275                 280                 285

Glu Lys Val Pro Glu Tyr Thr Leu Thr Ile Gln Ala Thr Asp Met Asp
290                 295                 300

Gly Asp Gly Ser Thr Thr Thr Ala Val Ala Val Val Glu Ile Leu Asp
305                 310                 315                 320

Ala Asn Asp Asn Ala Pro Met Phe Asp Pro Gln Lys Tyr Glu Ala His
            325                 330                 335

Val Pro Glu Asn Ala Val Gly His Glu Val Gln Arg Leu Thr Val Thr
            340                 345                 350

Asp Leu Asp Ala Pro Asn Ser Pro Ala Trp Arg Ala Thr Tyr Leu Ile
            355                 360                 365

Met Gly Gly Asp Asp Gly Asp His Phe Thr Ile Thr Thr His Pro Glu
            370                 375                 380

Ser Asn Gln Gly Ile Leu Thr Thr Arg Lys Gly Leu Asp Phe Glu Ala
385                 390                 395                 400

Lys Asn Gln His Thr Leu Tyr Val Glu Val Thr Asn Glu Ala Pro Phe
            405                 410                 415
```

-continued

```
Val Leu Lys Leu Pro Thr Ser Thr Ala Thr Ile Val Val His Val Glu
            420                 425                 430

Asp Val Asn Glu Ala Pro Val Phe Val Pro Ser Lys Val Val Glu
            435                 440                 445

Val Gln Glu Gly Ile Pro Thr Gly Glu Pro Val Cys Val Tyr Thr Ala
        450                 455                 460

Glu Asp Pro Asp Lys Glu Asn Gln Lys Ile Ser Tyr Arg Ile Leu Arg
465                 470                 475                 480

Asp Pro Ala Gly Trp Leu Ala Met Asp Pro Asp Ser Gly Gln Val Thr
                485                 490                 495

Ala Val Gly Thr Leu Asp Arg Glu Asp Glu Gln Phe Val Arg Asn Asn
            500                 505                 510

Ile Tyr Glu Val Met Val Leu Ala Met Asp Asn Gly Ser Pro Pro Thr
            515                 520                 525

Thr Gly Thr Gly Thr Leu Leu Leu Thr Leu Ile Asp Val Asn Asp His
        530                 535                 540

Gly Pro Val Pro Glu Pro Arg Gln Ile Thr Ile Cys Asn Gln Ser Pro
545                 550                 555                 560

Val Arg Gln Val Leu Asn Ile Thr Asp Lys Asp Leu Ser Pro His Thr
                565                 570                 575

Ser Pro Phe Gln Ala Gln Leu Thr Asp Ser Asp Ile Tyr Trp Thr
            580                 585                 590

Ala Glu Val Asn Glu Glu Gly Asp Thr Val Val Leu Ser Leu Lys Lys
            595                 600                 605

Phe Leu Lys Gln Asp Thr Tyr Asp Val His Leu Ser Leu Ser Asp His
610                 615                 620

Gly Asn Lys Glu Gln Leu Thr Val Ile Arg Ala Thr Val Cys Asp Cys
625                 630                 635                 640

His Gly His Val Glu Thr Cys Pro Gly Pro Trp Lys Gly Gly Phe Ile
                645                 650                 655

Leu Pro Val Leu Gly Ala Val Leu Ala Leu Leu Phe Leu Leu Leu Val
            660                 665                 670

Leu Leu Leu Leu Val Arg Lys Lys Arg Lys Ile Lys Glu Pro Leu Leu
            675                 680                 685

Leu Pro Glu Asp Asp Thr Arg Asp Asn Val Phe Tyr Tyr Gly Glu Glu
            690                 695                 700

Gly Gly Gly Glu Glu Asp Gln Asp Tyr Asp Ile Thr Gln Leu His Arg
705                 710                 715                 720

Gly Leu Glu Ala Arg Pro Glu Val Val Leu Arg Asn Asp Val Ala Pro
                725                 730                 735

Thr Ile Ile Pro Thr Pro Met Tyr Arg Pro Arg Pro Ala Asn Pro Asp
                740                 745                 750

Glu Ile Gly Asn Phe Ile Ile Glu Asn Leu Lys Ala Ala Asn Thr Asp
            755                 760                 765

Pro Thr Ala Pro Pro Tyr Asp Thr Leu Leu Val Phe Asp Tyr Glu Gly
            770                 775                 780

Ser Gly Ser Asp Ala Ala Ser Leu Ser Ser Leu Thr Ser Ser Ala Ser
785                 790                 795                 800

Asp Gln Asp Gln Asp Tyr Asp Tyr Leu Asn Glu Trp Gly Ser Arg Phe
                805                 810                 815

Lys Lys Leu Ala Asp Met Tyr Gly Gly Gly Glu Asp Asp
            820                 825
```

```
<210> SEQ ID NO 122
<211> LENGTH: 822
<212> TYPE: PRT
<213> ORGANISM: Rattus norvegicus

<400> SEQUENCE: 122

Met Glu Leu Leu Ser Gly Pro Leu Val Phe Leu Leu Leu Leu Leu Gln
1               5                   10                  15

Val Cys Trp Leu Arg Ser Val Val Ser Glu Ser Tyr Arg Glu Asp Phe
            20                  25                  30

Ile Arg Glu Ala Gly Val Thr Leu Glu Val Gly Gly Thr Asp Leu Glu
        35                  40                  45

Pro Ser Gln Ala Leu Glu Lys Glu Ala Leu Ala Gly His Glu Val Leu
    50                  55                  60

Gly Ala Asp Ser Gly Gly Ile Ile Thr Leu Asn Arg Glu Thr Val Gln
65                  70                  75                  80

Gly Gly Lys Gly Val Met Asn Ser Pro Pro Ser Arg Ile Leu Arg Arg
                85                  90                  95

Arg Lys Arg Glu Trp Val Met Pro Pro Ile Ser Val Pro Glu Asn Gly
            100                 105                 110

Lys Gly Pro Phe Pro Gln Arg Leu Asn Gln Leu Lys Ser Asn Lys Asp
        115                 120                 125

Arg Gly Thr Lys Leu Phe Tyr Ser Ile Thr Gly Pro Gly Ala Asp Ser
    130                 135                 140

Pro Pro Glu Gly Val Phe Thr Ile Glu Lys Glu Thr Gly Trp Leu Leu
145                 150                 155                 160

Leu Asn Met Pro Leu Asp Arg Glu Lys Ile Val Lys Tyr Glu Leu Phe
                165                 170                 175

Gly His Ala Val Ser Glu Asn Gly Ala Ser Val Glu Glu Pro Met Asn
            180                 185                 190

Ile Ser Ile Ile Val Thr Asp Gln Asn Asp Asn Lys Pro Lys Phe Thr
        195                 200                 205

Gln Asp Thr Phe Arg Gly Ser Val Pro Glu Gly Val Met Pro Gly Thr
    210                 215                 220

Ser Val Met Gln Val Thr Ala Thr Asp Glu Asp Ala Ile Asn Thr
225                 230                 235                 240

Tyr Asn Gly Val Val Ala Tyr Ser Ile His Ser Gln Glu Pro Lys Glu
                245                 250                 255

Pro His Asp Leu Met Phe Thr Ile His Lys Ser Thr Gly Thr Ile Ser
            260                 265                 270

Val Ile Ser Ser Gly Leu Asp Arg Glu Lys Val Pro Glu Tyr Thr Leu
        275                 280                 285

Thr Ile Gln Ala Thr Asp Met Asp Gly Asp Gly Ser Thr Thr Thr Ala
    290                 295                 300

Glu Ala Val Val Gln Ile Leu Asp Thr Asn Asp Asn Ala Pro Glu Phe
305                 310                 315                 320

Gln Pro Gln Lys Tyr Glu Ala Trp Val Pro Glu Asn Ala Val Gly His
                325                 330                 335

Glu Val Gln Arg Leu Thr Val Thr Asp Leu Asp Ser Pro Asn Ser Pro
            340                 345                 350

Ala Trp Arg Ala Thr Tyr His Ile Val Gly Gly Asp Gly Asp His
        355                 360                 365

Phe Thr Val Ala Thr His Pro Glu Thr Asn Gln Gly Ile Leu Thr Thr
    370                 375                 380
```

```
Lys Lys Gly Leu Asp Phe Glu Ala Gln Asn Gln His Thr Leu Tyr Ile
385                 390                 395                 400

Glu Val Thr Asn Glu Ala Ser Phe Ala Val Lys Leu Pro Thr Ala Thr
            405                 410                 415

Ala Thr Val Val Val His Val Glu Asp Val Asn Glu Ala Pro Val Phe
            420                 425                 430

Val Pro Pro Ser Lys Val Ile Glu Ala Gln Glu Gly Ile Ser Ile Gly
            435                 440                 445

Glu Leu Val Cys Val Tyr Thr Ala Gln Asp Pro Asp Lys Glu Glu Gln
            450                 455                 460

Lys Ile Ser Tyr Ser Ile Leu Arg Asp Pro Ala Ser Trp Leu Ala Val
465                 470                 475                 480

Asp Pro Asp Ser Gly Gln Ile Thr Ala Ala Gly Ile Leu Asp Arg Glu
            485                 490                 495

Asp Glu Gln Phe Val Lys Asn Asp Ile Tyr Glu Val Met Val Leu Ala
            500                 505                 510

Thr Asp Asn Gly Asn Pro Pro Thr Thr Gly Thr Gly Thr Leu Leu Leu
            515                 520                 525

Thr Leu Thr Asp Ile Asn Asp His Gly Pro Ile Pro Glu Pro Arg Gln
            530                 535                 540

Ile Ile Ile Cys Asn Gln Ser Pro Val Pro Gln Val Leu Asn Ile Thr
545                 550                 555                 560

Asp Lys Asp Leu Ser Pro Asn Ser Ser Pro Phe Gln Ala Gln Leu Thr
            565                 570                 575

His Asp Ser Asp Ile Tyr Trp Met Ala Glu Val Ser Glu Lys Gly Asp
            580                 585                 590

Thr Val Ala Leu Ser Leu Lys Lys Phe Leu Lys Gln Asp Thr Tyr Asp
            595                 600                 605

Leu His Leu Ser Leu Ser Asp His Gly Asn Arg Glu Gln Leu Thr Met
            610                 615                 620

Ile Arg Ala Thr Val Cys Asp Cys His Gly Gln Val Leu Asn Asp Cys
625                 630                 635                 640

Pro Arg Pro Trp Lys Gly Gly Phe Ile Leu Pro Val Leu Gly Ala Val
            645                 650                 655

Leu Ala Leu Leu Thr Leu Leu Leu Ala Leu Leu Leu Val Arg Lys
            660                 665                 670

Lys Arg Lys Val Lys Glu Pro Leu Leu Leu Pro Glu Asp Asp Thr Arg
            675                 680                 685

Asp Asn Val Phe Tyr Tyr Gly Glu Glu Gly Gly Glu Glu Asp Gln
690                 695                 700

Asp Tyr Asp Ile Thr Gln Leu His Arg Gly Leu Glu Ala Arg Pro Glu
705                 710                 715                 720

Val Val Leu Arg Asn Asp Val Ala Pro Thr Phe Ile Pro Thr Pro Met
            725                 730                 735

Tyr Arg Pro Arg Pro Ala Asn Pro Asp Glu Ile Gly Asn Phe Ile Ile
            740                 745                 750

Glu Asn Leu Lys Ala Ala Asn Thr Asp Pro Thr Ala Pro Pro Tyr Asp
            755                 760                 765

Ser Leu Leu Val Phe Asp Tyr Glu Gly Ser Gly Ser Asp Ala Ala Ser
            770                 775                 780

Leu Ser Ser Leu Thr Ser Ser Thr Ser Asp Gln Asp Gln Asp Tyr Asn
785                 790                 795                 800

Tyr Leu Thr Glu Trp Gly Ser Arg Phe Lys Lys Leu Ala Asp Met Tyr
```

Gly Gly Gly Glu Asp Asp
          820

<210> SEQ ID NO 123
<211> LENGTH: 822
<212> TYPE: PRT
<213> ORGANISM: Mus musculus

<400> SEQUENCE: 123

Met Glu Leu Leu Ser Gly Pro His Ala Phe Leu Leu Leu Leu Gln
1               5                   10                  15

Val Cys Trp Leu Arg Ser Val Val Ser Glu Pro Tyr Arg Ala Gly Phe
            20                  25                  30

Ile Gly Glu Ala Gly Val Thr Leu Glu Val Glu Gly Thr Asp Leu Glu
        35                  40                  45

Pro Ser Gln Val Leu Gly Lys Val Ala Leu Ala Gly Gln Gly Met His
    50                  55                  60

His Ala Asp Asn Gly Asp Ile Ile Met Leu Thr Arg Gly Thr Val Gln
65                  70                  75                  80

Gly Gly Lys Asp Ala Met His Ser Pro Pro Thr Arg Ile Leu Arg Arg
                85                  90                  95

Arg Lys Arg Glu Trp Val Met Pro Pro Ile Phe Val Pro Glu Asn Gly
            100                 105                 110

Lys Gly Pro Phe Pro Gln Arg Leu Asn Gln Leu Lys Ser Asn Lys Asp
        115                 120                 125

Arg Gly Thr Lys Ile Phe Tyr Ser Ile Thr Gly Pro Gly Ala Asp Ser
    130                 135                 140

Pro Pro Glu Gly Val Phe Thr Ile Glu Lys Glu Ser Gly Trp Leu Leu
145                 150                 155                 160

Leu His Met Pro Leu Asp Arg Glu Lys Ile Val Lys Tyr Glu Leu Tyr
                165                 170                 175

Gly His Ala Val Ser Glu Asn Gly Ala Ser Val Glu Glu Pro Met Asn
            180                 185                 190

Ile Ser Ile Ile Val Thr Asp Gln Asn Asp Asn Lys Pro Lys Phe Thr
        195                 200                 205

Gln Asp Thr Phe Arg Gly Ser Val Leu Glu Gly Val Met Pro Gly Thr
    210                 215                 220

Ser Val Met Gln Val Thr Ala Thr Asp Glu Asp Asp Ala Val Asn Thr
225                 230                 235                 240

Tyr Asn Gly Val Val Ala Tyr Ser Ile His Ser Gln Glu Pro Lys Glu
                245                 250                 255

Pro His Asp Leu Met Phe Thr Ile His Lys Ser Thr Gly Thr Ile Ser
            260                 265                 270

Val Ile Ser Ser Gly Leu Asp Arg Glu Lys Val Pro Glu Tyr Arg Leu
        275                 280                 285

Thr Val Gln Ala Thr Asp Met Asp Gly Glu Gly Ser Thr Thr Thr Ala
    290                 295                 300

Glu Ala Val Val Gln Ile Leu Asp Ala Asn Asp Asn Ala Pro Glu Phe
305                 310                 315                 320

Glu Pro Gln Lys Tyr Glu Ala Trp Val Pro Glu Asn Glu Val Gly His
                325                 330                 335

Glu Val Gln Arg Leu Thr Val Thr Asp Leu Asp Val Pro Asn Ser Pro
            340                 345                 350

```
Ala Trp Arg Ala Thr Tyr His Ile Val Gly Gly Asp Gly Asp His
            355                 360                 365

Phe Thr Ile Thr Thr His Pro Glu Thr Asn Gln Gly Val Leu Thr Thr
    370                 375                 380

Lys Lys Gly Leu Asp Phe Glu Ala Gln Asp Gln His Thr Leu Tyr Val
385                 390                 395                 400

Glu Val Thr Asn Glu Ala Pro Phe Ala Val Lys Leu Pro Thr Ala Thr
                405                 410                 415

Ala Thr Val Val His Val Lys Asp Val Asn Glu Ala Pro Val Phe
            420                 425                 430

Val Pro Pro Ser Lys Val Ile Glu Ala Gln Glu Gly Ile Ser Ile Gly
            435                 440                 445

Glu Leu Val Cys Ile Tyr Thr Ala Gln Asp Pro Asp Lys Glu Asp Gln
            450                 455                 460

Lys Ile Ser Tyr Thr Ile Ser Arg Asp Pro Ala Asn Trp Leu Ala Val
465                 470                 475                 480

Asp Pro Asp Ser Gly Gln Ile Thr Ala Ala Gly Ile Leu Asp Arg Glu
                485                 490                 495

Asp Glu Gln Phe Val Lys Asn Asn Val Tyr Glu Val Met Val Leu Ala
                500                 505                 510

Thr Asp Ser Gly Asn Pro Pro Thr Gly Thr Gly Thr Leu Leu Leu
            515                 520                 525

Thr Leu Thr Asp Ile Asn Asp His Gly Pro Ile Pro Glu Pro Arg Gln
            530                 535                 540

Ile Ile Ile Cys Asn Gln Ser Pro Val Pro Gln Val Leu Asn Ile Thr
545                 550                 555                 560

Asp Lys Asp Leu Ser Pro Asn Ser Ser Pro Phe Gln Ala Gln Leu Thr
                565                 570                 575

His Asp Ser Asp Ile Tyr Trp Met Ala Glu Val Ser Glu Lys Gly Asp
                580                 585                 590

Thr Val Ala Leu Ser Leu Lys Lys Phe Leu Lys Gln Asp Thr Tyr Asp
            595                 600                 605

Leu His Leu Ser Leu Ser Asp His Gly Asn Arg Glu Gln Leu Thr Met
    610                 615                 620

Ile Arg Ala Thr Val Cys Asp Cys His Gly Gln Val Phe Asn Asp Cys
625                 630                 635                 640

Pro Arg Pro Trp Lys Gly Gly Phe Ile Leu Pro Ile Leu Gly Ala Val
                645                 650                 655

Leu Ala Leu Leu Thr Leu Leu Ala Leu Leu Leu Leu Val Arg Lys
            660                 665                 670

Lys Arg Lys Val Lys Glu Pro Leu Leu Leu Pro Glu Asp Asp Thr Arg
                675                 680                 685

Asp Asn Val Phe Tyr Tyr Gly Glu Glu Gly Gly Gly Glu Glu Asp Gln
            690                 695                 700

Asp Tyr Asp Ile Thr Gln Leu His Arg Gly Leu Glu Ala Arg Pro Glu
705                 710                 715                 720

Val Val Leu Arg Asn Asp Val Val Pro Thr Phe Ile Pro Thr Pro Met
                725                 730                 735

Tyr Arg Pro Arg Pro Ala Asn Pro Asp Glu Ile Gly Asn Phe Ile Ile
            740                 745                 750

Glu Asn Leu Lys Ala Ala Asn Thr Asp Pro Thr Ala Pro Pro Tyr Asp
            755                 760                 765

Ser Leu Leu Val Phe Asp Tyr Glu Gly Ser Gly Ser Asp Ala Ala Ser
```

-continued

```
            770                 775                 780
Leu Ser Ser Leu Thr Thr Ser Ala Ser Asp Gln Asp Gln Asp Tyr Asn
785                 790                 795                 800

Tyr Leu Asn Glu Trp Gly Ser Arg Phe Lys Lys Leu Ala Asp Met Tyr
                805                 810                 815

Gly Gly Gly Glu Asp Asp
            820

<210> SEQ ID NO 124
<211> LENGTH: 595
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 124

Met Lys Phe Leu Val Asn Val Ala Leu Val Phe Met Val Val Tyr Ile
1               5                   10                  15

Ser Tyr Ile Tyr Ala Asp His Gln Thr Ser Leu Tyr Lys Lys Ala Gly
                20                  25                  30

Phe Glu Gly Asp Arg Thr Asp Trp Val Val Ala Pro Ile Ser Val Pro
            35                  40                  45

Glu Asn Gly Lys Gly Pro Phe Pro Gln Arg Leu Asn Gln Leu Lys Ser
50                  55                  60

Asn Lys Asp Arg Asp Thr Lys Ile Phe Tyr Ser Ile Thr Gly Pro Gly
65                  70                  75                  80

Ala Asp Ser Pro Pro Glu Gly Val Phe Ala Val Glu Lys Glu Thr Gly
                85                  90                  95

Trp Leu Leu Leu Asn Lys Pro Leu Asp Arg Glu Glu Ile Ala Lys Tyr
            100                 105                 110

Glu Leu Phe Gly His Ala Val Ser Glu Asn Gly Ala Ser Val Glu Asp
        115                 120                 125

Pro Met Asn Ile Ser Ile Ile Val Thr Asp Gln Asn Asp His Lys Pro
    130                 135                 140

Lys Phe Thr Gln Asp Thr Phe Arg Gly Ser Val Leu Glu Gly Val Leu
145                 150                 155                 160

Pro Gly Thr Ser Val Met Gln Val Thr Ala Thr Asp Glu Asp Asp Ala
                165                 170                 175

Ile His Thr Tyr Asn Gly Val Val Ala Tyr Ser Ile His Ser Gln Glu
            180                 185                 190

Pro Lys Asp Pro His Asp Leu Met Phe Thr Ile His Arg Ser Thr Gly
        195                 200                 205

Thr Ile Ser Val Ile Ser Ser Gly Leu Asp Arg Glu Lys Val Pro Glu
    210                 215                 220

Tyr Thr Leu Thr Ile Gln Ala Thr Asp Met Asp Gly Asp Gly Ser Thr
225                 230                 235                 240

Thr Thr Ala Val Ala Val Val Glu Ile Leu Asp Ala Asn Asp Asn Ala
                245                 250                 255

Pro Val Phe Asp Pro Gln Lys Tyr Glu Ser His Val Pro Glu Asn Ala
            260                 265                 270

Val Gly His Glu Val Gln Arg Leu Thr Val Thr Asp Leu Asp Ala Pro
        275                 280                 285

Asn Ser Pro Ala Trp Arg Ala Thr Tyr Leu Ile Val Gly Gly Asp Asp
    290                 295                 300
```

Gly Asp His Phe Thr Ile Ala Thr His Pro Glu Ser Asn Gln Gly Ile
305                 310                 315                 320

Leu Thr Thr Arg Lys Gly Leu Asp Phe Glu Ala Lys Asn Gln His Thr
            325                 330                 335

Leu Tyr Val Glu Val Thr Asn Glu Ala Pro Phe Val Leu Lys Leu Pro
        340                 345                 350

Thr Ser Thr Ala Thr Ile Val His Val Glu Asp Val Asn Glu Ala
    355                 360                 365

Pro Val Phe Val Pro Pro Ser Lys Val Val Glu Val Gln Glu Gly Ile
    370                 375                 380

Pro Thr Gly Glu Ala Val Cys Val Tyr Thr Ala Lys Asp Pro Asp Lys
385                 390                 395                 400

Glu Asn Gln Lys Ile Ser Tyr Arg Ile Leu Arg Asp Pro Ala Gly Trp
                405                 410                 415

Leu Ala Met Asp Pro Asp Ser Gly Gln Val Thr Val Ala Gly Thr Leu
            420                 425                 430

Asp Arg Glu Asp Glu Arg Phe Val Arg Asn Asn Ile Tyr Glu Val Met
        435                 440                 445

Val Leu Ala Val Asp Asn Gly Ser Pro Pro Thr Thr Gly Thr Gly Thr
450                 455                 460

Leu Leu Leu Thr Leu Ile Asp Val Asn Asp His Gly Pro Val Pro Glu
465                 470                 475                 480

Pro Arg Glu Ile Thr Ile Cys Asn Gln Ser Pro Glu Ser Gln Val Leu
                485                 490                 495

Asn Ile Thr Asp Lys Asp Leu Ser Pro His Thr Ser Pro Phe Gln Ala
            500                 505                 510

Gln Leu Thr Asp Asp Ser Asp Ile Tyr Trp Met Ala Glu Val Asn Glu
        515                 520                 525

Lys Asp Asp Thr Val Val Leu Ser Leu Lys Lys Phe Leu Lys Gln Asp
530                 535                 540

Thr Tyr Asp Val His Leu Ser Leu Ser Asp His Gly Asn Lys Leu Gln
545                 550                 555                 560

Leu Thr Val Ile Arg Ala Thr Val Cys Asp Cys His Gly His Val Glu
                565                 570                 575

Lys Cys Pro Asp Pro Trp Lys Gly Gly Ala His His His His
            580                 585                 590

His Gly Ala
        595

<210> SEQ ID NO 125
<211> LENGTH: 595
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 125

Met Lys Phe Leu Val Asn Val Ala Leu Val Phe Met Val Val Tyr Ile
1               5                   10                  15

Ser Tyr Ile Tyr Ala Asp His Gln Thr Ser Leu Tyr Lys Lys Ala Gly
            20                  25                  30

Phe Glu Gly Asp Arg Thr Asp Trp Val Val Ala Pro Ile Ser Val Pro
        35                  40                  45

Glu Asn Gly Lys Gly Pro Phe Pro Gln Arg Leu Asn Gln Leu Lys Ser
    50                  55                  60

```
Asn Lys Asp Arg Asp Thr Lys Ile Phe Tyr Ser Ile Thr Gly Pro Gly
 65                  70                  75                  80

Ala Asp Ser Pro Pro Glu Gly Val Phe Ala Val Glu Lys Glu Thr Gly
                 85                  90                  95

Trp Leu Leu Leu Asn Lys Pro Leu Asp Arg Glu Glu Ile Ala Lys Tyr
            100                 105                 110

Glu Leu Phe Gly His Ala Val Ser Glu Asn Gly Ala Ser Val Glu Asp
        115                 120                 125

Pro Met Asn Ile Ser Ile Ile Val Thr Asp Gln Asn Asp His Lys Pro
    130                 135                 140

Lys Phe Thr Gln Asp Thr Phe Arg Gly Ser Val Leu Glu Gly Val Leu
145                 150                 155                 160

Pro Gly Thr Ser Val Met Gln Val Thr Ala Thr Asp Glu Asp Asp Ala
                165                 170                 175

Ile His Thr Tyr Asn Gly Val Val Ala Tyr Ser Ile His Ser Gln Glu
            180                 185                 190

Pro Lys Asp Pro His Asp Leu Met Phe Thr Ile His Arg Ser Thr Gly
        195                 200                 205

Thr Ile Ser Val Ile Ser Ser Gly Leu Asp Arg Glu Lys Val Pro Glu
210                 215                 220

Tyr Thr Leu Thr Ile Gln Ala Thr Asp Met Asp Gly Asp Gly Ser Thr
225                 230                 235                 240

Thr Thr Ala Val Ala Val Val Glu Ile Leu Asp Ala Asn Asp Asn Ala
                245                 250                 255

Pro Val Phe Asp Pro Gln Lys Tyr Glu Ser His Val Pro Glu Asn Ala
                260                 265                 270

Val Gly His Glu Val Gln Arg Leu Thr Val Thr Asp Leu Asp Ala Pro
            275                 280                 285

Asn Ser Pro Ala Trp Arg Ala Thr Tyr Leu Ile Val Gly Gly Asp Asp
    290                 295                 300

Gly Asp His Phe Thr Ile Ala Thr His Pro Glu Ser Asn Gln Gly Ile
305                 310                 315                 320

Leu Thr Thr Arg Lys Gly Leu Asp Phe Glu Ala Lys Asn Gln His Thr
                325                 330                 335

Leu Tyr Val Glu Val Thr Asn Glu Ala Pro Phe Val Leu Lys Leu Pro
            340                 345                 350

Thr Ser Thr Ala Thr Ile Val Val His Val Glu Asp Val Asn Glu Ala
        355                 360                 365

Pro Val Phe Val Pro Pro Ser Lys Val Val Glu Val Gln Glu Gly Ile
    370                 375                 380

Pro Thr Gly Glu Ala Val Cys Val Tyr Thr Ala Lys Asp Pro Asp Lys
385                 390                 395                 400

Glu Asn Gln Lys Ile Ser Tyr Arg Ile Leu Arg Asp Pro Ala Gly Trp
                405                 410                 415

Leu Ala Met Asp Pro Asp Ser Gly Gln Val Thr Val Ala Gly Thr Leu
            420                 425                 430

Asp Arg Glu Asp Glu Arg Phe Val Arg Asn Asn Ile Tyr Glu Val Met
        435                 440                 445

Val Leu Ala Val Asp Asn Gly Ser Pro Pro Thr Thr Gly Thr Gly Thr
    450                 455                 460

Leu Leu Leu Thr Leu Ile Asp Val Asn Asp His Gly Pro Val Pro Glu
465                 470                 475                 480
```

Pro Arg Glu Ile Thr Ile Cys Asn Gln Ser Pro Glu Ser Gln Val Leu
                485                 490                 495

Asn Ile Thr Asp Lys Asp Leu Ser Pro His Thr Ser Pro Phe Gln Ala
            500                 505                 510

Gln Leu Thr Asp Asp Ser Asp Ile Tyr Trp Met Ala Glu Val Asn Glu
            515                 520                 525

Lys Asp Asp Thr Val Val Leu Ser Leu Lys Lys Phe Leu Lys Gln Gly
            530                 535                 540

Thr Tyr Asp Val His Leu Ser Leu Ser Asp His Gly Asn Lys Glu Gln
545                 550                 555                 560

Leu Thr Val Ile Arg Ala Thr Val Cys Asp Cys His Gly His Val Glu
                565                 570                 575

Lys Cys Pro Asp Pro Trp Lys Gly Gly Gly Ala His His His His His
            580                 585                 590

His Gly Ala
    595

<210> SEQ ID NO 126
<211> LENGTH: 829
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126

Met Gly Leu Pro Arg Gly Pro Leu Ala Ser Leu Leu Leu Leu Gln Val
1               5                   10                  15

Cys Trp Leu Gln Cys Ala Ala Ser Glu Pro Cys Arg Ala Val Phe Arg
                20                  25                  30

Glu Ala Glu Val Thr Leu Glu Ala Gly Gly Ala Glu Gln Glu Pro Gly
            35                  40                  45

Gln Ala Leu Gly Lys Val Phe Met Gly Cys Pro Gly Gln Glu Pro Ala
        50                  55                  60

Leu Phe Ser Thr Asp Asn Asp Asp Phe Thr Val Arg Asn Gly Glu Thr
65                  70                  75                  80

Val Gln Glu Arg Arg Ser Leu Lys Glu Arg Asn Pro Leu Lys Ile Phe
                85                  90                  95

Pro Ser Lys Arg Ile Leu Arg Arg His Lys Arg Asp Trp Val Val Ala
            100                 105                 110

Pro Ile Ser Val Pro Glu Asn Gly Lys Gly Pro Phe Pro Gln Arg Leu
        115                 120                 125

Asn Gln Leu Lys Ser Asn Lys Asp Arg Asp Thr Lys Ile Phe Tyr Ser
    130                 135                 140

Ile Thr Gly Pro Gly Ala Asp Ser Pro Pro Glu Gly Val Phe Ala Val
145                 150                 155                 160

Glu Lys Glu Thr Gly Trp Leu Leu Leu Asn Lys Pro Leu Asp Arg Glu
                165                 170                 175

Glu Ile Ala Lys Tyr Glu Leu Phe Gly His Ala Val Ser Glu Asn Gly
            180                 185                 190

Ala Ser Val Glu Asp Pro Met Asn Ile Ser Ile Ile Val Thr Asp Gln
        195                 200                 205

Asn Asp His Lys Pro Lys Phe Thr Gln Asp Thr Phe Arg Gly Ser Val
    210                 215                 220

Leu Glu Gly Val Leu Pro Gly Thr Ser Val Met Gln Val Thr Ala Thr
225                 230                 235                 240

```
Asp Glu Asp Asp Ala Ile Tyr Thr Tyr Asn Gly Val Val Ala Tyr Ser
            245                 250                 255

Ile His Ser Gln Glu Pro Lys Asp Pro His Asp Leu Met Phe Thr Ile
            260                 265                 270

His Arg Ser Thr Gly Thr Ile Ser Val Ile Ser Ser Gly Leu Asp Arg
            275                 280                 285

Glu Lys Val Pro Glu Tyr Thr Leu Thr Ile Gln Ala Thr Asp Met Asp
            290                 295                 300

Gly Asp Gly Ser Thr Thr Thr Ala Val Ala Val Glu Ile Leu Asp
305                 310                 315                 320

Ala Asn Asp Asn Ala Pro Met Phe Asp Pro Gln Lys Tyr Glu Ala His
                325                 330                 335

Val Pro Glu Asn Ala Val Gly His Glu Val Gln Arg Leu Thr Val Thr
                340                 345                 350

Asp Leu Asp Ala Pro Asn Ser Pro Ala Trp Arg Ala Thr Tyr Leu Ile
                355                 360                 365

Met Gly Gly Asp Asp Gly Asp His Phe Thr Ile Thr Thr His Pro Glu
        370                 375                 380

Ser Asn Gln Gly Ile Leu Thr Thr Arg Lys Gly Leu Asp Phe Glu Ala
385                 390                 395                 400

Lys Asn Gln His Thr Leu Tyr Val Glu Val Thr Asn Glu Ala Pro Phe
                405                 410                 415

Val Leu Lys Leu Pro Thr Ser Thr Ala Thr Ile Val Val His Val Glu
                420                 425                 430

Asp Val Asn Glu Ala Pro Val Phe Val Pro Pro Ser Lys Val Val Glu
            435                 440                 445

Val Gln Glu Gly Ile Pro Thr Gly Glu Pro Val Cys Val Tyr Thr Ala
        450                 455                 460

Glu Asp Pro Asp Lys Glu Asn Gln Lys Ile Ser Tyr Arg Ile Leu Arg
465                 470                 475                 480

Asp Pro Ala Gly Trp Leu Ala Met Asp Pro Asp Ser Gly Gln Val Thr
                485                 490                 495

Ala Val Gly Thr Leu Asp Arg Glu Asp Glu Gln Phe Val Arg Asn Asn
            500                 505                 510

Ile Tyr Glu Val Met Val Leu Ala Met Asp Asn Gly Ser Pro Pro Thr
        515                 520                 525

Thr Gly Thr Gly Thr Leu Leu Leu Thr Leu Ile Asp Val Asn Asp His
        530                 535                 540

Gly Pro Val Pro Glu Pro Arg Gln Ile Thr Ile Cys Asn Gln Ser Pro
545                 550                 555                 560

Val Arg Gln Val Leu Asn Ile Thr Asp Lys Asp Leu Ser Pro His Thr
            565                 570                 575

Ser Pro Phe Gln Ala Gln Leu Thr Asp Asp Ser Asp Ile Tyr Trp Thr
                580                 585                 590

Ala Glu Val Asn Glu Glu Gly Asp Thr Val Val Leu Ser Leu Lys Lys
            595                 600                 605

Phe Leu Lys Gln Asp Thr Tyr Asp Val His Leu Ser Leu Ser Asp His
        610                 615                 620

Gly Asn Lys Glu Gln Leu Thr Val Ile Arg Ala Thr Val Cys Asp Cys
625                 630                 635                 640

His Gly His Val Glu Thr Cys Pro Gly Pro Trp Lys Gly Gly Phe Ile
                645                 650                 655
```

```
Leu Pro Val Leu Gly Ala Val Leu Ala Leu Phe Leu Leu Val
                660                 665                 670

Leu Leu Leu Leu Val Arg Lys Lys Arg Lys Ile Lys Glu Pro Leu Leu
675                 680                 685

Leu Pro Glu Asp Asp Thr Arg Asp Asn Val Phe Tyr Tyr Gly Glu Glu
    690                 695                 700

Gly Gly Gly Glu Glu Asp Gln Asp Tyr Asp Ile Thr Gln Leu His Arg
705                 710                 715                 720

Gly Leu Glu Ala Arg Pro Glu Val Val Leu Arg Asn Asp Val Ala Pro
                725                 730                 735

Thr Ile Ile Pro Thr Pro Met Tyr Arg Pro Arg Pro Ala Asn Pro Asp
                740                 745                 750

Glu Ile Gly Asn Phe Ile Ile Glu Asn Leu Lys Ala Ala Asn Thr Asp
                755                 760                 765

Pro Thr Ala Pro Pro Tyr Asp Thr Leu Leu Val Phe Asp Tyr Glu Gly
    770                 775                 780

Ser Gly Ser Asp Ala Ala Ser Leu Ser Ser Leu Thr Ser Ser Ala Ser
785                 790                 795                 800

Asp Gln Asp Gln Asp Tyr Asp Tyr Leu Asn Glu Trp Gly Ser Arg Phe
                805                 810                 815

Lys Lys Leu Ala Asp Met Tyr Gly Gly Gly Glu Asp Asp
                820                 825

<210> SEQ ID NO 127
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

Gly Pro Asp Trp Val Val Ala Pro Ile Ser Val Pro Glu Asn Gly Lys
1               5                   10                  15

Gly Pro Phe Pro Gln Arg Leu Asn Gln Leu Lys Ser Asn Lys Asp Arg
                20                  25                  30

Asp Thr Lys Ile Phe Tyr Ser Ile Thr Gly Pro Gly Ala Asp Ser Pro
            35                  40                  45

Pro Glu Gly Val Phe Ala Val Glu Lys Glu Thr Gly Trp Leu Leu Leu
        50                  55                  60

Asn Lys Pro Leu Asp Arg Glu Glu Ile Ala Lys Tyr Glu Leu Phe Gly
65                  70                  75                  80

His Ala Val Ser Glu Asn Gly Ala Ser Val Glu Asp Pro Met Asn Ile
                85                  90                  95

Ser Ile Ile Val Thr Asp Gln Asn Asp His Lys Pro Lys Phe Thr Gln
                100                 105                 110

Asp Thr Phe Arg Gly Ser Val Leu Glu Gly Val Leu Pro Gly Thr Ser
            115                 120                 125

Val Met Gln Val Thr Ala Thr Asp Glu Asp Asp Ala Ile Tyr Thr Tyr
        130                 135                 140

Asn Gly Val Val Ala Tyr Ser Ile His Ser Gln Glu Pro Lys Asp Pro
145                 150                 155                 160

His Asp Leu Met Phe Thr Ile His Arg Ser Thr Gly Thr Ile Ser Val
                165                 170                 175

Ile Ser Ser Gly Leu Asp Arg Glu Lys Val Pro Glu Tyr Thr Leu Thr
                180                 185                 190
```

Ile Gln Ala Thr Asp Met Asp Gly Asp Gly Ser Thr Thr Ala Val
        195                 200                 205

Ala Val Val Glu Ile Leu Asp Ala Asn Asp Asn
        210                 215

<210> SEQ ID NO 128
<211> LENGTH: 244
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 128

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Gln
            20                  25                  30

Ser Ala Ala Trp Asn Trp Ile Arg Gln Ser Pro Ser Arg Gly Leu Glu
        35                  40                  45

Trp Leu Gly Arg Ile Tyr Tyr Arg Ser Lys Trp Tyr Asn Asp Tyr Ala
50                  55                  60

Leu Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Gly Glu Gly Tyr Gly Arg Glu Gly Phe Ala Ile
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Glu Phe Asp Tyr Lys Asp Asp Asp Lys Gly Ala Pro His His
225                 230                 235                 240

His His His His

<210> SEQ ID NO 129
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 129

Asp Ile Gln Met Thr Gln Ser Pro Ser Ser Leu Ser Ala Ser Val Gly
1               5                   10                  15

```
Asp Arg Val Thr Ile Thr Cys Arg Ala Ser Gln Thr Ile Ser Asn Thr
             20                  25                  30

Leu Ala Trp Tyr Gln Gln Lys Pro Gly Lys Ala Pro Lys Leu Leu Ile
         35                  40                  45

Tyr Ala Ala Ser Asn Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Leu Ser Trp Phe Thr
                 85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Ala
    210

<210> SEQ ID NO 130
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 130

His His His His His His
1               5

<210> SEQ ID NO 131
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Arg Gly Asp Ser
1

<210> SEQ ID NO 132
<211> LENGTH: 22
<212> TYPE: PRT
<213> ORGANISM: Human immunodeficiency virus

<400> SEQUENCE: 132

Tyr Gly Arg Lys Lys Arg Arg Gln Arg Arg Leu Tyr Arg Ser Pro
1               5                   10                  15

Ala Met Pro Glu Asn Leu
```

-continued

```
                20

<210> SEQ ID NO 133
<211> LENGTH: 101
<212> TYPE: PRT
<213> ORGANISM: Homo sapiens

<400> SEQUENCE: 133

Asp Trp Val Val Ala Pro Ile Ser Val Pro Glu Asn Gly Lys Gly Pro
1               5                   10                  15

Phe Pro Gln Arg Leu Asn Gln Leu Lys Ser Asn Lys Asp Arg Asp Thr
            20                  25                  30

Lys Ile Phe Tyr Ser Ile Thr Gly Pro Gly Ala Asp Ser Pro Pro Glu
        35                  40                  45

Gly Val Phe Ala Val Glu Lys Glu Thr Gly Trp Leu Leu Leu Asn Lys
    50                  55                  60

Pro Leu Asp Arg Glu Glu Ile Ala Lys Tyr Glu Leu Phe Gly His Ala
65                  70                  75                  80

Val Ser Glu Asn Gly Ala Ser Val Glu Asp Pro Met Asn Ile Ser Ile
                85                  90                  95

Ile Val Thr Asp Gln
            100

<210> SEQ ID NO 134
<211> LENGTH: 101
<212> TYPE: PRT
<213> ORGANISM: Macaca fascicularis

<400> SEQUENCE: 134

Asp Trp Val Val Ala Pro Ile Ser Val Pro Glu Asn Gly Lys Gly Pro
1               5                   10                  15

Phe Pro Gln Arg Leu Asn Gln Leu Lys Ser Asn Lys Asp Arg Asp Thr
            20                  25                  30

Lys Ile Phe Tyr Ser Ile Thr Gly Pro Gly Ala Asp Ser Pro Pro Glu
        35                  40                  45

Gly Val Phe Ala Val Glu Lys Glu Thr Gly Trp Leu Leu Leu Asn Lys
    50                  55                  60

Pro Leu Asp Arg Glu Glu Ile Ala Lys Tyr Glu Leu Phe Gly His Ala
65                  70                  75                  80

Val Ser Glu Asn Gly Ala Ser Val Glu Asp Pro Met Asn Ile Ser Ile
                85                  90                  95

Ile Val Thr Asp Gln
            100

<210> SEQ ID NO 135
<211> LENGTH: 59
<212> TYPE: PRT
<213> ORGANISM: Homo sapiens

<400> SEQUENCE: 135

Cys Pro Glu Asn Glu Lys Gly Pro Phe Pro Lys Asn Leu Val Gln Ile
1               5                   10                  15

Lys Ser Asn Lys Asp Lys Glu Gly Lys Val Phe Tyr Ser Ile Thr Gly
            20                  25                  30

Gln Gly Ala Asp Thr Pro Pro Val Gly Val Phe Ile Ile Glu Arg Glu
        35                  40                  45

Thr Gly Trp Leu Lys Val Thr Glu Pro Leu Asp
    50                  55
```

```
<210> SEQ ID NO 136
<211> LENGTH: 59
<212> TYPE: PRT
<213> ORGANISM: Homo sapiens

<400> SEQUENCE: 136

Leu Pro Glu Asn Ser Arg Gly Pro Phe Pro Gln Glu Leu Val Arg Ile
1               5                   10                  15

Arg Ser Asp Arg Asp Lys Asn Leu Ser Leu Arg Tyr Ser Val Thr Gly
            20                  25                  30

Pro Gly Ala Asp Gln Pro Pro Thr Gly Ile Phe Ile Ile Asn Pro Ile
        35                  40                  45

Ser Gly Gln Leu Ser Val Thr Lys Pro Leu Asp
    50                  55

<210> SEQ ID NO 137
<211> LENGTH: 59
<212> TYPE: PRT
<213> ORGANISM: Homo sapiens

<400> SEQUENCE: 137

Val Pro Glu Asn Gly Lys Gly Pro Phe Pro Gln Arg Leu Asn Gln Leu
1               5                   10                  15

Lys Ser Asn Lys Asp Arg Asp Thr Lys Ile Phe Tyr Ser Ile Thr Gly
            20                  25                  30

Pro Gly Ala Asp Ser Pro Pro Glu Gly Val Phe Ala Val Glu Lys Glu
        35                  40                  45

Thr Gly Trp Leu Leu Leu Asn Lys Pro Leu Asp
    50                  55

<210> SEQ ID NO 138
<211> LENGTH: 59
<212> TYPE: PRT
<213> ORGANISM: Homo sapiens

<400> SEQUENCE: 138

Val Pro Glu Asn Ser Arg Gly Pro Phe Pro Gln Gln Leu Val Arg Ile
1               5                   10                  15

Arg Ser Asp Lys Asp Asn Asp Ile Pro Ile Arg Tyr Ser Ile Thr Gly
            20                  25                  30

Val Gly Ala Asp Gln Pro Pro Met Glu Val Phe Ser Ile Asp Ser Met
        35                  40                  45

Ser Gly Arg Met Tyr Val Thr Arg Pro Met Asp
    50                  55

<210> SEQ ID NO 139
<211> LENGTH: 54
<212> TYPE: PRT
<213> ORGANISM: Homo sapiens

<400> SEQUENCE: 139

Ile Asp Glu Glu Lys Asn Thr Ser Leu Pro His His Val Gly Lys Ile
1               5                   10                  15

Lys Ser Ser Val Ser Arg Lys Asn Ala Lys Tyr Leu Leu Lys Gly Glu
            20                  25                  30

Tyr Val Gly Lys Val Phe Arg Val Asp Ala Glu Thr Gly Asp Val Phe
        35                  40                  45

Ala Ile Glu Arg Leu Asp
    50
```

```
<210> SEQ ID NO 140
<211> LENGTH: 56
<212> TYPE: PRT
<213> ORGANISM: Homo sapiens

<400> SEQUENCE: 140

Leu Leu Glu Glu Tyr Thr Gly Ser Asp Tyr Gln Tyr Val Gly Lys Leu
1               5                   10                  15

His Ser Asp Gln Asp Arg Gly Asp Gly Ser Leu Lys Tyr Ile Leu Ser
            20                  25                  30

Gly Asp Gly Ala Gly Asp Leu Phe Ile Ile Asn Glu Asn Thr Gly Asp
        35                  40                  45

Ile Gln Ala Thr Lys Arg Leu Asp
    50                  55

<210> SEQ ID NO 141
<211> LENGTH: 56
<212> TYPE: PRT
<213> ORGANISM: Homo sapiens

<400> SEQUENCE: 141

Val Leu Glu Glu Tyr Met Gly Ser Asp Pro Leu Tyr Val Gly Lys Leu
1               5                   10                  15

His Ser Asp Val Asp Lys Gly Asp Gly Ser Ile Lys Tyr Ile Leu Ser
            20                  25                  30

Gly Glu Gly Ala Ser Ser Ile Phe Ile Ile Asp Glu Asn Thr Gly Asp
        35                  40                  45

Ile His Ala Thr Lys Arg Leu Asp
    50                  55

<210> SEQ ID NO 142
<211> LENGTH: 56
<212> TYPE: PRT
<213> ORGANISM: Homo sapiens

<400> SEQUENCE: 142

Val Leu Glu Glu Phe Ser Gly Pro Glu Pro Ile Leu Val Gly Arg Leu
1               5                   10                  15

His Thr Asp Leu Asp Pro Gly Ser Lys Lys Ile Lys Tyr Ile Leu Ser
            20                  25                  30

Gly Asp Gly Ala Gly Thr Ile Phe Gln Ile Asn Asp Val Thr Gly Asp
        35                  40                  45

Ile His Ala Ile Lys Arg Leu Asp
    50                  55

<210> SEQ ID NO 143
<211> LENGTH: 56
<212> TYPE: PRT
<213> ORGANISM: Homo sapiens

<400> SEQUENCE: 143

Leu Leu Glu Glu Tyr Thr Gly Thr Asp Thr Gln Tyr Val Gly Lys Leu
1               5                   10                  15

His Thr Asp Gln Asp Lys Gly Asp Gly Asn Leu Lys Tyr Ile Leu Thr
            20                  25                  30

Gly Asp Gly Ala Gly Ser Leu Phe Val Ile Asp Glu Asn Thr Gly Asp
        35                  40                  45

Ile His Ala Ala Lys Lys Leu Asp
    50                  55
```